US008257946B2

(12) United States Patent
Satchell

(10) Patent No.: US 8,257,946 B2
(45) Date of Patent: Sep. 4, 2012

(54) CYSTEINE PROTEASE AUTOPROCESSING OF FUSION PROTEINS

(75) Inventor: Karla J. F. Satchell, Evanston, IL (US)

(73) Assignee: Northwestern University, Evanston, IL (US)

(*) Notice: Subject to any disclaimer, the term of this patent is extended or adjusted under 35 U.S.C. 154(b) by 0 days.

(21) Appl. No.: 13/183,071

(22) Filed: Jul. 14, 2011

(65) Prior Publication Data

US 2011/0294160 A1 Dec. 1, 2011

Related U.S. Application Data

(63) Continuation of application No. 12/630,603, filed on Dec. 3, 2009, now abandoned.

(60) Provisional application No. 61/119,489, filed on Dec. 3, 2008.

(51) Int. Cl.
*C12P 21/06* (2006.01)

(52) U.S. Cl. ...................................... 435/69.1

(58) Field of Classification Search ........................ None
See application file for complete search history.

(56) References Cited

U.S. PATENT DOCUMENTS

| 7,045,677 | B2 | 5/2006 | Cottingham et al. |
| 7,176,287 | B2 | 2/2007 | Hamilton et al. |
| 7,276,355 | B2 | 10/2007 | Furutani et al. |
| 7,378,512 | B2 | 5/2008 | Rumenapf et al. |
| 7,396,664 | B2 | 7/2008 | Daly et al. |

OTHER PUBLICATIONS

Altschul et al., "Basic local alignment search tool", Journal of Molecular Biology, Oct. 5, 1990, 215(3):403-410.
Boardman et al., "*Vibrio cholerae* Strains with Mutations in an Atypical Type I Secretion System Accumulate RTX Toxin Intracellularly", Journal of Bacteriology, Dec. 2004, 186(23):8137-8143.
Cordero et al., "RTX Toxin Actin Cross-Linking Activity in clinical and Environmental Isolates of *Vibrio cholerae*", Journal of Clinical Microbiology, Jul. 2007, 45(7):2289-2292.
Cordero et al., "The Actin Cross-Linking Domain of the *Vibrio cholerae* RTX Toxin Directly Catalyzes the Covalent Cross-Linking of Actin", Journal of Biological Chemistry, Oct. 27, 2006, 281(43)32366-32374.
Deutscher et al., "Section VII: Purification Procedures: Chromatographic Methods", Methods in Enzymology: Guide to Protein Purification, 1990, 182:309-392.
Egerer et al., "Auto-catalytic Cleavage of Clostridium difficile Toxins A and B Depends on Cysteine Protease Activity", Journal of Biological Chemistry, Aug. 31, 2007, 282(35):25314-25321.
Fullner et al., "Genetic Characterization of a New Type IV-A Pilus Gene Cluster Found in Both Classical and El Tor Biotypes of *Vibrio cholerae*", Infection and Immunity, Mar. 1999, 67(3):1393-1404.
Fullner et al., "In vivo covalent cross-linking of cellular actin by the *Vibrio cholerae* RTX toxin", EMBO Journal, 2000, 19(20):5315-5323.

Fullner-Satchell, "MiniReview: MARTX, Multifunctional Autoprocessing Repeats-in-Toxin Toxins", Infection and Immunity, Nov. 2007, 75(11):5079-5084.
Fullner et al., "The Contribution of Accessory Toxins of *Vibrio cholerae* O1 El Tor to the Proinflammatory Response in a Murine Pulmonary Cholera Model", Journal of Experimental Medicine, Jun. 3, 2002, 195(11):1455-1462.
Fullner et al., "*Vibrio cholerae*I-Induced Cellular Responses of Polarized T84 Intestinal Epithelial Cells Are Dependent on Production of Cholera Toxin and the RTX Toxin", Infection and Immunity, Oct. 2001, 69(10):6310-6317.
Haines et al., "Role of Toll-Like Receptor 4 in the Proinflammatory Response to *Vibrio cholerae* O1 El Tor Strains Deficient in Production of Cholera Toxin and Accessory Toxins", Infection and Immunity, Sep. 2005, 73(9):6157-6164.
Kudryashov et al., "Characterization of the Enzymatic Activity of the Actin Cross-Linnking Domain from the *Vibrio cholerae* MARTXvc Toxin", Journal of Biological Chemistry, Jan. 4, 208, 283(1):445-452.
Kudryashov et al., "Connecting actin monomers by iso-peptide bond is a toxicity mechanism of the *Vibrio cholerae* MARTX toxin", PNAS, Nov. 25, 2008, 105(47):18537-18542.
Lin et al., "Identification of a *Vibrio cholerae* RTX toxin gene cluster that is tightly linked to the cholera toxin prophage", PNAS, Feb. 1999, 96:1071-1076.
Mel, et al., "Association of Protease Activity in *Vibrio cholerae* Vaccine Strains with Decreases in Transcellular Epithelial Resistance of Polarized T84 Intestinal Epithelial Cells", Infection and Immunity, Nov. 2000, 78(11):6487-6492.
Olivier et al., "Hemolysin and the Multifunctional Autoprocessing RTX Toxin Are Virulence Factors during Intestinal Infection of Mice with *Vibrio cholerae* El Tor O1 Strains", Infection and Immunity, Oct. 2007(b), 75(10):5035-5042.
Olivier et al., "Prolonged Colonization of Mice by *Vibrio cholerae* El Tor O1 Depends on Accessory Toxins", Infection and Immunity, Oct. 2007(a), 75(10):5043-5051.
Olivier et al., "Successful Small Intestine Colonization of Adult Mice by *Vibrio Cholerae* Requires Ketamine Anesthesia and Accessory Toxins", Public Library of Science, Oct. 2009, 4(10):1-6.
Osickova et al., "An Amphipathic alpha-Helix Including Glutamates 509 and 516 Is Crucial for Membrane Translocation of Adenylate Cyclase Toxin and Modulates Formation and Cation Selectivity of Its Membrane Channels", Journal of Biological Chemistry, Dec. 31, 1999, 274(53):37644-37650.

(Continued)

*Primary Examiner* — Nashaat Nashed
(74) *Attorney, Agent, or Firm* — Andrus, Sceales, Starke & Sawall, LLP

(57) ABSTRACT

Disclosed are fusion proteins, polynucleotides that encode the disclosed fusion proteins, and methods for expressing and autoprocessing of the disclosed fusion proteins to obtain a target protein. The disclosed fusion proteins include an autoproteolytic cysteine protease fused to a heterologous polypeptide, which may be isolated as the target protein. Preferably, the protease activity of the cysteine protease is inducible. Suitable autoproteolytic cysteine proteases for the fusion proteins include the cysteine protease of the *Vibrio cholerae* RTX toxin.

19 Claims, 7 Drawing Sheets

OTHER PUBLICATIONS

Prochazkova et al., "Structure-Function Analysis of Inositol Hexakisphosphate-induced Autoprocessing of the *Vibrio cholerae* Multifunctional Autoprocessing RTX Toxin", Journal of Biological Chemistry, Aug. 29, 2008, 283 (35):23656-23664.

Pfeifer et al., "Cellular Uptake of *Clostridium difficile* Toxin B", Journal of Biological Chemistry, Nov. 7, 2003, 278(45):44535-44541.

Reineke et al., "Autocatalytic cleavage of *Clostridium difficile* toxin B", Nature, Mar. 22, 2007, 446:415-419.

Rupnik et al., "Characterization of the cleavage site and function of resulting cleavage fragments after limited proteolysis of *Clostridium difficile* toxin B (TcdB) by host cells", Microbiology, 2005, 151:199-208.

Sheahan et al., "Autoprocessing of the *Vibrio cholerae* RTX toxin by the cysteine protease domain", EMBO Journal, 2007, 26(10):2552-2561.

Sheahan et al., "Inactivation of small Rho GTPases by the multifunctional RTX toxin from *Vibrio cholerae*", Cellular Microbiology, May 2007, 9(5):1324-1335.

Sheahan et al., "Identification of a domain within the multifunctional *Vibrio cholerae* RTX toxin that covalently cross-links actin", PNAS, Jun. 29, 2004, 101(26):9798-9803.

Shen et al., "Simplified, Enhanced Protein Purification Using an Inducible, Autoprocessing Enzyme Tag", Public Library of Science, Dec. 2009, 4(12):1-11.

Stols et al., "A New Vector for High-Throughput, Ligation-Independent Cloning Encoding a Tobacco Etch Virus Protease Cleavage Site", Protein Expression and Purification, 2002, 25:8-15.

Tatusova et al., "BLAST 2 sequences, a new tool for comparing protein and nucleotide sequences", FEMS Microbiology Letters, May 15, 1999, 174(2):247-250.

Watnick et al., "A Role for the Mannose-Sensitive Hemagglutinin in Biofilm Formation by *Vibrio cholerae* El Tor", Journal of Bacteriology, Jun. 1999, 181(11):3606-3609.

CYSTEINE PROTEASE AUTOPROCESSING OF FUSION PROTEINS

CROSS-REFERENCE TO RELATED APPLICATIONS

The present application is a continuation of U.S. application Ser. No. 12/630,603, filed on Dec. 3, 2009, which application was published on Jun. 3, 2010, as US2010/0137563, and claims the benefit under 35 U.S.C. §119(e) to U.S. Provisional Patent Application Number 61/119,489, filed on Dec. 3, 2008, the contents of which are incorporated herein by reference in their entireties.

STATEMENT REGARDING FEDERALLY SPONSORED RESEARCH OR DEVELOPMENT

This invention was made with U.S. Government Support from the following agency: NIH/NIAID, Grant No. R01AI051490. The U.S. Government has certain rights in the invention.

BACKGROUND

Purification of recombinant proteins from *Escherichia coli* and other model organisms is an essential component of biochemical and structural biology research. Over the past few decades, numerous strategies have been developed to allow easy purification of recombinant proteins by addition of a fusion protein or protein tag that allows rapid affinity purification. For some proteins, the fusion or tag poses a problem as the additional peptide sequences can interfere with function of the protein in biochemical assays or prevent the protein from forming compact crystals. If this occurs, the tag must often be removed after purification. This process of tag removal can be a cumbersome process.

Recently, a cysteine protease domain (CPD) embedded in a large protein toxin of *Vibrio cholerae* and other bacterial organisms was discovered that is inactive until induced by addition of the chemical compound inositol hexakisphosphate, also known as inositol-6-phosphate, InsP6, IP6, or phytic acid. Here, it is shown that a target protein can be purified as part of a fusion protein that includes the target protein fused to the CPD and a C-terminal peptide tag of 6-histidine residues. After purification of the fusion protein, the inducer molecule InsP6 is added and the protease and the peptide tag are removed from the fusion protein via autoproteolysis. The remaining portion of the fusion protein includes the target protein and an additional alanine and leucine residue added to the C-terminus of the target protein.

These disclosed strategies for purification of recombinant proteins followed by removal of a peptide tag may be adapted into any available cloning or purification systems. The molecule InsP6 is not produced by bacteria, hence, this strategy may be desirable for any recombinant protein produced in *E. coli* or other bacterial expression systems. This strategy also is desirable for any recombinant protein produced in plant, fungal, insect, or animal host cell expression systems in which the host cell is modified to block synthesis of InsP6.

SUMMARY

Disclosed are fusion proteins, polynucleotides that encode the disclosed fusion proteins, and methods for expressing and autoprocessing of the disclosed fusion proteins to obtain a target protein. The disclosed fusion proteins include an autoproteolytic cysteine protease fused to a heterologous polypeptide, which may be isolated as the target protein. In some embodiments, the protease activity of the cysteine protease is inducible. Suitable autoproteolytic cysteine proteases for the fusion proteins include the cysteine protease of the *Vibrio cholerae* RTX toxin. Examples of heterologous polypeptides may include target proteins, including but not limited to, industrial enzymes (process enzymes), enzymes targeted for use in consumer products, or proteins with pharmaceutical activity.

The fusion protein may include: (a) a first polypeptide; and (b) a second polypeptide fused to the C-terminus of the first peptide, where the first polypeptide is heterologous with respect to the second polypeptide and the second polypeptide has an amino acid sequence that includes the cysteine protease domain of the *Vibrio cholerae* RTX toxin or a cysteine proteases domain from a conserved or related toxin as contemplated herein. In some embodiments, the second polypeptide has an amino acid sequence that is at least 95% identical to any of SEQ ID NOs:1-17 (or at least 96%, 97%, 98%, or 99% identical to any of SEQ ID NOs:1-17), and the second polypeptide has cysteine protease activity when induced by inositol hexakisphosphate such that the second polypeptide is autocleaved (e.g., between amino acids 2 and 3 of the second polypeptide).

The fusion protein further may include a peptide tag fused at the C-terminus of the second polypeptide. Suitable peptide tags may include, but are not limited to a 6×His tag, a hemaglutinin tag, a FLAG tag, a glutathione-S-transferase tag, a green fluorescent protein tag, a maltose binding protein tag, a chitin binding protein tag, or another functional sequence of amino acids.

In the fusion protein, the first polypeptide and the second polypeptide may be directly fused. Alternatively, the first polypeptide and second polypeptide may be fused indirectly via a peptide linker (e.g., a linker which optionally is flexible and which optionally has one or more glycine or serine residues or any other compatible amino acid sequence).

Also disclosed are polynucleotides coding for the disclosed fusion proteins. For example, contemplated polynucleotides may include DNA or RNA molecules. The disclosed polynucleotides may be recombinant and may include one or more heterologous polynucleotide sequences fused to the polynucleotide sequence coding for the fusion protein. In some embodiments, contemplated recombinant polynucleotides include a promoter sequence operably linked to a polynucleotide coding for the disclosed fusion protein.

Also disclosed are vectors that include the recombinant polynucleotides. The vectors further may include selectable markers and may be utilized to transform a host cell (e.g., an isolated bacterial, plant, fungal, insect, or animal cell).

Also disclosed are methods for producing the disclosed fusion proteins. The methods may include: (a) culturing or fermenting a cell under conditions suitable for expression of the fusion protein, where the cell is transformed with a recombinant polynucleotide, and the recombinant polynucleotide includes a promoter sequence operably linked to a polynucleotide encoding the fusion protein; and (b) recovering the fusion protein so expressed. The fusion protein further may include a peptide tag as contemplated herein and the method further may include contacting the peptide tag with a molecule or resin that binds the peptide tag (e.g., in order to activate, isolate, separate, or purify the fusion protein). In some embodiments, the method further may include: (c) contacting the recovered fusion protein and inositol hexakisphosphate, thereby inducing cleavage of the fusion protein within the second polypeptide to provide: (i) a cleaved fragment of the fusion protein including the first polypeptide; and (ii) a cleaved fragment of the fusion protein including at least a portion of the second polypeptide. In some embodiments, the recovered fusion protein and the inositol hexakisphosphate are contacted in a reaction mixture comprising a protease inhibitor (e.g., a protease inhibitor that inhibits non-specific protease activity in the reaction mixture). Suitable proteases may include but are not limited to chloromethyl ketones and N-ethylmaleimide. In further embodiments, the method may include: (d) separating the cleaved fragment of the fusion protein that includes the first polypeptide and the cleaved fragment of the fusion protein that includes at least a portion of the second polypeptide. For example, where the fusion protein includes a peptide tag fused at the C-terminus of the second polypeptide, the peptide tag may be contacted with a molecule or resin that binds the peptide tag to remove the cleaved fragment of the fusion protein that includes at least a portion of the second polypeptide.

Also disclosed are kits for preparing and using the fusion proteins contemplated herein. In some embodiments, the kit includes: (1) an expression vector as contemplated herein for expressing the fusion protein; optionally (2) reagents for activating, isolating, separating, or purifying the fusion protein or cleavage products thereof (e.g., resins or columns that bind to the peptide tag present on the fusion protein); and optionally (3) an inducer compound (e.g., inositol hexakisphosphate).

DETAILED DESCRIPTION

Figure 1:
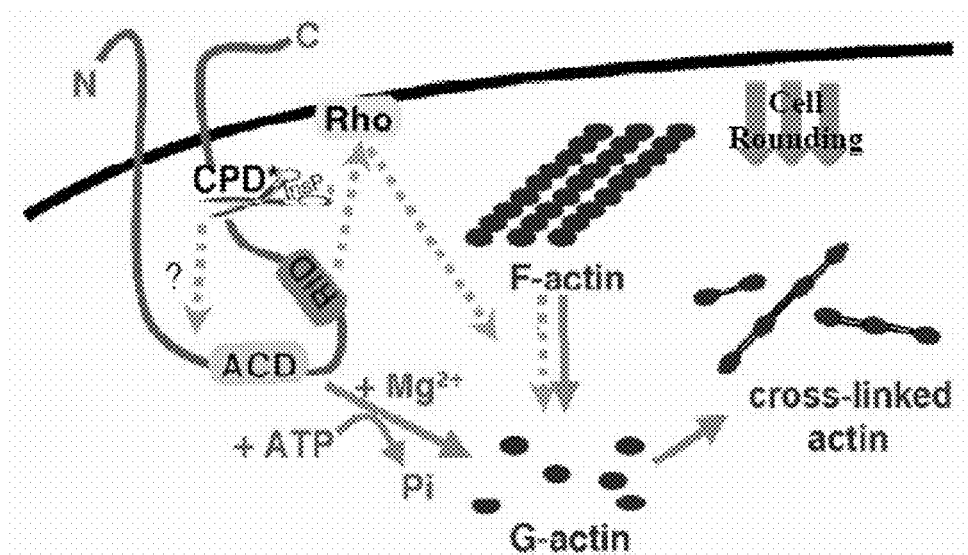
FIG. 1. Model for mechanism of MARTX-Vc-mediated cell rounding.

The subject matter disclosed herein is described using several definitions and description, as set forth below and throughout the application.

Unless otherwise noted, the terms used herein are to be understood according to conventional usage by those of ordinary skill in the relevant art. In addition to the definitions of terms provided below, it is to be understood that as used in the specification, embodiments, and in the claims, "a", "an", and "the" can mean one or more, depending upon the context in which it is used.

As used herein, "about," "approximately," "substantially," and "significantly" are terms that will be understood by persons of ordinary skill in the art and will vary to some extent on the context in which they are used. If there are uses of the term which are not clear to persons of ordinary skill in the art given the context in which the term is used or that are not clear in the context of the present disclosure, "about" or "approximately" will mean up to plus or minus 10% of the particular term and "substantially" and "significantly" will mean more than plus or minus 10% of the particular term.

Disclosed herein are fusion proteins that include an autoproteolytic cysteine protease fused to a heterologous polypeptide. As used herein, a "heterologous polypeptide" is a polypeptide that is not naturally cleaved by the autoproteolytic cysteine protease (e.g., a non-*Vibrio cholerae* RTX polypeptide). Preferably, the enzyme activity of the autoproteolytic cysteine protease is inducible. Suitable autoproteolytic cysteine proteases for the fusion proteins include the cysteine protease domain (CPD) of the *Vibrio cholerae* RTX toxin or cysteine protease domains from conserved or related toxins (e.g., the conserved toxin in large clostridial glucosylating toxins TcdB, TcdA, TcnA, and TcsL; putative toxins from *V. vulnificus, Yersinia* sp., *Photorhabdus* sp., and *Xenorhabdus* sp.; and a filamentous/hemagglutinin-like protein FhaL from *Bordetella* sp.). Examples of heterologous polypeptides may include, target proteins, including but not limited to, industrial enzymes (process enzymes), enzymes targeted for use in consumer products, or proteins with pharmaceutical activity. Fusion proteins and methods of making and using fusion proteins are disclosed in U.S. Pat. Nos. 7,378,512; 7,276,355; 7,176,287; and 7,045,677; the contents of which are incorporated herein by reference in their entireties.

Typically, the protease of the disclosed fusion proteins is fused in frame to the C-terminus of the heterologous polypeptide. The heterologous protein and the protease may be directly fused or indirectly fused via a linking peptide. For example, a linking peptide may comprise at least 1, 2, 3, 4, 5, 10, 15, or 20 amino acids. Suitable linkers may comprise any sequence of amino acids. Preferred linkers have neutral structural properties. For example, a linker preferably has a neutral pH and comprises relatively small-sized amino acids (e.g., glycine and serine). A preferred linker may comprise the sequence (GGGGS) (SEQ ID NO:18) or 1, 2, or 3 tandem repeats thereof.

In some embodiments, the enzyme activity of the autoproteolytic cysteine protease of the fusion protein is inducible (e.g., where the proteolytic activity of the protease is induced by contacting the protease with a chemical reagent such as inositol hexakisphosphate in a processing reaction). For example, the fusion protein may be expressed and subsequently the autoproteolytic activity of the protease may be induced in a processing reaction mixture such that the protease cleaves itself. The portion of the fusion protein comprising the heterologous polypeptide may be separated from the other cleaved portion of the fusion protein (i.e., the portion comprising the protease or the majority of the protease). Preferably, the fusion protein further comprises a peptide tag at the C-terminus of the protease, which may be utilized to isolate, separate, or purify the fusion protein or to isolate, separate, or purify the C-terminal portion of the fusion protein. In some embodiments, non-specific protease activity of the fusion protein may be inhibited by including in the processing reaction a protease inhibitor, including but not limited to chloromethyl ketones and N-ethylmaleimide. As contemplated herein, "non-specific protease activity" means cleavage by the autoprotease at a position other than between amino acids 2 and 3 of the autoprotease (or cleavage by another protease in the processing reaction mixture a position other than between amino acids 2 and 3 of the autoprotease).

Preferably, the protease inhibitor does not inhibit or does not substantially inhibit specific protease activity of the autoprotease (i.e., cleavage by the autoprotease at the position between amino acids 2 and 3 of the autoprotease). As contemplated herein, a protease inhibitor that does not substantially inhibit the specific protease activity of the autoprotease is a protease inhibitor that does not inhibit the specific protease activity of the autoprotease by more than 50% (preferably that does not inhibit the specific protease activity of the autoprotease by more than 40%, 30%, 20%, or 10%).

Also disclosed are nucleic acid molecules that encode the disclosed fusion proteins. For example, contemplated are nucleic add molecules (e.g., DNA or RNA) which code for a fusion protein in which the fusion protein comprises a first polypeptide fused at its C-terminus to a second polypeptide as disclosed herein.

A preferred nucleic acid molecule is one that encodes the fusion protein contemplated herein in which the encoded second polypeptide of the fusion protein comprises the amino acid sequence of any of SEQ ID NOs:1-17 or the amino acid sequence of a variant, mutant, or derivative thereof with autoproteolytic cysteine protease activity. Variants or derivatives with autoproteolytic cysteine protease activity may include variants or derivative having one or more amino acid substitutions, deletions, additions and/or amino acid insertions, provided that autoproteolytic activity is retained.

The autoproteolytic cysteine protease activity of the disclosed fusion protein or polypeptides can be assayed by methods shown herein or by methods known in the art (e.g., by an in vitro system). For example, a DNA construct encoding a fusion protein or polypeptide may be transcribed into RNA and translated into protein with the aid of an in vitro translation kit. The resulting protein may be labeled by incorporating a detectable amino acid (e.g., a radioactive amino acid). Protease activity may be induced by adding inositol hexakisphosphate to the protein. If a fusion protein or polypeptide exhibits autoproteolysis, the resulting cleavage products can be detected using methods known in the art. For example, the protein can be loaded onto a protein gel (for example SDS-PAGE) and subjected to electrophoresis. The gel may be subsequently stained with suitable dyes or subjected to autoradiography. Alternatively, a Western blot and immunostaining may be performed. Cleavage of the protein can be assessed on the basis of the intensity of the resulting protein bands.

Also contemplated are bacterial, plant, fungal, insect, or animal host cell expression vectors that express the disclosed fusion proteins. Vectors may be used to transform appropriate host cells (e.g., *E. coli*). The transformed host cell may be cultivated or fermented such that the fusion protein is expressed constitutively or after adding a reagent that induces expression (e.g., via an inducible promoter). The fusion protein may exhibit autoproteolysis after expression. To assess the efficiency of autoproteolytic cleavage, a sample comprising the fusion protein may be taken after the end of the cultivation or induction phase and analyzed by SDS-PAGE or other methods.

Expression vectors as contemplated herein may include control sequences that modulate expression of the fusion protein. Expression control sequences may include constitutive or inducible promoters (e.g., T3, T7, Lac, trp, or phoA), ribosome binding sites, or transcription terminators.

The vectors disclosed herein may be utilized to transform host cells. Suitable host cells include bacterial, plant, fungal, insect, or animal host cell. Suitable bacteria include, but are not limited to: Gram-negative bacteria such as *Escherichia* species (e.g., *E. coli*), other Gram-negative bacteria, (e.g., *Pseudomonas* sp., such as *Pseudomonas aeruginosa*, or *Caulobacter* sp., such as *Caulobacter crescentus*), or Gram-positive bacteria (e.g., *Bacillus* sp., in particular *Bacillus subtilis*).

Also disclosed are methods for expressing, preparing, isolating, separating, or purifying fusion protein or polypeptides. In some embodiments, the methods may be utilized to produce the heterologous polypeptide of the fusion protein as disclosed herein. The steps of the methods may include: (i) cultivating or fermenting a transformed host cell (e.g., a bacterial host cell as contemplated herein) which comprises an expression vector (as contemplated herein) which in turn comprises a nucleic acid molecule encoding a fusion protein (as contemplated herein), wherein cultivation occurs under conditions which cause expression of the fusion protein and further autoproteolytic cleavage of the fusion protein; and (ii) isolating, separating, or purifying the cleaved heterologous polypeptide portion of the fusion protein. The transformed bacteria may be cultivated or fermented using methods known in the art in order to express the fusion protein. The cleaved heterologous polypeptide portion of the fusion protein may be isolated, separated, or purified by methods known in the art (see, e.g., M. P. Deutscher, in: Methods in Enzymology: Guide to Protein Purification, Academic Press Inc., (1990), 309-392). An exemplary isolation, separation, or purification method may include one or more of the following steps: a cell disruption step, a clarification step (e.g., via centrifugation or filtration), a chromatographic separation step, a dialysis step, and a precipitation step.

The terms "nucleic acid" and "nucleic acid sequence" refer to a nucleotide, oligonucleotide, polynucleotide (which terms may be used interchangeably), or any fragment thereof. These phrases also refer to DNA or RNA of genomic or synthetic origin (which may be single-stranded or double-stranded and may represent the sense or the antisense strand). These phrases also refer to peptide nucleic acid (PNA), or to any DNA-like or RNA-like material.

The terms "amino acid" and "amino acid sequence" refer to an oligopeptide, peptide, polypeptide, or protein sequence (which terms may be used interchangeably), or a fragment of any of these, and to naturally occurring or synthetic molecules. Where "amino acid sequence" is recited to refer to a sequence of a naturally occurring protein molecule, "amino acid sequence" and like terms are not meant to limit the amino acid sequence to the complete native amino acid sequence associated with the recited protein molecule.

The amino acid sequences contemplated herein may include conservative amino acid substitutions relative to a reference amino acid sequence. For example, a variant, mutant, or derivative polypeptide may include conservative amino acid substitutions relative to a reference polypeptide. "Conservative amino acid substitutions" are those substitutions that are predicted to interfere least with the properties of the reference polypeptide. In other words, conservative amino acid substitutions substantially conserve the structure and the function of the reference protein. Table 1 provides a list of exemplary conservative amino acid substitutions.

TABLE 1

| Original Residue | Conservative Substitution |
|---|---|
| Ala | Gly, Ser |
| Arg | His, Lys |
| Asn | Asp, Gln, His |
| Asp | Asn, Glu |
| Cys | Ala, Ser |
| Gln | Asn, Glu, His |

TABLE 1-continued

| Original Residue | Conservative Substitution |
|---|---|
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Thr | Ser, Val |
| Trp | Phe, Tyr |
| Tyr | His, Phe, Trp |
| Val | Ile, Leu, Thr |

Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

A "deletion" refers to a change in the amino acid or nucleotide sequence that results in the absence of one or more amino acid residues or nucleotides. A deletion removes at least 1, 2, 3, 4, 5, 10, 20, 50, 100, or 200 amino acids residues or nucleotides. A deletion may include an internal deletion or a terminal deletion (e.g., an N-terminal truncation or a C-terminal truncation of a reference polypeptide or a 5'-terminal or 3'-terminal truncation of a reference polynucleotide).

A "fragment" is a portion of an amino acid sequence or a polynucleotide which is identical in sequence to but shorter in length than a reference sequence. A fragment may comprise up to the entire length of the reference sequence, minus at least one nucleotide/amino acid residue. For example, a fragment may comprise from 5 to 1000 contiguous nucleotides or contiguous amino acid residues of a reference polynucleotide or reference polypeptide, respectively. In some embodiments, a fragment may comprise at least 5, 10, 15, 20, 25, 30, 40, 50, 60, 70, 80, 90, 100, 150, 250, or 500 contiguous nucleotides or contiguous amino acid residues of a reference polynucleotide or reference polypeptide, respectively. Fragments may be preferentially selected from certain regions of a molecule. The term "at least a fragment" encompasses the full length polynucleotide or full length polypeptide.

A "full length" polynucleotide sequence is one containing at least a translation initiation codon (e.g., methionine) followed by an open reading frame and a translation termination codon. A "full length" polynucleotide sequence encodes a "full length" polypeptide sequence.

"Homology" refers to sequence similarity or, interchangeably, sequence identity, between two or more polynucleotide sequences or two or more polypeptide sequences. Homology, sequence similarity, and percentage sequence identity may be determined using methods in the art and described herein.

The terms "percent identity" and "% identity," as applied to polynucleotide sequences, refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. Percent identity for a nucleic acid sequence may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403 410), which is available from several sources, including the NCBI, Bethesda, Md., at its website. The BLAST software suite includes various sequence analysis programs including "blastn," that is used to align a known polynucleotide sequence with other polynucleotide sequences from a variety of databases. Also available is a tool called "BLAST 2 Sequences" that is used for direct pairwise comparison of two nucleotide sequences. "BLAST 2 Sequences" can be accessed and used interactively at the NCBI website. The "BLAST 2 Sequences" tool can be used for both blastn and blastp (discussed below).

Percent identity may be measured over the length of an entire defined polynucleotide sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or Sequence Listing, may be used to describe a length over which percentage identity may be measured.

A "variant," "mutant," or "derivative" of a particular nucleic acid sequence may be defined as a nucleic acid sequence having at least 50% sequence identity to the particular nucleic acid sequence over a certain length of one of the nucleic acid sequences using blastn with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of nucleic acids may show, for example, at least 60%, at least 70%, at least 80%, at least 85%, at least 90%, at least 91%, at least 92%, at least 93%, at least 94%, at least 95%, at least 96%, at least 97%, at least 98%, or at least 99% or greater sequence identity over a certain defined length.

Nucleic acid sequences that do not show a high degree of identity may nevertheless encode similar amino acid sequences due to the degeneracy of the genetic code. It is understood that changes in a nucleic acid sequence can be made using this degeneracy to produce multiple nucleic acid sequences that all encode substantially the same protein.

The phrases "percent identity" and "% identity," as applied to polypeptide sequences, refer to the percentage of residue matches between at least two polypeptide sequences aligned using a standardized algorithm. Methods of polypeptide sequence alignment are well-known. Some alignment methods take into account conservative amino acid substitutions. Such conservative substitutions, explained in more detail above, generally preserve the charge and hydrophobicity at the site of substitution, thus preserving the structure (and therefore function) of the polypeptide. Percent identity for amino acid sequences may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403 410), which is available from several sources, including the NCBI, Bethesda, Md., at its website. The BLAST software suite includes various sequence analysis programs including "blastp," that is used to align a known amino acid sequence with other amino acids sequences from a variety of databases.

Percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

A "variant," "mutant," or "derivative" of a particular polypeptide sequence is defined as a polypeptide sequence having at least 50% sequence identity to the particular polypeptide sequence over a certain length of one of the polypeptide sequences using blastp with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of polypeptides may show, for example, at least 60%, at least 70%, at least 80%, at least 90%, at least 91%, at least 92%, at least 93%, at least 94%, at least 95%, at least 96%, at least 97%, at least 98%, or at least 99% or greater sequence identity over a certain defined length of one of the polypeptides. A "variant" or a "derivative" may have substantially the same functional activity as a reference polypeptide. For example, a variant or derivative of a cysteine protease may have cysteine protease activity (e.g., autoproteolytic cysteine protease activity).

The words "insertion" and "addition" refer to changes in an amino acid or nucleotide sequence resulting in the addition of one or more amino acid residues or nucleotides, respectively. An insertion or addition may refer to 1, 2, 3, 4, 5, 10, 20, 30, 40, 50, 60, 70, 80, 90, 100, 150, or 200 amino acid residues or nucleotides.

"Operably linked" refers to the situation in which a first nucleic acid sequence is placed in a functional relationship with a second nucleic acid sequence. For instance, a promoter is operably linked to a coding sequence if the promoter affects the transcription or expression of the coding sequence. Operably linked DNA sequences may be in close proximity or contiguous and, where necessary to join two protein coding regions, in the same reading frame.

A "recombinant nucleic acid" is a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques such as those described in Sambrook, J. et al. (1989) Molecular Cloning: A Laboratory Manual, 2$^{nd}$ ed., vol. 1 3, Cold Spring Harbor Press, Plainview N.Y. The term recombinant includes nucleic acids that have been altered solely by addition, substitution, or deletion of a portion of the nucleic acid. Frequently, a recombinant nucleic acid may include a nucleic acid sequence operably linked to a promoter sequence. Such a recombinant nucleic acid may be part of a vector that is used, for example, to transform a cell.

"Substantially isolated or purified" nucleic acid or amino acid sequences are contemplated herein. The term "substantially isolated or purified" refers to nucleic acid or amino acid sequences that are removed from their natural environment, and are at least 60% free, preferably at least 75% free, and more preferably at least 90% free, even more preferably at least 95% free from other components with which they are naturally associated.

"Transformation" describes a process by which exogenous DNA is introduced into a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, bacteriophage or viral infection, electroporation, heat shock, lipofection, and particle bombardment. The term "transformed cells" includes stably transformed cells in which the inserted DNA is capable of replication either as an autonomously replicating plasmid or as part of the host chromosome, as well as transiently transformed cells which express the inserted DNA or RNA for limited periods of time.

A "composition comprising a given amino acid sequence" and a "composition comprising a given polynucleotide sequence" refer broadly to any composition containing the given polynucleotide or amino acid sequence. The composition may comprise a dry formulation or an aqueous solution. The compositions may be stored in any suitable form including, but not limited to, freeze-dried form and may be associated with a stabilizing agent such as a carbohydrate. The compositions may be aqueous solution containing salts (e.g., NaCl), detergents (e.g., sodium dodecyl sulfate; SDS), and other components (e.g., Denhardt's solution, dry milk, salmon sperm DNA, and the like).

The contemplated fusion proteins may include at least a fragment of an amino acid sequence of a proven or putative cysteine protease. (See Sheahan K.L. et al., "Autoprocessing of the *Vibrio cholerae* RTX toxin by the cysteine protease domain," EMBO J. 2007 May 16;26(10):2552-61, at page 2553, FIG. 1 and supplemental Table 1, the content of which is incorporated herein by reference in its entirety). Proven and putative cysteine protease domains for incorporation into the fusion proteins contemplated herein include, but are not limited to Vibrio-type RTX toxins such as toxins from *V. cholerae* (VcRtx) (SEQ ID NO:1); *V. vulnificus* (VvRtx) (SEQ ID NO:2), *V. splendidus* (VsRtx) (SEQ ID NO:3), *Xenorhabdus nematophila* (XnRtx) (SEQ ID NO:8), *X bovienii* (XbRtx) (SEQ ID NO:9), and *Photorhabdus luminescens* (Plu1344 (SEQ ID NO:4), Plu1341 (SEQ ID NO:5), Plu3217 (SEQ ID NO:6), and Plu3324 (SEQ ID NO:7)); clostridial-type toxins such as *Clostridium difficile* toxin A (TcdA) (SEQ ID NO:12), toxin B (TcdB) (SEQ ID NO:13), *C. sordellii* cytotoxin L (TcsL) (SEQ ID NO:15) and *C. noveyi* alpha toxin (TcnA) (SEQ ID NO:14); putative *Yersinia* toxins *Y. pseudotuberculosis* YPTB3219 (YpRtx) (SEQ ID NO:10) and *Y. mollaretti* Mfp2 (YmMfp2) (SEQ ID NO:11); and four domains arranged in tandem in *B. pertussis* putative adhesin FhaL (FhaL1-4) (SEQ ID NO:16). Contemplated fusion proteins may include at least a fragment of the proven and putative autoproteases disclosed in Table 2, in particular the listed amino acid fragment.

TABLE 2

| Protein | Abbreviation | Gen Bank Accession number | SEQ ID NO: | Amino Acid Fragment |
|---|---|---|---|---|
| Group 1: Vibrio-type RTX toxins | | | | |
| V. cholerae RTX toxin | VcRtx | gi │ 4455065 | 1 | 3420-3619 |
| V. vulnificus RTX toxin | VvRtx | gi │ 37676690 | 2 | 4110-4288 |
| V. splendidus putative RTX toxin | VsRtx | gi │ 84386478 | 3 | 3751-3975 |
| P. luminescens putative RTX toxins | Plu1341 | gi │ 37525303 | 4 | 2579-2764 |
| | Plu1344 | gi │ 36784731 | 5 | 2965-3163 |
| | Plu3217 | gi │ 36786533 | 6 | 2425-2620 |
| | Plu3324 | gi │ 37686635 | 7 | 2440-2626 |
| Group 2: Putative toxins from Yersinia | | | | |
| Y. pseudotuberculosis putative toxin | YpRtx | gi │ 51590811 | 10 | 1058-1271 |
| Y. mollaretti putative toxin | YmMfp2 | gi │ 77962640 | 11 | 1-224 |
| Group 3: Clostridial glucosylating toxins | | | | |
| C. difficile Toxin A | TcdA | gi │ 98593 | 12 | 535-769 |
| C. difficile Toxin B | TcdB | gi │ 761714 | 13 | 536-768 |
| C. noveyi alpha toxin | TcnA | gi │ 755724 | 14 | 532-813 |
| C. sordellii cytotoxin L | TcsL | gi │ 1000695 | 15 | 526-825 |
| Group 4. Type V secreted adhesin | | | | |
| Bordetella pertussis putative adhesin | cpd1 | gi │ 33563918 | 16 | 2551-2716 |
| FhaL | cpd2 | gi │ 33563918 | 16 | 3079-3119 |
| | cdp3 | gi │ 33563918 | 16 | 3375-3971 |
| | cpd4 | gi │ 33563918 | 16 | 3397-3562 |

In some embodiments, the disclosed fusion proteins may include at least a fragment of the amino acid sequence of the MARTX toxin of *V. cholerae* as the second polypeptide of the fusion protein. (See, e.g., Satchell, K. J., "MARTX, Multifunctional Autoprocessing Repeats-in-Toxin Toxins," Infection and Immunity, November 2007, p. 5079-5084; Sheahan K. L. et al., "Autoprocessing of the *Vibrio cholerase* RTX toxin by the cysteine protease domain," EMBO J. 2007 May 16; 26(10):2552-61; Prochazkova K. et al., "Structure-function analysis of inositol hexakisphosphate-induced autoprocessing of the *Vibrio cholerae* multifunctional autoprocessing RTX toxin," J. Biol. Chem. 2008 Aug. 29; 283(35); Prochazkova et al., "Structural and molecular mechanism for autoprocessing of MARTX toxin of *Vibrio Cholerae* at multiple sites," J. Biol. Chem. 2009 2009 Sep. 25; 284(39):26557-68 Epub 2009 Jul. 20; the contents of which are incorporated by reference in their entireties). The entire MARTX toxin of *V. cholerae* is 4545 amino acids. (See Table 2 above where the MARTX toxin is referred to as "VcRtx," and GenBank Accession No. gi│4455065, the content of which is incorporated herein by reference in its entirety). In some embodiments, the disclosed fusion proteins comprise amino acid sequence 3376-3637 of MARTX (e.g., as the contemplated protease domain or C-terminal second polypeptide of the presently disclosed fusion proteins), or a variant, mutant, or derivative thereof having cysteine protease activity. In other embodiments, the disclosed fusion proteins comprise amino acid sequence 3427-3637 of MARTX (SEQ ID NO:17) (e.g., as the contemplated protease domain or C-terminal second polypeptide of the presently disclosed fusion proteins), or a variant, mutant, or derivative thereof having cysteine protease activity. In other embodiments, the disclosed fusion proteins comprise amino acid sequence 3432-3637 of MARTX (e.g., as the contemplated protease domain or C-terminal second polypeptide of the presently disclosed fusion proteins), or a variant, mutant, or derivative thereof having cysteine protease activity. In even further embodiments, the disclosed fusion proteins comprise amino acid sequence 3441-3637 of MARTX (e.g., as the contemplated protease domain or C-terminal second polypeptide of the presently disclosed fusion proteins), or a variant; mutant, or derivative thereof having cysteine protease activity.

EXAMPLES

The following examples are illustrative and are not intended to limit the disclosed subject matter.

Example 1

Background
*Vibrio cholerae* MARTX toxin. The life-threatening diarrheal disease cholera is caused by toxigenic strains of the Gram-negative organism *Vibrio cholerae*. In addition to the well-characterized ADP-ribosylating cholera toxin (CT), *V. cholerae* secretes a novel cytotoxin that is the founding member of a new family of the RTX (repeats-in-toxin) family (Satchell, 2007). This toxin of *V. cholerae* contributes to virulence in mice and has been shown to be important for the bacterium to establish prolonged colonization of the small intestine (Olivier et al., 2007b; Olivier et al., 2007a). Hence, it has been proposed that this toxin is important for initiation of disease in cholera patients and is likely an important factor for prolonged colonization in asymptomatic carriers and thereby is important for dissemination of the pathogen.

Beyond its potential importance for pathogenesis, the Multifunctional-Autoprocessing RTX toxin of *V. cholerae* (MARTX-Vc) is of intrinsic interest due to its novel biochemical properties and mode of action. At 4545 aa and a predicted size of >480 kDa, MARTX-Vc is one of the largest single polypeptide toxins. However, unlike other RTX toxins, MARTX-Vc is not a pore-forming toxin, but rather induces actin depolymerization and cell rounding (Satchell, 2007).

Current knowledge about the process of cell rounding by MARTX-Vc is diagrammed in FIG. 1. Based on the mechanism of translocation of RTX toxin *Bordetella pertussis* adenylate cyclase (Osickova et al., 1999), it is predicted that MARTX-Vc self-inserts into the eukaryotic cytoplasmic membrane and then transfers activity domains to the cytoplasm. Thus far, at least three activities have been described for this toxin conferred by three discrete activity domains:

1. Cross-linking activity. The toxin has been shown to covalently crosslink actin into oligomers (Fullner and Mekalanos, 2000). This activity is associated with the actin crosslinking domain (ACD) that is shared with a type 6 secretion effector of *V. cholerae* and with the putative MARTX toxin of *Aeromonas hydrophila* (MARTX-Ah) (Satchell, 2007; Sheahan et al., 2004). It has been shown that the substrate for crosslinking is free monomeric G-actin and crosslinking occurs dependent upon the hydrolysis of ATP. It has been hypothesized that cell rounding then occurs by depletion of the free G-actin pool leading to an equilibrium shift that drives the depolymerization of assembled actin fibers (Kudryashov et al., 2008; Cordero et al., 2006).

2. RhoGTPase inactivation. It also has been demonstrated that the toxin inactivates RhoGTPases, the master regulators of actin cytoskeletal assembly, by a mechanism that is distinct from all other known Rho-modulating toxins. This activity is associated with a Rho-inactivation domain (RID) that is shared with the MARTX toxin from *V. vulnificus* (MARTX-Vv) and the putative MARTX toxins from *Xenorhabdus* sp. (Satchell, 2007; Sheahan and Satchell, 2007).

3. Cysteine protease domain (CPD) autoproteolysis. It also has been shown that the toxin has an autoprocessing activity associated with it cysteine protease domain (CPD). This enzymatic region of the protein cleaves the toxin after binding cytosolic stimulatory factor inositol hexakisphosphate (InsP6), a molecule found exclusively in the eukaryotic cell cytosol. Thus, processing would be induced only after translocation to the eukaryotic cell cytosol to release the ACD and RID to access the substrates (Sheahan et al., 2007).

Figure 2:
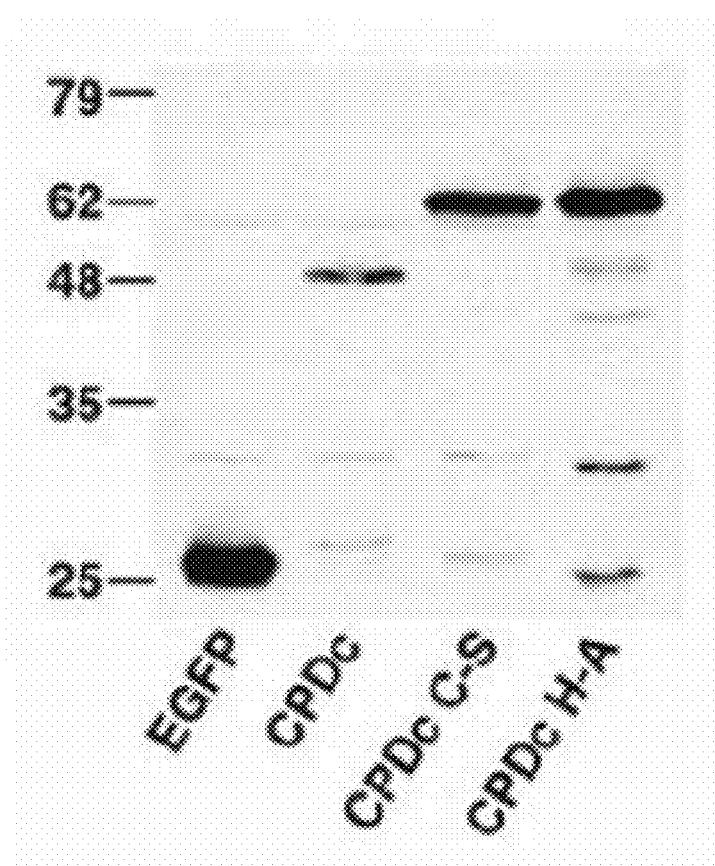
FIG. 2. HEp-2 cells transfected with CPD fused to EGFP (CPDc) do not have full-length CPD:EGFP as detected by Western blotting with anti-EGFP antibody. Mutagenesis of C3568 (CPDc C-S) or H3519 (CPDc H-A) resulted in proteins at the expected mol. wt.

Identification of the CPD. Transient expression of aa 3376-3637 of the MARTX-Vc toxin in eukaryotic cells resulted in cells that appeared condensed and necrotic. A Western blot of cell lysates with anti-GFP antibody revealed the CPD:EGFP fusion protein expressed from plasmid pCPDc runs on SDS-PAGE at 48 kDa, approx. 9 kDa smaller than predicted (FIG. 2). Since one of only two Cys residues in the entire toxin is located within this region, it was hypothesized that Cys3568 was important for cytotoxicity. Indeed, cytotoxicity was not observed after transfection of a mutant plasmid carrying a C3568S mutation. The fusion protein expressed from pCPDc C-S ran on SDS-PAGE at the expected size of 57 kDa. A His3519A mutant also ran at the predicted mol. wt. (FIG. 2) These results showed this domain is an autoprotease with a His-Cys catalytic dyad in vivo (Sheahan et al., 2007).

Figure 3:
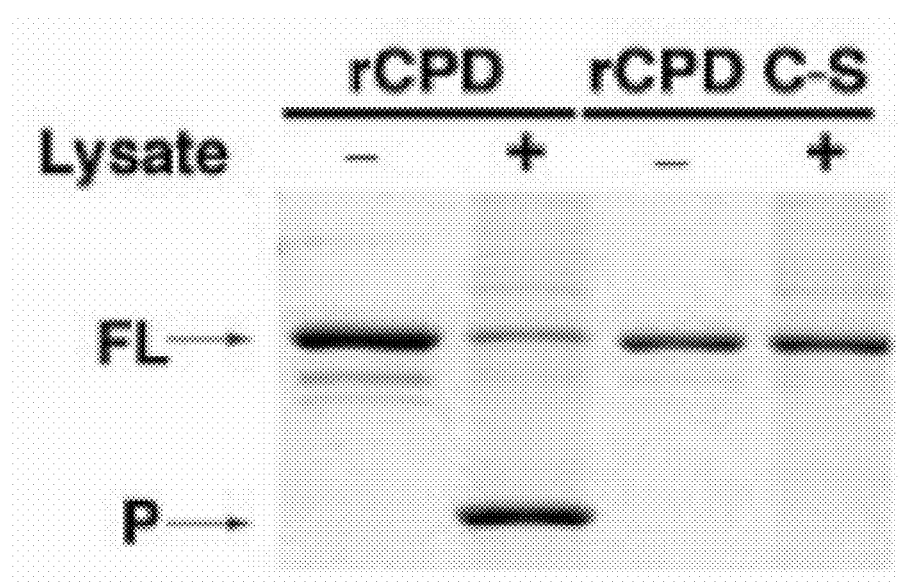
FIG. 3. Purified recombinant CPD (rCPD) or the C3568S mutant (rCPD C-S) were incubated at 37° C. for 2 hr in the (+)presence or (−)absence of a nuclear-free cell lysate. Arrows indicated full-length (FL) and processed (P) forms of rCPD.

Induced autoprocessing of the CPD. In order to demonstrate that the CPD is an autoprocessing cysteine protease, recombinant CPD and recombinant protein carrying the C3568S mutation were purified (rCPD and rCPD C-S, respectively). Both proteins purified from *E. coli* at the full length and were resolved on SDS-PAGE at the predicted m.w. of 34 kDa demonstrating that rCPD was not cleaved in *E. coli* or during purification. Cleavage occurred only after addition a nuclear-free eukaryotic cell lysate, which stimulated autoprocessing of rCPD, but not rCPD C-S (FIG. 3) (Sheahan et al., 2007).

Figure 4:
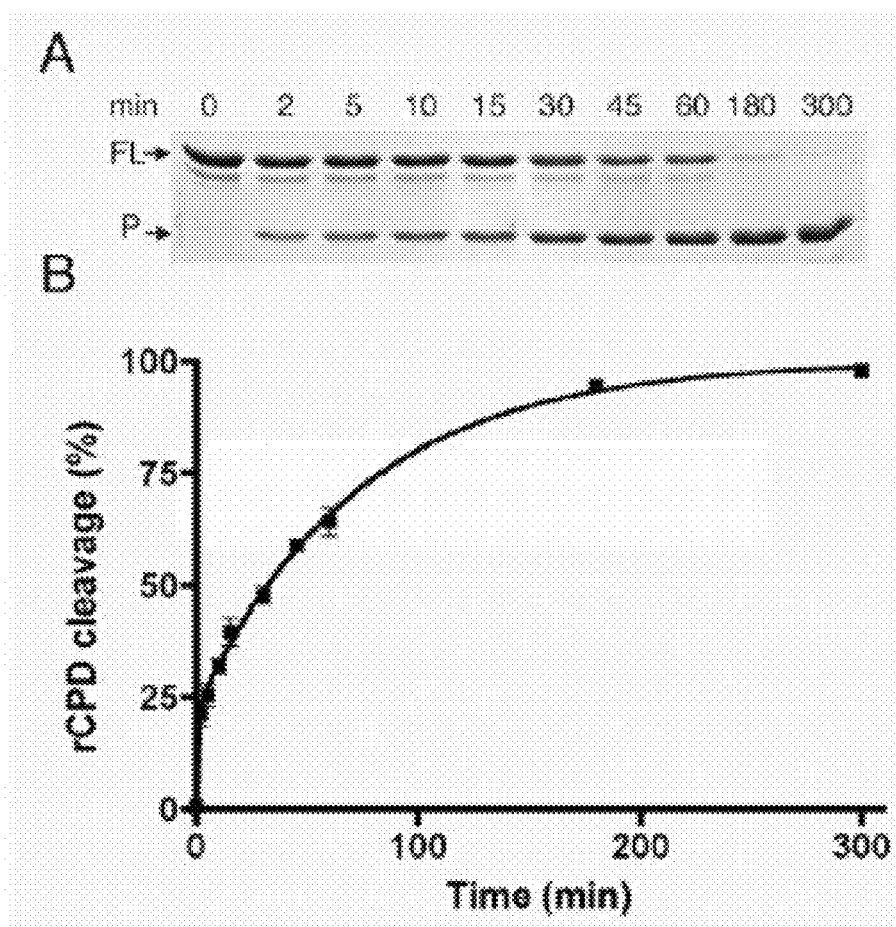
FIG. 4. Demonstrates autoprocessing of rCPD at its N-terminus after addition of 100 µM InsP6.

Homologous CPDs have been identified in 18 large bacterial proteins including all MARTX toxins, four clostridial glucosylating toxins, 2 putative toxins from *Yersinia* sp., and an adhesin from *Bordetella* sp. (Sheahan et al., 2007). Of particular note is *Clostridum difficile* Toxin B (TcdB). This toxin has previously been demonstrated to undergo processing after translocation to release the glucosyl transferase catalytic domain (Rupnik et al., 2005; Pfeifer et al., 2003). A recent paper showed that autocatalytic processing of TcdB occurs after addition of inositol hexakisphosphate (InsP6), also known as inositol-6-phosphate, IP6, or phytic acid (Reineke et al., 2007). In a subsequent paper, InsP6-induced autoprocessing of both TcdA and TcdB was shown to be due to its cysteine protease domain, the same domain shared with MARTX-Vc (Egerer et al., 2007). Based on the TcdB results, InsP6 was assessed to determine whether it also induces autoprocessing of rCPD. Indeed, InsP6 induces autoprocessing of rCPD and has a binding constant for InsP6 of 0.6 µM. InsP6-induced autoprocessing of rCPD occurred in a time- and concentration-dependent manner (FIG. 4, Prochazkova K., and Satchell K. J., "Structure-function analysis of inositol hexakisphosphate-induced autoprocessing of the *Vibrio cholerae* multifunctional autoprocessing RTX toxin," J. Biol. Chem., 2008 Aug. 29; 283(35):23656-64).

Figure 5:
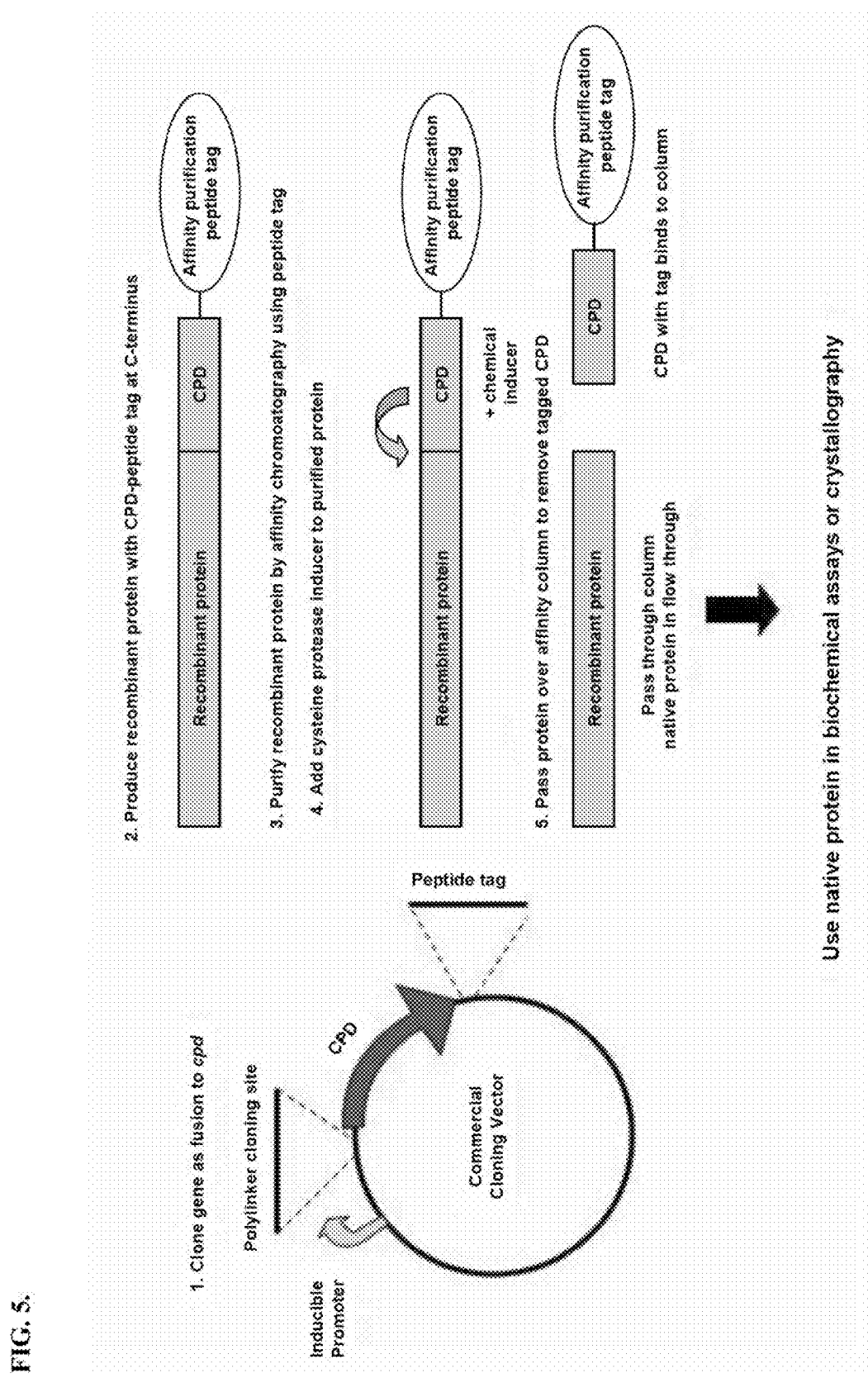
FIG. 5. Production of recombinant protein as part of a fusion protein and subsequent cleavage at CPD.

Application of CPD to recombinant protein purification. The CPD of *V. cholerae* is not active in bacteria and is inducible only by adding the inducing compound inositol 6 phosphate in a processing reaction. As such, a recombinant protein fused at the N-terminus of the CPD was created and a peptide tag was added at the C-terminus of the CPD. It was hypothesized that the recombinant protein could be purified via the peptide tag which subsequently could be removed by inducing the CPD, allowing rapid production of native recombinant protein. The concept is diagrammed in FIG. 5 below. The recovered recombinant protein after cleavage includes two additional C-terminal amino acids from the CPD (i.e., an alanine-leucine dipeptide). CPD cleavage of the fusion protein could be induced on a column, after purification of the fusion protein, or during dialysis of the fusion protein. The peptide tag remains associated with the CPD and thus the tagged CPD may be removed from the recombinant protein by affinity chromatography. In some embodiments, protease inhibitors may be included in the processing reaction, including but not limited to chloromethyl ketones or N-ethylmaleimide. For example, protease inhibitors may be utilized to prevent cleavage at a site other than the specific site for CPD cleavage (e.g., at a position other than between amino acids 2 and 3 of the CPD).

Figure 6:
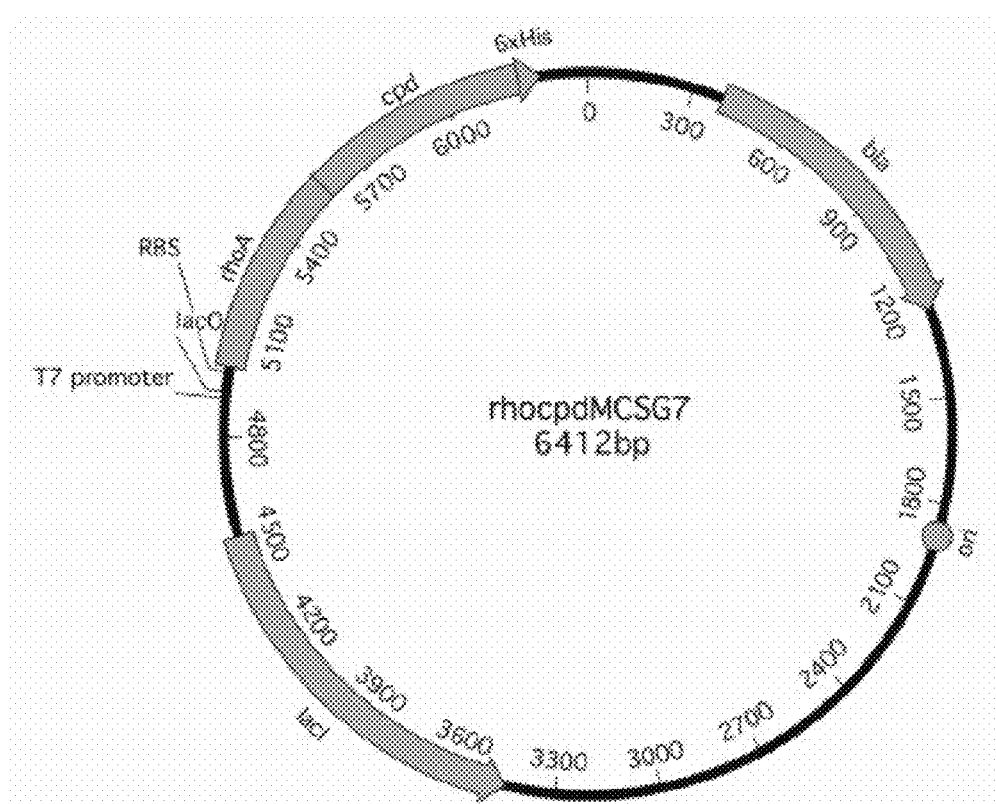
FIG. 6. Diagram of overexpression plasmid created to generate a fusion of RhoA to CPD:6×His.

In one example, a T7 overexpression plasmid was utilized to fuse the eukaryotic protein RhoA to CPD with a C-terminal 6×His Tag. A map of this vector is diagrammed in FIG. 6. This vector was created from pMCSG7 (Stols et al., 2002).

Figure 7:
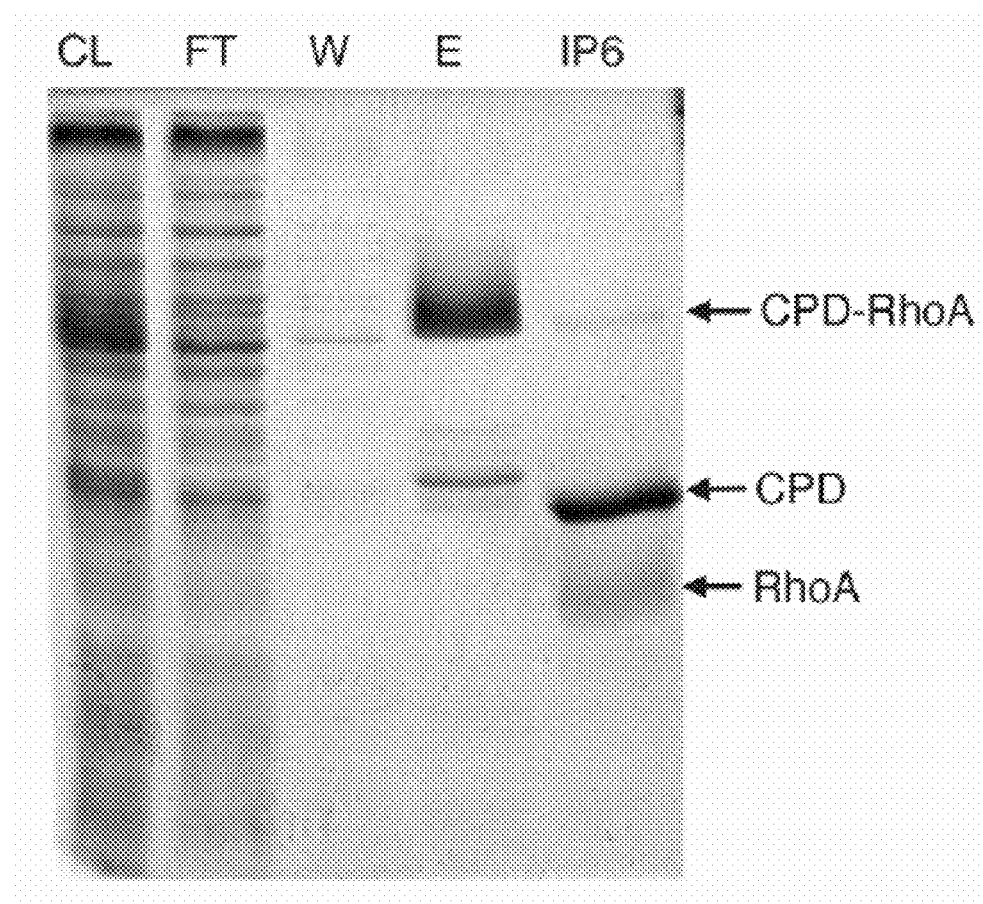
FIG. 7. Clarified lysate (CL) was loaded onto nickel column and Flow through (FT) and wash (W) fractions were collected. Protein was eluted in 250 mM imidazole and Rho was cleaved from CPD:6×His by addition of Inositol 6 phosphate (IP6).

The vector was transformed to *E. coli* BL21(DE3) and bacteria were grown and induced with IPTG. RhoA:CPD:6× His fusion protein was purified from 100 ml cell lysate on an AKTA HisTrap column with elution in 250 mM imidazole. Eluted protein was incubated in 1 µM phytic acid (InsP6) from Sigma for 1 hr at 37° C. Result of cleavage is shown in FIG. 7.

REFERENCES

Cordero, C. L., Kudryashov, D. S., Reisler, E. and Satchell, K. J. (2006) The actin cross-linking domain of the *Vibrio cholerae* RTX toxin directly catalyzes the covalent cross-linking of actin. *J Biol. Chem.* 281: 32366-32374.

Egerer, M., Giesemann, T., Jank, T., Satchell, K. J. and Aktories, K. (2007) Auto-catalytic cleavage of *Clostridium difficile* toxins A and B depends on a cysteine protease activity. *J Biol Chem* epub Jun. 25, 2007.

Fullner, K. J. and Mekalanos, J. J. (2000) In vivo covalent crosslinking of actin by the RTX toxin of *Vibrio cholerae*. *EMBO J.* 19: 5315-5323.

Kudryashov, D. S., Cordero, C. L., Reisler, E. and Satchell, K. J. (2008) Characterization of the enzymatic activity of the actin cross-linking domain from the *Vibrio cholerae* MAR-TXVc toxin. *J Biol. Chem.* 283: 445-452.

Olivier, V., Salzman, N. H. and Satchell, K. J. (2007a) Prolonged colonization of mice by *Vibrio cholerae* El Tor O1 depends on accessory toxins. *Infect Immun.* 75: 5043-5051.

Olivier, V., Haines, G. K., 3rd, Tan, Y. and Satchell, K. J. (2007b) Hemolysin and the multifunctional autoprocessing RTX toxin are virulence factors during intestinal infection of mice with *Vibrio cholerae* El Tor O1 strains. *Infect Immun.* 75: 5035-5042.

Osickova, A., Osicka, R., Maier, E., Benz, R. and Sebo, P. (1999) An amphipathic alpha-helix including glutamates 509 and 516 is crucial for membrane translocation of adenylate cyclase toxin and modulates formation and cation selectivity of its membrane channels. *J. Biol. Chem.* 274: 37644-37650.

Pfeifer, G., Schirmer, J., Leemhuis, J., Busch, C., Meyer, D. K., Aktories, K. and Barth, H. (2003) Cellular uptake of *Clostridium difficile* toxin B. Translocation of the N-terminal catalytic domain into the cytosol of eukaryotic cells. *J Biol. Chem.* 278: 44535-44541.

Reineke, J., Tenzer, S., Rupnik, M., Koschinski, A., Hasselmayer, O., Schrattenholz, A., et al (2007) Autocatalytic cleavage of *Clostridium difficile* toxin B. *Nature.* 446: 415-419.

Rupnik, M., Pabst, S., Rupnik, M., von Eichel-Streiber, C., Urlaub, H. and Soling, H. D. (2005) Characterization of the cleavage site and function of resulting cleavage fragments after limited proteolysis of *Clostridium difficile* toxin B (TcdB) by host cells. *Microbiology.* 151: 199-208.

Satchell, K. J. (2007) MARTX: Multifunctional-Autoprocessing RTX Toxins. *Infect Immun.* 75: 5079-5084.

Sheahan, K. L. and Satchell, K. J. (2007) Inactivation of small Rho GTPases by the multifunctional RTX toxin from *Vibrio cholerae. Cell Microbiol.* 9: 1324-1335.

Sheahan, K. L., Cordero, C. L. and Satchell, K. J. (2004) Identification of a domain within the multifunctional *Vibrio cholerae* RTX toxin that covalently cross-links actin. *Proc. Natl. Acad. Sci. USA.* 101: 9798-9803.

Sheahan, K. L., Cordero, C. L. and Satchell, K. J. (2007) Autoprocessing of the *Vibrio cholerae* RTX toxin by the cysteine protease domain. *EMBO J.* 26: 2552-2561.

Stols, L., Gu, M., Dieckman, L., Raffen, R., Collart, F. R. and Donnelly, M. I. (2002) A new vector for high-throughput, ligation-independent cloning encoding a tobacco etch virus protease cleavage site. *Protein Expr Purif.* 25: 8-15.

Example 2

Reference is made to the article Prochazkova K., and Satchell K. J., "Structure-function analysis of inositol hexakisphosphate-induced autoprocessing of the *Vibrio cholerae* multifunctional autoprocessing RTX toxin," published in the Journal of Biological Chemistry, volume 283(35), pages 23656-64, on Aug. 29, 2008, the content of which was disclosed and incorporated by reference in U.S. Provisional Patent Application No. 61/119,489, filed on Dec. 3, 2008.

The invention claimed is:

1. A method for producing a recombinant polypeptide, the method comprising:
   (a) culturing a prokaryotic cell transformed with a recombinant polynucleotide, the recombinant polynucleotide encoding a fusion protein comprising:
      (i) the recombinant polypeptide; and
      (ii) an inducible autoproteolytic cysteine protease fused to the C-terminus of the recombinant polypeptide;
   (b) isolating the fusion protein from the cell;
   (c) inducing the autoproteolytic cysteine protease of the isolated fusion protein in a reaction mixture by adding a solution consisting_essentially of inositol hexakisphosphate to the reaction mixture to cleave the isolated fusion protein and produce a cleaved fragment comprising the recombinant polypeptide; and
   (d) isolating the cleaved fragment comprising the recombinant polypeptide.

2. The method of claim 1, wherein the encoded fusion protein further comprises a peptide tag fused at the C-terminus of the inducible autoproteolytic cysteine protease and the fusion protein is recovered by contacting the fusion protein with a resin that binds the peptide tag.

3. The method of claim 1, wherein the peptide tag is a 6×His tag, a hemaglutinin tag, a FLAG tag, a glutathione-S-transferase tag, a green fluorescent protein tag, a maltose binding protein tag, or a chitin binding protein tag.

4. The method of claim 1, wherein the fusion protein comprises a fragment of V. cholerae RTX toxin (SEQ ID NO:1), V. vulnificus RTX toxin (SEQ ID NO:2), V. splendidus putative RTX toxin (SEQ ID NO:3), P. luminescens putative RTX toxin (SEQ ID NO:4-7), Xenorhabdus nematophila (XnRtx) (SEQ ID NO:8), X bovienii (XbRtx) (SEQ ID NO:9), Y. pseudotuberculosis putative toxin (SEQ ID NO:10), Y. mollaretti putative toxin (SEQ ID NO:11), C. difficile Toxin A (SEQ ID NO:12), C. difficile Toxin B (SEQ ID NO:13), C. noveyi alpha toxin (SEQ ID NO:14), C. sordellii cytotoxin L (SEQ ID NO:15), or Bordetella pertussis putative adhesin FhaL (SEQ ID NO:16), and the fragment has inducible autoproteolytic cysteine protease activity.

5. The method of claim 1, wherein the inducible autoproteolytic cysteine protease fused to the C-terminus of the recombinant polypeptide has an amino acid sequence that is at least 95% identical to SEQ ID NO:17, and has cysteine protease activity when induced by inositol hexakisphosphate.

6. The method of claim 5, wherein the inducible autoproteolytic cysteine protease has an amino acid sequence that is at least 97% identical to SEQ ID NO:17.

7. The method of claim 5, wherein the inducible autoproteolytic cysteine protease has an amino acid sequence that is at least 99% identical to SEQ ID NO:17.

8. The method of claim 5, wherein the inducible autoproteolytic cysteine protease has an amino acid sequence of SEQ ID NO:17.

9. The method of claim 8, wherein the inducible autoproteolytic cysteine protease is cleaved between amino acids 2 and 3 of SEQ ID NO:17.

10. The method of claim 1, wherein the recombinant polypeptide and the inducible autoproteolytic cysteine protease are directly fused.

11. The method of claim 1, wherein the recombinant polypeptide and the inducible autoproteolytic cysteine protease are fused indirectly via a peptide linker.

12. A method for producing a recombinant polypeptide, the method comprising:
   (a) culturing a prokaryotic cell transformed with a recombinant polynucleotide, the recombinant polynucleotide encoding a fusion protein comprising:

(i) the recombinant polypeptide; and
(ii) an inducible autoproteolytic cysteine protease fused to the C-terminus of the recombinant polypeptide;
(b) isolating the fusion protein from the cell;
(c) inducing the autoproteolytic cysteine protease of the isolated fusion protein in a reaction mixture by adding a solution to the reaction mixture to cleave the isolated fusion protein and produce a cleaved fragment comprising the recombinant polypeptide, wherein the solution consists essentially of hexakisphosphate and a protease inhibitor that inhibits non-specific protease activity and does not inhibit the autoproteolytic cysteine protease; and
(d) isolating the cleaved fragment comprising the recombinant polypeptide.

13. The method of claim 12, wherein the encoded fusion protein further comprises a peptide tag fused at the C-terminus of the inducible autoproteolytic cysteine protease and the fusion protein is recovered by contacting the fusion protein with a resin that binds the peptide tag.

14. The method of claim 12, wherein the fusion protein comprises a fragment of *V. cholerae* RTX toxin (SEQ ID NO:1), *V. vulnificus* RTX toxin (SEQ ID NO:2), *V. splendidus* putative RTX toxin (SEQ ID NO:3), *P. luminescens* putative RTX toxin (SEQ ID NO:4-7), *Xenorhabdus nematophila* (XnRtx) (SEQ ID NO:8), *X. bovienii* (XbRtx) (SEQ ID NO:9), *Y. pseudotuberculosis* putative toxin (SEQ ID NO:10), *Y. mollaretti* putative toxin (SEQ ID NO:11), *C. difficile* Toxin A (SEQ ID NO:12), *C. difficile* Toxin B (SEQ ID NO:13), *C. noveyi* alpha toxin (SEQ ID NO:14), *C. sordellii cytotoxin* L (SEQ ID NO:15), or *Bordetella pertussis* putative adhesin FhaL (SEQ ID NO:16), and the fragment has inducible autoproteolytic cysteine protease activity.

15. The method of claim 12, wherein the inducible autoproteolytic cysteine protease fused to the C-terminus of the recombinant polypeptide has an amino acid sequence that is at least 95% identical to SEQ ID NO:17, and has cysteine protease activity when induced by inositol hexakisphosphate.

16. The method of claim 15, wherein the inducible autoproteolytic cysteine protease has an amino acid sequence of SEQ ID NO:17.

17. The method of claim 16, wherein the inducible autoproteolytic cysteine protease is cleaved between amino acids 2 and 3 of SEQ ID NO:17.

18. The method of claim 12, wherein the recombinant polypeptide and the inducible autoproteolytic cysteine protease are directly fused.

19. The method of claim 12, wherein the recombinant polypeptide and the inducible autoproteolytic cysteine protease are fused indirectly via a peptide linker.

* * * * *

UNITED STATES PATENT AND TRADEMARK OFFICE
CERTIFICATE OF CORRECTION

| | |
|---|---|
| PATENT NO. | : 8,257,946 B2 |
| APPLICATION NO. | : 13/183071 |
| DATED | : September 4, 2012 |
| INVENTOR(S) | : Karla J. Fuller-Satchell |

It is certified that error appears in the above-identified patent and that said Letters Patent is hereby corrected as shown below:

In the Specification:

Column 1, lines 15-21 please remove the government support clause as government funding does not apply to this invention.

Signed and Sealed this
Twenty-third Day of April, 2013

Teresa Stanek Rea
*Acting Director of the United States Patent and Trademark Office*

SEQUENCE LISTING

```
<160> NUMBER OF SEQ ID NOS: 18

<210> SEQ ID NO 1
<211> LENGTH: 4545
<212> TYPE: PRT
<213> ORGANISM: Vibrio cholerae
<220> FEATURE:
<221> NAME/KEY: misc_feature
<222> LOCATION: (1555)..(1555)
<223> OTHER INFORMATION: Xaa can be any naturally occurring amino acid
<220> FEATURE:
<221> NAME/KEY: misc_feature
<222> LOCATION: (4440)..(4440)
<223> OTHER INFORMATION: Xaa can be any naturally occurring amino acid

<400> SEQUENCE: 1

Met Gly Lys Pro Phe Trp Arg Ser Val Glu Tyr Phe Phe Thr Gly Asn
1               5                   10                  15

Tyr Ser Ala Asp Asp Gly Asn Asn Asn Ile Val Ala Ile Gly Phe Gly
            20                  25                  30

Gly Gln Ile His Ala Tyr Gly Gly Asp His Val Thr Val Gly Ser
        35                  40                  45

Ile Gly Ala Thr Val Tyr Thr Gly Ser Gly Asn Asp Thr Val Val Gly
    50                  55                  60

Gly Ser Ala Tyr Leu Lys Val Glu Asp Ser Thr Gly His Leu Ile Val
65                  70                  75                  80

Lys Gly Ala Ala Gly Tyr Ala Asp Ile Asn Lys Ser Gly Asp Gly Asn
                85                  90                  95

Val Ser Phe Ala Gly Ala Ala Gly Val Ser Ile Asp His Leu Gly
            100                 105                 110

Asn His Gly Asp Val Ser Tyr Gly Gly Ala Ala Ala Tyr Asn Gly Ile
        115                 120                 125
```

```
Thr Arg Lys Gly Leu Ser Gly Asn Val Thr Phe Ala Gly Ala Gly Gly
    130                 135                 140

Tyr Asn Ala Leu Trp His Glu Thr Asn Gln Gly Asn Leu Ser Phe Thr
145                 150                 155                 160

Gly Ala Gly Ala Gly Asn Lys Leu Asp Arg Thr Trp Ser Asn Arg Tyr
                165                 170                 175

Gln Gly Ser His Gly Asp Val Thr Phe Asp Gly Ala Gly Ala Ala Asn
            180                 185                 190

Ser Ile Ser Ser Arg Val Glu Thr Gly Asn Ile Thr Phe Arg Gly Ala
        195                 200                 205

Gly Ala Asp Asn His Leu Val Arg Lys Gly Lys Val Gly Asp Ile Thr
    210                 215                 220

Leu Gln Gly Ala Gly Ala Ser Asn Arg Ile Glu Arg Thr His Gln Ala
225                 230                 235                 240

Glu Asp Val Tyr Thr Gln Thr Arg Gly Asn Ile Arg Phe Glu Gly Val
                245                 250                 255

Gly Gly Tyr Asn Ser Leu Tyr Ser Asp Val Ala His Gly Asp Ile His
                260                 265                 270

Phe Ser Gly Gly Gly Ala Tyr Asn Thr Ile Ile Arg Lys Gly Ser Gly
            275                 280                 285

Asn Asp Phe Ala Lys Glu Gly Met Thr Asn Ala Lys Ala Asp Glu Ile
290                 295                 300

Val Leu Thr Lys Ala Val Met Ser Gly Ser Trp Ile Gly Gln Asp His
305                 310                 315                 320

His Val Thr Ala Val Lys Ser Ala Ser Glu Pro Asn Thr Tyr Leu Phe
                325                 330                 335

Ala Phe Ala Asp Ser Thr Tyr Thr Lys Ile Asn Lys Val Gln Leu Arg
            340                 345                 350

Asn Asp Pro Gln Thr Gly Glu Leu Lys Tyr Tyr Ser Thr Ala Trp Tyr
        355                 360                 365

Lys Glu Val Asn His Leu Ser Asn Leu Ala Asn Gln Asp Ile Ser Asp
    370                 375                 380

Asn Gly Gly Phe Thr Ala Val Asn Ile Asn Gly Ala Tyr Thr Leu Ser
385                 390                 395                 400

Asp Leu Lys Val Glu His Gln Gln Ser Val Thr Val His Ala Val Glu
                405                 410                 415

Lys Ser Leu Thr Glu Tyr Glu Trp Val Thr Tyr Ala Asn Gly Ala Val
            420                 425                 430

Ile Asp Ala Lys Glu Val Ser Leu Ser Asp Ala Lys Met Gly Gly His
        435                 440                 445

Ala Ile Tyr Ala Asp Gly Thr Lys Val Asp Val Lys Ala Val Lys Ser
    450                 455                 460

Asn Arg Gln Pro Asn Thr Tyr Ile Tyr Ala Lys Val Leu Gly Pro Tyr
465                 470                 475                 480

Thr Lys Ile Val Val Val Glu Leu Ala Asn Asp Pro Glu Thr Gly Ala
                485                 490                 495

Leu Lys Tyr Gln Ala Arg Ser Trp Tyr Lys Glu Gly Asp His Thr Ala
            500                 505                 510

Asn Ile Ala Asn Gln Asp Ile Ser Ser Ala Thr Gly Tyr Asn Pro Met
        515                 520                 525

Gly Lys Gly Gly Tyr Ser Leu Ser Asp Leu His Tyr Ser Val Asn Ala
    530                 535                 540

Val Arg Ser Thr Ser Glu Thr Val Ala Asp Ile Glu Glu Tyr Thr Asp
545                 550                 555                 560
```

```
Gln Thr Leu Phe Lys Pro Ala Asn Asp Ser Gly Glu Ser Ser Gly Asp
                565                 570                 575

Val Arg Phe Asn Gly Ala Gly Gly Asn Val Ile Lys Ser Asn Val
        580                 585                 590

Thr Arg Gly Asn Val His Phe Asn Gly Gly Ile Ala Asn Val Ile
    595                 600                 605

Leu His Ser Ser Gln Phe Gly Asn Thr Glu Phe Asn Gly Gly Ala
    610                 615                 620

Ala Asn Val Ile Val Lys Ser Gly Glu Gly Asp Leu Thr Phe Arg
625                 630                 635                 640

Gly Ala Gly Leu Ala Asn Val Leu Val His Gln Ser Glu Gln Gly Lys
                645                 650                 655

Met Asp Val Tyr Ala Gly Gly Ala Val Asn Val Leu Val Arg Leu Gly
                660                 665                 670

Asp Gly Gln Tyr Leu Ala His Leu Leu Ala Tyr Gly Asn Ile Ser Val
                675                 680                 685

Gln Lys Gly Ser Gly Asp Ser Arg Val Val Met Leu Gly Gly Tyr Asn
            690                 695                 700

Thr His Thr Gln Ile Gly Ser Gly Asn Gly Leu Trp Leu Ala Ala Gly
705                 710                 715                 720

Gly Phe Asn Val Met Thr Gln Val Gly Lys Gly Asp Val Ala Ala Val
                725                 730                 735

Leu Ala Gly Gly Ala Asn Val Leu Thr Lys Met Gly Glu Gly Glu Leu
                740                 745                 750

Thr Ser Gly Met Leu Gly Gly Ala Asn Val Ile Thr His Ile Ser Asn
            755                 760                 765

Asp Asp Gln Leu Ser Asn Thr Thr Ala Val Ala Leu Gly Gly Ala Asn
            770                 775                 780

Ile Leu Thr Lys Lys Gly Lys Gly Asn Thr Leu Ala Val Met Gly Gly
785                 790                 795                 800

Gly Ala Asn Val Leu Thr His Val Gly Asp Gly Thr Thr Thr Gly Val
                805                 810                 815

Met Val Gly Gly Ala Asn Ile Leu Thr Lys Val Gly Asn Gly Asp Thr
            820                 825                 830

Thr Gly Ile Leu Leu Gly Val Gly Asn Val Leu Thr His Val Gly Asp
            835                 840                 845

Gly Gln Thr Leu Gly Val Met Gly Ala Ala Gly Asn Ile Phe Thr Lys
            850                 855                 860

Val Gly Asp Gly Thr Ser Ile Ala Val Met Ile Gly Ala Gly Asn Ile
865                 870                 875                 880

Phe Thr His Val Gly Glu Gly Asn Ala Trp Ala Leu Met Gly Gly Leu
                885                 890                 895

Gly Asn Val Phe Thr Lys Val Gly Asn Gly Asp Ala Leu Ala Leu Met
                900                 905                 910

Val Ala Glu Ala Asn Val Phe Thr His Ile Gly Asp Gly Met Ser Val
            915                 920                 925

Ala Leu Met Leu Ala Lys Gly Asn Val Ala Thr Lys Val Gly Asn Gly
            930                 935                 940

Thr Thr Leu Ala Ala Met Val Gly Asn Val Asn Ile Phe Thr His Ile
945                 950                 955                 960

Gly His Gly Ser Thr Phe Ala Ala Met Ile Gly Gln Ala Asn Ile Met
                965                 970                 975

Thr Lys Val Gly Asn Asp Leu Thr Ala Ala Leu Met Val Gly Lys Ala
```

-continued

```
                980             985              990
Asn Ile Met Thr His Val Gly Asp Gly Thr Ser Leu Gly Leu Phe Ala
            995             1000              1005
Gly Glu Val Asn Val Met Thr Lys Val Gly Asn Gly Thr Thr Leu
    1010             1015            1020
Ala Ala Met Phe Gly Lys Ala Asn Ile Met Thr His Val Gly Asp
    1025             1030            1035
Gly Leu Thr Gly Val Leu Ala Leu Gly Glu Ala Asn Ile Val Thr
    1040             1045            1050
Lys Leu Gly Asp Asp Phe Met Gly Val Val Ala Ala Lys Ala
    1055             1060            1065
Asn Val Val Thr His Val Gly Asp Ala Thr Thr Ala Ala Val Leu
    1070             1075            1080
Ala Gly Lys Gly Asn Ile Leu Thr Lys Val Gly Glu Gly Thr Thr
    1085             1090            1095
Val Gly Leu Leu Ile Ser Asp Val Gly Asn Val Met Thr His Val
    1100             1105            1110
Gly Asp Gly Thr Thr Ile Gly Ile Ala Lys Gly Lys Ala Asn Leu
    1115             1120            1125
Ile Thr Lys Val Gly Asp Gly Leu Gly Val Asn Val Thr Trp Gly
    1130             1135            1140
Gln Ala Asn Val Phe Thr Gln Val Gly Asp Gly Asp Arg Tyr Asn
    1145             1150            1155
Phe Ala Lys Gly Glu Ala Asn Leu Ile Thr Lys Val Gly Asp Gly
    1160             1165            1170
Gln Glu Val Ser Val Val Gln Gly Glu Ala Asn Ile Ile Thr His
    1175             1180            1185
Val Gly Asn Gly Asp Asp Tyr Thr Gly Ala Trp Gly Lys Ala Asn
    1190             1195            1200
Val Ile Thr Lys Val Gly His Gly Gln Asn Val Val Leu Ala Lys
    1205             1210            1215
Gly Glu Ala Asn Ile Val Thr Gln Val Gly Asp Gly Asp Ser Phe
    1220             1225            1230
Asn Ala Leu Trp Ser Lys Gly Asn Ile Val Thr Lys Val Gly Asp
    1235             1240            1245
Gly Met Gln Val Thr Ala Ala Lys Gly Gln Ala Asn Ile Thr Thr
    1250             1255            1260
Thr Val Gly Asn Gly Leu Asn Val Thr Ala Ala Tyr Gly Asp Ala
    1265             1270            1275
Asn Ile Asn Thr Lys Val Asp Gly Val Ser Val Asn Val Ala
    1280             1285            1290
Trp Gly Lys Tyr Asn Ile Asn Thr Lys Val Gly Asp Gly Leu Asn
    1295             1300            1305
Val Ala Val Met Lys Gly Lys Ala Asn Ala Asn Ile His Val Gly
    1310             1315            1320
Asp Gly Leu Asn Ile Asn Ala Ser Tyr Ala Gln Asn Asn Val Ala
    1325             1330            1335
Ile Lys Val Gly Asn Gly Asp Phe Tyr Ser Leu Ala Val Ala Ser
    1340             1345            1350
Ser Asn Thr Ser Ser Asn Lys Leu Ser Ala Leu Phe Asp Asn Ile
    1355             1360            1365
Lys Gln Thr Val Leu Gly Val Gly Gly Ser Gln Ala Ile Asn Tyr
    1370             1375            1380
```

-continued

Leu Val Gln Gly Asp Glu Ala Ser Ser Ser Gly Thr His Lys Gly
1385                1390                1395

Arg Gly Ala Ile Ala Thr Pro Glu Ile Thr Lys Leu Asp Gly Phe
1400                1405                1410

Gln Met Asp Ala Ile Lys Glu Val Ser Ser Asp Leu Gly Asp Ser
1415                1420                1425

Leu Thr Gly Ser Val Thr Lys Val Asp Thr Pro Asp Leu Asn Lys
1430                1435                1440

Met Gln His Ala Leu Asn Val Asp Ser Ser Val Gln Ala Pro
1445                1450                1455

Asn Leu Ile Val Asn Gly Asp Phe Glu Leu Gly Glu His Gly Trp
1460                1465                1470

Gln Ser Thr His Gly Val Glu Ala Ser Tyr Ala Gly Ser Val Tyr
1475                1480                1485

Gly Val Glu Gly Glu Gly His Gly Ala Arg Val Thr Glu Leu Asp
1490                1495                1500

Thr Tyr Thr Asn Thr Ser Leu Tyr Gln Asp Leu Ala Asn Leu Ala
1505                1510                1515

Gln Gly Glu Val Ile Ala Val Ser Phe Asp Phe Ala Lys Arg Ala
1520                1525                1530

Gly Leu Ser Asn Asn Glu Gly Ile Glu Val Leu Trp Asn Gly Glu
1535                1540                1545

Val Val Phe Ser Ser Ser Xaa Asp Glu Ser Ala Trp Gln Gln Lys
1550                1555                1560

Asn Leu Lys Leu Thr Ala Gln Ala Gly Ser Asn Arg Ile Glu Phe
1565                1570                1575

Lys Gly Thr Gly His Asn Asp Gly Leu Gly Tyr Ile Leu Asp Asn
1580                1585                1590

Val Val Ala Thr Ser Glu Ser Gln Gln Ala Asn Ala Ile Arg
1595                1600                1605

Glu His Ala Thr Gln Asn Pro Ala Ala Gln Asn Ala Leu Ser Asp
1610                1615                1620

Lys Glu Arg Ala Glu Ala Asp Arg Gln Arg Leu Glu Gln Glu Lys
1625                1630                1635

Gln Lys Gln Leu Asp Ala Val Ala Gly Ser Gln Ser Gln Leu Glu
1640                1645                1650

Ser Thr Asp Gln Gln Ala Leu Glu Asn Asn Gly Gln Ala Gln Arg
1655                1660                1665

Asp Ala Val Lys Glu Glu Ser Glu Ala Val Thr Ala Glu Leu Ala
1670                1675                1680

Lys Leu Ala Gln Gly Leu Asp Val Leu Asp Gly Gln Ala Thr His
1685                1690                1695

Thr Gly Glu Ser Gly Asp Gln Trp Arg Asn Asp Phe Ala Gly Gly
1700                1705                1710

Leu Leu Asp Gly Val Gln Ser Gln Leu Asp Asp Ala Lys Gln Leu
1715                1720                1725

Ala Asn Asp Lys Ile Ala Ala Ala Lys Gln Thr Leu Ser Asp Asn
1730                1735                1740

Asn Ser Lys Val Lys Glu Ser Val Ala Lys Ser Glu Ala Gly Val
1745                1750                1755

Ala Gln Gly Glu Gln Asn Arg Ala Gly Val Glu Gln Asp Ile Ala
1760                1765                1770

Asp Ala Gln Ala Asp Ala Glu Lys Arg Lys Ala Asp Ala Leu Ala
1775                1780                1785

-continued

```
Lys Gly Lys Asp Ala Gln Gln Ala Glu Ser Asp Ala His His Ala
    1790                1795                1800
Val Asn Asn Ala Gln Ser Arg Gly Asp Arg Asp Val Gln Leu Ala
    1805                1810                1815
Glu Asn Lys Ala Asn Gln Ala Gln Ala Asp Ala Gln Gly Ala Lys
    1820                1825                1830
Gln Asn Glu Gly Asp Arg Pro Asp Arg Gln Gly Val Thr Gly Ser
    1835                1840                1845
Gly Leu Ser Gly Asn Ala His Ser Val Glu Gly Ala Gly Glu Thr
    1850                1855                1860
Asp Ser His Val Asn Thr Asp Ser Gln Thr Asn Ala Asp Gly Arg
    1865                1870                1875
Phe Ser Glu Gly Leu Thr Glu Gln Glu Gln Glu Ala Leu Glu Gly
    1880                1885                1890
Ala Thr Asn Ala Val Asn Arg Leu Gln Ile Asn Ala Gly Ile Arg
    1895                1900                1905
Ala Lys Asn Ser Val Ser Ser Met Thr Ser Met Phe Ser Glu Thr
    1910                1915                1920
Asn Ser Lys Ser Ile Val Val Pro Thr Lys Val Ser Pro Glu Pro
    1925                1930                1935
Glu Arg Gln Glu Val Thr Arg Arg Asp Val Arg Ile Ser Gly Val
    1940                1945                1950
Asn Leu Glu Ser Leu Ser Ala Val Gln Gly Ser Gln Pro Thr Gly
    1955                1960                1965
Gln Leu Ala Ser Lys Ser Val Pro Gly Phe Lys Ser His Phe Ala
    1970                1975                1980
Ser Thr Ser Ile Gly Ile Glu Asn Glu Leu Ser Gly Leu Val Val
    1985                1990                1995
Val Leu Pro Lys Asn Ser Ala Gln Thr Phe Gly Tyr Val His Asp
    2000                2005                2010
Ser Gln Gly Asn Pro Leu Phe Met Leu Thr Lys Asp Met Asn Gln
    2015                2020                2025
Gly Gly Tyr Ser Asn Pro Val Gly Ile Asn Asp Ile Gln Gly Val
    2030                2035                2040
Asn Asn Trp Gln Thr His Thr Ile Glu Leu Val Thr Tyr Pro Ser
    2045                2050                2055
Glu Ile Ser Asp Thr Ala Ala Val Glu Ser Arg Lys Glu Ala Met
    2060                2065                2070
Leu Trp Leu Ala Lys Glu Phe Thr Asp His Ile Asn Gln Ser Asn
    2075                2080                2085
His Gln Ser Leu Pro His Leu Val Ser Asp Gly Arg Phe Thr
    2090                2095                2100
Leu Val Ile Ser Asn Ser Lys His Leu Ile Ala Ala Gly Asn Gly
    2105                2110                2115
Thr Ser Ile Asp Ala Gln Gly Lys Thr Ile Gly Met Thr Pro Ser
    2120                2125                2130
Gly Gln Gln Ala Thr Met Ala Ile Ser Ala Lys Glu Phe Gly Thr
    2135                2140                2145
Ser Ser Ser Pro Glu Val Arg Leu Leu Glu Ser Ala Pro Trp Tyr
    2150                2155                2160
Gln Ala Gly Leu Arg Asp Glu Phe Leu Ala Asn Ala Lys Asn Thr
    2165                2170                2175
Thr Leu Asp Asp Pro Ala Thr Ala Gln Asn Val Tyr Ala Tyr Leu
```

-continued

```
                2180                2185                2190
Thr Ser Val Tyr Ser Lys Thr Ala Asp Leu Ala Lys Glu Tyr Gly
    2195                2200                2205
Ile Tyr Ile Asn Asp Trp Asp Pro Ala Ser Glu Gly Phe Ser Pro
    2210                2215                2220
Asn Ala Gln Gly Leu Thr Asp Pro Lys Val Lys Asn Ala Trp Ser
    2225                2230                2235
Ile Leu Pro Arg Thr Lys Pro Val Arg Met Leu Glu Leu Leu Ser
    2240                2245                2250
Ala Glu Asp Ser Arg Tyr Val Arg Gln Gln Ile Ala Glu Lys Leu
    2255                2260                2265
Lys Gly Thr Tyr Ser Glu Ser Leu Ala Lys Asn Val Phe Glu Tyr
    2270                2275                2280
Phe Gln Tyr Gly Gly Glu Val Ala Gly His Gly Ile Asn Asn Ala
    2285                2290                2295
Thr Thr Gly Ser Val Gln Gln Pro Glu Pro Ala Ile Leu Phe Glu
    2300                2305                2310
Phe Arg Ser Val Pro Ser Ala Leu Ser Asp Phe Val Pro Lys Thr
    2315                2320                2325
Ala Ser Thr Val Lys Val Asp Val Lys Ala Leu Asp His Phe Asp
    2330                2335                2340
Ser Ala Ser Arg Lys Ala Ile Ile Thr Glu Val Asn Ala Leu Val
    2345                2350                2355
Ser Gly Ser Glu Asp Phe Asp Ala Trp Tyr Gln Glu Tyr Arg Ala
    2360                2365                2370
Ser Lys Gly Gln Pro Pro Val Lys Asn Pro Lys Ser Ser Ala Ser
    2375                2380                2385
Ala Asn His Lys Ala Glu Trp Leu Met Thr Gln His Ala Glu Gln
    2390                2395                2400
Trp Ala Lys Ile Thr Ala Pro Tyr Thr Asp Asn His Glu Thr Leu
    2405                2410                2415
Thr Ser Thr Lys Leu Ala Ser Asn Asp Lys Glu Glu Leu His Ala
    2420                2425                2430
Leu Gly Glu Thr Ser Asn Leu Glu Asn Asn Lys Gln Gln Glu Asn
    2435                2440                2445
Val Ala Ser Ile Ile Asn Thr Met Leu Asn Asp Met Leu Pro Phe
    2450                2455                2460
Tyr Ala Leu Arg Thr Glu Arg Asn Leu Leu Val Gln Glu Gly Asp
    2465                2470                2475
Glu Gly Phe Glu Val Arg Ala Trp Pro Gly Thr Glu Asp Lys Ser
    2480                2485                2490
Lys Thr Ile Ile Leu Glu Asp Pro Glu Asp Ala Ala Gln His Lys
    2495                2500                2505
Ala Ile Glu Arg Phe Ile Leu Ala Asn Phe Asp Asn Phe Glu Gln
    2510                2515                2520
Met Pro Asp Glu Leu Phe Leu Val Asp Asn Lys Val Ile Ser His
    2525                2530                2535
His Glu Gly Arg Thr His Val Leu Ala Gln Lys Val Asp Gly Ala
    2540                2545                2550
Trp Gln Tyr Asn Ala Thr Val Glu Leu Met Ser Val Thr Glu Leu
    2555                2560                2565
Leu Asp Ala Ala Asn Val Thr Gly Lys Ile Arg Gly Glu Ser Tyr
    2570                2575                2580
```

```
Gln Gln Val Ile Asp Ala Leu Thr Asp Tyr His Ala Ser Ile Thr
    2585                2590                2595

Glu His Ala Asp Tyr Glu Pro Glu Ser Val Glu Lys Leu Leu Asn
2600                2605                2610

Leu Arg Lys Lys Ile Glu Gly Tyr Val Leu Gly His Pro Asp Ser
    2615                2620                2625

Gly Arg Val Glu Ala Met Asn Ser Leu Leu Asn Gln Val Asn Thr
2630                2635                2640

Arg Leu Asp Glu Val Ser Leu Leu Ser Val Ala Glu Gln Thr Ile
    2645                2650                2655

Gln Ala Gln Asn Ser Phe Ser Arg Leu Tyr Asp Gln Leu Glu Ala
2660                2665                2670

Ala Asn Leu Lys Glu Ser Lys His Leu Tyr Leu Asp Gln Asn Gly
    2675                2680                2685

Asp Phe Val Thr Lys Gly Lys Gly Asn Leu Ala Asn Ile Asp Leu
2690                2695                2700

Leu Gly Ser Arg Glu Ala Val Leu Glu Lys Val Lys Leu Thr Val
    2705                2710                2715

Ser Asn Glu Tyr Gly Gln Thr Val Ala Asp Thr Ile Phe Ala Gly
2720                2725                2730

Leu Ser Ala Lys Asp Leu Ala Lys Asp Gly Lys Gly Val Asp Ile
    2735                2740                2745

Ala Gly Leu Asn Lys Val His Gln Ala Ile Glu Gln His Leu Ser
2750                2755                2760

Pro Val Ser Ala Thr Leu Tyr Ile Trp Lys Pro Ser Asp His Ser
    2765                2770                2775

Ala Leu Gly His Ala Ala Leu Gln Ile Gly Gln Gly Arg Thr Gln
2780                2785                2790

Leu Glu Gly Gln Ala Ala Ala Asp Phe Asn Gln Gln Asn Tyr Val
    2795                2800                2805

Ser Trp Trp Pro Leu Gly Ser Lys Ser Ser Asn Ile Ser Asn Ile
2810                2815                2820

Leu Asn Val Ala Thr Lys Asp Gln Pro Asp Leu Lys Leu Arg Trp
    2825                2830                2835

Ser Asp Phe Ser Gln Pro Ala His Gln Asn Asp Thr Leu Glu His
2840                2845                2850

Asp Val Ala Ser Glu Glu Asn Asp Gly Phe Gly Leu His Asp Gly
    2855                2860                2865

Asp Ile Lys Leu Lys Arg Phe Ile Glu Lys Leu Asn Ala Ala Lys
2870                2875                2880

Gly Ile Asp Ala Ser Phe Lys Glu Ala Ser Glu Gly Tyr Ala Ser
    2885                2890                2895

Val Leu Leu Gly Asn Pro Asp Met Leu Glu Thr Thr Ser Ile Pro
2900                2905                2910

Ala His Val Phe Gln Pro Phe Val Glu Gln Trp Asn Asp Thr Ser
    2915                2920                2925

Tyr Asp Met Met Asp Val Ala His Arg Phe Ala Gln Glu Leu Arg
2930                2935                2940

Leu Gln Ala Gln Arg Ser Asp Pro Glu Leu Leu Glu Lys Arg
    2945                2950                2955

Ile Gly Asn Val Ile Arg Gln Phe Ala Glu Arg Ala Leu Glu Glu
2960                2965                2970

Ile Glu Thr Phe Lys Ala Ser Gln Ala Asp Gln Gly Arg Val Phe
    2975                2980                2985
```

```
Arg Ile Asn Leu Glu Gly Leu Asp Val Ala Ala Met Gln Ala Glu
    2990            2995                3000

Trp His Arg Leu Ser Asn Asp Pro Asp Ala Arg Tyr Gln Leu Leu
    3005            3010                3015

Thr Lys Asn Cys Ser Ser Thr Val Ala Lys Val Leu Lys Ala Gly
    3020            3025                3030

Gly Ala Asp Lys Leu Ile Gly His Thr Trp Leu Pro Lys Phe Gly
    3035            3040                3045

Val Trp Thr Pro Thr Glu Leu Phe Asn Phe Gly Gln Ala Leu Gln
    3050            3055                3060

Glu Ala Gln Leu Glu Ile Ala Ala Lys Lys Gln Ser His Gln Val
    3065            3070                3075

Thr Asp Val Leu Asp Ala Leu Ser Gly Asn Glu Lys Pro Lys Glu
    3080            3085                3090

Asn Val Ala Ile Glu Asn Asp Gly Thr Pro Pro Arg Asp Lys Glu
    3095            3100                3105

Ser Leu Ser Pro Leu Thr Arg Phe Leu Asn Asn Glu Leu Tyr Gly
    3110            3115                3120

Asp Lys Glu Ala Arg Arg Lys Ile Gly Glu Ile Thr Gln Thr Leu
    3125            3130                3135

Leu Asp His Ala Val Glu Lys Gly Glu Ser Gln Lys Ile Thr Leu
    3140            3145                3150

Gln Gly Glu Ala Gly Arg Leu Thr Gly Tyr Tyr His Gln Gly Thr
    3155            3160                3165

Ala Pro Ser Glu Gly Glu Thr Ser Ser Pro Ser Gly Lys Val Val
    3170            3175                3180

Leu Phe Leu His Gly Ser Gly Ser Ser Ala Glu Glu Gln Ala Ser
    3185            3190                3195

Ala Ile Arg Asn His Tyr Gln Lys Gln Gly Ile Asp Met Leu Ala
    3200            3205                3210

Val Asn Leu Arg Gly Tyr Gly Glu Ser Asp Gly Pro Ser Glu
    3215            3220                3225

Lys Gly Leu Tyr Gln Asp Ala Arg Thr Met Phe Asn Tyr Leu Val
    3230            3235                3240

Asn Asp Lys Gly Ile Asp Pro Ser Asn Ile Ile His Gly Tyr
    3245            3250                3255

Ser Met Gly Gly Pro Ile Ala Ala Asp Leu Ala Arg Tyr Ala Ala
    3260            3265                3270

Gln Asn Gly Gln Ala Val Ser Gly Leu Leu Leu Asp Arg Pro Met
    3275            3280                3285

Pro Ser Met Thr Lys Ala Ile Thr Ala His Glu Val Ala Asn Pro
    3290            3295                3300

Ala Gly Ile Val Gly Ala Ile Ala Lys Ala Val Asn Gly Gln Phe
    3305            3310                3315

Ser Val Glu Lys Asn Leu Glu Gly Leu Pro Lys Glu Thr Ser Ile
    3320            3325                3330

Leu Leu Leu Thr Asp Asn Glu Gly Leu Gly Asn Glu Gly Glu Lys
    3335            3340                3345

Leu Arg Thr Lys Leu Thr Ala Ser Gly Tyr Asn Val Thr Gly Glu
    3350            3355                3360

Gln Thr Phe Tyr Gly His Ala Ser Asn Arg Leu Met Ser Gln
    3365            3370                3375

Tyr Ala Asp Gln Ile Val Ser Gly Leu Ser Ser Ser Ala Ser Val
```

|  | 3380 |  |  |  | 3385 |  |  |  | 3390 |  |
|---|---|---|---|---|---|---|---|---|---|---|

Asp Glu Asp Leu Asp Gln Gln Gly Leu Asp Thr Thr Ser Thr Lys
3395                3400                3405

Asp Gln Gly Ile Ser Asn Lys Asn Asp His Leu Gln Val Val Asp
3410                3415                3420

Ser Lys Glu Ala Leu Ala Asp Gly Lys Ile Leu His Asn Gln Asn
3425                3430                3435

Val Asn Ser Trp Gly Pro Ile Thr Val Thr Pro Thr Thr Asp Gly
3440                3445                3450

Gly Glu Thr Arg Phe Asp Gly Gln Ile Ile Val Gln Met Glu Asn
3455                3460                3465

Asp Pro Val Val Ala Lys Ala Ala Asn Leu Ala Gly Lys His
3470                3475                3480

Ala Glu Ser Ser Val Val Val Gln Leu Asp Ser Asp Gly Asn Tyr
3485                3490                3495

Arg Val Val Tyr Gly Asp Pro Ser Lys Leu Asp Gly Lys Leu Arg
3500                3505                3510

Trp Gln Leu Val Gly His Gly Arg Asp His Ser Glu Thr Asn Asn
3515                3520                3525

Thr Arg Leu Ser Gly Tyr Ser Ala Asp Glu Leu Ala Val Lys Leu
3530                3535                3540

Ala Lys Phe Gln Gln Ser Phe Asn Gln Ala Glu Asn Ile Asn Asn
3545                3550                3555

Lys Pro Asp His Ile Ser Ile Val Gly Cys Ser Leu Val Ser Asp
3560                3565                3570

Asp Lys Gln Lys Gly Phe Gly His Gln Phe Ile Asn Ala Met Asp
3575                3580                3585

Ala Asn Gly Leu Arg Val Asp Val Ser Val Arg Ser Ser Glu Leu
3590                3595                3600

Ala Val Asp Glu Ala Gly Arg Lys His Thr Lys Asp Ala Asn Gly
3605                3610                3615

Asp Trp Val Gln Lys Ala Glu Asn Asn Lys Val Ser Leu Ser Trp
3620                3625                3630

Asp Ala Gln Gly Glu Val Val Ala Lys Asp Glu Arg Ile Arg Asn
3635                3640                3645

Gly Ile Ala Glu Gly Asp Ile Asp Leu Ser Arg Ile Gly Val Asn
3650                3655                3660

Asn Val Asp Glu Pro Ala Arg Gly Ala Ile Gly Asp Asn Asn Asp
3665                3670                3675

Val Phe Asp Ala Pro Glu Lys Arg Lys Pro Glu Thr Glu Val Ile
3680                3685                3690

Ala Asn Ser Ser Ser Ser Asn Gln Phe Ser Tyr Ser Gly Asn Ile
3695                3700                3705

Gln Val Asn Val Gly Glu Gly Glu Phe Thr Ala Val Asn Trp Gly
3710                3715                3720

Thr Ser Asn Val Gly Ile Lys Val Gly Thr Gly Gly Phe Lys Ser
3725                3730                3735

Leu Ala Phe Gly Asp Asn Asn Val Met Val His Ile Gly Asp Gly
3740                3745                3750

Glu Ser Lys His Ser Val Asp Ile Gly Gly Tyr Gln Ala Leu Glu
3755                3760                3765

Gly Ala Gln Met Phe Leu Gly Asn Arg Asn Val Ser Phe Asn Phe
3770                3775                3780

| | | | | | | | | | | |
|---|---|---|---|---|---|---|---|---|---|---|
|Gly|His|Ser|Asn|Asp|Leu|Ile|Leu|Met|Met|Asp|Lys|Ser|Ile|Pro|
|   |   |3785|   |   |   |3790|   |   |   |3795|   |   |   |   |
|Thr|Pro|Pro|Leu|Val|Asn|Pro|Phe|Asp|Gly|Ala|Ala|Arg|Ile|Ser|
|   |3800|   |   |   |   |3805|   |   |   |3810|   |   |   |   |
|Gly|Val|Leu|Gln|Gly|Ile|Ala|Thr|Ser|Gly|Glu|Gly|Glu|Asp|Trp|
|   |3815|   |   |   |   |3820|   |   |   |3825|   |   |   |   |
|Leu|Ala|Ala|Gln|Glu|Gln|Gln|Trp|Thr|Leu|Ser|Gly|Ala|Lys|Lys|
|   |3830|   |   |   |   |3835|   |   |   |3840|   |   |   |   |
|Phe|Val|Lys|Asp|Met|Ser|Gly|Leu|Asp|Gln|Ser|Ser|Val|Asp|   |
|   |3845|   |   |   |   |3850|   |   |   |3855|   |   |   |   |

```
Gly His Ser Asn Asp Leu Ile Leu Met Met Asp Lys Ser Ile Pro
        3785            3790            3795

Thr Pro Pro Leu Val Asn Pro Phe Asp Gly Ala Ala Arg Ile Ser
    3800             3805            3810

Gly Val Leu Gln Gly Ile Ala Thr Ser Gly Glu Gly Glu Asp Trp
    3815             3820            3825

Leu Ala Ala Gln Glu Gln Gln Trp Thr Leu Ser Gly Ala Lys Lys
    3830             3835            3840

Phe Val Lys Asp Met Ser Gly Leu Asp Gln Ser Ser Val Asp
    3845             3850            3855

Tyr Thr Thr Leu Val Glu Leu Asp Ser Gln Asn Glu Arg Asp Ser
    3860             3865            3870

Arg Gly Leu Lys His Asp Ala Glu Ala Thr Leu Asn Lys Gln Tyr
    3875             3880            3885

Asn Gln Trp Leu Ser Gly Asn Gly Asn Ser Gly Thr Ser Gln Leu
    3890             3895            3900

Ser Arg Ala Asp Lys Leu Arg Gln Ala Asn Glu Lys Leu Ala Phe
    3905             3910            3915

Asn Phe Ala Val Gly Gly Gln Gly Ala Asp Ile Gln Val Thr Thr
    3920             3925            3930

Gly Asn Trp Asn Phe Met Phe Gly Asp Asn Ile Gln Ser Ile Leu
    3935             3940            3945

Asp Thr Asn Leu Gly Ser Leu Phe Gly Leu Met Thr Gln Gln Phe
    3950             3955            3960

Thr Ala Thr Gly Gln Ala Lys Thr Thr Phe Thr Tyr Thr Pro Gln
    3965             3970            3975

Asp Leu Pro Arg Gln Leu Lys Asn Lys Leu Leu Gly Gln Leu Ala
    3980             3985            3990

Gly Val Gly Ala Glu Thr Thr Leu Ala Asp Ile Phe Gly Val Asp
    3995             4000            4005

Tyr Thr Ala Ser Gly Gln Ile Val Ser Arg Asn Gly Gln Ala Val
    4010             4015            4020

Asp Gly Val Ala Ile Leu Lys Glu Met Leu Glu Val Ile Gly Glu
    4025             4030            4035

Phe Ser Gly Asp Gln Leu Gln Ala Phe Val Asp Pro Ala Lys Leu
    4040             4045            4050

Leu Asp Ser Leu Lys Ala Gly Ile Asp Met Gly Ala Asp Gly Ile
    4055             4060            4065

Lys Ser Phe Ala Glu Thr His Gly Leu Lys Glu Lys Ala Pro Glu
    4070             4075            4080

Glu Glu Lys Asp Asn Ser Ser Val Ser Val Asn Gly Ala Asn Val
    4085             4090            4095

Asn Ser Ala Gln Gly Ala Thr Val Ala Asp Gly Asn Thr Glu Thr
    4100             4105            4110

Ala Glu Thr Gln Asp Arg Ala Phe Gly Phe Asn Ser Leu Asn Leu
    4115             4120            4125

Pro Asn Leu Phe Ala Thr Ile Phe Ser Gln Asp Lys Gln Lys Glu
    4130             4135            4140

Met Lys Ser Leu Val Glu Asn Leu Lys Gln Asn Leu Thr Ala Asp
    4145             4150            4155

Leu Leu Asn Met Lys Glu Lys Thr Phe Asp Phe Leu Arg Asn Ser
    4160             4165            4170

Gly His Leu Gln Gly Asp Gly Asp Ile Asn Ile Ser Leu Gly Asn
    4175             4180            4185
```

Tyr Asn Phe Asn Trp Gly Gly Asp Gly Lys Asp Leu Gly Ala Tyr
4190            4195                4200

Leu Gly Asp Asn Asn Phe Trp Gly Arg Gly Asp Asp Val
4205            4210                4215

Phe Tyr Ala Thr Gly Lys Ser Asn Ile Phe Thr Gly Gly Glu Gly
4220            4225                4230

Asn Asp Met Gly Val Leu Met Gly Arg Glu Asn Met Met Phe Gly
4235            4240                4245

Gly Asp Gly Asn Asp Thr Ala Val Val Ala Gly Arg Ile Asn His
4250            4255                4260

Val Phe Leu Gly Ala Gly Asp Asp Gln Ser Phe Val Phe Gly Glu
4265            4270                4275

Gly Gly Glu Ile Asp Thr Gly Ser Gly Arg Asp Tyr Val Val Thr
4280            4285                4290

Ser Gly Asn Phe Asn Arg Val Asp Thr Gly Asp Gln Asp Tyr
4295            4300                4305

Ser Val Thr Ile Gly Asn Asn Asn Gln Val Glu Leu Gly Ala Gly
4310            4315                4320

Asn Asp Phe Ala Asn Ile Phe Gly Asn Tyr Asn Arg Ile Asn Ala
4325            4330                4335

Gly Ala Gly Asn Asp Val Val Lys Leu Met Gly Tyr His Ala Val
4340            4345                4350

Leu Asn Gly Gly Asp Gly Asp Asp His Leu Ile Ala Thr Ala Ile
4355            4360                4365

Ser Lys Phe Ser Gln Phe Asn Gly Gly Glu Gly Arg Asp Leu Met
4370            4375                4380

Val Leu Gly Gly Tyr Gln Asn Thr Phe Lys Gly Gly Thr Asp Val
4385            4390                4395

Asp Ser Phe Val Val Ser Gly Asp Val Ile Asp Asn Leu Val Glu
4400            4405                4410

Asp Ile Arg Ser Glu Asp Asn Ile Val Phe Asn Gly Ile Asp Trp
4415            4420                4425

Gln Lys Leu Trp Phe Glu Arg Ser Gly Tyr Asp Xaa Lys Leu Ser
4430            4435                4440

Ile Leu Arg Asp Pro Ser Asn Asp Ser Asp Gln Ser Lys Phe Glu
4445            4450                4455

His Ile Gly Ser Val Thr Phe Ser Asp Tyr Phe Asn Gly Asn Arg
4460            4465                4470

Ala Gln Val Val Ile Gly Met Ser Glu Lys Asp Leu Ser Gly Glu
4475            4480                4485

Arg Glu Tyr Thr Met Leu Ser Asp Ser Ala Ile Asp Ala Leu Val
4490            4495                4500

Gln Ala Met Ser Gly Phe Glu Pro Gln Ala Gly Asp Asn Gly Phe
4505            4510                4515

Ile Asp Ser Leu Glu Ser Lys Ser Gln Ala Ala Ile Ser Met Ala
4520            4525                4530

Trp Ser Asp Val Val His Lys Lys Gly Leu Met Val
4535            4540                4545

<210> SEQ ID NO 2
<211> LENGTH: 5206
<212> TYPE: PRT
<213> ORGANISM: Vibrio vulnificus

<400> SEQUENCE: 2

```
Met Gly Lys Pro Phe Trp Arg Ser Val Glu Tyr Phe Phe Thr Gly Asn
1               5                   10                  15

Tyr Ser Ala Asp Asp Gly Asn Asn Ser Ile Val Ala Ile Gly Phe Gly
            20                  25                  30

Gly Glu Ile His Ala Tyr Gly Asp Asp His Val Thr Val Gly Ser
        35                  40                  45

Ile Gly Ala Thr Val Tyr Thr Gly Ser Gly Asn Asp Thr Val Val Gly
    50                  55                  60

Gly Ser Ala Tyr Leu Arg Val Glu Asp Thr Thr Gly His Leu Ser Val
65                  70                  75                  80

Lys Gly Ala Ala Gly Tyr Ala Asp Ile Asn Lys Ser Gly Asp Gly Asn
                85                  90                  95

Val Ser Phe Ala Gly Ala Ala Gly Val Ser Ile Asp His Leu Gly
            100                 105                 110

Asn His Gly Asp Val Ser Tyr Gly Gly Ala Ala Tyr Asn Gly Ile
        115                 120                 125

Thr Arg Lys Gly Leu Ser Gly Asn Val Thr Phe Lys Gly Ala Gly Gly
    130                 135                 140

Tyr Asn Ala Leu Trp His Glu Thr Asn Gln Gly Asn Leu Ser Phe Ala
145                 150                 155                 160

Gly Ala Gly Ala Gly Asn Lys Leu Asp Arg Thr Trp Phe Asn Arg Tyr
                165                 170                 175

Gln Gly Ser Arg Gly Asp Val Thr Phe Asp Gly Ala Gly Ala Ala Asn
            180                 185                 190

Ser Ile Ser Ser Arg Val Glu Thr Gly Asn Ile Thr Phe Arg Gly Ala
        195                 200                 205

Gly Ala Asp Asn His Leu Val Arg Lys Gly Lys Val Gly Asp Ile Thr
    210                 215                 220

Leu Gln Gly Ala Gly Ala Ser Asn Arg Ile Glu Arg Thr Arg Gln Ala
225                 230                 235                 240

Glu Asp Val Tyr Ala Gln Thr Arg Gly Asn Ile Arg Phe Glu Gly Val
            245                 250                 255

Gly Gly Tyr Asn Ser Leu Tyr Ser Asp Val Ala His Gly Asp Ile His
            260                 265                 270

Phe Ser Gly Gly Gly Ala Tyr Asn Thr Ile Thr Arg Lys Gly Ser Gly
        275                 280                 285

Ser Ser Phe Asp Ala Gln Gly Met Glu Tyr Ala Lys Ala Glu Asp Ile
    290                 295                 300

Val Leu Thr Ala Ala Gln Met His Gly Leu Ser Ile Asp Asn Gly Asn
305                 310                 315                 320

Lys Phe His Ala Val Thr Ala Val Lys Ser Glu Arg Glu Pro Asn Thr
                325                 330                 335

Tyr Leu Phe Ala Ile Ala Asp Gly Thr Tyr Thr Lys Ile Asn Lys Val
            340                 345                 350

Arg Leu Tyr Asn Asp Pro Glu Thr Gly Lys Leu Lys Tyr Tyr Ser Glu
        355                 360                 365

Ala Trp Phe Lys Arg Gly Asn His Leu Ala Glu Leu Ala Arg Ser Asp
    370                 375                 380

Val Ser Ser Ala Gly Gly Phe Glu Val Asn Pro Ile Asn Gly Gly Tyr
385                 390                 395                 400

Thr Leu Ser Asn Ile Ala Val Glu His Gln Gln Ser Leu Thr Val His
            405                 410                 415

Ala Val Glu Lys Asp Leu Thr Glu Tyr Glu Trp Val Thr Tyr Ala Asn
```

```
            420                 425                 430
Gly Ala Leu Ile Asp Ala Lys Asp Val Ala Leu Ser Glu Ala Lys Met
            435                 440                 445
Gly Gly His Ala Ile Ser Thr Asp Gly Thr Thr Val Asp Val Gln Ala
            450                 455                 460
Val Lys Ser Asn Arg Lys Pro Asn Thr Tyr Val Tyr Ala Lys Val Leu
465                 470                 475                 480
Gly Pro Tyr Thr Lys Ile Val Val Glu Leu Ala Asn Asp Pro Lys
                485                 490                 495
Thr Gly Ala Leu Lys Tyr Gln Ala Arg Ser Trp Tyr Lys Glu Gly Asn
            500                 505                 510
His Thr Ala Asn Leu Ala Asn Glu Asp Ile Ser Ser Ala Asn Gly Tyr
            515                 520                 525
His Ser Met Gly Lys Gly Gly Tyr Ser Leu Ser Asp Leu His Tyr Ser
            530                 535                 540
Val Asn Ala Val Arg Ser Thr Ser Glu Thr Val Ala Asp Ile Asp Glu
545                 550                 555                 560
Tyr Thr Asp Gln Thr Leu Phe Lys Pro Ala Thr Asp Ser Gly Glu Ser
                565                 570                 575
Ser Gly Asp Val Arg Phe Asn Gly Ala Gly Gly Asn Val Ile Lys
            580                 585                 590
Ser Asn Val Thr Arg Gly Asn Val Tyr Phe Asn Gly Gly Ile Ala
            595                 600                 605
Asn Val Ile Leu His Ser Ser Gln Phe Gly His Thr Glu Phe Asn Gly
            610                 615                 620
Gly Gly Ala Ala Asn Val Ile Val Lys Ser Gly Glu Glu Gly Asp Leu
625                 630                 635                 640
Thr Phe Arg Gly Ala Gly Leu Ala Asn Val Leu Val His Gln Ser Lys
                645                 650                 655
Gln Gly Lys Met Asp Val Tyr Ala Gly Gly Ala Val Asn Val Leu Val
            660                 665                 670
Arg Ile Gly Asp Gly Gln Tyr Leu Ala His Leu Leu Ala Tyr Gly Asn
            675                 680                 685
Ile Ser Val His Lys Gly Asn Gly Asn Ser Arg Val Val Met Leu Gly
            690                 695                 700
Gly Tyr Asn Thr His Thr Gln Ile Gly Ser Gly Asn Gly Leu Trp Leu
705                 710                 715                 720
Ala Ala Gly Gly Phe Asn Val Met Thr Gln Val Gly Lys Gly Asp Val
                725                 730                 735
Ala Ser Val Leu Ala Gly Gly Ala Asn Val Leu Thr Lys Val Gly Asp
            740                 745                 750
Gly Asp Leu Thr Ala Gly Met Leu Gly Gly Ala Asn Val Ile Thr His
            755                 760                 765
Ile Ser Gly Asp Asn Glu Thr Ser Asn Thr Thr Ala Val Ala Leu Gly
            770                 775                 780
Gly Ala Asn Ile Leu Thr Lys Lys Gly Lys Gly Asn Thr Leu Ala Val
785                 790                 795                 800
Met Gly Gly Gly Ala Asn Val Leu Thr His Val Gly Asp Gly Thr Thr
                805                 810                 815
Thr Gly Val Met Val Gly Gly Ala Asn Ile Leu Thr Lys Val Gly Asn
            820                 825                 830
Gly Asp Thr Thr Gly Ile Met Leu Gly Val Gly Asn Val Leu Thr His
            835                 840                 845
```

-continued

Val Gly Asp Gly Gln Thr Leu Gly Val Met Gly Ala Ala Gly Asn Ile
        850                 855                 860

Phe Thr Lys Val Gly Asp Gly Thr Ser Ile Ala Val Met Ile Gly Ala
865                 870                 875                 880

Gly Asn Ile Phe Thr His Val Gly Glu Gly Asn Ala Trp Ala Leu Met
                885                 890                 895

Gly Gly Leu Gly Asn Val Phe Thr Lys Val Gly Asn Gly Asp Ala Leu
            900                 905                 910

Ala Leu Met Val Ala Glu Ala Asn Val Phe Thr His Ile Gly Asp Gly
        915                 920                 925

Met Ser Val Ala Leu Met Leu Ala Lys Gly Asn Val Ala Thr Lys Val
    930                 935                 940

Gly Asn Gly Thr Thr Leu Ala Ala Met Val Gly Asn Ala Asn Ile Phe
945                 950                 955                 960

Thr His Val Gly Ser Gly Ser Thr Phe Ala Ala Met Ile Gly Gln Ala
                965                 970                 975

Asn Ile Met Thr Lys Val Gly Asn Asp Leu Thr Ala Ala Leu Met Val
            980                 985                 990

Gly Lys Ala Asn Ile Tyr Thr His Val Gly Asp Gly Thr Ser Leu Gly
        995                 1000                1005

Ile Phe Ala Gly Glu Val Asn Val Ile Thr Lys Val Gly Asn Gly
    1010                1015                1020

Thr Thr Leu Ala Ala Met Phe Gly Lys Ala Asn Ile Met Thr His
    1025                1030                1035

Val Gly Asp Gly Leu Thr Gly Val Leu Ala Leu Gly Glu Ala Asn
    1040                1045                1050

Ile Val Thr Lys Val Gly Asp Phe Met Gly Val Val Ala Ala
    1055                1060                1065

Ala Lys Ala Asn Val Val Thr His Val Gly Asp Ala Thr Thr Ala
    1070                1075                1080

Ala Val Leu Ala Gly Lys Gly Asn Ile Leu Thr Lys Val Gly Glu
    1085                1090                1095

Gly Thr Thr Val Gly Leu Leu Ile Ser Asp Ile Gly Asn Val Met
    1100                1105                1110

Thr His Val Gly Asp Gly Thr Ile Gly Ile Ala Lys Gly Lys
    1115                1120                1125

Ala Asn Ile Ile Thr Lys Val Gly Asp Gly Leu Gly Val Asn Val
    1130                1135                1140

Ala Trp Gly Gln Ala Asn Val Phe Thr Gln Val Gly Asp Gly Asp
    1145                1150                1155

Arg Tyr Asn Phe Ala Lys Gly Glu Ala Asn Ile Ile Thr Lys Val
    1160                1165                1170

Gly Asp Gly Gln Glu Val Ser Val Val Gln Gly Lys Ala Asn Ile
    1175                1180                1185

Ile Thr His Val Gly Asn Gly Asp Asp Tyr Thr Gly Ala Trp Gly
    1190                1195                1200

Lys Ala Asn Val Ile Thr Lys Val Gly Asn Gly Arg Asn Val Val
    1205                1210                1215

Leu Ala Lys Gly Glu Ala Asn Ile Val Thr Gln Val Gly Asp Gly
    1220                1225                1230

Asp Ser Phe Asn Ala Leu Trp Ser Lys Gly Asn Ile Val Thr Lys
    1235                1240                1245

Val Gly Asp Gly Met Gln Val Thr Ala Ala Lys Gly Lys Ala Asn
    1250                1255                1260

-continued

```
Ile Thr Thr Thr Val Gly Asp Gly Leu Ser Val Thr Ala Ala Tyr
1265                1270                1275

Gly Asp Ala Asn Ile Asn Thr Lys Val Gly Asp Gly Val Ser Val
    1280                1285                1290

Asn Val Ala Trp Gly Lys Tyr Asn Ile Asn Thr Lys Val Gly Asp
    1295                1300                1305

Gly Leu Asn Val Ala Val Met Lys Gly Lys Ala Asn Ala Asn Ile
    1310                1315                1320

His Val Gly Asp Gly Leu Asn Ile Asn Ala Ser Tyr Ala Gln Asn
    1325                1330                1335

Asn Val Ala Ile Lys Val Gly Asn Gly Asp Phe Tyr Ser Leu Ala
    1340                1345                1350

Val Ala Ser Ser Asn Thr Ser Ser Asn Lys Leu Ser Ala Leu Phe
    1355                1360                1365

Asp Asn Ile Lys Gln Thr Leu Leu Gly Val Gly Gly Ser Gln Ala
    1370                1375                1380

Ile Asn Tyr Leu Val Gln Gly Asp Glu Ala Ser Ser Ser Gly Thr
    1385                1390                1395

Gln Lys Gly Arg Gly Ala Ile Ala Thr Pro Glu Ile Thr Lys Leu
    1400                1405                1410

Asp Gly Phe Gln Met Glu Ala Ile Glu Glu Val Gly Ser Asp Leu
    1415                1420                1425

Gly Asp Ser Leu Thr Gly Ser Val Thr Lys Val Asp Thr Pro Asp
    1430                1435                1440

Leu Asn Lys Met Gln Asn Ala Leu Asp Val Asp Gly Ser Ala Asp
    1445                1450                1455

Gln Thr Gln Ala Pro Asn Leu Ile Val Asn Gly Asp Phe Glu Gln
    1460                1465                1470

Gly Asp Arg Gly Trp Lys Ser Thr His Gly Val Glu Ala Ser Tyr
    1475                1480                1485

Ser Gly Asn Val Tyr Gly Val Asn Gly Glu Gly His Gly Ala Arg
    1490                1495                1500

Val Thr Glu Leu Asp Thr Tyr Thr Asn Thr Ser Leu Tyr Gln Asp
    1505                1510                1515

Leu Thr Asp Leu Thr Glu Gly Glu Val Ile Ala Val Ser Phe Asp
    1520                1525                1530

Phe Ala Lys Arg Ala Gly Leu Ser Asn Asn Glu Gly Ile Glu Val
    1535                1540                1545

Leu Trp Asn Gly Glu Val Val Phe Ser Ser Gly Asp Ala Ser
    1550                1555                1560

Ala Trp Gln Gln Lys Thr Leu Lys Leu Thr Ala His Ala Gly Ser
    1565                1570                1575

Asn Arg Ile Glu Phe Lys Gly Thr Gly His Asn Asp Gly Leu Gly
    1580                1585                1590

Tyr Ile Leu Asp Asn Val Val Ala Lys Ser Glu Ser Ser Gln Gln
    1595                1600                1605

Ala Asn Ala Val Ser Glu His Ala Thr Gln Asn Gln Ala Ser Gln
    1610                1615                1620

Asn Ala Leu Ser Asp Lys Glu Cys Ala Glu Ala Asp Arg Gln Arg
    1625                1630                1635

Leu Glu Gln Glu Lys Gln Lys Gln Leu Asp Ala Val Ala Gly Ser
    1640                1645                1650

Gln Ser Gln Leu Glu Ser Thr Asp Gln Gln Ala Leu Glu Asn Asn
```

-continued

```
             1655                1660                1665

Gly Gln Ala Gln Arg Asp Ala Val Lys Glu Ser Glu Ala Val
         1670                1675                1680

Thr Ala Glu Leu Thr Lys Leu Ala Gln Gly Leu Asp Val Leu Asp
         1685                1690                1695

Gly Gln Ala Thr His Thr Gly Glu Ser Gly Asp Gln Trp Arg Asn
         1700                1705                1710

Asp Phe Ala Gly Gly Leu Leu Asp Gly Val Gln Ser Gln Leu Asp
         1715                1720                1725

Asp Ala Lys Gln Leu Ala Asn Asp Lys Ile Ala Ala Ala Lys Gln
         1730                1735                1740

Thr Gln Ser Asp Asn Asn Ser Lys Val Lys Glu Ser Val Ala Lys
         1745                1750                1755

Ser Glu Ala Gly Val Ala Lys Gly Glu Gln Asn Arg Ala Gly Ala
         1760                1765                1770

Glu Gln Asp Ile Ala Glu Ala Lys Ala Asp Ala Glu Thr Arg Lys
         1775                1780                1785

Ala Asp Ala Val Ala Lys Ser Asn Asp Ala Lys Gln Ala Glu Ser
         1790                1795                1800

Asp Ala His Ser Ala Ala Asn Asp Ala Gln Ser Arg Gly Asp Arg
         1805                1810                1815

Asp Ala Met Asn Ala Glu Asn Lys Ala Asn Gln Ala Gln Asn Asp
         1820                1825                1830

Ala Lys Gly Thr Lys Gln Asn Glu Gly Asp Arg Pro Asp Arg Glu
         1835                1840                1845

Gly Val Ala Gly Ser Gly Leu Ser Gly Asn Ala His Ser Val Glu
         1850                1855                1860

Gly Ala Gly Glu Thr Gly Ser His Val Asn Thr Asp Ser Pro Thr
         1865                1870                1875

Asn Ala Asp Gly Arg Phe Ser Glu Gly Leu Ser Glu Gln Glu Gln
         1880                1885                1890

Glu Ala Leu Glu Gly Ala Thr Asn Ala Val Asn Arg Leu Gln Ile
         1895                1900                1905

Asn Ala Gly Ile Arg Gly Lys Asn Ser Gly Ser Thr Ile Thr Ser
         1910                1915                1920

Met Phe Thr Glu Thr Asn Ser Asp Ser Ile Val Val Pro Thr Thr
         1925                1930                1935

Ala Ser Gln Asp Val Val Arg Gln Glu Ile Arg Ile Ser Gly Val
         1940                1945                1950

Asn Leu Glu Gly Leu Gly Glu Thr Ser His Asp Ser Ala Glu Ser
         1955                1960                1965

Leu Val Ala Ala Arg Ala Glu Lys Val Ala Asn Leu Tyr Arg Trp
         1970                1975                1980

Leu Asp Thr Asp Asn Asp Val Ala Thr Asp Lys Tyr Val Pro Val
         1985                1990                1995

Pro Gly Phe Glu Arg Val Asp Ala Asp Val Ser Asp Glu Val Lys
         2000                2005                2010

Gln Arg Met Ile Gln Ser Met Ser Gly Tyr Ile Glu His Thr Asp
         2015                2020                2025

Asn Gln Val Pro Lys Asp Gln Ala Glu Ala Leu Ala Thr Leu Phe
         2030                2035                2040

Val Glu Ser Thr Leu Asp Tyr Asp Trp Asp Lys Arg Val Glu Phe
         2045                2050                2055
```

```
Leu Thr Lys Leu Glu Ser Tyr Gly Tyr Ser Phe Glu Ala Pro His
2060                2065                2070

Ala Glu Lys Ser Ile Val Ser Phe Trp Ser Gly Lys Asn Phe Lys
2075                2080                2085

Gln Tyr Arg Asp Val Leu Asp Asn Ala Gln Thr Asp Gly Lys Lys
2090                2095                2100

Val Val Tyr Asp Ile Asp Val Lys Gly Asn Ala Phe Ala Ile Asp
2105                2110                2115

Leu Asn Lys His Leu Met Arg Trp Gly Gly Leu Phe Leu Asp Pro
2120                2125                2130

Asp Asn Ala Glu Gln Asn Gln Leu Lys Ser Ser Ile Asp Ala Ala
2135                2140                2145

Thr Phe Ser Asn Thr Gly Phe Trp Ser Ser Val Tyr Ala Thr Gly
2150                2155                2160

Ala Gln Asn Asp Val Tyr Val Ile Ala Glu Gly Gly Val Arg Leu
2165                2170                2175

Gly Asn Tyr Phe Trp Asn Val Glu Leu Pro Ala Leu Arg Gln Leu
2180                2185                2190

Gln Arg Glu Gly Leu Val Gly Glu Ile Arg Leu Leu Asp Lys Pro
2195                2200                2205

Val Ser Glu Tyr Lys Asp Leu Pro Ala Asp Gln Ile Gly Arg Arg
2210                2215                2220

Leu Thr Asp Ala Gly Val Ala Val Lys Val Arg Phe Asp Ala Leu
2225                2230                2235

Ser His Glu Arg Gln Ala Glu Leu Leu Ala Asp Asn Pro Asp Gly
2240                2245                2250

Tyr Lys Ala Asp Thr Leu Val Glu Leu Asp Val Lys Leu Ser Ala
2255                2260                2265

Ile Asp Ser Met Leu Arg Glu Ser Leu Pro Phe Tyr Ser Leu Arg
2270                2275                2280

Thr Glu Arg Asn Leu Leu Val Gln Glu Gly Glu Glu Gly Phe Glu
2285                2290                2295

Val Arg Ser Trp Pro Gly Ile Asp Gly Lys Ser Lys Thr Ile Leu
2300                2305                2310

Leu Asp Asn Pro Glu Asp Ala Ala Gln Gln Lys Ser Ile Glu Arg
2315                2320                2325

Phe Ile Leu Ala Asn Phe Asp Asn Phe Glu Gln Met Pro Asp Glu
2330                2335                2340

Leu Phe Leu Val Asp Asn Lys Val Leu Ser His His Asp Gly Arg
2345                2350                2355

Thr Arg Ile Ile Ala Gln Lys Glu Asp Gly Ala Trp Thr Tyr Asn
2360                2365                2370

Thr Asn Val Glu Leu Met Ser Val Thr Glu Leu Leu Asp Ala Ala
2375                2380                2385

His Val Asn Gly Lys Val Arg Gly Asp Ser Tyr Gln Gln Val Ile
2390                2395                2400

Asp Ala Leu Thr Glu Tyr His Ala Ser Thr Val Glu His Ala Asp
2405                2410                2415

Tyr Glu Leu Glu Ser Val Glu Lys Leu Leu Asn Leu Arg Lys Gln
2420                2425                2430

Ile Glu Gly Tyr Val Leu Gly His Pro Asp Ser Gly Arg Val Glu
2435                2440                2445

Ala Met Asn Ser Leu Leu Asn Gln Val Asn Ser Arg Leu Glu Glu
2450                2455                2460
```

-continued

```
Val Ser Val Leu Ala Val Ser Glu Gln Ser Ile Lys Ala His Asp
2465                2470                2475

Ser Phe Ser Arg Leu Tyr Asp Gln Leu Asp Asn Ala Asn Leu Lys
2480                2485                2490

Glu Ser Lys His Leu Tyr Leu Asp Gly Asn Gly Asp Phe Val Thr
2495                2500                2505

Lys Gly Lys Gly Asn Leu Ala Thr Ile Asp Gln Leu Gly Gly Ser
2510                2515                2520

Asp Ala Val Leu Glu Lys Val Lys Ala Ala Val Thr His Glu Tyr
2525                2530                2535

Gly Gln Val Val Ala Asp Thr Ile Phe Ala Gly Leu Ser Ala Asn
2540                2545                2550

Asp Leu Ala Lys Asp Gly Lys Gly Ile Asp Ile Ala Gly Leu Asn
2555                2560                2565

Lys Val His Gln Ala Ile Glu Gln His Met Ser Pro Val Ser Ala
2570                2575                2580

Thr Met Tyr Ile Trp Lys Pro Ser Asp His Ser Ala Leu Gly His
2585                2590                2595

Ala Ala Leu Gln Ile Gly Gln Gly Arg Thr Gln Leu Glu Gly Gln
2600                2605                2610

Ala Ala Ala Asp Phe Asn Lys Gln Asn Tyr Val Ser Trp Trp Pro
2615                2620                2625

Leu Gly Ser Lys Ser Ser Asn Ile Arg Asn Ile Phe Asn Val Ala
2630                2635                2640

Thr Glu Asp Gln Pro Asp Leu Lys Leu Arg Trp Ser Asp Phe Ser
2645                2650                2655

Gln Pro Ala His Gln Asn Asp Thr Leu Glu His Asp Met Ala Ser
2660                2665                2670

Glu Glu Asn Asp Gly Phe Gly Leu Lys Asp Gly Glu Thr Lys Leu
2675                2680                2685

Lys Arg Phe Ile Glu Lys Leu Asn Ala Ala Lys Gly Ile Asp Ala
2690                2695                2700

Ser Tyr Lys Asp Ala Ser Glu Gly Tyr Ala Ser Val Leu Leu Gly
2705                2710                2715

Asn Pro Asp Met Leu Ala Ser Thr Gly Ile Pro Ala His Val Phe
2720                2725                2730

Gln Pro Phe Val Asp Gln Trp Asn Asp Thr Ser Tyr Asp Met Met
2735                2740                2745

Asp Val Ala Asn Arg Phe Ala Glu Glu Leu Gln Lys Gln Ala Gln
2750                2755                2760

Ala Ser Gly Asp Pro Ala Leu Val Glu Lys Arg Ile Asp Asn Val
2765                2770                2775

Val Arg Leu Phe Ala Glu Arg Ala Leu Glu Glu Ile Glu Ala Phe
2780                2785                2790

Lys Ala Ser Gln Ala Asp Glu Gly Arg Val Phe Arg Ile Asn Leu
2795                2800                2805

Glu Gly Leu Asp Val Ala Ala Met Gln Ala Glu Trp Asn Arg Leu
2810                2815                2820

Ser Asn Asp Pro Asp Ala Arg Tyr Gln Leu Leu Thr Lys Asn Cys
2825                2830                2835

Ser Ser Thr Val Ala Lys Val Leu Lys Ala Gly Gly Ala Asp Lys
2840                2845                2850

Leu Ile Gly His Thr Trp Arg Pro Lys Phe Gly Val Trp Thr Pro
```

-continued

```
            2855                2860                2865

Thr Glu Leu Phe Asn Phe Gly Gln Ala Leu Gln Glu Ala Gln Leu
            2870                2875                2880

Glu Ile Ala Ala Lys Lys Gln Ser His Gln Val Thr Asp Val Leu
            2885                2890                2895

Asp Ala Leu Ser Gly Asn Glu Lys His Lys Glu Asn Val Ala Ile
            2900                2905                2910

Glu Asn Asp Gly Thr Pro Pro Arg Asp Lys Glu Ser Leu Ser Pro
            2915                2920                2925

Leu Thr Arg Phe Leu Asn Asn Glu Leu Tyr Gly Glu Lys Asp Ala
            2930                2935                2940

Arg Arg Lys Ile Gly Glu Ile Thr Gln Thr Leu Leu Asp His Ala
            2945                2950                2955

Val Glu Asn Gly Glu Ser Gln Lys Val Thr Leu Lys Gly Glu Val
            2960                2965                2970

Gly Arg Leu Thr Gly Tyr Tyr His Gln Gly Ala Ala Ser Ser Glu
            2975                2980                2985

Gly Glu Thr Ser Ala Thr Ser Gly Lys Val Val Leu Phe Leu His
            2990                2995                3000

Gly Ser Gly Ser Ser Ala Glu Glu Gln Ala Ser Glu Ile Arg Asn
            3005                3010                3015

His Tyr Gln Lys Gln Gly Ile Asp Met Leu Ala Val Asn Leu Arg
            3020                3025                3030

Gly Tyr Gly Glu Ser Asp Gly Gly Pro Ser Glu Lys Gly Leu Tyr
            3035                3040                3045

Gln Asp Ala Arg Thr Met Phe Asn Tyr Leu Val Asn Asp Lys Gly
            3050                3055                3060

Ile Asp Pro Ser Asn Ile Ile Ile His Gly Tyr Ser Met Gly Gly
            3065                3070                3075

Pro Ile Ala Ala Asp Leu Ala Arg Tyr Ala Ala Gln Asn Gly Gln
            3080                3085                3090

Ala Val Ser Gly Leu Leu Leu Asp Arg Pro Met Pro Ser Met Thr
            3095                3100                3105

Lys Ala Ile Thr Ala His Glu Met Ala Asn Pro Ala Gly Ile Val
            3110                3115                3120

Gly Ala Ile Ala Lys Ala Val Asn Gly Gln Phe Ser Val Glu Lys
            3125                3130                3135

Asn Leu Lys Gly Leu Pro Lys Glu Thr Pro Ile Leu Leu Leu Thr
            3140                3145                3150

Asp Asn Glu Gly Leu Gly Glu Glu Gly Glu Lys Leu Arg Ala Lys
            3155                3160                3165

Leu Ala Ile Ala Gly Tyr Asn Val Thr Gly Glu Gln Thr Phe Tyr
            3170                3175                3180

Gly His Glu Ala Ser Asn Arg Leu Met Gly Gln Tyr Ala Asp Gln
            3185                3190                3195

Ile Val Ser Gly Leu Phe Asn Ala Glu Gln Ala Ala Val Glu Ala
            3200                3205                3210

Gly Glu Val Leu Lys Gly Leu Glu Lys Asp Phe Lys Arg Tyr Gly
            3215                3220                3225

Asp Ala Leu Lys Pro Asp Thr Ser Val Pro Gly Lys Ser Lys Asp
            3230                3235                3240

Ile Arg Thr Thr Lys Asp Phe Leu Asn Gly Tyr Lys Asn Asp His
            3245                3250                3255
```

-continued

```
Ala Lys Glu Ile Val Asp Gly Phe Arg Ser Asp Met Ser Ile Lys
3260                3265                3270
Gln Leu Val Asp Leu Phe Val Lys Gly Asn Trp Ser Ala Glu Gln
3275                3280                3285
Lys Gly Ala Leu Ala Trp Glu Ile Glu Ser Arg Ala Leu Lys Val
3290                3295                3300
Thr Phe Gln Asn Lys Ser Glu Lys Tyr Asn Arg Leu Phe Arg Glu
3305                3310                3315
Ile Ala Ser Ala Gly Val Val Asp Ala Lys Ala Thr Glu Gln Leu
3320                3325                3330
Ala Pro Gln Leu Met Leu Leu Asn Leu Ser Asn Asp Gly Phe Gly
3335                3340                3345
Gly Arg Cys Asp Pro Leu Ser Lys Leu Val Leu Ala Lys Gln
3350                3355                3360
Leu Glu Asn Asp Gly Gln Val Gly Val Ala Arg Gln Leu Leu Glu
3365                3370                3375
Lys Met Tyr Ser Ala Ala Ala Val Leu Ser Asn Pro Thr Leu Tyr
3380                3385                3390
Ser Asp Ser Glu Lys Ala Asn Ala Ser Lys Leu Leu Ser Ser Leu
3395                3400                3405
Ala Ala Ile His Ala Lys Asn Pro Met His Asp Thr Ser Met Lys
3410                3415                3420
Val Trp Gln Glu Lys Leu Glu Gly Lys Gln Ala Leu Thr Val Asn
3425                3430                3435
Gly Val Val Glu Lys Ile Thr Asp Ala Ser Ala Asn Gly Lys Pro
3440                3445                3450
Val Leu Leu Glu Leu Asp Ala Pro Gly His Ala Met Ala Ala Trp
3455                3460                3465
Ala Lys Gly Ser Gly Asp Asp Arg Val Tyr Gly Phe Tyr Asp Pro
3470                3475                3480
Asn Ala Gly Ile Val Glu Phe Ser Ser Ala Glu Lys Phe Gly Asp
3485                3490                3495
Tyr Leu Thr Arg Phe Phe Gly Lys Ser Asp Leu Asn Met Ala Gln
3500                3505                3510
Ser Tyr Lys Leu Gly Lys Asn Asp Ala Gly Glu Ala Ile Phe Asn
3515                3520                3525
Arg Val Val Met Asp Gly Asn Thr Leu Ala Ser Tyr Lys Pro
3530                3535                3540
Thr Phe Gly Asp Lys Thr Thr Met Gln Gly Ile Leu Asp Leu Pro
3545                3550                3555
Val Phe Asp Ala Thr Pro Ile Lys Lys Pro Thr Gly Gly Val Ala
3560                3565                3570
Ser Asp Leu Glu Ala Leu Gly Asp Lys Thr Lys Val Val Val Asp
3575                3580                3585
Leu Ala Gln Ile Phe Thr Val Gln Glu Leu Lys Glu Arg Ala Lys
3590                3595                3600
Val Phe Ala Lys Pro Ile Gly Ala Ser Tyr Gln Gly Ile Leu Asp
3605                3610                3615
Gln Leu Asp Leu Val His Gln Ala Lys Gly Arg Asp Gln Ile Ala
3620                3625                3630
Ala Ser Phe Glu Leu Asn Lys Lys Ile Asn Asp Tyr Ile Ala Glu
3635                3640                3645
His Pro Thr Ser Gly Arg Asn Gln Ala Leu Thr Gln Leu Lys Lys
3650                3655                3660
```

```
Gln Val Thr Asn Ala Leu Phe Ile Gly Lys Met Gln Val Ala Gln
    3665                3670                3675

Ala Gly Ile Asp Ala Ile Ala Gln Thr Arg Pro Glu Leu Ala Ala
    3680                3685                3690

Arg Ile Phe Met Val Ala Ile Glu Glu Ala Asn Gly Lys His Val
    3695                3700                3705

Gly Leu Thr Asp Met Met Val Arg Trp Ala Asn Glu Asp Pro Tyr
    3710                3715                3720

Leu Ala Pro Lys His Gly Tyr Lys Gly Glu Thr Pro Ser Asp Leu
    3725                3730                3735

Gly Phe Asp Ala Lys Tyr His Val Asp Leu Gly Glu His Tyr Ala
    3740                3745                3750

Asp Phe Lys Gln Trp Leu Glu Thr Ser Gln Ser Asn Gly Leu Leu
    3755                3760                3765

Ser Lys Ala Thr Leu Asp Glu Ser Thr Lys Thr Val His Leu Gly
    3770                3775                3780

Tyr Ser Tyr Gln Glu Leu Gln Asp Leu Thr Gly Ala Glu Ser Val
    3785                3790                3795

Gln Met Ala Phe Tyr Phe Leu Lys Glu Ala Ala Lys Lys Ala Asp
    3800                3805                3810

Pro Ile Ser Gly Asp Ser Ala Glu Met Ile Leu Leu Lys Lys Tyr
    3815                3820                3825

Ala Asp Gln Ser Tyr Leu Ser Gln Leu Asp Ser Asp Arg Met Asp
    3830                3835                3840

Gln Ile Glu Gly Ile Tyr Arg Ser Ser His Glu Thr Asp Ile Asp
    3845                3850                3855

Ala Trp Asp Arg Arg Tyr Ser Gly Thr Gly Tyr Asp Glu Leu Thr
    3860                3865                3870

Asn Lys Leu Ala Ser Ala Thr Gly Val Asp Glu Gln Leu Ala Val
    3875                3880                3885

Leu Leu Asp Asp Arg Lys Gly Leu Leu Ile Gly Glu Val His Gly
    3890                3895                3900

Ser Asp Val Asn Gly Leu Arg Phe Val Asn Glu Gln Met Asp Ala
    3905                3910                3915

Leu Lys Lys Gln Gly Val Thr Val Ile Gly Leu Glu His Leu Arg
    3920                3925                3930

Ser Asp Leu Ala Gln Pro Leu Ile Asp Arg Tyr Leu Ala Thr Gly
    3935                3940                3945

Val Met Ser Ser Glu Leu Ser Ala Met Leu Lys Thr Lys His Leu
    3950                3955                3960

Asp Val Thr Leu Phe Glu Asn Ala Arg Ala Asn Gly Met Arg Ile
    3965                3970                3975

Val Ala Leu Asp Ala Asn Ser Ser Ala Arg Pro Asn Val Gln Gly
    3980                3985                3990

Thr Glu His Gly Leu Met Tyr Arg Ala Gly Ala Ala Asn Asn Ile
    3995                4000                4005

Ala Val Glu Val Leu Gln Asn Leu Pro Asp Gly Glu Lys Phe Val
    4010                4015                4020

Ala Ile Tyr Gly Lys Ala His Leu Gln Ser His Lys Gly Ile Glu
    4025                4030                4035

Gly Phe Val Pro Gly Ile Thr His Arg Leu Asp Leu Pro Ala Leu
    4040                4045                4050

Lys Val Ser Asp Ser Asn Glu Phe Thr Val Glu Gln Asp Asp Val
```

```
                4055                4060                4065

Ser Leu Arg Val Val Tyr Asp Asp Val Ala Asn Lys Pro Lys Ile
    4070                4075                4080

Thr Phe Lys Asp Ser Leu Ser Gly Ala Asn Thr Ala Leu His Asn
    4085                4090                4095

Gln Asn Val Asn Asp Trp Glu Arg Val Val Thr Pro Thr Ala
    4100                4105                4110

Asp Gly Gly Glu Ser Arg Phe Asp Gly Gln Ile Ile Val Gln Met
    4115                4120                4125

Glu Asn Asp Asp Val Val Ala Lys Ala Ala Asn Leu Ala Gly
    4130                4135                4140

Lys His Pro Glu Ser Val Val Gln Ile Asp Ser Asp Gly
    4145                4150                4155

Asn Tyr Arg Val Val Tyr Gly Asp Pro Ser Lys Leu Asp Gly Lys
    4160                4165                4170

Leu Arg Trp Gln Leu Val Gly His Gly Arg Asp Asp Ser Glu Ser
    4175                4180                4185

Asn Asn Thr Arg Leu Ser Gly Tyr Ser Ala Asp Glu Leu Ala Val
    4190                4195                4200

Lys Leu Ala Lys Phe Gln Gln Ser Phe Asn Gln Ala Glu Asn Ile
    4205                4210                4215

Asn Asn Lys Pro Asp His Ile Ser Ile Val Gly Cys Ser Leu Val
    4220                4225                4230

Ser Asp Asp Lys Gln Lys Gly Phe Gly His Gln Phe Ile Asn Ala
    4235                4240                4245

Met Asp Ala Asn Gly Leu Arg Val Asp Val Ser Val Arg Ser Ser
    4250                4255                4260

Glu Leu Ala Val Asp Glu Ala Gly Arg Lys His Thr Lys Asp Ala
    4265                4270                4275

Asn Gly Asp Trp Val Gln Lys Ala Glu Asn Asn Lys Val Ser Leu
    4280                4285                4290

Ser Trp Asp Glu Gln Gly Glu Val Val Ala Lys Asp Glu Arg Ile
    4295                4300                4305

Arg Asn Gly Ile Ala Glu Gly Asp Ile Asp Leu Ser Arg Ile Gly
    4310                4315                4320

Val Ser Asp Val Asp Glu Pro Ala Arg Gly Ala Ile Gly Asp Asn
    4325                4330                4335

Asn Asp Val Phe Asp Ala Pro Glu Lys Arg Lys Ala Glu Thr Glu
    4340                4345                4350

Thr Ser Ser Ser Ser Ala Asn Asn Lys Leu Ser Tyr Ser Gly Asn
    4355                4360                4365

Ile Gln Val Asn Val Gly Asp Gly Glu Phe Thr Ala Val Asn Trp
    4370                4375                4380

Gly Thr Ser Asn Val Gly Ile Lys Val Gly Thr Gly Gly Phe Lys
    4385                4390                4395

Ser Leu Ala Phe Gly Asp Asn Asn Val Met Val His Ile Gly Asn
    4400                4405                4410

Gly Glu Ser Lys His Ser Phe Asp Ile Gly Gly Tyr Gln Ala Leu
    4415                4420                4425

Glu Gly Ala Gln Met Phe Ile Gly Asn Arg Asn Val Ser Phe Asn
    4430                4435                4440

Leu Gly Arg Ser Asn Asp Leu Ile Val Met Met Asp Lys Ser Ile
    4445                4450                4455
```

-continued

```
Pro Thr Pro Pro Leu Val Asn Pro Phe Asp Gly Ala Ala Arg Ile
    4460            4465            4470

Ser Gly Val Leu Gln Ser Ile Ala Thr Ser Gly Glu Gly Gln Asp
    4475            4480            4485

Trp Leu Ala Ala Gln Glu Gln Gln Trp Thr Leu Ser Gly Ala Lys
    4490            4495            4500

Lys Phe Val Lys Asp Met Ser Gly Leu Asp Gln Ser Ser Ser Val
    4505            4510            4515

Asp Tyr Thr Ser Leu Val Glu Leu Asp Ser Gln Asn Glu Arg Ser
    4520            4525            4530

Ser Arg Gly Leu Lys His Asp Ala Glu Ala Leu Asn Lys Gln
    4535            4540            4545

Tyr Asn Gln Trp Leu Ser Gly Asn Ser Asp Ser Asp Thr Ser Lys
    4550            4555            4560

Leu Ser Arg Ala Asp Lys Leu Arg Gln Ala Asn Glu Lys Leu Ala
    4565            4570            4575

Phe Asn Phe Ala Val Gly Gly Gln Gly Ala Asp Ile Gln Val Thr
    4580            4585            4590

Thr Gly Asn Trp Asn Phe Met Phe Gly Asp Asn Ile Gln Ser Ile
    4595            4600            4605

Leu Asp Thr Asn Leu Gly Ser Leu Phe Gly Leu Met Thr Gln Gln
    4610            4615            4620

Phe Ser Ala Thr Gly Gln Ala Lys Thr Thr Phe Thr Tyr Thr Pro
    4625            4630            4635

Glu Asp Leu Pro Arg Gln Leu Lys Asn Lys Leu Leu Gly Gln Leu
    4640            4645            4650

Ala Gly Val Gly Ala Glu Thr Thr Leu Ala Asp Ile Phe Gly Val
    4655            4660            4665

Asp Tyr Thr Ala Ser Gly Gln Ile Val Ser Arg Asn Gly Glu Ala
    4670            4675            4680

Val Asp Gly Val Ala Ile Leu Lys Glu Met Leu Glu Val Ile Gly
    4685            4690            4695

Glu Phe Ser Gly Asp Gln Leu Gln Ala Phe Val Asp Pro Ala Lys
    4700            4705            4710

Leu Leu Asp Ser Leu Lys Ala Gly Ile Asn Met Gly Ala Asp Gly
    4715            4720            4725

Ile Lys Ser Phe Ala Glu Thr His Gly Leu Lys Glu Lys Ala Pro
    4730            4735            4740

Glu Glu Glu Glu Asp Asn Ser Ser Val Ser Val Asn Gly Ala Ser
    4745            4750            4755

Val Asn Ser Ala Gln Gly Ala Thr Val Ala Asp Gly Ser Thr Glu
    4760            4765            4770

Thr Ala Glu Thr Pro Asp Arg Ala Phe Gly Phe Asn Ser Leu Asn
    4775            4780            4785

Leu Pro Asn Leu Phe Ala Thr Ile Phe Ser Gln Asp Lys Gln Lys
    4790            4795            4800

Glu Met Lys Ser Leu Val Glu Asn Leu Lys Glu Asn Leu Thr Ala
    4805            4810            4815

Asp Leu Leu Asn Met Lys Glu Lys Thr Phe Asp Phe Leu Arg Asn
    4820            4825            4830

Ser Gly His Leu Gln Gly Asp Gly Asp Ile Asn Ile Ser Leu Gly
    4835            4840            4845

Asn Tyr Asn Phe Asn Trp Gly Gly Asp Gly Lys Asp Leu Gly Ala
    4850            4855            4860
```

```
Tyr Leu Gly Asp Asn Asn Asn Phe Trp Gly Gly Arg Gly Asp Asp
    4865                4870                    4875

Val Phe Tyr Ala Thr Gly Thr Ser Asn Ile Phe Thr Gly Gly Glu
    4880                4885                    4890

Gly Asn Asp Met Gly Val Leu Met Gly Arg Glu Asn Met Met Phe
    4895                4900                    4905

Gly Gly Asp Gly Asn Asp Thr Ala Val Val Ala Gly Arg Ile Asn
    4910                4915                    4920

His Val Phe Leu Gly Ala Gly Asp Asp Gln Ser Phe Val Phe Gly
    4925                4930                    4935

Glu Gly Gly Glu Ile Asp Thr Gly Ser Gly Arg Asp Tyr Val Val
    4940                4945                    4950

Thr Ser Gly Asn Phe Asn Arg Val Asp Thr Gly Asp Asp Gln Asp
    4955                4960                    4965

Tyr Ser Val Thr Ile Gly Asn Asn Asn Gln Val Glu Leu Gly Ala
    4970                4975                    4980

Gly Asn Asp Phe Ala Asn Val Phe Gly Asn Tyr Asn Arg Ile Asn
    4985                4990                    4995

Ala Ser Ala Gly Asn Asp Val Val Lys Leu Met Gly Tyr His Ala
    5000                5005                    5010

Val Leu Asn Gly Gly Glu Gly Glu Asp His Leu Ile Ala Ala Ala
    5015                5020                    5025

Ile Ser Lys Phe Ser Gln Phe Asn Gly Gly Glu Gly Arg Asp Leu
    5030                5035                    5040

Met Val Leu Gly Gly Tyr Gln Asn Thr Phe Lys Gly Gly Thr Asp
    5045                5050                    5055

Val Asp Ser Phe Val Val Ser Gly Asp Val Ile Asp Asn Leu Val
    5060                5065                    5070

Glu Asp Ile Arg Ser Glu Asp Asn Ile Val Phe Asn Gly Ile Asp
    5075                5080                    5085

Trp Gln Lys Leu Trp Phe Glu Arg Ser Gly Tyr Asp Leu Lys Leu
    5090                5095                    5100

Ser Ile Leu Arg Asp Pro Ala Ser Asp Ser Asp Gln Ala Lys Phe
    5105                5110                    5115

Glu His Ile Gly Ser Val Thr Phe Ser Asp Tyr Phe Asn Gly Asn
    5120                5125                    5130

Arg Ala Gln Val Ile Ile Ala Met Gly Glu Lys Asp Ala Thr Gly
    5135                5140                    5145

Glu Arg Glu Tyr Thr Thr Leu Ser Glu Ser Ala Ile Asp Ala Leu
    5150                5155                    5160

Val Gln Ala Met Ser Gly Phe Asp Pro Gln Ala Gly Asp Asn Gly
    5165                5170                    5175

Phe Ile Asp Asn Leu Asp Ser Lys Ser Arg Val Ala Ile Thr Thr
    5180                5185                    5190

Ala Trp Ala Asp Val Val His Lys Lys Gly Ile Thr Val
    5195                5200                    5205

<210> SEQ ID NO 3
<211> LENGTH: 4872
<212> TYPE: PRT
<213> ORGANISM: Vibrio splendidus

<400> SEQUENCE: 3

Met Gly Lys Pro Phe Trp Arg Ser Val Glu Tyr Phe Phe Thr Gly Asn
1               5                   10                  15
```

```
Tyr Ser Ala Asp Glu Gly Asn Asn Ile Val Ala Ile Gly Phe Gly
             20                  25                  30

Gly Glu Ile His Ala Arg Gly Gly Asp Asp His Val Thr Val Gly Ser
             35                  40                  45

Ile Gly Ala Thr Val Tyr Thr Gly Ser Gly Asn Asp Thr Val Val Gly
 50                  55                  60

Gly Ala Ala Tyr Leu Arg Val Glu Asp Ser Val Gly Asn Leu Asn Val
 65                  70                  75                  80

Lys Gly Ala Ala Gly Tyr Ala Asp Ile Asn Lys Ser Gly Asp Gly Asn
                 85                  90                  95

Val Ser Phe Ala Gly Ala Ala Gly Gly Val Ser Ile Asp His Leu Gly
            100                 105                 110

Asn Arg Gly Asp Val Asn Tyr Gly Gly Val Ala Ala Tyr Asn Gly Ile
            115                 120                 125

Thr Arg Lys Gly Leu Ser Gly Asn Val Thr Phe Gly Gly Ala Gly Gly
            130                 135                 140

Tyr Asn Ser Leu Trp His Glu Thr Asn Gln Gly Asn Leu Ser Phe Thr
145                 150                 155                 160

Gly Ala Gly Ala Gly Asn Lys Leu Asp Arg Thr Trp Phe Asn Gln Tyr
                165                 170                 175

Gln Gly Ser Arg Gly Asn Val Thr Phe Asp Gly Val Gly Ala Ala Asn
            180                 185                 190

Ser Ile Ser Ser Arg Val Glu Thr Gly Asn Ile Thr Phe Arg Gly Ala
            195                 200                 205

Gly Ala Asp Asn His Leu Val Arg Lys Gly Lys Val Gly Asp Ile Thr
            210                 215                 220

Leu Gln Gly Ala Gly Ala Ser Asn Arg Ile Glu Arg Thr Arg Gln Ser
225                 230                 235                 240

Asp Asp Val Tyr Val Glu Thr Arg Gly Asn Ile Arg Phe Glu Gly Val
                245                 250                 255

Gly Gly Tyr Asn Ser Ile Tyr Ser Asp Val Ala His Gly Asp Ile His
            260                 265                 270

Phe Ser Gly Gly Gly Ala Tyr Asn Lys Ile Thr Arg Lys Gly Ser Gly
            275                 280                 285

Asn Asp Phe Lys Gly Glu Gly Leu Ala Asn Ala Asn Ala Asp Glu Ile
            290                 295                 300

Val Leu Thr Lys Ala Val Met Ser Gly Ser Trp Val Gly Gln Asn His
305                 310                 315                 320

Gln Val Thr Gly Ile Ser Ser Ser Arg Glu Pro Asn Thr Tyr Leu Phe
                325                 330                 335

Ala Phe Ala Asp Asp Thr Tyr Thr Lys Ile Asn Lys Val Gln Leu Arg
            340                 345                 350

Asn Asp Pro Gln Thr Gly Leu Leu Glu Tyr Tyr Ser Thr Ala Trp Tyr
            355                 360                 365

Lys Ala Gly Asn His Leu Asp Asn Leu Ser Asp Leu Asp Ile Ser Ser
            370                 375                 380

Gln Gly Gly Phe Asn Ala Val Asn Ile Asn Gly Ala Tyr Thr Leu Ser
385                 390                 395                 400

Asp Leu Thr Val Glu His Gln Gln Pro Val Thr Val His Ala Ile Glu
                405                 410                 415

Lys Asp Leu Thr Glu Tyr Glu Trp Val Thr Tyr Ala Asn Gly Ala Leu
            420                 425                 430

Ile Asp Ala Glu Asp Val Val Leu Ala Asp Ala Lys Met Gly Gly His
```

```
                435                 440                 445
Ala Ile Ser Thr Asn Gly Thr Thr Val Asp Val Lys Gly Val Lys Ser
450                 455                 460

Asn Arg Lys Ser Asn Thr Tyr Val Tyr Ala Lys Val Leu Gly Pro Tyr
465                 470                 475                 480

Thr Lys Ile Val Val Val Glu Leu Ala Asn Asp Ser Glu Thr Gly Glu
                485                 490                 495

Leu Lys Tyr Gln Ala Arg Ser Trp Tyr Lys Glu Gly Asn Tyr Thr Gly
                500                 505                 510

Asn Leu Ala Asn Glu Asp Ile Ser Ser Ala Asn Gly Tyr His Ser Met
            515                 520                 525

Gly Arg Gly Gly Tyr Ser Leu Ser Asp Leu Gln Tyr Ser Val Asn Ala
530                 535                 540

Val Arg Ser Thr Ser Glu Thr Val Ala Asp Ile Asp Glu Tyr Asn Glu
545                 550                 555                 560

Gln Ala Leu Ile Lys Pro Ala Thr Asp Thr Gly Glu Ser Ser Gly Asp
                565                 570                 575

Val Arg Phe Asn Gly Val Gly Gly Asn Val Ile Lys Ser Asn Val
                580                 585                 590

Thr Arg Gly Asp Val His Phe Asn Gly Gly Ile Ala Asn Val Ile
                595                 600                 605

Leu His Ser Ser Lys Phe Gly Asp Thr Glu Phe Ile Gly Gly Ala
610                 615                 620

Ala Asn Val Ile Val Lys Ser Gly Asp Glu Gly Asp Leu Thr Phe Arg
625                 630                 635                 640

Gly Ala Gly Leu Ala Asn Val Leu Val His Gln Ser Lys Gln Gly Lys
                645                 650                 655

Met Asp Val Tyr Ala Gly Gly Ala Val Asn Val Leu Val Arg Ile Gly
                660                 665                 670

Asp Gly Glu Tyr Leu Ala His Leu Leu Ala Tyr Gly Asn Ile Ser Val
            675                 680                 685

His Lys Gly Asn Gly Asn Ser Arg Leu Thr Met Leu Gly Gly Tyr Asn
        690                 695                 700

Thr His Thr Gln Ile Gly Ser Gly Asn Gly Leu Trp Leu Ala Val Gly
705                 710                 715                 720

Gly Phe Asn Val Met Thr Gln Val Gly Lys Gly Asp Ile Ala Ser Val
                725                 730                 735

Leu Val Gly Gly Ala Asn Val Met Thr Lys Val Gly Asp Gly Asp Leu
            740                 745                 750

Thr Ala Gly Met Leu Gly Gly Ala Asn Ile Ile Thr His Ile Ser Gly
        755                 760                 765

Asp Asp Thr Ala Ser Asn Thr Thr Ala Val Ala Leu Gly Gly Ala Asn
770                 775                 780

Ile Leu Thr Lys Lys Gly Asn Gly Asn Ala Leu Ala Val Met Gly Gly
785                 790                 795                 800

Gly Ala Asn Val Leu Thr His Ile Gly Asp Gly Ser Thr Thr Gly Val
                805                 810                 815

Met Val Gly Gly Ala Asn Ile Leu Thr Lys Val Gly Asp Gly Asp Thr
                820                 825                 830

Thr Gly Ile Met Leu Gly Ile Gly Asn Val Leu Thr His Val Gly Asp
            835                 840                 845

Gly Gln Thr Ile Gly Val Met Gly Ala Ala Gly Asn Ile Phe Thr Lys
850                 855                 860
```

-continued

```
Val Gly Asp Gly Thr Ser Ile Ala Ala Met Ile Gly Val Gly Asn Ile
865                 870                 875                 880

Phe Thr His Val Gly Glu Gly Asn Ala Trp Ala Leu Met Gly Gly Leu
            885                 890                 895

Gly Asn Val Phe Thr Lys Val Gly His Gly Asp Ala Leu Ala Leu Met
        900                 905                 910

Val Ala Glu Ala Asn Val Phe Thr His Ile Gly Asp Gly Thr Thr Val
    915                 920                 925

Ala Leu Met Val Ala Lys Gly Asn Ile Ala Thr Lys Val Gly Asn Gly
930                 935                 940

Thr Ser Ile Ala Ala Met Val Gly Asn Ala Asn Ile Phe Thr Gln Val
945                 950                 955                 960

Gly Asn Gly Ser Thr Phe Ala Ala Met Leu Gly Gln Ala Asn Ile Met
            965                 970                 975

Thr Lys Val Gly Asn Asp Leu Thr Ala Ala Leu Met Ile Gly Lys Ala
        980                 985                 990

Asn Ile Tyr Thr His Val Gly Asp Gly Thr Ser Leu Gly Leu Phe Ala
    995                 1000                1005

Gly Glu Leu Asn Val Met Thr Lys Val Gly Asn Gly Thr Thr Leu
    1010                1015                1020

Ala Ala Met Phe Gly Lys Ala Asn Ile Met Thr His Val Gly Asp
    1025                1030                1035

Gly Leu Thr Gly Val Leu Ala Leu Gly Glu Ala Asn Ile Ile Thr
    1040                1045                1050

Lys Val Gly Asp Asp Phe Met Gly Val Ala Ala Ala Lys Ala
    1055                1060                1065

Asn Val Val Thr His Val Gly Asp Ala Thr Thr Ala Ala Val Leu
    1070                1075                1080

Ala Gly Lys Gly Asn Ile Leu Thr Lys Val Gly Glu Gly Thr Thr
    1085                1090                1095

Val Gly Leu Leu Ile Ser Lys Val Gly Asn Val Met Thr His Val
    1100                1105                1110

Gly Asp Gly Thr Thr Ile Gly Leu Ala Lys Gly Lys Ala Asn Ile
    1115                1120                1125

Ile Thr Lys Val Gly Asp Gly Leu Gly Val Asn Val Ala Trp Gly
    1130                1135                1140

Gln Ala Asn Ile Phe Thr His Val Gly Asp Gly Asp Arg Tyr Asn
    1145                1150                1155

Phe Ala Lys Gly Glu Ala Asn Ile Ile Thr Lys Val Gly Asp Gly
    1160                1165                1170

Gln Glu Val Ser Val Val Gln Gly Lys Ala Asn Val Ile Thr His
    1175                1180                1185

Val Gly Asn Gly Asp Asp Tyr Thr Gly Ala Trp Gly Lys Ala Asn
    1190                1195                1200

Ile Ile Thr Lys Val Gly Asp Gly Arg Asn Val Val Leu Ala Lys
    1205                1210                1215

Gly Glu Ala Asn Ile Ile Thr Gln Val Gly Asp Gly Asp Ser Phe
    1220                1225                1230

Asn Ala Leu Trp Ser Lys Gly Asn Ile Val Thr Lys Val Gly Asp
    1235                1240                1245

Gly Met Gln Val Thr Ala Ala Lys Gly Lys Ala Asn Ile Thr Thr
    1250                1255                1260

Thr Val Gly Asn Gly Leu Ser Val Thr Ala Ala Tyr Gly Asp Ala
    1265                1270                1275
```

```
Asn Ile Asn Thr Lys Ile Gly Asp Gly Ile Ser Val Asn Val Ala
    1280            1285                1290
Trp Gly Lys Tyr Asn Val Asn Thr Lys Val Gly Asp Gly Leu Asn
    1295            1300                1305
Val Ala Val Met Lys Gly Lys Ala Asn Val Asn Ile His Val Gly
    1310            1315                1320
Asp Gly Leu Gly Ile Asn Ala Ser Tyr Ala Arg Asn Asn Val Ala
    1325            1330                1335
Ile Lys Val Gly Asn Gly Asp Phe Tyr Ser Leu Ala Val Ala Ser
    1340            1345                1350
Ser Asn Thr Ser Ser Asn Lys Leu Ser Ala Leu Phe Asp Asn Ile
    1355            1360                1365
Lys Gln Thr Leu Leu Gly Val Gly Gly Ser Gln Ala Ile Asn Tyr
    1370            1375                1380
Leu Val Gln Gly Asp Glu Ala Ser Ser Ser Gly Ile Gln Lys Gly
    1385            1390                1395
Arg Gly Ala Ile Ser Thr Pro Glu Ile Thr Lys Leu Asp Gly Phe
    1400            1405                1410
Ala Leu Asp Glu Ile Glu Glu Val Gly Ser Asp Leu Gly Asp Gly
    1415            1420                1425
Leu Ser Gly Ser Val Thr Asn Val Glu Thr Pro Asp Leu Ser Ser
    1430            1435                1440
Met Glu Asn Glu Leu Asn Ile Glu Glu Ser Ser Asp Gln Ala Gln
    1445            1450                1455
Ala Pro Asn Leu Ile Val Asn Gly Asp Phe Glu Gln Gly Gly Asp
    1460            1465                1470
Gly Trp Glu Ser Thr His Gly Val Glu Ala Ser Tyr Ser Ser Ser
    1475            1480                1485
Ala Tyr Gly Val Ser Gly Glu Gly His Gly Ser Arg Val Thr Glu
    1490            1495                1500
Leu Asp Thr Tyr Thr Asn Thr Ser Leu Ser Gln Asp Leu Thr Asp
    1505            1510                1515
Leu Ala Glu Gly Glu Val Ile Ala Val Ser Phe Asp Phe Ala Lys
    1520            1525                1530
Arg Ala Gly Ile Ser Ser Asn Glu Gly Ile Glu Val Leu Trp Asn
    1535            1540                1545
Gly Asp Val Val Phe Ser Thr Ser Gly Asp Glu Ala Ala Trp Gln
    1550            1555                1560
Gln Lys Thr Leu Lys Leu Thr Ala Asn Ser Gly Ser Asn Arg Ile
    1565            1570                1575
Glu Phe Lys Gly Thr Gly His Asn Asp Gly Leu Gly Tyr Val Leu
    1580            1585                1590
Asp Asn Val Val Ala Lys Ser Glu Thr Ser His Gln Ala Asn Ala
    1595            1600                1605
Val Ala Asp Asn Ala Glu Gln Asn Gln Ala Ala Lys Asn Ala Met
    1610            1615                1620
Ser Asp Lys Glu Arg Ala Glu Ala Asp Arg Gln Arg Leu Glu Gln
    1625            1630                1635
Glu Lys Gln Lys Gln Leu Glu Ala Val Ser Gly Ser Gln Ala Gln
    1640            1645                1650
Leu Glu Ser Thr Asp Gln Ala Leu Glu Ser Asn Gly Gln Ala
    1655            1660                1665
Gln Arg Asp Ala Val Asn Glu Glu Ser Lys Ala Val Thr Lys Asp
```

```
              1670                1675                1680

Leu  Thr  Ala  Met  Ala  Gln  Gly  Leu  Asp  Val  Leu  Asp  Asn  Lys  Ala
     1685                1690                1695

Glu  Tyr  Thr  Gly  Val  Ser  Gly  Asp  His  Trp  Arg  Asp  Arg  Phe  Ala
     1700                1705                1710

Gly  Gly  Leu  Leu  Lys  Asp  Val  Gln  Thr  Gln  Leu  Asp  Asn  Ala  Lys
     1715                1720                1725

Asp  Val  Ser  Gly  Glu  Gln  Ile  Ala  Asp  Ala  Lys  Gln  Ala  His  Lys
     1730                1735                1740

Asp  Asn  Gln  Lys  Asn  Val  Asn  Asp  Ser  Val  Ala  Lys  Ser  Glu  Ala
     1745                1750                1755

Gly  Val  Ala  Lys  Gly  Glu  Asp  Asn  Arg  Ser  Ser  Ala  Glu  Gln  Asp
     1760                1765                1770

Ile  Ala  Asp  Ala  Lys  Ala  Asp  Ala  Arg  Lys  Ala  Glu  Ala
     1775                1780                1785

Thr  Thr  Lys  Thr  Asn  Glu  Ala  Lys  Gln  Ala  Glu  Ser  Asn  Ala  Asn
     1790                1795                1800

Asn  Ser  Ala  Arg  Asp  Ala  Glu  Glu  Arg  Gly  Asn  Ser  Asp  Ala  Arg
     1805                1810                1815

Asn  Ala  Glu  Asn  Lys  Ala  His  Gln  Ala  Gln  Ala  Asp  Ala  Lys  Gly
     1820                1825                1830

Ser  Lys  Gln  Asn  Glu  Ser  Asp  Arg  Pro  Asp  Arg  Gln  Gly  Ala  Ser
     1835                1840                1845

Gly  Ser  Gly  Leu  Ser  Asn  Glu  Ser  His  Phe  Thr  Gln  Ser  Glu  Glu
     1850                1855                1860

Thr  Thr  Ser  Ser  Asp  Val  Asp  Thr  Val  Asn  Pro  Gln  Ser  Ala  Asp
     1865                1870                1875

Gly  Arg  Phe  Ser  Glu  Gly  Leu  Thr  Asp  Gln  Glu  Gln  Glu  Ala  Leu
     1880                1885                1890

Asp  Gly  Ala  Val  Gln  Ala  Val  Asn  Arg  Leu  Gln  Ile  Asn  Ala  Gly
     1895                1900                1905

Ile  Arg  Ser  Lys  Asn  Thr  Gly  Ser  Ser  Val  Thr  Ser  Leu  Phe  Thr
     1910                1915                1920

Glu  Ser  Asn  Ala  Asp  Ser  Ile  Val  Leu  Pro  Thr  Thr  His  Ser  Gln
     1925                1930                1935

Asp  Val  Ala  Arg  Lys  Glu  Ile  Arg  Ile  Ser  Gly  Val  Asn  Leu  Tyr
     1940                1945                1950

Gly  Leu  Gly  Glu  Thr  Ala  Asp  Val  Ser  Ala  Ser  Ile  Thr  Lys  Asn
     1955                1960                1965

Val  Asp  Gly  Phe  Lys  Phe  Ser  Leu  Leu  Gly  Pro  Asp  Asp  Val  Arg
     1970                1975                1980

Phe  Val  Asp  Ser  Thr  Lys  Arg  His  Leu  Gly  Lys  Leu  Ser  Thr  Asp
     1985                1990                1995

Leu  Pro  Ser  Lys  Glu  Leu  Lys  Ala  Val  Arg  Ser  His  Ile  Gln  Ser
     2000                2005                2010

Ile  Gln  Arg  Ile  Pro  Ser  Glu  Ser  Asn  Leu  Ala  Val  Leu  Glu  Leu
     2015                2020                2025

Ala  Val  Glu  Gln  Trp  Gln  Gln  Asn  Asn  Pro  Lys  Glu  Phe  Ala  Gln
     2030                2035                2040

Arg  Gly  Glu  Met  Val  Lys  Thr  Leu  Gln  Phe  Glu  Ile  Val  Ser  Leu
     2045                2050                2055

Gln  Ser  His  Ile  Gln  Lys  Asn  Arg  Ser  Lys  Asp  Ala  Gly  Ile  Phe
     2060                2065                2070
```

-continued

```
Gly Ile Ala Ile Asp Pro Lys Ser Val Glu Ala Phe Glu Ser Lys
2075                2080                2085

Val Val Phe Asp Gly Val Gly Arg Val Ile Gly Leu Val Glu Pro
2090                2095                2100

Leu Ala Asp Ala Gln Ile Asn Ser Leu Lys Ser Leu Glu Val Val
2105                2110                2115

Ser Pro Thr Leu Thr Asn Ser Thr Ser Asp Arg Glu Thr Ala Lys
2120                2125                2130

Thr Glu Ser Glu Ser Ile Val Glu Phe Ile Tyr Lys Leu Gly Gln
2135                2140                2145

Val Glu Ser Thr Glu Thr Ser Thr Ser Glu Ile Asn Lys Leu Ala
2150                2155                2160

Glu Gln Ala Lys Thr Leu Trp Met Ser Gly Asn Val Thr Gln Asp
2165                2170                2175

Ser Ala Val Lys Leu Phe Thr Glu Ala Asn Asp Lys Leu Ala Ala
2180                2185                2190

His Pro Lys Leu Gln Val Leu Ala Ser Lys Leu Leu Phe Asp Ala
2195                2200                2205

Lys Lys Glu Lys Glu Ile Gly Gln Tyr Phe Asp Asn Leu Phe Gly
2210                2215                2220

Arg Arg Phe Asp Ser Glu Ile Ala His Glu Leu Val Lys Thr Pro
2225                2230                2235

Thr Asp Lys Ala Ile Asn Thr Ser Ala Gln Ile Gly Asn Ser Leu
2240                2245                2250

Val Asn Asp Phe Asp Glu Trp Met His Ser Leu Leu Pro Asp Ala
2255                2260                2265

Ala Asp Asp Ala Leu Arg Ala Glu Arg Ile Gln Thr Lys Met Glu
2270                2275                2280

Glu Phe Ala Gln Ala Ile Ala Gln Asp Glu Arg Pro Trp Phe Ser
2285                2290                2295

Arg Val Pro Thr Leu Thr Gln Phe Leu Asp Thr Pro Ser His Ala
2300                2305                2310

Asn Phe Lys Thr Met Met Thr Gln Val Asp Asp Gly Phe Gly Val
2315                2320                2325

Ile Lys Val Pro Phe Leu Ala Val Lys Met Ala Ile Thr Pro Gly
2330                2335                2340

Leu Gly Met Glu Met Ala Pro Trp Lys Ala Glu Gly Asp Arg Phe
2345                2350                2355

Tyr Gln Asn Val Ile Thr Lys Ala Arg Ser Thr Asn Thr Val Ile
2360                2365                2370

Ser Ser Gly Val Asp Gly Glu Asn Gln Val Asn Leu Ile Glu Lys
2375                2380                2385

Lys Thr Ser Asp Tyr Gly Thr Ala Leu His Tyr Gln Pro Lys Gly
2390                2395                2400

Asp Thr Tyr Asp Asp Phe Lys Glu Gly Arg Ser Val Ala Asp Gly
2405                2410                2415

Arg Ile Leu Asn Pro Gly Lys Lys Thr Thr Phe Glu Ser Asn Ala
2420                2425                2430

Leu Asn Asn Gly Leu Ser Val Val Thr Gly Ala Ser Gly Ser Thr
2435                2440                2445

Asn Ile Met Thr His Leu Asn Gln Tyr Ile Ala Ser Lys Asn Pro
2450                2455                2460

Gly Phe Ser Val Asp Gln Ala Tyr Leu Asn Thr Leu Ser Phe Leu
2465                2470                2475
```

Val Phe Asp Gly Gly His Ser Val Asn Glu Ser Leu Ala Val Tyr
2480                2485                2490

Lys Ala Leu Gln Glu Thr Gly Asp Asp Arg Lys Ala Val Leu Glu
2495                2500                2505

Ser Tyr Thr Ala Asn Tyr Gln Asp Leu Ile Asp Leu Val Asp Asp
2510                2515                2520

Ser Ser Lys Gly Thr Val Arg Asp Ala Leu Asp Asn Ala Leu Gly
2525                2530                2535

Lys Thr Leu Glu Phe Tyr Lys Glu His Ala Asn Ser Ala Ser Asn
2540                2545                2550

Glu Leu Glu Ala Leu Gly Gly Lys Arg Lys Pro Ile Ser Glu Arg
2555                2560                2565

Asn Lys Glu Asn Val Ala Ile Glu Asn Asp Gly Thr Pro Pro Arg
2570                2575                2580

Asp Lys Glu Ser Val Ser Pro Leu Thr Arg Phe Leu Asn Asn Glu
2585                2590                2595

Leu Phe Gly Thr Lys Asp Ala Arg Arg Lys Val Gly Asp Ile Thr
2600                2605                2610

Glu Thr Leu Leu Gly Phe Ala Val Glu Lys Gly Glu Ser Gln Lys
2615                2620                2625

Val Thr Leu Lys Gly Glu Ala Gly Arg Leu Ser Gly Tyr Phe His
2630                2635                2640

Lys Gly Ala Lys Ala Ser Glu Gly Glu Glu Ser Val Gly Asn Gly
2645                2650                2655

Lys Val Val Leu Phe Leu His Gly Ser Gly Ser Ser Ser Glu Glu
2660                2665                2670

Gln Ala Ser Ala Ile Arg Ser His Tyr His Lys Gln Asn Ile Asp
2675                2680                2685

Met Leu Ala Val Asn Met Arg Gly Tyr Gly Glu Ser Asp Gly Gly
2690                2695                2700

Pro Ser Glu Lys Gly Leu Tyr Gln Asp Ala Arg Thr Met Phe Lys
2705                2710                2715

Tyr Leu Val Asn Asp Lys Gly Ile Asp Pro Ser Asn Ile Ile Ile
2720                2725                2730

His Gly Tyr Ser Met Gly Gly Pro Ile Ala Ala Asp Leu Ala Arg
2735                2740                2745

Phe Ala Ala Gln Asn Gly Gln Ala Val Ser Gly Leu Leu Leu Asp
2750                2755                2760

Arg Pro Met Pro Ser Met Thr Lys Ala Ile Thr Ala His Glu Val
2765                2770                2775

Ala Asn Pro Ala Gly Ile Val Gly Ala Leu Ser Lys Ala Val Asn
2780                2785                2790

Gly Gln Phe Ser Val Glu Lys Asn Leu Lys Gly Leu Pro Lys Asp
2795                2800                2805

Ala Pro Ile Met Leu Leu Thr Asp Asn Glu Gly Leu Gly Gly Glu
2810                2815                2820

Gly Glu Lys Leu Arg Ala Lys Leu Ala Val Ser Gly Phe Asn Val
2825                2830                2835

Thr Gly Glu Gln Thr Phe Tyr Gly His Glu Ala Ser Asn Arg Leu
2840                2845                2850

Met Ser Gln Tyr Ala Glu Gln Ile Val Ser Gly Leu Phe Asp Ala
2855                2860                2865

Asp Arg Val Ser Ala Asp Ala Ser Asp Val Leu Lys Gly Ile Lys

-continued

|  |  |  | 2870 |  |  |  | 2875 |  |  |  | 2880 |
|---|---|---|---|---|---|---|---|---|---|---|---|

Asn Asp Leu Ser Arg Tyr Gly Glu Ala Leu Lys Pro Asp Thr Lys
2885                     2890                     2895

Val Pro Gly Lys Ser Lys Asp Ile Arg Thr Thr Lys Asp Phe Leu
2900                     2905                     2910

Asn Gly Tyr Lys Ile Asp His Ala Lys Asp Ile Val Glu Gly Phe
2915                     2920                     2925

Arg Pro Asp Met Asn Ile Lys Gln Leu Val Asp Leu Leu Val Glu
2930                     2935                     2940

Gly Asn Trp Ser Ala Glu Gln Lys Gly Ala Leu Ala Trp Glu Val
2945                     2950                     2955

Glu Ser Arg Gly Leu Lys Ala Thr Phe Gln Ala Lys Ser Glu Lys
2960                     2965                     2970

His Asn Arg Leu Phe Arg Asp Val Ala Ser Ser Gly Val Thr Asp
2975                     2980                     2985

Ala Lys Ala Ser Glu Gln Leu Ala Pro Gln Leu Leu Leu Leu Asn
2990                     2995                     3000

Leu Ser Asn Asp Gly Phe Gly Gly Arg Cys Asp Pro Leu Ser Lys
3005                     3010                     3015

Leu Ile Leu Val Ala Lys Gln Leu Glu Ser Asp Gly Gln Val Gly
3020                     3025                     3030

Val Ala Arg Lys Leu Leu Glu Lys Met Tyr Ser Thr Ala Ala Val
3035                     3040                     3045

Leu Ser Asn Pro Thr Leu Tyr Ser Glu Thr Glu Arg Ala Asn Ala
3050                     3055                     3060

Ser Lys Leu Met Asp Ser Leu Ala Ala Ile His Thr Lys Asn Pro
3065                     3070                     3075

Met His Asp Thr Ser Met Lys Val Trp Gln Glu Lys Leu Glu Gly
3080                     3085                     3090

Lys Lys Ala Leu Thr Val Thr Gly Val Ile Glu Lys Ile Thr Asp
3095                     3100                     3105

Val Ser Val Asp Asn Lys Pro Val Leu Leu Glu Leu Asp Ala Pro
3110                     3115                     3120

Gly His Ala Met Ala Ala Trp Ala Lys Gly Asp Gly Glu Asn Arg
3125                     3130                     3135

Val Tyr Gly Phe Tyr Asp Pro Asn Ala Gly Val Val Glu Phe Ser
3140                     3145                     3150

Ser Lys Asp Lys Phe Ser Thr Tyr Leu Thr Arg Phe Phe Gly Lys
3155                     3160                     3165

Ser Asp Leu Asp Met Ala Gln Arg Tyr Arg Leu Pro Lys Asn Asp
3170                     3175                     3180

Val Gly Glu Ala Ile Phe Asn Arg Val Val Met Asp Gly Asn
3185                     3190                     3195

Thr Leu Ala Thr Tyr Lys Pro Thr Leu Gly Asp Lys Thr Thr Leu
3200                     3205                     3210

Gln Gly Ile Leu Asp Leu Pro Val Phe Asp Ala Thr Pro Ile Lys
3215                     3220                     3225

Lys Ser Thr Glu Val Lys Val Thr Asp Leu Glu Ser Leu Gly Asn
3230                     3235                     3240

Lys Thr Lys Leu Val Val Asp Leu Ser Thr Ile Met Thr Lys Gln
3245                     3250                     3255

Glu Leu Lys Asp Gly Gly Lys Val Phe Ala Lys Pro Ile Gly Ala
3260                     3265                     3270

-continued

Ser Tyr Gln Ala Ile Leu Asp Gln Val Glu Leu Val His Ser Phe
3275                3280                3285

Ile Gly Arg Asp Gln Val Gly Ala Ser Phe Glu Leu Asn Lys Gln
3290                3295                3300

Ile Asn Asn Tyr Leu Ala Glu His Pro Thr Ser Gly Arg Asn Leu
3305                3310                3315

Ala Leu Thr Thr Leu Lys Glu Gln Val Ser Thr Ala Leu Phe Ser
3320                3325                3330

Gly Lys Met Lys Val Thr Gln Glu Ser Ile Asp Ala Ile Ala Gln
3335                3340                3345

Thr Arg Thr Asp Val Ala Ala Arg Ile Tyr Val Val Ala Met Glu
3350                3355                3360

Glu Ala Asn Gly Glu His Val Gly Leu Thr Asp Met Met Val Arg
3365                3370                3375

Trp Ala Asn Glu Asp Pro Tyr Leu Ser Pro Lys Gln Gly Tyr Ala
3380                3385                3390

Gly Glu Thr Pro Ser Asp Leu Gly Phe Asp Ala Lys Tyr His Ile
3395                3400                3405

Glu Leu Gly Glu Gln Tyr Ser Asp Phe Lys Leu Trp Leu Glu Lys
3410                3415                3420

Ser Gln Ser Ala Asp Leu Leu Ser Lys Ala Val Leu Asp Glu Ala
3425                3430                3435

Thr Gln Thr Val His Leu Gly Tyr Ser Tyr Gln Glu Leu Gln Asp
3440                3445                3450

Leu Thr Gly Val Glu Ser Val Gln Met Ala Phe Tyr Phe Leu Lys
3455                3460                3465

Glu Ala Ala Lys Lys Ser Asp Ser Thr Thr Ser Asp Ser Ala Glu
3470                3475                3480

Met Ile Leu Leu Lys Lys Phe Ala Asp Gln Gly Tyr Ile Ser Gln
3485                3490                3495

Leu Glu Thr Asp Arg Met Asp His Ile Glu Gly Ile Tyr Arg Ser
3500                3505                3510

Ser His Glu Thr Asp Val Asp Asn Trp Asp Arg Arg Tyr Ser Gly
3515                3520                3525

Ala Gly Tyr Asp Glu Leu Ser Asp Lys Leu Ala Gly Ala Asn Gly
3530                3535                3540

Gly Val Glu Glu Gln Leu Ser Val Leu Leu Asn Glu Arg Lys Gly
3545                3550                3555

Leu Leu Ile Gly Glu Val His Gly Ser Asp Val Asn Gly Leu Arg
3560                3565                3570

Phe Val Asn Glu Gln Met Asp Ala Leu Lys Lys Gln Gly Val Thr
3575                3580                3585

Val Ile Gly Leu Glu His Leu Arg Ser Asp Leu Ala Gln Pro Leu
3590                3595                3600

Ile Asp Asn Tyr Leu Ser Thr Gly Ile Met Ser Ser Glu Leu Ser
3605                3610                3615

Ala Met Ile Lys Thr Lys His Leu Asp Ile Thr Leu Phe Glu Asn
3620                3625                3630

Ala Arg Ala Asn Gly Met Arg Ile Leu Ala Leu Asp Ala Asn Ser
3635                3640                3645

Thr Ala Arg Pro Thr Val Gln Gly Thr Glu His Gly Leu Met Tyr
3650                3655                3660

Arg Ala Gly Ala Ala Asn Asn Val Ala Val Asp Ala Leu Gln Ala
3665                3670                3675

```
Leu Pro Asp Gly Glu Lys Phe Val Ala Ile Tyr Gly Lys Ala His
    3680            3685                3690

Leu Gln Ser His Lys Gly Ile Glu Ser Phe Val Pro Gly Ile Thr
    3695            3700                3705

His Arg Leu Gly Leu Pro Ala Leu Lys Val Ser Ala Ser Asp Gln
    3710            3715                3720

Phe Val Ile Glu Gln Asp Asp Lys Thr Leu Arg Thr Val Tyr Asp
    3725            3730                3735

Asp Val Ala Asn Lys Pro Lys Ile Asp Phe Arg Ala Ser Leu Asn
    3740            3745                3750

Gly Ser Asp Asp Thr Val Lys Asn Lys Asp Val Asn Ser Trp Glu
    3755            3760                3765

Arg Leu Ile Val Ser Pro Gln Ser Asp Gly Gly Glu Thr Arg Phe
    3770            3775                3780

Asp Gly Gln Ile Ile Ile Gln Met Glu Asn Asp Ser Ser Val Ser
    3785            3790                3795

Lys Ala Ala Glu Asn Leu Ala Gly Lys His Pro Asp Ser Thr Val
    3800            3805                3810

Val Val Gln Leu Asp Ser Asp Gly Asn Tyr Arg Val Val Tyr Gly
    3815            3820                3825

Asp Pro Ser Lys Leu Pro Lys Asp Lys Ser Thr Gly Gln Leu Arg
    3830            3835                3840

Trp Gln Leu Val Gly His Gly Arg Asp Glu Ser Glu Asn Asn Asn
    3845            3850                3855

Thr His Leu Ser Gly Tyr Ser Ala Asp Glu Leu Ala Val Lys Leu
    3860            3865                3870

Ala Ala Phe Asn Gln Ala Phe Ser Glu Ala Glu Asn Val Lys Ala
    3875            3880                3885

Ser Pro Asp Tyr Ile Ser Val Val Gly Cys Ser Leu Ile Ser Asp
    3890            3895                3900

Asp Lys Gln Asn Gly Phe Gly Arg Leu Leu Ile Gln Ser Met Gly
    3905            3910                3915

Asp Asn Asp Ile Arg Ser Asp Val Ser Val Arg Ser Ser Glu Val
    3920            3925                3930

Ala Val Asp Ser Asn Gly Arg Lys His Thr His Asp Glu Asn Gly
    3935            3940                3945

His Trp Val Gln Lys Glu Lys Ser Asn Lys Val Thr Leu Ser Trp
    3950            3955                3960

Asp Glu Gln Gly Glu Val Thr Glu Lys His Glu Arg Ile Arg Asn
    3965            3970                3975

Gly Ile Ala Glu Gly Asp Ile Asp Leu Ser Arg Val Gly Thr Ser
    3980            3985                3990

Asp Val Asp Glu Thr Ala Arg Gly Ala Ile Ala Glu Asn Ser Asp
    3995            4000                4005

Val Phe Asn Ala Pro Glu Lys Arg Lys Asn Asp Thr Glu Ser Ser
    4010            4015                4020

Ser Ser Gly Ser Ser Lys Ser Lys Leu Ser Tyr Ser Gly Asn Ile
    4025            4030                4035

Gln Val Asn Val Gly Asp Gly Glu Phe Thr Ala Val Asn Trp Gly
    4040            4045                4050

Thr Ser Asn Val Ser Val Lys Val Gly Thr Gly Gly Phe Lys Ser
    4055            4060                4065

Leu Ala Phe Gly Asp Asn Asn Val Met Val His Val Gly Asp Gly
```

```
                    4070            4075            4080
Glu Ser Lys His Ser Phe Asp Ile Gly Gly Tyr Gln Ala Leu Glu
    4085            4090            4095

Gly Ala Gln Met Phe Ile Gly Asn Arg Asn Val Ser Phe Asn Leu
    4100            4105            4110

Gly Gln Ser Asn Asp Leu Ile Val Met Met Asp Lys Ser Ile Pro
    4115            4120            4125

Thr Pro Pro Leu Val Asn Pro Phe Asp Gly Ala Ser Arg Ile Ser
    4130            4135            4140

Gly Val Leu Lys Ser Ile Ala Ser Ser Gly Glu Gly Gln Asp Trp
    4145            4150            4155

Leu Ala Ala Gln Glu Gln Gln Trp Thr Leu Ser Gly Ala Lys Lys
    4160            4165            4170

Phe Val Lys Asp Met Ser Gly Leu Asp Gln Ser Ser Ser Val Asp
    4175            4180            4185

Tyr Thr Ser Leu Val Asp Leu Asp Ser Gln Asn Glu Arg Ser Ser
    4190            4195            4200

Arg Gly Leu Lys Asn Asp Ala Glu Ala Thr Leu Asn Lys Gln Tyr
    4205            4210            4215

Asn Gln Trp Leu Gly Gly Ser Asp Asn Ser Asp Ser Ser Lys Met
    4220            4225            4230

Ser Arg Ala Asp Lys Phe Arg Gln Ala Asn Glu Lys Leu Ala Phe
    4235            4240            4245

Asn Phe Ala Val Gly Gly Gln Gly Ala Asp Ile Gln Val Thr Thr
    4250            4255            4260

Gly Asn Trp Asn Phe Met Phe Gly Asp Asn Ile Gln Ser Ile Leu
    4265            4270            4275

Asp Thr Asn Leu Gly Ser Leu Phe Gly Leu Met Thr Gln Gln Phe
    4280            4285            4290

Ser Thr Thr Gly Gln Ala Lys Thr Thr Phe Thr Tyr Ser Pro Glu
    4295            4300            4305

Asp Leu Pro Arg Gln Leu Lys Asn Lys Leu Leu Gly Gln Leu Ala
    4310            4315            4320

Gly Val Gly Ala Glu Thr Thr Leu Gly Asp Ile Phe Gly Val Asp
    4325            4330            4335

Tyr Thr Ala Ala Gly His Ile Val Ser Arg Thr Gly Glu Ser Val
    4340            4345            4350

Asp Gly Val Ala Ile Leu Lys Glu Met Leu Glu Val Val Gly Glu
    4355            4360            4365

Phe Ser Gly Asp Gln Leu Gln Ala Phe Val Asp Pro Ala Lys Leu
    4370            4375            4380

Leu Asp Ser Leu Glu Ser Gly Val Asn Met Gly Ala Asp Gly Ile
    4385            4390            4395

Lys Thr Phe Ala Glu Thr His Gly Leu Lys Glu Lys Ala Pro Glu
    4400            4405            4410

Glu Glu Glu Asp Asn Ser Ser Val Ser Val Asn Gly Thr Asn Val
    4415            4420            4425

Ala Gly Ala Gln Asp Asn Gly Asp Ala Ile Thr Ala Asp Ser Ser
    4430            4435            4440

Ala Lys Glu Asp Arg Ala Phe Gly Phe Asn Ser Leu Asn Leu Pro
    4445            4450            4455

Asn Leu Phe Ala Thr Ile Phe Ser Glu Asn Lys Gln Thr Glu Met
    4460            4465            4470
```

```
Lys Ser Leu Val Glu Asn Leu Lys Glu Asn Leu Thr Ala Asp Leu
4475                4480                4485

Leu Asn Met Lys Glu Lys Thr Phe Asp Phe Leu Arg Asn Ser Gly
4490                4495                4500

His Leu Gln Gly Asp Gly Asp Ile Asn Val Ser Leu Gly Asn Tyr
4505                4510                4515

Asn Phe Asn Trp Gly Gly Gly Lys Asp Leu Gly Ala Tyr Leu
4520                4525                4530

Gly Asp Asn Asn Asn Phe Trp Gly Gly Arg Gly Asp Asp Val Tyr
4535                4540                4545

Tyr Ala Thr Gly Thr Ser Asn Ile Phe Thr Gly Gly Glu Gly Asn
4550                4555                4560

Asp Met Gly Val Leu Met Gly Arg Glu Asn Met Met Phe Gly Gly
4565                4570                4575

Glu Gly Asn Asp Thr Ala Val Val Ala Gly Arg Ile Asn His Val
4580                4585                4590

Phe Leu Gly Ala Gly Asp Asp Glu Ser Phe Val Phe Gly Glu Gly
4595                4600                4605

Gly Glu Ile Asp Thr Gly Thr Gly Arg Asp Tyr Val Val Thr Ser
4610                4615                4620

Gly Asn Tyr Asn Arg Val Asp Thr Gly Gly Asp Gln Asp Tyr Ser
4625                4630                4635

Val Thr Ile Gly Asn Asn Asn Gln Val Glu Leu Gly Ala Gly Asn
4640                4645                4650

Asp Phe Ala Asn Val Phe Gly Asn Tyr Asn Arg Ile Asn Ala Ser
4655                4660                4665

Gly Gly Asn Asp Val Val Lys Leu Met Gly Tyr Asn Ala Val Leu
4670                4675                4680

Asn Gly Gly Glu Gly Asp Asp His Leu Ile Ala Ala Ala Leu Ser
4685                4690                4695

Lys Phe Ser Gln Leu Asn Gly Gly Glu Gly Ser Asp Val Met Val
4700                4705                4710

Leu Gly Gly Phe Gln Asn Thr Phe Lys Gly Gly Thr Gly Val Asp
4715                4720                4725

Ser Phe Val Val Ser Gly Asp Val Ile Asp Asn Leu Val Glu Asp
4730                4735                4740

Ile Arg Ser Glu Asp Asn Ile Val Phe Asn Gly Ile Asp Trp Gln
4745                4750                4755

Lys Leu Trp Leu Glu Arg Ser Gly Tyr Asp Leu Lys Leu Ser Ile
4760                4765                4770

Leu Arg Asp Pro Glu Ser Asp Thr Asp Gln Ala Lys Phe Glu His
4775                4780                4785

Ile Gly Ser Val Thr Phe Asn Asp Tyr Phe Asn Gly Asn Arg Ala
4790                4795                4800

Gln Val Val Val Ala Met Gly Asp Gln Gly Thr Ser Gln Asp His
4805                4810                4815

Thr Val Leu Ser Asn Asn Ala Val Asp Ala Leu Val Gln Ala Met
4820                4825                4830

Ser Ala Phe Glu Pro Gln Ala Gly Asp Asn Gly Phe Ile Asp Asn
4835                4840                4845

Leu Asp Ser Lys Ser Arg Val Ala Ile Thr Thr Ala Trp Ser Asp
4850                4855                4860

Val Ser Lys Gly Asn Ser Val Ile Ser
4865                4870
```

<210> SEQ ID NO 4
<211> LENGTH: 3672
<212> TYPE: PRT
<213> ORGANISM: Photorhabdus luminescens

<400> SEQUENCE: 4

```
Met Gly Lys Ser Ser Asn Arg Ser Thr Glu Tyr Ile Phe Thr Gly Lys
1               5                   10                  15

Tyr Tyr Asp Asp Asp Asn Ile Asp Asn Ser Ile Thr Ala Ile Gly
            20                  25                  30

Ile Gly Gly Asn Val Tyr Ala Tyr Gly Gly Asp Asp Val Thr Val
        35                  40                  45

Gly Ser Phe Lys Val Asp Val Tyr His Thr Asp Gly Asp Leu Ala Val
50                  55                  60

Lys Gly Ala Ser Gly Tyr Thr Gly Ile His Lys Thr Gly Asn Gly Gly
65                  70                  75                  80

Leu Ser Phe Ala Gly Ala Ala Gly Ala Val Phe Ile Asn His Thr Gly
                85                  90                  95

Glu Thr Gly Asn Leu Asn Tyr Ser Gly Val Ala Gly Tyr Asn Lys Leu
            100                 105                 110

Val Arg Lys Gly Leu Ser Gly Asp Ser Ser Phe Lys Gly Gly Gly Gly
        115                 120                 125

Tyr Asn Gln Leu Trp His Glu Thr Asn Arg Gly Asp Leu Asp Phe Ala
130                 135                 140

Gly Ala Gly Ala Gly Asn Asn Ile Asp Arg Thr Trp Phe Asn Arg Tyr
145                 150                 155                 160

Gln Asp Ser Gln Gly Asn Val Ile Phe Asn Gly Ala Gly Val Thr Asn
                165                 170                 175

Asn Ile Asn Ser Arg Val Glu Ser Gly Asp Ile Ile Leu His Gly Ile
            180                 185                 190

Gly Thr Asp Asn His Ile Val Arg Arg Gly Arg Asn Gly Asp Ile Leu
        195                 200                 205

Leu Arg Gly Val Gly Ala Ala Asn Arg Ile Glu Arg Ile Arg His Ser
210                 215                 220

Glu Asp Lys Tyr Gly Gln Thr Gln Gly Asp Ile Thr Leu Glu Gly Ala
225                 230                 235                 240

Gly Gly Tyr Asn Thr Leu Tyr Ser Asp Val Ala His Gly Asn Ile His
                245                 250                 255

Phe Thr Gly Thr Gly Val Tyr Asn Lys Ile Ala Arg Val Gly Val Arg
            260                 265                 270

Asn Glu Ile Glu Phe Ala Gln Ala Lys Asp Ile Ile Met Thr Ser Ala
        275                 280                 285

Thr Met Glu Gly Asp Gly Thr Gln Gln Ser Arg Gln Val Lys Ala Val
290                 295                 300

Lys Ser Ala Val Glu Pro Asp Thr Tyr Leu Phe Ala Ile Ala Asn Asn
305                 310                 315                 320

Ile Asn Thr Lys Val Val Ala Val Arg Leu Arg Asn Asn Pro Asp Thr
                325                 330                 335

Gly Lys Leu Arg Tyr Tyr Ala Thr Ser Trp Tyr Lys Gln Gly Asp His
            340                 345                 350

Leu Glu Asp Ile Ala Lys Glu Asn Ile Asn Thr Asn Asn Gly Phe Ile
        355                 360                 365

Pro Val Lys Gly Asp Asp Thr Ile Thr Leu Ala Asn Ile Asn Val Val
370                 375                 380
```

```
Tyr Arg Gln Lys Asn Thr Ile Gln Gly Val Val Lys Ala Leu Leu Thr
385                 390                 395                 400

Asp Lys Trp Gly Asn Tyr Ala Arg Gly Ile Asn Ile Lys Ala Glu Asp
            405                 410                 415

Val Ile Leu Ala Ser Ala Lys Ile Gly Gly Asp Thr Leu Ser Ser Asn
                420                 425                 430

Gly Leu Lys Ile Asp Val Ser Pro Val Lys Ser Asn Thr Gln Pro Asn
            435                 440                 445

Thr Tyr Val Tyr Ala Ile Phe Leu Asp Pro Tyr Thr Lys Val Val Glu
        450                 455                 460

Val Lys Leu Ala Asn Asp Ser Glu Thr Gly Arg Leu Lys Tyr Ile Ala
465                 470                 475                 480

Arg Ser Trp Tyr Lys Lys Gly Asp His Thr Gly Arg Ile Ala Asn Glu
                485                 490                 495

Thr Phe Ser Tyr Pro Tyr Gly Tyr Arg Leu Ile Arg Ala Gly Tyr Thr
                500                 505                 510

Val Ser Glu Leu His Tyr Lys Leu Asn Val Thr Asp Asp Ile Thr Asp
            515                 520                 525

Cys Leu Thr Asp Leu Lys Ser Tyr Phe Glu Gln Asp Val Ile Lys Ser
        530                 535                 540

Ser Lys Ser Gly Gly Asp Ser Ser Gly Asn Ile Tyr Phe Ser Gly Ala
545                 550                 555                 560

Gly Gly Gly Asn Ile Ile Lys Ser Asp Val Thr Arg Gly Asp Ile Asn
                565                 570                 575

Phe Thr Gly Leu Gly Ala Ala Asn Val Ile Leu His Asp Ser Lys Phe
                580                 585                 590

Gly Asp Thr His Phe Asp Gly Ala Gly Ala Ala Asn Val Ile Val Lys
            595                 600                 605

Lys Gly Glu Lys Gly Asp Leu Thr Phe Arg Gly Thr Gly Leu Ala Asn
610                 615                 620

Val Leu Val His Arg Gly Gln Ser Gly Lys Met Asp Val Tyr Ala Gly
625                 630                 635                 640

Gly Ala Val Asn Val Leu Val Arg Ile Gly Asp Gly Gln Tyr Leu Ala
                645                 650                 655

His Leu Leu Ala Tyr Gly Asn Ile Ser Ile His Lys Gly Asn Gly Ser
            660                 665                 670

Ser Arg Val Arg Met Leu Gly Gly Tyr Asn Thr His Thr Gln Ile Gly
            675                 680                 685

Asn Gly Asp Gly Asn Trp Ser Gly Lys Gly Gly Phe Asn Val Ile Thr
690                 695                 700

Gln Ala Gly Lys Gly Ser Ile Ser Ser Val Leu Leu Gly Gly Ala Asn
705                 710                 715                 720

Ala Leu Thr Lys Leu Gly Ala Gly Ser Leu Val Ala Gly Met Leu Gly
            725                 730                 735

Gly Ala Asn Ile Ile Ser His Leu Ser Glu Glu Thr Glu Thr Ser Asn
                740                 745                 750

Thr Thr Ala Ile Ala Leu Gly Ala Ser Ile Leu Thr Lys Lys Gly
        755                 760                 765

Thr Gly His Ala Gln Ala Val Met Gly Gly Ala Asn Val Leu Thr
        770                 775                 780

His Ile Gly Asp Gly Asn Thr Thr Gly Val Met Leu Gly Gly Ala Asn
785                 790                 795                 800

Ile Leu Thr Lys Val Gly Ser Gly Asp Ser Thr Gly Ile Met Phe Gly
```

```
                        805                 810                 815
Ile Gly Asn Val Leu Thr His Val Gly Asp Gly Leu Thr Leu Gly Val
                820                 825                 830
Met Ala Ala Ala Gly Asn Ile Phe Thr Lys Val Gly Glu Gly Thr Ser
                835                 840                 845
Ile Ala Ala Leu Thr Gly Thr Gly Asn Leu Phe Thr His Ile Gly Lys
                850                 855                 860
Gly Asp Val Trp Ala Leu Met Gly Gly Ala Val Asn Val Phe Thr Lys
865                 870                 875                 880
Val Gly Asp Gly Asp Ala Leu Ala Leu Met Val Ala Ala Gly Asn Val
                885                 890                 895
Phe Thr His Ile Gly Asp Gly Thr Ser Val Ala Leu Met Gln Ala Glu
                900                 905                 910
Gly Asn Ile Ala Thr Lys Val Gly Asn Gly Met Thr Leu Ala Ala Met
                915                 920                 925
Ile Gly Lys Ala Asn Ile Phe Thr His Val Gly Glu Gly Asn Thr Phe
                930                 935                 940
Ala Ala Leu Ile Gly Gly Ala Asn Val Leu Thr Lys Val Gly Asn Asp
945                 950                 955                 960
Gln Thr Ala Ala Leu Met Ile Gly Lys Ala Asn Ile Tyr Ser His Val
                965                 970                 975
Gly Asn Gly Pro Ser Ile Gly Leu Phe Ala Gly Glu Leu Asn Val Met
                980                 985                 990
Thr Lys Val Gly Glu Gly Thr Thr Leu Ala Ala Met Phe Gly Arg Ala
                995                 1000                1005
Asn Ile Met Thr His Val Gly Asp Gly Leu Thr Gly Val Leu Ala
                1010                1015                1020
Leu Gly Glu Ala Asn Ile Val Thr Lys Val Gly Asn Asp Phe Met
                1025                1030                1035
Gly Val Val Ala Thr Val Lys Ala Asn Val Ile Thr His Val Gly
                1040                1045                1050
Asn Ala Val Thr Ala Ser Ile Leu Phe Gly Lys Gly Asn Ile Leu
                1055                1060                1065
Thr Lys Val Gly Asp Gly Thr Thr Val Gly Leu Leu Val Ser Asp
                1070                1075                1080
Val Gly Asn Val Met Thr His Ile Gly Glu Gly Ser Thr Val Gly
                1085                1090                1095
Phe Ala Lys Gly Lys Ala Asn Leu Ile Thr Lys Ile Gly Asp Gly
                1100                1105                1110
Ala Gly Val Asn Ala Ala Trp Gly Glu Ala Asn Ile Leu Thr Gln
                1115                1120                1125
Val Gly Asn Gly Asp Arg Tyr Asn Phe Ala Lys Gly Gln Ala Asn
                1130                1135                1140
Leu Met Thr Lys Val Gly Lys Gly Gln Glu Val Thr Val Val Gln
                1145                1150                1155
Gly Asp Ala Asn Ile Ile Thr His Val Gly Asn Gly Asp Asp Tyr
                1160                1165                1170
Thr Gly Ala Trp Gly Lys Ala Asn Val Val Thr Lys Val Gly Asp
                1175                1180                1185
Gly Arg Asn Val Val Leu Ala Lys Gly Lys Ala Asn Ile Ile Thr
                1190                1195                1200
Gln Val Gly Gln Gly Asp Ser Phe Asn Ala Leu Trp Ser Glu Gly
                1205                1210                1215
```

-continued

```
Asn Ile Val Thr Lys Val Gly Asp Gly Met Gln Val Thr Val Ala
1220            1225                1230

Lys Gly Lys Ala Asn Val Thr Thr Thr Val Gly Asn Gly Leu Asn
1235            1240                1245

Val Thr Ala Ala His Gly Asp Ser Asn Ile Asn Thr His Val Gly
1250            1255                1260

Asn Gly Val Ser Val Asn Leu Ala Trp Gly Lys His Asn Ile Asn
1265            1270                1275

Thr Lys Val Gly Asn Gly Leu Asn Val Ala Val Met Lys Gly Gln
1280            1285                1290

Ser Asn Ala Asn Ile Gln Val Gly His Gly Leu Ala Val Asn Ala
1295            1300                1305

Ser Tyr Ala Arg Asn Asn Val Ala Ile Lys Ile Gly Glu Gly Asp
1310            1315                1320

Phe Tyr Ser Leu Ala Val Ala Ala Ser Asn Thr Glu Ser Asn Lys
1325            1330                1335

Leu Ala Ala Phe Phe Asn Asn Ile Lys Gln Thr Val Leu Gly Val
1340            1345                1350

Met Gly Ser Gln Ala Ile Asn Tyr Leu Val Gln Gly Glu Glu Val
1355            1360                1365

Asn Thr Phe Gly Ile His Lys Gly Arg Gly Ala Ile His Leu Ala
1370            1375                1380

Glu Val Ser Thr Ile Asp Gly Phe Gln Met Glu Ala Ile Ala Pro
1385            1390                1395

Val Ser Ser Asp Leu Asn Tyr Arg Leu Asn Gly Thr Val Thr Ala
1400            1405                1410

Val Glu Thr Pro Asp Val Asp Val Ile Glu Ser Val Leu Asn Gln
1415            1420                1425

Lys Thr Arg Ser Ile Ser Asp Gln Asn Asn Asn Leu Ile Ile Asn
1430            1435                1440

Gly Asp Phe Glu Gln Gly Lys Leu Gly Trp Gln Ser Thr His Gly
1445            1450                1455

Ile Glu Ala Tyr Gly Ser Ala Ser Ala Tyr Gly Leu Val Ile Ala
1460            1465                1470

Gly His Gly Glu Arg Val Ser Glu Leu Asp Ala Glu Arg Asn Thr
1475            1480                1485

Thr Ile Tyr Gln Asp Leu Gln Asn Leu Ser Glu Gly Glu Val Ile
1490            1495                1500

Ser Leu Ser Phe Asp Phe Ala His Arg Ser Asn Thr Tyr Val Ile
1505            1510                1515

Asn Asn Gly Met Glu Val Phe Trp Asn Gly Gln Trp Val Phe Ser
1520            1525                1530

Ala Ser Gly Asn Ala Ile Glu Trp Lys Ser Lys Thr Leu Glu Leu
1535            1540                1545

Ile Ala Arg Ala Gly Ser Asn Arg Ile Glu Phe Lys Gly Thr Gly
1550            1555                1560

Leu Asn Asp Gly Val Gly Tyr Val Leu Asp Asn Val Val Ala Lys
1565            1570                1575

Ser Glu Asn Pro Leu Gln Thr Asp Val Val Thr Glu His Ala Lys
1580            1585                1590

Gln Asp Lys Ala Ala Gln Asn Ala Leu Asn Asp Lys Glu Lys Ala
1595            1600                1605

Glu Lys Asp Arg Gln Leu Leu Glu Gln Glu Gln Glu Lys Gln Leu
1610            1615                1620
```

-continued

```
Ala Gly Ile Ala Lys Ser Gln Ser Gln Leu Glu Leu Thr Asp Gln
        1625                1630                1635
Ala Ala Val Ser Gln Asn Gly Leu Thr Gln Arg Asn Ala Ile Glu
        1640                1645                1650
Ala Glu Ala Gln Ala Glu Thr Gly Lys Leu Ile Ser Met Thr Gln
        1655                1660                1665
Gly Leu Ala Val Leu Asp Asn His Ala Ser Tyr Ser Gly Gln Ser
        1670                1675                1680
Gly Asp Pro Trp Arg Asn Pro Phe Ala Ala Glu Phe Leu Asn His
        1685                1690                1695
Val Gln Asn Glu Leu Tyr Tyr Val Lys Phe Ile Ala Gln Lys Lys
        1700                1705                1710
Leu Ala Asn Ala Arg Gln Ala Ile Ala Asp Asn Gln Gln Gln Val
        1715                1720                1725
Lys Lys Ala Val Ala Lys Ala Glu Ala Gly Val Ala Gln Ser Glu
        1730                1735                1740
Gln His Cys Val Ser Ala Lys Gln Asp Ile Ala Ala Ala Gln Glu
        1745                1750                1755
Lys Ala Glu Leu Arg Lys Ile Glu Ala Val Leu Gln Gln Gln Gln
        1760                1765                1770
Ala Lys Glu Ala Glu Asn Asp Ala Asn Ile Ala Tyr Gln Gly Ala
        1775                1780                1785
Glu Tyr Arg Gly Lys His Asp Ile Ala Val Ala Glu Ser Lys Ile
        1790                1795                1800
Thr Gln Val Gln Val Asp Ala Lys Val Ala Lys Gln Ser Asp Ser
        1805                1810                1815
Arg Pro Asp Arg Thr Gly Ala Gly Gly Ser Gly Leu Ser Gly Lys
        1820                1825                1830
Ala Tyr Glu Ser Thr Gly Ala Gly Glu Thr Gly Ser His Ile Asp
        1835                1840                1845
Pro Glu Leu Val Pro Glu Ala Glu Lys Lys Phe Tyr Glu Gly Leu
        1850                1855                1860
Ser Glu Glu Glu Leu Gln Ala Leu Asp Ser Val Glu Gln Leu Val
        1865                1870                1875
Asp His Leu Lys Ile Asn Ala Ser Ile His Ala Glu Asn Thr Gly
        1880                1885                1890
Val Leu Thr Ala Ser Lys Phe Ala Lys Gly Gln Ser Gly Ser Met
        1895                1900                1905
Val Met Pro Ala Ser Asn Ser Pro Gly Glu Phe Val Arg Arg Val
        1910                1915                1920
Pro Arg Ile Ser Gly Ile Asn Leu Lys Ser Leu Gly Asp Asp Ile
        1925                1930                1935
Lys Leu Gly Gln Lys Gly Asn Ser Ala Ile Phe Glu Ser Ala Lys
        1940                1945                1950
Phe Asn Leu Leu Lys Glu Gly Ser Lys Leu Phe Ile Asn Pro Asp
        1955                1960                1965
Glu Arg Thr Leu Gly Gln Lys Arg Pro Leu Ser Gln Ala Met Thr
        1970                1975                1980
Ala Val Arg Asp Ile Phe Tyr Lys Thr Met Ser His Phe Asp Glu
        1985                1990                1995
Glu His Val Leu Gln Phe Glu Gln Val Ile Ala Asp Trp Gln Gln
        2000                2005                2010
His Ser Pro Lys Glu Phe Ala Leu Arg Ala Asn Gln Val Asn Leu
```

```
                2015                2020                2025

Ile Arg Phe Arg Met Gly Arg Val Met Glu Tyr Leu Gln Ala Gln
    2030                2035                2040

Arg Ala Glu Ser Ala Lys Val Leu Gly Ile Ala Val Ser Pro Gln
    2045                2050                2055

Arg Ala Glu Gln Leu Ser Gln Arg Val Ile Phe Asp Gly Thr Gly
    2060                2065                2070

Arg Val Val Gly Leu Lys Gly Ser Val Thr Gln Asp Glu Ile Asn
    2075                2080                2085

His Leu Ile Glu Trp Lys Ile Thr Pro Leu Thr Arg Ala Asn Ser
    2090                2095                2100

Thr Ala Glu Arg Glu Ala Pro Lys Thr Glu Ser Glu Ser Leu Ile
    2105                2110                2115

Ala Phe Met Ser Arg Leu Glu Ala Ala Asn Ile Pro Glu Ala Met
    2120                2125                2130

Pro Leu Ile Glu Gln Ala Arg Gly Leu Trp Leu Ile Gly Gln Val
    2135                2140                2145

Thr Ser Lys Glu Thr Ile Lys Leu Phe Asn Asp Ala Ala Ser Gln
    2150                2155                2160

Leu Gln Ala Tyr Pro Glu Leu Gln Ala Leu Val Leu Ser Leu Gln
    2165                2170                2175

Ala Asp Ala His Lys Lys Ser Thr Thr Gln Tyr Ile Asp Asn
    2180                2185                2190

Leu Phe Gly Arg Arg Phe Asp Ser Glu Val Ala His Thr Leu Val
    2195                2200                2205

Lys Thr Ala Ser Pro Asp Ala Ile Ala Val Ser Lys Arg Ile Gly
    2210                2215                2220

Gln Phe Leu Val Gln Glu Phe Glu Leu Tyr Met Gln Asn Thr Ala
    2225                2230                2235

Ser Ser Thr Ile Arg Asp Gly Gln Ile Thr Asn Gly Gln Met Ala
    2240                2245                2250

Ile Arg Met His Ala Phe Ala Glu Lys Ile Lys Lys Asp Ile Arg
    2255                2260                2265

Pro Trp Phe Ser Arg Val Pro Glu Leu Thr Thr Phe Leu Gln Lys
    2270                2275                2280

Pro Thr Leu Asp Asn Phe Lys Ile Met Met Thr Lys Val Asp Asn
    2285                2290                2295

Gly Phe Glu Met Ile Lys Ile Pro Phe Leu Ala Val Lys Met Ser
    2300                2305                2310

Asn Thr Asp Gly Met Gly Leu His Leu Ser Gln Trp Lys Ala Glu
    2315                2320                2325

Ala Asp Ile Phe Tyr Arg Gly Glu Ile Tyr Lys Ala Arg Ser Thr
    2330                2335                2340

Ser Asn Thr Leu Thr His Arg Ala Asp Val Thr His Thr Val Glu
    2345                2350                2355

Leu Ile Asp Gln Gln Thr Asn Asp Tyr Gly Ile Ala Leu Pro Tyr
    2360                2365                2370

Gln Pro Ser Gly Asp Gln Tyr Asp Asp Phe Leu Ser Gly Arg Lys
    2375                2380                2385

Val Ala Ala Gly Ser Val Leu Thr Pro Gly Gln Glu Thr Val Leu
    2390                2395                2400

Glu Arg Asn Ala Leu Ala Gln Gly His Ser Val Val Thr Gly Ala
    2405                2410                2415
```

-continued

Ser Gly Ser Thr Asn Ile Met Val His Leu Asn Asn Tyr Ile Ala
2420                    2425                2430

Arg Gln Asp Pro Thr Phe Ser Gln Glu Gln Ala Tyr Leu Asn Thr
2435                    2440                2445

Leu Ala Phe Leu Val Phe Asp Gly Gly His Ser Val Asn Glu Ser
2450                    2455                2460

Leu Val Val Tyr Lys Ala Leu Gln Ala Thr Ser Asp Glu Arg Arg
2465                    2470                2475

Gln Val Leu Gln His Tyr Thr Ala Ser Tyr Met Asp Leu Met Asp
2480                    2485                2490

Ile Ala Gly Asp Lys Gly Glu Arg Trp Ile Asn Gln Ala Leu Asn
2495                    2500                2505

Ser Ala Phe Glu Lys Thr Leu His Phe Tyr Arg Glu Asn Thr Pro
2510                    2515                2520

Glu Arg Lys Arg Asn Asp Val Pro Val Glu Ala Leu Gln Ala Leu
2525                    2530                2535

Ser Gly Lys Asn Gly Thr Ser Glu Ser Leu Phe Ile Lys Asp Gly
2540                    2545                2550

Gly Thr Ser Pro Gln Asp Lys Ala Ala Leu Asn Pro Val Thr Arg
2555                    2560                2565

Phe Phe Asn Asn Glu Leu Tyr Gly Phe Lys Glu Asp Lys Asn Gln
2570                    2575                2580

Asp Arg Val Lys Asn Ser Gln Gln Lys Asn Asp Asn Arg Gly Thr
2585                    2590                2595

Arg Phe Asp Gly Gln Ile Ile Ile Gln Met Glu Asp Asp Pro Ile
2600                    2605                2610

Val Ala Lys Ala Ala Ile Asn Leu Ala Gly Lys His Pro Asp Ser
2615                    2620                2625

Ser Val Val Lys Leu Asp Ala Asp Gly Lys Tyr His Val Ile
2630                    2635                2640

Asp Gly Asp Pro Ala Gly Leu Ser Gly Lys Leu Arg Trp Gln Ile
2645                    2650                2655

Val Gly His Gly Arg Asp Glu Ser Thr Gln Asn Asn Thr Arg Leu
2660                    2665                2670

Ser Gly Tyr Arg Ala Asp Glu Leu Ala Ile Lys Leu Lys Gln Phe
2675                    2680                2685

Ser Gln Asp Phe Glu Gln Ala Gly Lys Pro Glu Arg Ile Ser Ile
2690                    2695                2700

Val Gly Cys Ser Leu Ile Ser Asp Asp Lys Gln Asn Gly Phe Ala
2705                    2710                2715

Tyr Arg Phe Met Phe Ala Leu Asp Lys Gln Gly Ile Arg Ser Glu
2720                    2725                2730

Val Ser Val Arg Arg Ser Asp Val Ala Val Asp Ala Thr Gly Arg
2735                    2740                2745

Lys Phe Thr Arg Asp Lys Asn Tyr Gln Trp Val Asn Arg Leu Asp
2750                    2755                2760

Asp Asn Lys Gln Val Leu Cys Trp Asn Glu Glu Gly Glu Leu Thr
2765                    2770                2775

Ala Thr Thr Glu Arg Glu Arg Cys Gly Val Ala Glu Ser Asp Ile
2780                    2785                2790

Asn Leu Ala Arg Val Gly Tyr Thr Glu Ala Asp Ser Val Thr Arg
2795                    2800                2805

Gly Ala Ile Ala Asp Asn His Asp Val Phe Ile Ala Pro Arg Lys
2810                    2815                2820

-continued

```
Arg Lys Asn Arg Ile Glu Pro Gly Ser Asn Pro Gln Ser Asp Lys
    2825              2830              2835
Pro Leu Ser Tyr Ala Gly Asn Ile Gln Val Asn Val Gly Asp Gly
    2840              2845              2850
Glu Phe Thr Ala Ile Asn Trp Gly Thr Ser Asn Val Gly Ile Lys
    2855              2860              2865
Val Gly Thr Gly Gly Phe Lys Ser Leu Ala Phe Gly Asp Asn Asn
    2870              2875              2880
Val Met Ala His Ile Gly Glu Gly Asp Ser Lys His Ser Val Asn
    2885              2890              2895
Leu Gly Gly Tyr Gln Ala Phe Glu Gly Ala Gln Val Phe Ile Gly
    2900              2905              2910
Thr Arg Asn Ile Ser Phe Asn Gln Gly Arg Ser Asn Asp Leu Ile
    2915              2920              2925
Val Met Met Asp Lys Ser Leu Ser Thr Pro Pro Leu Val Asn Pro
    2930              2935              2940
Phe Asp Gly Thr Ala Arg Ile Ser Gly Val Leu Lys Ser Ile Ala
    2945              2950              2955
Arg Ser Gly Glu Glu Gln Asn Trp Leu Ala Val Gln Asp Gln Gln
    2960              2965              2970
Trp Thr Leu Ser Gly Ala Glu Lys Phe Val Arg Asp Met Ser Gly
    2975              2980              2985
Leu Asp Gln Thr Ser Ser Val Asp Tyr Lys Thr Leu Val Asp Leu
    2990              2995              3000
Asp Ala Gln His Glu Arg Ser Ser Arg Gly Leu Lys Ser Asp Thr
    3005              3010              3015
Glu Thr Ala Leu Asn Lys Lys Tyr His Arg Trp Leu Ser Asp Asn
    3020              3025              3030
Ser Asn Asp Ile Asp Thr Ser Lys Met Ser Arg Val Asp Lys Phe
    3035              3040              3045
Arg Gln Ala Asn Glu Lys Leu Ile Phe Asn Phe Ala Val Gly Gly
    3050              3055              3060
Arg Gly Ala Asp Ile Gln Val Thr Thr Gly Ser Trp Asn Phe Met
    3065              3070              3075
Phe Gly Asp His Ile Gln Ser Ile Leu Asp Thr Asn Leu Gly Ser
    3080              3085              3090
Leu Phe Gly Leu Met Thr Gln Gln Tyr Ser Ala Thr Gly Ile Ala
    3095              3100              3105
Lys Thr Thr Phe Thr Tyr Lys Pro Gln Asp Leu Pro Arg Gln Leu
    3110              3115              3120
Lys Asn Lys Leu Leu Gly Arg Leu Ala Ser Val Asn Ala Glu Thr
    3125              3130              3135
Thr Leu Ala Asp Ile Phe Gly Val Asp Cys Thr Pro Glu Gly Gln
    3140              3145              3150
Ile Val Ala Arg Thr Gly Glu Pro Val Asp Gly Thr Ala Ile Leu
    3155              3160              3165
Arg Glu Met Leu Glu Met Ile Lys Gln Phe Gly Gly Asp Gln Phe
    3170              3175              3180
Arg Val Phe Ala Asp Pro Asp Lys Trp Ile Glu Gly Leu Lys Gln
    3185              3190              3195
His Ile Asp Met Gly Ala Asp Gly Ile Lys Ser Phe Leu Ile Ser
    3200              3205              3210
His Gly Leu Lys Glu Lys Ala Pro Asp Glu Asn Arg Glu Glu Ser
```

-continued

```
                   3215                3220                3225

Val Pro Gly Val Ile Asn Ser Gly Asn Ser Gln Val Asp Asn Lys
3230                3235                3240

Pro Glu Arg Ala Leu Gly Phe His Ser Leu Asn Leu Pro Asn Leu
3245                3250                3255

Phe Ala Thr Ile Phe Asn Arg Asn Lys Gln Glu Glu Met Arg Ser
3260                3265                3270

Leu Val Thr Asn Leu Lys Glu Asn Leu Thr Ala Asp Leu Leu Asn
3275                3280                3285

Met Glu Gln Lys Thr Phe Asp Phe Leu Arg Asn Ser Gly His Leu
3290                3295                3300

His Asp Asp Gly Asp Ile His Ile Ser Leu Gly Asn Tyr Asn Phe
3305                3310                3315

Asn Trp Gly Gly Asp Gly Lys Asp Leu Gly Ala Tyr Leu Gly Asp
3320                3325                3330

Asn Asn Asn Phe Trp Gly Gly Arg Gly Glu Asp Val Tyr Tyr Ala
3335                3340                3345

Ile Gly Ile Ser Asn Leu Phe Thr Gly Gly Glu Gly Asn Asp Leu
3350                3355                3360

Gly Val Leu Met Gly Arg Glu Asn Trp Met Phe Gly Gly His Gly
3365                3370                3375

Asp Asp Thr Ala Val Ile Ala Gly Arg Ile Asn Tyr Ala Phe Met
3380                3385                3390

Gly Glu Gly Asn Asp Gln Thr Phe Val Phe Gly Glu Gly Gly Leu
3395                3400                3405

Ile Asp Ala Gly Ser Gly Tyr Asp Tyr Val Val Thr Ala Gly Asn
3410                3415                3420

Tyr Asn Arg Val Glu Thr Gly Glu Asp Gln Asp Tyr Ala Val Thr
3425                3430                3435

Ile Gly Asn Asn Asn Trp Val Glu Leu Gly Ala Gly His Asp Phe
3440                3445                3450

Gly Trp Val Phe Gly Asn Asp Asn Arg Ile Asp Gly Asn Thr Gly
3455                3460                3465

Asp Asp Val Ile Lys Leu Met Gly Tyr His Ala Val Ile Asn Gly
3470                3475                3480

Gly Glu Gly Asp Asp His Leu Ile Ala Ala Thr Ile Ser Lys Phe
3485                3490                3495

Ser Gln Phe Asp Gly Gly Gly Gly Gln Asp Leu Leu Val Leu Gly
3500                3505                3510

Gly Tyr Gln Asn His Phe Gln Gly Gly Ala Gly Val Asp Ser Phe
3515                3520                3525

Val Val Ser Gly Gln Val Ile Asp Ser Gln Val Asp Asp Ile Asn
3530                3535                3540

Ala Glu Asp Met Ile Ala Phe Asn Asp Ile Asp Trp Gln Asp Leu
3545                3550                3555

Trp Phe Gln Arg Ser Gly Tyr Asp Leu Val Leu Ser Val Asn Arg
3560                3565                3570

Pro Thr Gln Asp Lys Thr Ala Gln Gly Ile Phe Glu Ser Ile Gly
3575                3580                3585

Ser Val Thr Phe Ser Asp Tyr Phe Asn Gly Asn Arg Ala Lys Leu
3590                3595                3600

Val Met Arg Met Gly Asp Lys Asn Ala Leu Gly Glu Arg Glu Phe
3605                3610                3615
```

-continued

```
Thr Ala Leu Ser Asp Asn Ala Val Asp Thr Leu Ile Gln Ala Met
    3620            3625                3630

Ser Ser Phe Ala Pro Thr Val Gly Asp Asn Gly Phe Ile Asp Asn
    3635            3640                3645

Leu Ala Ser Gln Ala Lys Ile Val Met Ala Thr Ala Trp Ala Asp
    3650            3655                3660

Thr Thr Glu Gly Lys Val Gln Phe Ala
    3665            3670

<210> SEQ ID NO 5
<211> LENGTH: 4070
<212> TYPE: PRT
<213> ORGANISM: Photorhabdus luminescens

<400> SEQUENCE: 5

Met Gly Lys Ser Ser Asn Arg Ser Thr Glu Tyr Phe Phe Thr Gly Lys
1               5                   10                  15

Tyr Tyr Asp Asp Asn Asp Gly Asn Ser Ile Ile Ala Ile Gly Ile Gly
            20                  25                  30

Gly Glu Val Tyr Ala Tyr Gly Gly Asp Asp Val Thr Ile Gly Ser
        35                  40                  45

Phe Lys Val Asp Val Tyr His Thr Asn Gly Glu Leu Ser Val Lys Gly
    50                  55                  60

Ala Ser Gly Tyr Thr Gly Ile Ser Lys Thr Asn Gly Gly Leu Ser
65                  70                  75                  80

Phe Ser Gly Ala Ala Gly Thr Ala Phe Ile Asp His Thr Gly Glu Thr
                85                  90                  95

Gly Asp Leu Ser Tyr Ser Gly Ala Ala Gly Tyr Asn Lys Leu Val Arg
            100                 105                 110

Lys Gly Ser Ser Gly Asp Thr Arg Phe Lys Gly Ala Gly Gly Tyr Asn
        115                 120                 125

Gln Leu Trp His Glu Thr Asp Gln Gly Asn Val Tyr Phe Ala Gly Ala
    130                 135                 140

Gly Ala Ala Asn Lys Ile Asp Arg Thr Trp Ser Asn Tyr Tyr Glu Gly
145                 150                 155                 160

Thr Gln Gly Asp Val Thr Phe Asn Gly Ala Gly Ala Ala Asn Ser Ile
                165                 170                 175

Asp Ser Arg Ile Glu Ser Gly Asp Ile Thr Leu Asn Gly Val Gly Ala
            180                 185                 190

Asp Asn His Ile Val Arg Lys Gly Arg Glu Gly Asn Ile Ile Leu His
        195                 200                 205

Gly Ala Gly Ala Ala Asn Arg Ile Glu Arg Thr Arg His Ser Glu Asp
    210                 215                 220

Gln Tyr Gly Gln Thr Gln Gly Asp Ile Thr Leu Glu Gly Ala Gly Gly
225                 230                 235                 240

Tyr Asn Lys Leu Tyr Ser Asp Val Ala His Gly Asn Ile His Phe Thr
                245                 250                 255

Gly Ala Gly Ala Tyr Asn Glu Ile Thr Arg Ala Gly Ala Arg Asn Glu
            260                 265                 270

Ile Glu Phe Ala Gln Ala Lys Asp Ile Val Met Thr Ser Ala Thr Met
        275                 280                 285

Glu Glu Arg Gly Ile Gln Gln Ser Gln Gln Val Lys Ala Val Lys Ser
    290                 295                 300

Glu Val Glu Pro Asp Thr Tyr Leu Phe Ala Ile Ala Asp Asn Val Asn
305                 310                 315                 320
```

```
Thr Lys Val Val Ala Val Arg Leu Gln Asn Asn Pro Asp Thr Gly Lys
                325                 330                 335

Leu Arg Tyr Tyr Ala Thr Ser Trp Tyr Lys Glu Gly Asn His Leu Lys
            340                 345                 350

Asp Ile Ala Lys Glu Asn Ile Asp Val Asn Asn Gly Phe Ile Ser Val
        355                 360                 365

Lys Gly Asp Asp Ala Ile Thr Leu Ala Asn Ile Asn Val Val Tyr Arg
    370                 375                 380

Gln Glu Thr Ile Val Gln Gly Val Glu Val Leu Leu Thr Asp Lys
385                 390                 395                 400

Trp Val Asn Tyr Ser Asp Gly Thr Asn Ile Lys Ala Lys Asn Val Thr
            405                 410                 415

Leu Gly Ser Ala Lys Met Gly Gly Tyr Ala Ile Ser Ser Asn Gly Leu
        420                 425                 430

Lys Ile Asp Val Ser Pro Val Lys Ser Asn Gln Gln Pro Asp Thr Tyr
    435                 440                 445

Val Tyr Ala Ile Phe Leu Glu Pro Tyr Thr Lys Val Val Glu Val Lys
    450                 455                 460

Leu Ala Asn Asp Asp Glu Thr Gly Lys Leu Lys Tyr Ile Ala Arg Ser
465                 470                 475                 480

Trp Tyr Lys Lys Gly Asp His Thr Gly Arg Leu Ala Asn Glu Arg Phe
            485                 490                 495

Ser Tyr Pro Arg Gly Tyr Gln Ser Ile Gly Ala Gly Tyr Thr Leu Ser
        500                 505                 510

Gln Leu His Tyr Asp Leu Asn Val Thr Asp Glu Ile Thr Asp Cys Leu
    515                 520                 525

Thr Asp Ile Glu Gly Tyr Ser Glu Gln Asp Val Ile Lys Ser Ser Lys
530                 535                 540

Asn Gly Gly Asp Ser Ser Gly Asn Ile Tyr Phe Ile Gly Ala Gly Gly
545                 550                 555                 560

Gly Asn Ile Ile Thr Ser Val Thr His Gly Asn Ile Asn Phe Thr
            565                 570                 575

Gly Ala Gly Ala Ala Asn Ile Ile Leu His Ser Ser Thr Phe Gly Asn
        580                 585                 590

Thr Tyr Phe Glu Gly Gly Gly Ala Asn Val Ile Val Lys Asn Gly
    595                 600                 605

Glu Glu Gly Asp Leu Ser Phe Arg Gly Ala Gly Leu Ala Asn Val Leu
610                 615                 620

Val His Gln Ser Gln Arg Gly Lys Met Asp Val Tyr Ala Gly Gly Ala
625                 630                 635                 640

Val Asn Val Leu Val Arg Val Gly Asp Gly Arg Tyr Leu Ala His Leu
            645                 650                 655

Leu Ser Tyr Gly Asn Ile Ser Ile His Lys Gly Asn Gly Asp Ser Arg
        660                 665                 670

Val Leu Met Leu Gly Gly Tyr Asn Thr His Thr Gln Ile Gly Asp Gly
    675                 680                 685

Ser Ala Asn Trp Phe Gly Ala Gly Phe Asn Val Ile Thr Gln Ala
    690                 695                 700

Gly Thr Gly Asp Ile Phe Ser Val Phe Leu Gly Gly Ala Asn Val Leu
705                 710                 715                 720

Thr Lys Leu Gly Ala Gly Asp Met Val Ala Gly Met Leu Gly Gly Ala
            725                 730                 735

Asn Ile Ile Thr His Leu Ser Asp Glu Thr Glu Thr Thr Asn Thr Thr
        740                 745                 750
```

```
Ala Ile Ala Leu Gly Gly Ala Asn Ile Phe Thr Lys Lys Gly Lys Gly
        755                 760                 765

His Thr Gln Ala Val Met Gly Gly Ala Asn Val Leu Thr His Ile
        770                 775                 780

Gly Asp Gly Asn Thr Thr Gly Val Met Leu Gly Ala Asn Ile Leu
785                 790                 795                 800

Thr Lys Val Gly Lys Gly Asp Met Thr Gly Ile Met Phe Gly Val Gly
                805                 810                 815

Asn Val Leu Thr His Val Gly Asp Gly Leu Thr Leu Gly Val Met Ala
                820                 825                 830

Ala Ala Gly Asn Ile Phe Thr Lys Val Gly Glu Gly Thr Ser Ile Ala
        835                 840                 845

Ala Met Ile Gly Ala Gly Asn Leu Phe Thr His Val Gly Lys Gly Asp
        850                 855                 860

Ala Trp Ala Leu Met Gly Gly Val Gly Asn Ile Phe Thr Lys Val Gly
865                 870                 875                 880

Asp Gly Asp Ala Leu Ala Leu Met Val Ala Ala Gly Asn Val Phe Thr
                885                 890                 895

His Ile Gly Asp Gly Thr Ser Val Ala Leu Met Leu Ala Lys Gly Asn
        900                 905                 910

Ile Ala Thr Lys Val Gly Asn Gly Met Thr Leu Ala Ala Met Ile Gly
        915                 920                 925

Lys Ala Asn Ile Phe Thr His Val Gly Glu Gly Asn Thr Phe Ala Ala
        930                 935                 940

Met Ile Gly Gly Ala Asn Val Leu Thr Lys Val Gly Asn Asp Leu Thr
945                 950                 955                 960

Ala Ala Leu Met Val Gly Lys Ala Asn Ile Tyr Ser His Val Gly Asn
                965                 970                 975

Gly Thr Ser Ile Gly Leu Phe Ala Gly Glu Leu Asn Val Met Thr Lys
                980                 985                 990

Val Gly Asn Gly Thr Thr Leu Ala Ala Met Phe Gly Lys Ala Asn Met
        995                 1000                1005

Met Thr His Val Gly Asp Gly Leu Thr Gly Val Leu Ala Leu Gly
        1010                1015                1020

Glu Ala Asn Ile Val Thr Lys Val Gly Asp Asp Phe Met Gly Val
        1025                1030                1035

Val Ala Ala Ala Lys Ala Asn Val Ile Thr His Val Gly Asp Ala
        1040                1045                1050

Thr Thr Ala Ala Ile Leu Phe Gly Lys Gly Asn Ile Leu Thr Lys
        1055                1060                1065

Val Gly Asp Gly Thr Thr Val Gly Leu Leu Ile Ser Asp Val Gly
        1070                1075                1080

Asn Val Met Thr His Val Gly Glu Gly Thr Thr Val Gly Phe Ala
        1085                1090                1095

Lys Gly Lys Ala Asn Leu Ile Thr Lys Ile Gly Asp Gly Ala Gly
        1100                1105                1110

Val Asn Ala Ala Trp Gly Glu Ala Asn Ile Leu Thr Gln Val Gly
        1115                1120                1125

Asn Gly Asp Arg Tyr Asn Phe Ala Lys Gly Lys Ala Asn Leu Met
        1130                1135                1140

Thr Lys Val Gly Lys Gly Gln Glu Val Thr Val Val Gln Gly Asp
        1145                1150                1155

Ala Asn Ile Ile Thr His Val Gly Asn Gly Asp Asp Tyr Thr Gly
```

|  |  |  |  |  |  |  |  |  |  |
|---|---|---|---|---|---|---|---|---|---|
| | | 1160 | | | 1165 | | | 1170 | |
| Ala | Trp | Gly | Lys | Ala | Asn | Val | Ile | Thr | Lys | Ile | Gly | Asp | Gly | Arg |
| 1175 | | | | 1180 | | | | 1185 | |
| Asn | Val | Val | Leu | Ala | Lys | Gly | Lys | Ala | Asn | Ile | Val | Thr | Gln | Val |
| 1190 | | | | 1195 | | | | 1200 | |
| Gly | Gln | Gly | Asp | Ser | Phe | Asn | Ala | Leu | Trp | Ser | Glu | Gly | Asn | Ile |
| 1205 | | | | 1210 | | | | 1215 | |
| Val | Thr | Lys | Val | Gly | Asp | Gly | Met | Gln | Val | Thr | Val | Ala | Lys | Gly |
| 1220 | | | | 1225 | | | | 1230 | |
| Lys | Ala | Asn | Val | Thr | Thr | Thr | Val | Gly | Asn | Gly | Leu | Asn | Val | Thr |
| 1235 | | | | 1240 | | | | 1245 | |
| Ala | Ala | His | Gly | Asp | Ala | Asn | Ile | Asn | Thr | His | Val | Gly | Asn | Gly |
| 1250 | | | | 1255 | | | | 1260 | |
| Val | Ser | Val | Asn | Leu | Ala | Trp | Gly | Lys | His | Asn | Ile | Asn | Thr | Lys |
| 1265 | | | | 1270 | | | | 1275 | |
| Val | Gly | Asn | Gly | Leu | Asn | Val | Ala | Val | Met | Lys | Gly | Gln | Ala | Asn |
| 1280 | | | | 1285 | | | | 1290 | |
| Ala | Asn | Ile | His | Val | Gly | Asp | Gly | Leu | Gly | Ile | Asn | Ala | Ser | Tyr |
| 1295 | | | | 1300 | | | | 1305 | |
| Ala | Arg | Asn | Asn | Val | Ala | Val | Lys | Ile | Gly | Asn | Gly | Asp | Phe | Tyr |
| 1310 | | | | 1315 | | | | 1320 | |
| Ser | Phe | Ser | Val | Thr | Asn | Ser | Asn | Lys | Leu | Ser | Ser | Leu | Phe | Glu |
| 1325 | | | | 1330 | | | | 1335 | |
| His | Ile | Lys | Gln | Thr | Thr | Leu | Gly | Val | Gly | Gly | Ser | Gln | Ala | Ile |
| 1340 | | | | 1345 | | | | 1350 | |
| Asn | Tyr | Leu | Val | His | Gly | Glu | Glu | Ala | Asn | Thr | Ser | Gly | Thr | His |
| 1355 | | | | 1360 | | | | 1365 | |
| Lys | Gly | Arg | Gly | Ala | Ile | Asn | Leu | Ala | Glu | Val | Ser | Gly | Ile | Asp |
| 1370 | | | | 1375 | | | | 1380 | |
| Gly | Phe | Gln | Met | Asp | Glu | Ile | Ala | Pro | Ile | Ser | Ser | Asp | Leu | Asn |
| 1385 | | | | 1390 | | | | 1395 | |
| His | Ser | Phe | Asn | Gly | Ala | Ile | Thr | Ala | Val | Glu | Thr | Pro | Asp | Val |
| 1400 | | | | 1405 | | | | 1410 | |
| Ser | Ser | Ile | Glu | Gly | Ala | Leu | Ser | Gln | Lys | Thr | Leu | Ser | Val | Ser |
| 1415 | | | | 1420 | | | | 1425 | |
| Asp | Gln | Asp | Glu | Asn | Leu | Ile | Val | Asn | Gly | Asp | Phe | Glu | Gln | Gly |
| 1430 | | | | 1435 | | | | 1440 | |
| Glu | Leu | Gly | Trp | Gln | Ser | Thr | His | Gly | Ile | Glu | Ala | Tyr | Asn | Pro |
| 1445 | | | | 1450 | | | | 1455 | |
| Ala | Ser | Asp | Tyr | Gly | Leu | Asp | Asn | Thr | Gly | Asp | Gly | Glu | Arg | Val |
| 1460 | | | | 1465 | | | | 1470 | |
| Ser | Lys | Phe | Asp | Val | Asp | Lys | Asn | Thr | Val | Ile | Trp | Gln | Glu | Leu |
| 1475 | | | | 1480 | | | | 1485 | |
| Gln | Asn | Leu | Ser | Glu | Gly | Glu | Val | Val | Ser | Leu | Thr | Phe | Asp | Phe |
| 1490 | | | | 1495 | | | | 1500 | |
| Met | Ser | His | Phe | Glu | Arg | Val | Asp | Arg | Asp | Leu | Ser | Gly | Ser | Gly |
| 1505 | | | | 1510 | | | | 1515 | |
| Ile | Met | Val | Leu | Trp | Asn | Gly | Lys | Ser | Val | Phe | Ser | Thr | Ser | Gly |
| 1520 | | | | 1525 | | | | 1530 | |
| Pro | Arg | Ala | Ile | Trp | Arg | Thr | Gln | Lys | Leu | Asp | Leu | Met | Ala | Lys |
| 1535 | | | | 1540 | | | | 1545 | |
| Ala | Gly | Thr | Asn | Arg | Ile | Glu | Phe | Lys | Gly | Thr | Gly | Gln | Asp | Asp |
| 1550 | | | | 1555 | | | | 1560 | |

-continued

```
Gly Phe Ser Tyr Ile Leu Asp Asn Ile Ile Val Lys Ser Glu Thr
1565                1570                1575

Ser Leu Ile Val Asn Asn Asp Leu Glu Gln Gly Lys Leu Asp Trp
1580                1585                1590

Gln Ser Thr Asn Asp Ile Ala Ala Tyr Ser Ser Val Ser Thr Asp
1595                1600                1605

Gly Pro Asn Asn Thr Arg Tyr Gly Glu Arg Val Ser Glu Leu Asp
1610                1615                1620

Val Asp Lys Asn Thr Thr Ile Tyr Gln Asp Leu Gln Asn Arg Ser
1625                1630                1635

Glu Gly Glu Val Ile Ser Leu Ser Phe Asp Phe Ala Asn Arg Pro
1640                1645                1650

Asp Ala Tyr Ser Val Asp Asn Gly Met Asp Val Phe Trp Asn Asp
1655                1660                1665

Lys Leu Val Phe Ser Thr Phe Gly Asp Ala Ala Lys Trp Gln Asn
1670                1675                1680

Lys Thr Leu Glu Leu Thr Ala Lys Ala Gly Ser Asn Arg Ile Glu
1685                1690                1695

Phe Lys Gly Thr Gly Leu Ser Asp Gly Val Gly Tyr Ile Leu Asp
1700                1705                1710

Asn Val Ile Ala Lys Ser Lys Ser Ser Gln Gln Ala Asn Ile Ile
1715                1720                1725

Thr Glu His Val Lys Gln Asp Lys Ala Ala Gln Asn Ala Leu Ser
1730                1735                1740

Asp Lys Glu Lys Ala Glu Lys Asp Arg Arg Leu Leu Glu Gln Glu
1745                1750                1755

Lys Glu Lys Gln Leu Ala Glu Ile Ala Lys Ser Gln Ser Gln Leu
1760                1765                1770

Glu Leu Thr Asp Gln Ala Ala Val Ser Gln Asn Gly Leu Thr Gln
1775                1780                1785

Arg Asn Ala Ile Glu Ala Glu Ala Gln Ala Glu Thr Asp Lys Leu
1790                1795                1800

Val Ser Met Thr Gln Gly Leu Asp Ala Leu Gly Asp Tyr Ala Asn
1805                1810                1815

Tyr Ser Gly Gln Ser Gly Asp Gln Trp Arg Asn Gln Phe Ala Ser
1820                1825                1830

Gln Phe Leu Asp His Ala Gln Asp Lys Leu Asn Asp Ile Lys Phe
1835                1840                1845

Ile Ala Gln Arg Lys Leu Met His Ala Arg Gln Ala Ile Thr Asp
1850                1855                1860

Asn Gln Gln His Val Lys Glu Ala Val Lys Lys Ser Glu Val Gly
1865                1870                1875

Val Ala Gln Ser Glu Gln His His Ala Ser Ala Lys Gln Asp Ile
1880                1885                1890

Ala Ala Ala Gln Lys Lys Ala Glu Leu Arg Lys Glu Glu Ala Leu
1895                1900                1905

Leu Gln Gln Gln Arg Ala Glu Lys Ala Glu Asn Asp Ala Asn Ile
1910                1915                1920

Ala Tyr Gln Gly Ala Glu Tyr Arg Gly Lys Arg Asp Ile Ala Ala
1925                1930                1935

Ala Glu Asn Lys Ile Ala Gln Val Gln Glu Asp Val Arg Gly Ala
1940                1945                1950

Lys Gln Ser Asp Ser Lys Pro Asp Arg Thr Gly Ala Gly Gly Ser
1955                1960                1965
```

Gly Leu Ser Gly Asn Gly Tyr Glu Ser Thr Gly Ala Gly Glu Thr
    1970            1975            1980

Gly Ser Tyr Ile Asp Pro Glu Leu Ile Pro Glu Ala Glu Lys Lys
    1985            1990            1995

Phe Tyr Lys Gly Leu Thr Glu Glu Glu Leu Gln Ala Leu Asp Asp
    2000            2005            2010

Ala Lys Gln Ala Val Asp Arg Leu Gln Ile Asn Ala Ser Ile Arg
    2015            2020            2025

Val Glu Asn Thr Gly Val Leu Thr Thr Ser Lys Phe Ala Lys Gly
    2030            2035            2040

Gln Ser Asp Asp Arg Val Ile Pro Thr Ser Asn Ser Ser Gly Glu
    2045            2050            2055

Arg Val Arg Arg Val Pro Arg Ile Ser Gly Ile Asn Leu Lys Ser
    2060            2065            2070

Leu Gly Asn Asp Val Lys Val Glu Gln Lys Asn Ser Ala Ile Phe
    2075            2080            2085

Glu Asn Ala Lys Phe Asn Leu Leu Lys Glu Gly Asn Lys Leu Phe
    2090            2095            2100

Ile Asn Pro Asn Val Arg Thr Leu Gly Arg Lys Arg Lys Leu Ser
    2105            2110            2115

Thr Ala Leu Ala Thr Val Arg Asp Thr Phe Tyr Lys Thr Met Ser
    2120            2125            2130

His Phe Asp Glu Glu His Ile Leu Leu Leu Glu Arg Ala Ile Ala
    2135            2140            2145

Asp Trp Gln Gln His Ser Pro Lys Glu Phe Ala Leu Arg Thr Asn
    2150            2155            2160

Gln Val Asn Leu Val Arg Phe Lys Met Gly Arg Met Ile Glu His
    2165            2170            2175

Leu Gln Ala Gln Arg Ala Glu Ser Ala Gly Val Leu Gly Ile Ala
    2180            2185            2190

Val Ala Pro Gln His Ala Glu His Leu Thr Gln Arg Val Ile Phe
    2195            2200            2205

Asp Gly Thr Gly Arg Val Val Gly Leu Lys Gly Gly Ile Thr Gln
    2210            2215            2220

Asn Glu Ile Asn Arg Leu Ile Glu Trp Gln Ile Thr Pro Leu Thr
    2225            2230            2235

Arg Thr Asn Ser Thr Ala Glu Arg Glu Ala Pro Lys Thr Glu Ser
    2240            2245            2250

Glu Ser Leu Ile Ala Phe Met Ser Arg Leu Glu Thr Ala Asn Ile
    2255            2260            2265

Pro Glu Ala Arg Phe Leu Ile Gly Arg Ala Arg Gly Leu Trp Leu
    2270            2275            2280

Thr Gly Gln Val Thr Ser Lys Glu Thr Ile Lys Leu Phe Asp Asp
    2285            2290            2295

Ala Ala Ser Gln Leu Gln Ala Tyr Pro Glu Leu His Gly Leu Val
    2300            2305            2310

Leu Ser Leu Gln Ala Asp Ala His Arg Glu Lys Ser Thr Thr Gln
    2315            2320            2325

Tyr Ile Asp Asn Leu Phe Gly Arg Arg Phe Asp Ser Glu Val Ala
    2330            2335            2340

His Thr Leu Val Lys Met Ala Ser Pro Asp Ala Leu Ala Thr Ser
    2345            2350            2355

Arg Arg Ile Gly Gln Phe Leu Val Gln Glu Phe Glu Leu Tyr Met

-continued

```
                  2360            2365            2370

Gln Ser Thr Ala Asp Ser Pro Val Leu Asp Gly Gln Ile Asp Ile
2375                2380                2385

Arg Met Gln Ala Phe Ala Glu Lys Ile Lys Lys Asp Ile Arg Pro
2390                2395                2400

Trp Phe Ser Arg Val Pro Glu Leu Thr Ala Phe Leu Gln Lys Pro
2405                2410                2415

Thr Leu Asp Asn Phe Lys Ile Met Met Thr Lys Val Asp Asn Gly
2420                2425                2430

Phe Glu Met Ile Lys Ile Pro Phe Leu Ala Val Lys Met Ser Asn
2435                2440                2445

Thr Asp Gly Met Gly Leu His Leu Ser Gln Trp Lys Ala Glu Ala
2450                2455                2460

Asp Ile Phe Tyr Arg Glu Glu Ile Tyr Lys Ala Arg Ser Thr Ser
2465                2470                2475

Ser Lys Leu Thr Asn Met Ala Asp Val Thr Tyr Lys Val Lys Leu
2480                2485                2490

Thr Glu Gln Gln Thr Asn Asp Tyr Gly Ile Ala Leu Pro Tyr Gln
2495                2500                2505

Pro Ser Gly Asp Gln Tyr Gly Asp Phe Leu Tyr Gly Arg Lys Val
2510                2515                2520

Ala Ala Gly Arg Val Leu Thr Pro Gly Gln Glu Thr Thr Leu Glu
2525                2530                2535

Arg Asn Ala Leu Ala Gln Gly His Ser Val Val Thr Gly Ala Ser
2540                2545                2550

Gly Ser Thr Asn Ile Met Val His Leu Asn Asn Tyr Ile Ala Ser
2555                2560                2565

Gln Asp Pro Thr Phe Ser Gln Glu Gln Ala Tyr Leu Asn Thr Leu
2570                2575                2580

Ala Phe Leu Val Phe Asp Gly His Ser Val Asn Glu Ser Leu
2585                2590                2595

Val Val Tyr Lys Ala Leu Gln Met Thr Gly Asp Glu Arg Arg Gln
2600                2605                2610

Val Leu Gln Asn Tyr Thr Ala Ser Tyr Met Asp Leu Met Asp Ile
2615                2620                2625

Ala Gly Asp Lys Gly Lys Leu Ser Ile Asn Gln Ala Leu Asn Asn
2630                2635                2640

Ala Phe Glu Lys Thr Gln His Leu Tyr Arg Glu Asn Thr Pro Glu
2645                2650                2655

Arg Glu Gln Asn Asp Ser Pro Val Glu Ala Leu Gln Ala Leu Ser
2660                2665                2670

Gly Lys Asn Gly Ala Ser Glu Ser Val Leu Ile Glu Asn Asp Asp
2675                2680                2685

Thr Pro Pro Arg Asp Lys Asp Ser Leu Asn Pro Val Thr Arg Phe
2690                2695                2700

Phe Asn Asn Glu Leu Tyr Gly Phe Lys Glu Asp Arg Arg His Ile
2705                2710                2715

Ser Asp Lys Thr Gln Thr Ile Leu Asn Asp Ala Val Ala Asn Gly
2720                2725                2730

Lys Ser Ser Lys Ile Thr Leu Lys Gly Glu Glu Gly Arg Leu Thr
2735                2740                2745

Gly Tyr Tyr His Gln Gly Asp Ile Lys Pro Asp Asp Ile Ser Thr
2750                2755                2760
```

-continued

| | | | | | | | | | | | |
|---|---|---|---|---|---|---|---|---|---|---|---|
|Ala|Ala|Glu|Lys|Lys|Val|Val|Leu|Phe|Leu|His|Gly|Ser|Gly|Leu|
|2765| | | |2770| | | |2775| | | |

Ala Ala Glu Lys Lys Val Val Leu Phe Leu His Gly Ser Gly Leu
2765                2770               2775

Ser Ala Glu Glu Gln Ala His Asp Ile Gln Ser His Tyr Gln Lys
2780                2785               2790

Gln Gly Ile Asp Ile Leu Ala Val Asn Met Arg Gly Tyr Gly Gly
2795                2800               2805

Ser Asp Gly Ser Pro Gly Glu Gln Gly Phe Tyr Gln Asp Ala Arg
2810                2815               2820

Thr Met Phe Arg Tyr Leu Val Gln Asp Arg Gly Ile Lys Pro Gly
2825                2830               2835

Asn Ile Ile Leu His Gly Tyr Ser Val Gly Gly Pro Val Ala Ala
2840                2845               2850

Asp Leu Ala Arg Tyr Ala Ser Gln Asn Asn Gln Ala Val Ser Gly
2855                2860               2865

Leu Leu Leu Asp Arg Pro Ile Ser Ser Met Thr Lys Thr Ile Thr
2870                2875               2880

Ala His Asp Val Pro Asn Pro Gly Gly Met Ile Gly Ala Leu Ala
2885                2890               2895

Lys Ala Met Asn Gly Gln Phe Ser Val Glu Lys Asn Leu Lys Gly
2900                2905               2910

Leu Pro Ile Asn Thr Pro Ile Met Leu Leu Thr Asp Asn Gln Gly
2915                2920               2925

Leu Gly His Glu Gly Glu Lys Leu Arg Ala Arg Leu Ala Ala Ser
2930                2935               2940

Gly Tyr Arg Val Ser Gly Gln Thr Phe Tyr Gly His Val Glu
2945                2950               2955

Ser Gly Ala Leu Met Ser Gln Tyr Thr Asp Arg Ile Val Ser Thr
2960                2965               2970

Leu Ser Asp Phe Gln Asn Lys Asn Arg Asp Gly Val Lys Asn Ser
2975                2980               2985

Trp Gln Lys Ser Asp Asn Arg Gly Thr Arg Phe Asp Gly Gln Ile
2990                2995               3000

Ile Ile Gln Met Glu Asn Asp Pro Ile Val Ala Lys Ala Ala Leu
3005                3010               3015

Asn Leu Ala Ser Lys His Arg Lys Ser Ser Val Val Val Lys Leu
3020                3025               3030

Asp Ser Asn Gly Lys Tyr His Val Ile Tyr Gly Asp Pro Ala Gly
3035                3040               3045

Leu Ser Gly Lys Leu Arg Trp Gln Ile Val Gly His Gly Arg Asn
3050                3055               3060

Glu Ser Ala Gln Asn Asn Thr Arg Leu Ser Gly Tyr Ser Ala Asp
3065                3070               3075

Glu Leu Ala Ile Lys Leu Lys Gln Phe Ser Gln Asn Phe Glu Gln
3080                3085               3090

Ala Gly Lys Pro Asp Arg Ile Ser Ile Val Gly Cys Ser Leu Ile
3095                3100               3105

Ser Asp Asp Lys Arg Asn Gly Phe Ala Tyr Arg Phe Ile Thr Ala
3110                3115               3120

Leu Asp Lys Gln Gly Ile Arg Ser Glu Val Ser Ala Arg Arg Ser
3125                3130               3135

Glu Val Ala Val Asp Ala Thr Gly Arg Lys Phe Thr Arg Asp Lys
3140                3145               3150

Asn His Gln Trp Val Asn Lys Leu Asp Asp Asn Lys Leu Val Leu
3155                3160               3165

```
Arg Trp Asn Glu Gln Asp Glu Leu Thr Thr Thr Glu Lys Leu
    3170                3175                3180

Arg Arg Gly Val Ala Glu Ser Asp Ile Asn Leu Ala Lys Val Gly
    3185                3190                3195

His Thr Glu Ala Asp Ser Ala Thr Arg Gly Ala Ile Ala Asp Asn
    3200                3205                3210

His Asp Val Phe Thr Ala Pro Gly Lys Arg Lys Asn Arg Val Glu
    3215                3220                3225

Leu Gly Ser Asn Pro Gln Ser Glu Pro Leu Gly Tyr Ala Gly Asn
    3230                3235                3240

Ile Gln Val Asn Val Gly Asp Gly Glu Phe Thr Ala Ile Asn Trp
    3245                3250                3255

Gly Thr Ser Asn Val Gly Ile Lys Val Gly Thr Gly Gly Phe Lys
    3260                3265                3270

Ser Leu Ala Phe Gly Asp Asn Asn Val Met Val His Ile Gly Glu
    3275                3280                3285

Gly Asp Ser Lys His Ser Val Asn Leu Ala Gly Tyr Gln Ala Leu
    3290                3295                3300

Glu Gly Ala Gln Met Phe Ile Gly Asn Arg Asn Val Ser Phe Asn
    3305                3310                3315

Gln Gly Arg Ser Asn Asp Leu Ile Val Met Met Asp Lys Ser Ile
    3320                3325                3330

Pro Thr Pro Pro Leu Val Asn Pro Phe Asp Gly Ala Ala Arg Ile
    3335                3340                3345

Thr Gly Val Leu Lys Ser Ile Ala His Ser Gly Glu Glu Arg Asn
    3350                3355                3360

Trp Leu Ala Ala Gln Asn Gln Gln Trp Thr Leu Ser Gly Ala Lys
    3365                3370                3375

Lys Phe Val Arg Asp Met Ser Gly Leu Asp Gln Thr Ser Ser Val
    3380                3385                3390

Asp Tyr Lys Thr Leu Val Asp Leu Asp Ser Gln Leu Lys Arg Ser
    3395                3400                3405

Ser Arg Gly Leu Lys Ser Asp Thr Glu Ala Ala Leu Asn Lys Lys
    3410                3415                3420

Tyr His Gln Trp Leu Asn Gly His Gly Asn Asn Ile Asp Thr Lys
    3425                3430                3435

Lys Met Ser Arg Val Asp Lys Phe Arg Gln Ala Asn Glu Lys Leu
    3440                3445                3450

Ala Phe Asn Phe Ala Val Gly Gly Gln Gly Ala Asp Ile Gln Val
    3455                3460                3465

Thr Thr Gly Ser Trp Asn Phe Met Phe Gly Asp His Ile Gln Ser
    3470                3475                3480

Ile Leu Asp Thr Asn Leu Gly Ser Leu Phe Gly Leu Met Thr Gln
    3485                3490                3495

Gln Tyr Ser Thr Thr Gly Leu Ala Lys Thr Thr Phe Thr Tyr Asn
    3500                3505                3510

Leu Gln Asp Leu Pro Arg Gln Leu Lys Asn Lys Leu Leu Gly Arg
    3515                3520                3525

Leu Ala Gly Val Asn Ala Glu Thr Thr Leu Ala Asp Ile Phe Gly
    3530                3535                3540

Val Asp Tyr Thr Pro Glu Gly Gln Ile Val Ala Arg Thr Gly Glu
    3545                3550                3555

Pro Val Asp Gly Lys Ala Ile Leu Arg Glu Met Leu Glu Val Ile
```

```
            3560            3565            3570
Lys Gln Phe Gly Gly Asp Gln Leu Ser Val Phe Thr Asp Pro Asp
    3575            3580            3585
Lys Leu Ile Glu Gly Leu Lys Gln Asn Ala Asn Met Ser Ala Asp
    3590            3595            3600
Gly Ile Glu Ser Phe Phe Val Ser His Gly Leu Lys Glu Lys Ala
    3605            3610            3615
Pro Asp Glu Asn Arg Glu Lys Ser Val Pro Asp Ala Val Asn Ser
    3620            3625            3630
Gly Lys Ser Gln Ala Asp Asp Lys Ser Glu Arg Ala Leu Gly Phe
    3635            3640            3645
Asn Ser Leu Asn Leu Pro Asn Leu Phe Ala Thr Ile Phe Ser Lys
    3650            3655            3660
Asp Lys Gln Gln Glu Met Lys Ser Leu Val Thr Asn Leu Lys Glu
    3665            3670            3675
Asn Leu Thr Ala Asp Leu Leu Asn Met Glu Gln Lys Thr Phe Asp
    3680            3685            3690
Phe Leu Arg Asn Ser Gly His Leu Gln Gly Asp Ser Asp Ile His
    3695            3700            3705
Ile Ser Leu Gly Asn Tyr Asn Phe Asn Trp Gly Gly Asp Gly Lys
    3710            3715            3720
Asp Leu Gly Ala Tyr Leu Gly Asp Asn Asn Phe Trp Gly Gly
    3725            3730            3735
Arg Gly Asp Asp Val Tyr Tyr Ser Ile Gly Thr Ser Asn Ile Phe
    3740            3745            3750
Thr Gly Gly Glu Gly Asp Asp Leu Gly Val Leu Met Gly Arg Glu
    3755            3760            3765
Asn Trp Met Phe Gly Gly Ser Gly Asp Asp Thr Ala Val Val Ala
    3770            3775            3780
Gly Arg Ile Asn His Val Phe Met Gly Glu Gly Asn Asp Gln Thr
    3785            3790            3795
Phe Val Phe Gly Glu Gly Gly Val Ile Asp Ala Gly Asn Gly Arg
    3800            3805            3810
Asp Tyr Val Val Thr Ser Gly Asn Tyr Asn Gln Val Asp Thr Gly
    3815            3820            3825
Glu Asp Gln Asp Tyr Ala Val Thr Ile Gly Asn Asn Asn Arg Val
    3830            3835            3840
Glu Leu Gly Glu Gly Asn Asp Phe Gly Arg Val Phe Gly Asn Asp
    3845            3850            3855
Asn Arg Ile Asp Gly Asn Met Gly Asn Asp Val Ile Lys Leu Met
    3860            3865            3870
Gly Tyr His Ala Val Ile Asn Gly Gly Glu Gly Asp Asp His Leu
    3875            3880            3885
Ile Ala Ala Thr Ile Ser Lys Phe Ser Gln Phe Asp Gly Gly Glu
    3890            3895            3900
Gly Gln Asp Leu Leu Val Leu Gly Gly Tyr Gln Asn His Phe Gln
    3905            3910            3915
Gly Gly Ala Gly Val Asp Ser Phe Val Val Ser Gly Lys Val Ile
    3920            3925            3930
Asp Ser Gln Val Asp Asp Ile Asn Ala Glu Asp Met Ile Ala Phe
    3935            3940            3945
Asn Asp Ile Asp Trp Gln Asp Leu Trp Phe Gln Arg Ser Gly Tyr
    3950            3955            3960
```

```
Asp Leu Val Leu Ser Val Asn Arg Pro Thr Gln Asp Lys Thr Ala
    3965                3970                3975

Gln Gly Leu Phe Glu Ser Val Gly Ser Val Thr Phe Arg Asp Tyr
    3980                3985                3990

Phe Asn Gly Asn Arg Ala Lys Leu Val Thr Gln Met Gly Arg Lys
    3995                4000                4005

Asp Ala Ser Gly Glu Arg Glu Phe Thr Ala Leu Ser Asp Asn Ala
    4010                4015                4020

Val Asp Thr Leu Ile Gln Ala Met Ser Ser Phe Ala Pro Thr Ala
    4025                4030                4035

Gly Asp Asn Gly Phe Ile Glu Ala Leu Asp Asn Arg Glu Lys Met
    4040                4045                4050

Ala Ile Thr Thr Ala Trp Ala Asp Thr Thr Ile Gly Lys Gly Lys
    4055                4060                4065

Phe Ala
    4070

<210> SEQ ID NO 6
<211> LENGTH: 3528
<212> TYPE: PRT
<213> ORGANISM: Photorhabdus luminescens

<400> SEQUENCE: 6

Met Phe Met Gly Lys Ser Ser Asn Arg Ser Ala Glu Tyr Phe Phe Thr
1               5                   10                  15

Gly Arg Tyr Tyr Asp Asp Asp Gly Asn Asn Ile Val Ala Ile Gly
                20                  25                  30

Val Gly Gly Ile Ile Tyr Ala Lys Gly Gly Asp Asp Arg Ile Thr Leu
            35                  40                  45

Gly Ser Ile Gly Ala Thr Val Tyr Ala Asp Ser Gly Asn Lys Val Val
        50                  55                  60

Asn Gly Gly Ala Gly Tyr Leu Lys Ile Val Asp Lys Glu Gly Asn Leu
65                  70                  75                  80

Ala Val His Gly Ala Ala Gly Tyr Ser Gly Ile Asp Lys Cys Gly Asn
                85                  90                  95

Gly Asn Ile Ser Phe Thr Gly Thr Ala Gly Gly Val Ser Met Asp His
                100                 105                 110

Arg Gly Asp His Gly Asp Leu Asn Phe Ser Gly Ala Ala Tyr Asn
            115                 120                 125

Gly Leu Asn Arg Gln Gly Gln Ser Gly Asn Val Thr Phe Asn Gly Val
        130                 135                 140

Gly Gly Tyr Asn Glu Leu Trp His Glu Thr Asn Gln Gly Asn Leu Asn
145                 150                 155                 160

Phe Ala Gly Ala Gly Ala Gly Asn Lys Ile Asp Arg Thr Trp Tyr Asp
                165                 170                 175

His Tyr Glu Lys Ser His Gly Asp Val Lys Phe Asp Gly Gly Ala
            180                 185                 190

Ala Asn Ser Ile Ser Ser Arg Val Glu Ser Gly Asn Ile Asn Phe Thr
        195                 200                 205

Gly Val Gly Ala Asp Asn His Leu Ile Arg Lys Gly Lys Glu Gly Asn
        210                 215                 220

Ile Ile Leu His Gly Ala Gly Ala Ser Asn Arg Ile Glu Arg Leu Arg
225                 230                 235                 240

Gln Asn Gln Asp Gln Tyr Glu Gln Thr His Gly Asn Ile Glu Phe Glu
                245                 250                 255
```

-continued

```
Gly Thr Gly Gly Tyr Asn Arg Ile Tyr Ser Asp Ile Ala His Gly Asp
            260                 265                 270

Ile Thr Phe Glu Gly Ala Gly Tyr Asn Glu Ile Ser Arg Ile Gly
        275                 280                 285

Glu Asp Ser Asp Ser Arg Asn Glu Ala Leu Tyr Ala Lys Ala Glu
    290                 295                 300

Glu Ile Val Leu Thr Thr Ala Met Met Gly Gly Ser Trp Ile Gln Gln
305                 310                 315                 320

Ser Gln Gln Val Thr Gly Ile Lys Ser Thr Ala Glu Pro Asp Thr Tyr
                325                 330                 335

Leu Phe Ala Phe Ala Asp Glu Met Tyr Thr Lys Ile Ser Lys Val Gln
            340                 345                 350

Leu Arg Asn Asp Pro Glu Thr Gly Lys Leu Ser Tyr Tyr Ala Thr Ser
            355                 360                 365

Trp Tyr Lys Glu Gly Asn His Leu Asn Asn Leu Ala Thr Glu Asn Ile
    370                 375                 380

Ser Ser Ser Asn Gly Phe Phe Asp Ile Arg Ser Asn Gly Gly Tyr Arg
385                 390                 395                 400

Leu Phe Asn Leu Ile Phe Glu His His His Pro Val Ile Ile Gln His
                405                 410                 415

Thr Val Glu Glu Asp Leu Gln Glu Asn Gln Trp Val Thr Tyr Ala Gly
            420                 425                 430

Gly Thr Asn Ala Arg Ala Glu Asn Val Met Leu Thr Asn Ala Lys Met
        435                 440                 445

His Gly Asn Ala Ile His Ser Gly Gly Leu Ile Leu Asp Val Ser Ala
    450                 455                 460

Val Lys Ser Asn Arg Gln Ala Asn Thr Tyr Ile Tyr Ala Lys Tyr Val
465                 470                 475                 480

Glu Ser Tyr Thr Lys Val Val Met Val Glu Leu Arg Asn Asp Ala Lys
                485                 490                 495

Thr Gly Ala Leu Gln Tyr Tyr Ala Ser Ala Trp Tyr Lys Ala Gly Asp
            500                 505                 510

His Thr Ser Asn Leu Ala Ala Glu Lys Val Ser Pro Gln Asn Gly Tyr
        515                 520                 525

Arg Ser Met Asp Ile Gly Gly Tyr Ser Leu Thr Asn Leu Gln Tyr Gln
    530                 535                 540

Val Asn Thr Val Arg Arg Val Ser Glu His Leu Ala Gln Thr Glu Glu
545                 550                 555                 560

Tyr Ser His Gln Glu Leu Val Lys Ser Ser Ala Asp Met Gly Asp Ser
                565                 570                 575

Ser Gly Asp Ile Asn Phe Lys Gly Met Gly Gly Gly Asn Val Ile Thr
            580                 585                 590

Ser Ser Val Thr Arg Gly Asn Ile Asn Phe Glu Gly Ala Gly Ala Ala
        595                 600                 605

Asn Val Ile Val Lys Lys Gly Glu Gln Gly Asp Leu Thr Phe Arg Gly
    610                 615                 620

Ala Gly Leu Ala Asn Val Leu Val His Gln Gly Gln Arg Gly Glu Met
625                 630                 635                 640

Asp Val Tyr Ala Gly Gly Ala Ala Asn Val Leu Val Arg Ile Gly Asp
                645                 650                 655

Gly Arg Tyr Leu Ala Arg Leu Leu Ala Ile Gly Asn Ile Ser Ile His
            660                 665                 670

Gln Gly Asn Gly Asp Ser Arg Val Ser Met Phe Gly Gly Tyr Asn Thr
        675                 680                 685
```

His Ser Gln Ile Gly Asn Gly Asn Ala Asn Trp Leu Gly Ala Gly Gly
    690                 695                 700

Phe Asn Val Met Thr Gln Thr Gly Lys Gly Lys Val Ser Ser Val Leu
705                 710                 715                 720

Ala Gly Gly Ala Asn Val Leu Thr Lys Leu Gly Ala Gly Asp Leu Asp
                725                 730                 735

Ala Gly Met Leu Gly Gly Ala Asn Ile Ile Thr His Leu Asn Asp Gly
                740                 745                 750

Glu Ile Ser Gly Thr Thr Ala Val Ala Leu Gly Gly Ala Asn Ile Leu
                755                 760                 765

Thr Lys Lys Gly Arg Gly Lys Ala Ile Ala Leu Met Gly Gly Gly Ala
        770                 775                 780

Asn Val Leu Thr His Ile Gly Asn Gly Ser Thr Thr Gly Met Met Leu
785                 790                 795                 800

Gly Gly Ala Asn Ile Leu Thr Lys Val Gly Asn Gly Asp Ala Thr Gly
                805                 810                 815

Ile Met Leu Gly Leu Gly Asn Val Leu Thr His Val Gly Ser Gly Gln
                820                 825                 830

Thr Leu Gly Val Met Gly Ala Ala Gly Asn Val Phe Thr Lys Val Gly
                835                 840                 845

Ser Gly Thr Thr Ile Ala Ala Met Ile Gly Ala Gly Asn Ile Phe Thr
        850                 855                 860

His Val Gly Asn Gly Asp Ala Trp Gly Leu Met Gly Gly Leu Gly Asn
865                 870                 875                 880

Val Phe Thr Lys Val Gly Asn Gly Lys Ala Leu Ala Leu Met Ile Ala
                885                 890                 895

Ala Gly Asn Val Phe Thr His Ile Gly Asp Glu Met Ser Val Ala Leu
                900                 905                 910

Met Leu Ala Lys Gly Asn Ile Ala Thr Lys Val Gly Asn Gly Met Met
            915                 920                 925

Leu Ala Ala Met Ile Gly Glu Ala Asn Val Met Thr His Ile Gly Asn
        930                 935                 940

Gly Ser Thr Phe Ala Ala Met Ile Gly Gln Gly Asn Ile Leu Thr Lys
945                 950                 955                 960

Val Gly Asn Asp Leu Ala Leu Gly Leu Met Val Gly Glu Ala Asn Ile
                965                 970                 975

Tyr Ser His Val Gly Asn Gly Thr Ser Ile Gly Leu Phe Ala Gly Glu
                980                 985                 990

Leu Asn Val Met Thr Arg Val Gly Asp Gly Thr Thr Leu Ala Ala Met
            995                 1000                1005

Phe Gly Gln Ala Asn Ile Met Thr His Ser Gly Asn Gly Leu Thr
    1010                1015                1020

Gly Val Leu Ala Leu Gly Glu Ala Asn Ile Val Thr Lys Val Gly
    1025                1030                1035

Asp Asp Phe Met Gly Val Val Ala Ala Ala Glu Ala Asn Val Ile
    1040                1045                1050

Thr His Lys Gly Ser Ser Thr Thr Ala Ala Val Leu Phe Gly Lys
    1055                1060                1065

Gly Asn Ile Leu Thr Lys Val Gly Asp Gly Thr Thr Val Gly Leu
    1070                1075                1080

Leu Ile Ser Asp Val Gly Asn Ile Met Thr His Val Gly Asp Gly
    1085                1090                1095

Thr Thr Val Gly Phe Ala Lys Gly Lys Ala Asn Ile Ile Thr Lys

-continued

```
            1100                1105                1110
Val Gly Asn Gly Thr Gly Val Asn Ala Val Trp Gly Asp Ala Asn
    1115                1120                1125

Ile Leu Thr Gln Val Gly Asp Gly Asp Arg Tyr Asn Phe Ala Lys
    1130                1135                1140

Gly Lys Ala Asn Ile Ile Thr Lys Val Gly Asn Asn Gln Glu Ile
    1145                1150                1155

Thr Val Val Gln Gly Asp Ala Asn Ile Ile Thr His Val Gly Gln
    1160                1165                1170

Gly Asp Asp Tyr Thr Gly Ala Trp Gly Lys Ala Asn Val Ile Thr
    1175                1180                1185

Lys Val Gly Asp Gly Arg Asn Val Val Leu Ala Lys Ala Asp Ala
    1190                1195                1200

Asn Ile Val Thr Gln Val Gly Asn Gly Asp Ser Phe Asn Ala Leu
    1205                1210                1215

Trp Ser Arg Gly Asn Ile Val Thr Lys Val Gly Asp Gly Met Gln
    1220                1225                1230

Val Thr Ala Ala Lys Gly Glu Ala Asn Ile Thr Thr Lys Val Gly
    1235                1240                1245

Asn Gly Leu Ser Val Thr Ala Thr His Gly Asp Phe Asn Ile Asn
    1250                1255                1260

Thr Asn Val Gly Asp Gly Ile Ser Ile Asn Ala Ala Trp Gly Glu
    1265                1270                1275

Tyr Asn Val Asn Thr Lys Val Gly Gln Gly Leu Asn Val Ala Ile
    1280                1285                1290

Met Lys Gly Lys Gly Asn Ala Asn Ile His Ile Gly Asp Gly Leu
    1295                1300                1305

Gly Ile Asn Ala Ser Tyr Ala Arg Asn Asn Leu Ala Ile Lys Val
    1310                1315                1320

Gly Asn Gly Asp Phe Tyr Thr Leu Ser Ile Ala Glu Ser Asn Thr
    1325                1330                1335

Gln Ser Asn Asn Leu Pro Phe Leu Phe Lys Ser Ile Lys Arg Thr
    1340                1345                1350

Val Leu Ser Val Glu Gly Ser Gln Ala Ile Asn Tyr Leu Ile His
    1355                1360                1365

Gly Asn Glu Ala Asn Ser Ser Gly Thr Tyr Arg Ser Arg Gly Ala
    1370                1375                1380

Ile Asn Leu Thr Glu Val Ser Ala Ile Asp Gly Phe Gln Met Asn
    1385                1390                1395

Ala Ile Asp Asp Val Gly Ser Asp Leu Arg Asp Lys Leu Ser Gly
    1400                1405                1410

Thr Val Thr Gln Val Glu Ile Pro Asp Thr Glu Ala Ile Gln Asn
    1415                1420                1425

Ala Leu His Ile Gly Asp Lys Val Asp Ser Thr Gln Ser Glu Ser
    1430                1435                1440

Ser Ser Gln Ala Asp Ala Val Ile Lys Gln Ala Lys Gln Asp Ser
    1445                1450                1455

Ala Glu Gln Asn Ala Leu Asn Asp Lys Glu Lys Ala Glu Glu Asn
    1460                1465                1470

Tyr Arg Ile Leu Glu Gln Glu Arg Asp Asn Gln Leu Lys Glu Ile
    1475                1480                1485

Ser Lys Pro Gln Phe Gln Leu Glu Ser Thr Asp Gln Asn Val Leu
    1490                1495                1500
```

-continued

Asn Thr Asn Gly Gln Val Gln Arg Asp Ala Ile Ser Gly Glu Ser
1505                1510                1515

Arg Ala Val Thr Lys Glu Leu Leu Ser Met Thr Gln Arg Leu Asn
1520                1525                1530

Ala Leu Asn Asp Asp Gly Asn Tyr Ala Gly Glu Leu Gly Asp Glu
1535                1540                1545

Trp Arg Asn Arg Phe Ala Val Gly Tyr Leu Asp Arg Ile Gln Glu
1550                1555                1560

Lys Leu Asp Asp Thr Lys Leu Ile Ser Gln Lys Lys Leu Ala Asp
1565                1570                1575

Leu Ser Pro Arg Phe Ile Asp Asn Gln Gln Val Lys Asn Ala
1580                1585                1590

Val Gly Lys Ser Glu Thr Gly Leu Glu Gln Ser Tyr His Asn Ile
1595                1600                1605

Lys Asn Ala Asp Asp Asn Ile Glu Asp Ala His Thr Lys Ala Lys
1610                1615                1620

Ser Arg Gln Lys Glu Ala Asp Leu Gln Arg Leu Arg Ala Thr Lys
1625                1630                1635

Ala Glu Ser Asp Ala Tyr Ala Val Tyr Glu Glu Ala Lys Gln Arg
1640                1645                1650

Gly Glu His Asp Ser Ser Val Ala Lys Asn Lys Ala Ala Gln Val
1655                1660                1665

Gln Ala Asp Ala Lys Gly Ala Lys Gln Thr Gly Asp Val Lys Pro
1670                1675                1680

Glu Arg Ser Gly Ala Thr Gly Ser Gly Leu Ser Gly Lys Ala Tyr
1685                1690                1695

Thr Pro Ile Asp Val Ala Lys Pro Lys Ser His Ile Asn Pro Glu
1700                1705                1710

Ala Lys Met Glu Ala Asn Gly Trp Asn Ser Glu Asp Leu Thr Leu
1715                1720                1725

Thr Ala Ala Asp Leu Ala Gly Leu Asn Ser Ala Gln Arg Ala Ile
1730                1735                1740

Asn Arg Leu Gln Ile Asn Arg Ser Ser Arg Pro Glu Asn Val Gly
1745                1750                1755

Ala Ser Ile Ile Ser Leu Leu Thr Gly Thr Pro Ser Asp Arg Val
1760                1765                1770

Val Glu Pro Ile Ser Asn Gln Thr Arg Lys Leu Ile Thr Thr Ala
1775                1780                1785

Pro Val Met Ser Gly Ile Asn Leu Gln Gly Leu Gly Gln Val Ile
1790                1795                1800

Gly Gly Asp Ser Phe Lys Ser His Ser Ser Ile Leu Arg Glu Phe
1805                1810                1815

Glu Pro Phe Leu Leu Ser Gln Gly Asp Lys Arg Phe Ile Ala Ser
1820                1825                1830

Thr Lys Arg Tyr Leu Gly Gln Ile Asn Thr Asp Arg Pro Ser Lys
1835                1840                1845

Ala Leu Val Ala Val Arg Glu Ala Phe Asn Asn Ala Ala Glu Gln
1850                1855                1860

Pro Asp Glu Gln His Val Leu Gln Leu Glu Gln Ala Leu Ala His
1865                1870                1875

Trp Gln Gln His Asp Pro Asn Glu Phe Ala Lys Arg Gly Arg Leu
1880                1885                1890

Val Lys Ser Leu Arg Phe Glu Met Gly Glu Leu Val Ala Tyr Leu
1895                1900                1905

```
Gln Ala Lys Arg Ala Glu Ser Ala Gly Ile Leu Gly Val Ser Leu
    1910            1915                1920

Ala Pro Asp His Val Ala Gln Phe Asp Gln Val Ser Phe Asp
    1925            1930                1935

Gly Phe Gly Arg Val Val Gly Leu Lys Gly Asp Ile Ala Gln Ser
    1940            1945                1950

Asp Ile His Arg Leu Thr Asp Leu Gln Ile Lys Pro Leu Thr Gln
    1955            1960                1965

Ile Asn Ser Ala Ala Glu Arg Glu Ala Pro Lys Thr Glu Ser Glu
    1970            1975                1980

Ser Leu Ile Val Phe Val Ser Arg Leu Gln Gln Glu Ala Ile Pro
    1985            1990                1995

Glu Gly Met Pro Leu Ile Glu Arg Ala Lys Asn Leu Trp Leu Ser
    2000            2005                2010

Gly Gln Val Thr Arg Gln Glu Thr Ile Lys Leu Phe Glu Asp Ala
    2015            2020                2025

Val Ser Gln Leu Gln Thr His Pro Glu Leu His Thr Leu Ala Gln
    2030            2035                2040

Gln Leu Leu Ala Asp Ala Arg Lys Glu Lys Thr Thr Gly Gln Tyr
    2045            2050                2055

Ile Asp Asn Leu Phe Gly Arg His Phe Asp Ser Glu Leu Ala Asp
    2060            2065                2070

Glu Leu Val Lys Thr Ala Pro Gln Asp Ala Met Thr Thr Ala Arg
    2075            2080                2085

Gln Thr Gly Gln Phe Leu Val Glu Arg Phe Glu Gln Trp Ile Gly
    2090            2095                2100

Gly Phe Tyr Pro Asp Val Ala Glu Arg Glu Lys Ile Ile Ala Lys
    2105            2110                2115

Lys Met Ala Gly Phe Ala Arg Ala Ile Asn Lys Asp Phe Arg Pro
    2120            2125                2130

Trp Phe Ser Arg Val Pro Glu Leu Thr Thr Phe Leu Asp Glu Pro
    2135            2140                2145

Thr Phe Ala Asn Phe Lys Ile Met Met Thr Gln Val Asp Asp Gly
    2150            2155                2160

Phe Ala Val Ile Lys Ile Pro Phe Leu Ala Val Lys Met Ala Ile
    2165            2170                2175

Thr Ser Gly Met Gly Met Gly Arg Ala Gln Trp Lys Val Ala Gly
    2180            2185                2190

Asp Arg Phe Tyr Glu Glu Val Ile Thr Lys Ala Arg Ser Thr Ser
    2195            2200                2205

Ser Gln Leu Thr Ser Gly Ala Asp Val Thr Tyr Asn Val Glu Ile
    2210            2215                2220

Thr Glu Lys Gln Thr Asn Asp Tyr Gly Thr Ala Leu Pro Tyr Gln
    2225            2230                2235

Pro Ala Asn Asn Lys His Asp Asp Phe Leu Tyr Gly Arg Lys Val
    2240            2245                2250

Ala Ala Gly Arg Ile Leu Val Pro Gly Trp Glu Thr Arg Phe Glu
    2255            2260                2265

His Asn Ala Leu Ala Gln Gly His Ser Val Val Thr Gly Ala Ser
    2270            2275                2280

Gly Ser Thr Asn Ile Met Val His Leu Asn Asn Tyr Ile Ala Ser
    2285            2290                2295

Glu Gln Ile Ala Ser Glu Gln Pro Thr Phe Ser Val Arg Gln Ser
```

```
                2300                    2305                    2310

Tyr Leu Asn Thr Leu Val Phe Leu Val Phe Asp Gly Gly His Ser
    2315                    2320                    2325

Val Asn Glu Ser Leu Ala Val Tyr Arg Ala Leu Gln Val Thr Asp
    2330                    2335                    2340

Asp Glu Gln Arg Lys Gln Leu Leu Asn Ser Tyr Thr Ala Asn Tyr
    2345                    2350                    2355

Arg Glu Leu Val Asp Ile Ala Gly Glu Gly Lys Val Trp Val
    2360                    2365                    2370

Ser Gln Ala Leu Asp Asn Ala Phe Arg Glu Thr Gly Glu Phe Tyr
    2375                    2380                    2385

Gln Lys His Ala Lys Val Lys Pro Gln Ser Arg Pro Ala Val Glu
    2390                    2395                    2400

Ala Leu Asp Trp Leu Ser Gly Lys Asn Lys Arg Pro Glu Pro Thr
    2405                    2410                    2415

Ile Ile Asp Asp Thr His Gln Asp Lys Lys Ile Ser Arg Leu Leu
    2420                    2425                    2430

Gly Asp Trp Gln Met Glu Gln Val Thr Pro Gln Ala Asp Gly Arg
    2435                    2440                    2445

Glu Thr Arg Phe Asp Gly Gln Ile Ile Ile Gln Met Glu Asp Asp
    2450                    2455                    2460

Pro Ile Val Ala Lys Ala Ala Ala Asn Leu Ala Gly Lys His Ser
    2465                    2470                    2475

Asp Ser Ser Val Val Gln Leu Asp Ser Lys Gly Lys Tyr Arg
    2480                    2485                    2490

Val Val Tyr Gly Asp Leu Thr Arg Leu Ser Gly Lys Leu Arg Trp
    2495                    2500                    2505

Gln Val Val Gly His Gly Arg Asp Thr Ser Glu Gln Asn Asn Ile
    2510                    2515                    2520

Arg Leu Ser Gly Tyr Thr Ala Asp Glu Leu Ala Thr Arg Leu Thr
    2525                    2530                    2535

Arg Phe Tyr Gln Asp Val Asn Gln Gly Lys Ser Ile Thr His Lys
    2540                    2545                    2550

Pro Asp His Ile Ser Ile Val Gly Cys Ser Leu Ile Ser Asp Asp
    2555                    2560                    2565

Lys Arg Asp Gly Phe Ala Arg Arg Phe Ile Thr Val Leu Asp Lys
    2570                    2575                    2580

Gln Gly Ile Arg Ser Asp Val Ser Ala Arg Ser Glu Val Ala
    2585                    2590                    2595

Val Asp Val Ser Gly Arg Lys Phe Thr Arg Asp Gln Asn Asn Gln
    2600                    2605                    2610

Trp Val Asn Asn Leu Pro Asp Asn Lys Ile Val Leu Ser Trp Tyr
    2615                    2620                    2625

Asp Gln Asn Glu Leu Ile Thr His Thr Glu Leu Val Arg Arg Gly
    2630                    2635                    2640

Ile Ala Glu Ser Asp Ile Asn Phe Ser Lys Val Gly Tyr Thr Glu
    2645                    2650                    2655

Ala Asp Thr Val Ile Asn Gly Ala Ile Ser Gly Asn Val Glu Leu
    2660                    2665                    2670

Phe Val Lys Pro Asn Lys Arg Glu Asn Thr Ile Gln Ile Asp Ser
    2675                    2680                    2685

Asn Glu Lys Thr Asn Asn Gln Leu Ser Tyr Ser Gly Asn Ile Gln
    2690                    2695                    2700
```

-continued

```
Val Asn Val Gly Asp Gly Glu Phe Thr Ala Leu Asn Trp Gly Thr
2705                2710                2715

Ser Asn Val Gly Ile Lys Val Gly Ser Gly Gly Phe Lys Ser Leu
    2720            2725                2730

Ala Phe Gly Asp Asn Asn Val Met Val His Ile Gly Asn Gly Asp
    2735                2740                2745

Ser Lys Gln Ser Phe Asp Ile Ala Gly Tyr Gln Ala Leu Glu Gly
    2750                2755                2760

Ala Gln Met Phe Ile Gly Asn Arg Asn Val Ser Phe Asn Gln Gly
    2765                2770                2775

Arg Ser Asn Asp Leu Ile Val Met Met Asp Lys Ser Ile Pro Thr
    2780                2785                2790

Pro Pro Leu Ile Asn Pro Phe Asp Gly Val Ala Arg Ile Ala Asp
    2795                2800                2805

Val Leu Gln Gly Val Ala Gly Ala Ser Glu Asp Gln Asp Trp Leu
    2810                2815                2820

Ala Ala Gln Asp Gln Gln Trp Thr Ile Ala Gly Ala Lys Lys Phe
    2825                2830                2835

Val Gln Asp Leu Ser Gly Leu Asp Gln Thr Ser Asn Val Asp Tyr
    2840                2845                2850

Asn Thr Leu Val Glu Leu Asp Ser Gln His Glu Arg Ser Ser Arg
    2855                2860                2865

Gly Leu Lys Tyr Asp Ala Glu Leu Thr Leu Asn Lys Lys Phe Asn
    2870                2875                2880

Gln Trp Leu Gly Glu His Gly Asn Gly Ala Asp Met Gly Lys Ile
    2885                2890                2895

Ser Arg Met Asp Lys Phe Arg Gln Ala Asn Gln Lys Leu Ala Phe
    2900                2905                2910

Asn Phe Ala Val Gly Gly Arg Gly Ala Asp Ile Gln Val Thr Thr
    2915                2920                2925

Gly Asn Trp Asn Leu Met Phe Gly Asp His Ile Gln Ser Ile Leu
    2930                2935                2940

Asp Thr Asn Leu Gly Ser Leu Phe Gly Leu Met Thr Gln Gln Tyr
    2945                2950                2955

Ser Ala Thr Gly Met Ala Lys Thr Thr Phe Thr Tyr Asn Pro Gln
    2960                2965                2970

Asp Leu Pro Arg Gln Leu Lys Asn Lys Leu Ile Gly Arg Leu Ala
    2975                2980                2985

Ser Val Asn Ala Asp Thr Thr Leu Ala Asp Ile Phe Gly Val Asn
    2990                2995                3000

Tyr Thr Ala Glu Gly Lys Ile Ile Ser Arg Thr Gly Glu Ser Val
    3005                3010                3015

Asp Gly Glu Ala Ile Leu Gln Glu Met Leu Glu Val Ile Gly Glu
    3020                3025                3030

Phe Ser Gly Asp Gln Leu Gln Ala Phe Ile Asn Pro Glu Thr Leu
    3035                3040                3045

Leu Asp Ser Leu Lys Ala Gly Ile Asp Met Gly Glu Glu Gly Val
    3050                3055                3060

Arg Ser Phe Ala Glu Ser His Gly Leu Lys Gln Lys Ala Pro Asp
    3065                3070                3075

Glu Arg Gln Glu Ser Gly Ser Ser Val Asn Ile Asn Gly Glu Asn
    3080                3085                3090

Val Gln Thr Asn Asn Lys Pro Lys Pro Ala Phe Gly Phe Asn Ser
    3095                3100                3105
```

-continued

Leu Asn Leu Pro Asn Leu Phe Ala Thr Met Phe Ser Glu Glu Lys
    3110                3115                3120

Gln Arg Glu Met Lys Ser Leu Val Ala Asn Leu Lys Glu Asn Leu
    3125                3130                3135

Thr Thr Asp Leu Leu Asn Met Glu Glu Lys Thr Phe Asp Phe Leu
    3140                3145                3150

Arg Asn Ser Gly His Leu Gln Gly Asp Gly Asp Ile His Val Ser
    3155                3160                3165

Leu Gly Asn Tyr Asn Phe Asn Trp Gly Gly Asp Gly Lys Asp Leu
    3170                3175                3180

Gly Thr Tyr Leu Gly Asp Asn Asn Phe Trp Gly Gly Arg Gly
    3185                3190                3195

Asp Asp Val Tyr Tyr Ser Leu Gly Thr Ser Asn Ile Phe Ser Gly
    3200                3205                3210

Gly Glu Gly Asn Asp Leu Gly Val Leu Met Gly Arg Glu Asn Trp
    3215                3220                3225

Met Phe Gly Gly Lys Gly Asp Thr Ala Val Val Ala Gly Arg
    3230                3235                3240

Ile Asn His Val Phe Met Gly Glu Gly Asn Asp Gln Thr Phe Val
    3245                3250                3255

Phe Gly Glu Gly Gly Phe Ile Asp Ala Gly Asn Gly Gln Asp Tyr
    3260                3265                3270

Val Val Thr Ala Gly Asn Tyr Asn Arg Met Asp Thr Gly Lys Gly
    3275                3280                3285

Gln Asp Tyr Ala Val Ile Ile Gly Asn Asn Gln Ala Glu Leu
    3290                3295                3300

Gly Gly Gly Asp Asp Phe Ala Arg Val Phe Gly Asn Asp Asn Arg
    3305                3310                3315

Leu Asp Gly Tyr Cys Gly Asn Asp Ala Ile Lys Leu Met Gly Tyr
    3320                3325                3330

His Ala Val Ile Asn Gly Gly Glu Gly Asp Asp His Leu Ile Ala
    3335                3340                3345

Ala Ala Ile Ser Lys Phe Ser Gln Leu Asp Gly Gly Glu Gly Gln
    3350                3355                3360

Asp Leu Leu Val Leu Gly Gly Tyr Gln Asn His Phe Arg Gly Gly
    3365                3370                3375

Ala Gly Val Asp Ser Phe Val Val Ser Glu Glu Val Ile Asp Asn
    3380                3385                3390

Arg Val Ser Asp Ile Asn Ala Glu Asp Met Ile Leu Phe Asn Gly
    3395                3400                3405

Val Asp Trp Gln Asn Leu Trp Leu Gln Arg Ser Gly Tyr Asp Leu
    3410                3415                3420

Val Leu Ser Val Lys Arg His Thr Gln Asp Asn Thr Ala Gln Gly
    3425                3430                3435

Arg Phe Glu Ser Glu Gly Ser Val Ile Phe Asn Asp Tyr Phe Asn
    3440                3445                3450

Gly Asn Arg Ala Lys Leu Val Thr Arg Met Ser Asp Lys Asn Ala
    3455                3460                3465

Ser Gly Glu Arg Glu Phe Thr Ala Leu Ser Asp Asn Ala Val Asp
    3470                3475                3480

Ser Leu Ile Gln Ala Met Ser Gly Phe Ala Pro Ala Val Gly Asp
    3485                3490                3495

Asn Gly Phe Ile Ala Gly Leu Asp Ser Gln Ala Lys Thr Ala Ile

```
                      3500              3505              3510
   Ala Thr  Ala Trp Thr Asp Val  Thr Ile Gly Lys Gly  Lys Phe Ala
       3515              3520              3525

<210> SEQ ID NO 7
<211> LENGTH: 3531
<212> TYPE: PRT
<213> ORGANISM: Photorhabdus luminescens

<400> SEQUENCE: 7

Met Gly Lys Ser Ser Asn Arg Ser Ala Glu Phe Phe Thr Gly Lys
1               5                   10                  15

Tyr Asp Asp Asp Gly Gly Asn Asn Ile Val Ala Ile Gly Leu Gly
                20                  25                  30

Gly Glu Ile Tyr Ala Lys Gly Gly Asn Asp His Ile Thr Val Gly Ser
                35                  40                  45

Leu Gly Ala Thr Ile Tyr Ala Ser Ser Gly Asp Lys Thr Val Asp Gly
50                  55                  60

Gly Ala Gly Tyr Leu Lys Ile Val Asn Ile Gly Gly Asp Leu Lys Val
65                  70                  75                  80

His Gly Ala Ala Gly Tyr Ala Ser Ile Asp Lys Asn Gly Asn Gly Asn
                85                  90                  95

Ile Ser Phe Ile Gly Ala Ala Gly Val Ser Met Asp His Arg Gly
                100                 105                 110

Ser Ser Gly Asn Leu Asn Phe Ser Gly Ala Ala Ala Tyr Asn Asn Leu
                115                 120                 125

Ser Arg Arg Gly Gln Ser Gly Asn Val Thr Phe Lys Gly Ile Gly Gly
                130                 135                 140

Tyr Asn Gly Leu Trp His Glu Thr His Gln Gly Asp Leu Asn Phe Asn
145                 150                 155                 160

Ala Ala Gly Ala Gly Asn Lys Ile Asp Arg Thr Trp His Asp Arg Tyr
                165                 170                 175

Glu Gly Ser Lys Gly Asn Val Ile Phe Val Gly Gly Ala Ala Asn
                180                 185                 190

Ser Ile Ser Ser Arg Val Glu Ser Gly Asn Ile Glu Phe Thr Gly Ala
                195                 200                 205

Gly Val Asp Asn His Ile Ile Arg Lys Gly Lys Glu Gly Asn Ile Ile
                210                 215                 220

Phe Gln Gly Ala Gly Ala Leu Asn Arg Ile Glu Arg Leu Arg Asp Ser
225                 230                 235                 240

Lys Asp Lys Tyr Glu Gln Thr Arg Gly Asn Ile Glu Phe Glu Gly Ala
                245                 250                 255

Gly Gly Tyr Asn Lys Val Tyr Ser Asp Ile Ala His Gly Asn Ile Arg
                260                 265                 270

Phe Ser Gly Ser Gly Gly Tyr Asn Glu Ile Ser Arg Ile Gly Glu Asp
                275                 280                 285

Ser Asp Ser Tyr Asn Lys Ala Leu Gly Tyr Ala Ser Ala Glu Lys Ile
                290                 295                 300

Val Leu Ile Thr Ala Lys Met Gly Ser Gln Lys Pro Gln Gln Val Thr
305                 310                 315                 320

Ala Ile Lys Ser Thr Thr Glu Ser Asn Thr Tyr Leu Phe Ala Phe Ala
                325                 330                 335

Asp Gly Lys Tyr Thr Lys Ile Ser Lys Val Gln Leu Lys Asn Asp Pro
                340                 345                 350

Lys Thr Asn Lys Leu Ser Tyr Tyr Ser Thr Ser Trp Arg Lys Asn Gly
```

```
                355                 360                 365
Asn Gln Leu Lys Asn Leu Ala Thr Glu Asn Ile Ser Leu Glu Asn Gly
        370                 375                 380

Tyr Asp Asp Ile Ser Asn Asp Gly Asp Tyr Arg Leu Ser Asn Leu Ile
385                 390                 395                 400

Phe Glu His His Gln Pro Val Thr Ile Gln His Thr Val Glu Glu Asp
                405                 410                 415

Leu Arg Glu Asn Gln Trp Val Thr Tyr Ala Ser Gly Thr Thr Ala Lys
                420                 425                 430

Ala Glu Asp Ile Lys Leu Ile Asp Ala Lys Met His Gly Arg Ser Ile
                435                 440                 445

His Ser Asn Gly Ser Val Leu Asp Val Ser Ala Val Lys Ser Asn Arg
        450                 455                 460

Arg Ser Asn Ala Tyr Val Tyr Ala Lys Tyr Val Glu Ser Tyr Thr Lys
465                 470                 475                 480

Val Val Val Val Glu Leu Lys Asn Asp Asp Lys Thr Gly Glu Leu Lys
                485                 490                 495

Tyr Tyr Ala Ser Ala Trp Tyr Lys Ala Gly Asp His Thr Arg Asp Leu
                500                 505                 510

Ala Asn Glu Asp Phe Ser Arg Ala Asn Gly Tyr Ser Ser Met Glu Val
        515                 520                 525

Gly Gly Tyr Ser Leu Thr Asn Leu Lys Tyr Gln Val Asp Thr Val Arg
        530                 535                 540

Arg Val Ser Glu His Leu Glu His Ile Glu Glu Asp Ser Leu Gln Glu
545                 550                 555                 560

Trp Val Lys Ser Ser Asn Ile Gly Asp Ser Ser Gly Asp Val Asn
                565                 570                 575

Phe Ser Gly Met Gly Gly Asn Leu Ile Lys Ser Ser Val Ile Asn
                580                 585                 590

Gly Asn Val Asn Phe Glu Gly Asp Gly Ile Ala Asn Val Ile Leu His
        595                 600                 605

Ser Ser Arg Ser Gly Asn Thr His Phe Glu Gly Ala Gly Ala Ala Asn
        610                 615                 620

Ile Ile Glu Lys Ser Gly Ile Asp Gly Asn Leu Thr Phe Arg Gly Ala
625                 630                 635                 640

Gly Leu Ala Asn Val Leu His Gln Ser Arg Asn Gly Glu Met Asp
                645                 650                 655

Val Tyr Ala Gly Gly Ala Ala Asn Val Leu Val Arg Val Gly Asp Gly
                660                 665                 670

Arg Tyr Leu Ala Arg Leu Leu Ala Ile Gly Asn Ile Ser Ile His Gln
                675                 680                 685

Gly Asn Gly Asp Ser Arg Val Val Met Leu Gly Gly Tyr Asn Thr His
        690                 695                 700

Thr Gln Ile Gly Lys Gly Ser Ala Asn Trp Leu Gly Ala Gly Gly Phe
705                 710                 715                 720

Asn Val Met Thr Gln Lys Gly Lys Gly Ser Ile Ser Ser Leu Leu Leu
                725                 730                 735

Gly Gly Ala Asn Val Leu Thr Lys Leu Gly Gly Asp Asn Leu Val Ser
                740                 745                 750

Gly Met Leu Gly Gly Ala Asn Ile Ile Thr His Ile Ser Gly Asp Asn
        755                 760                 765

Glu Ile Ser Asp Thr Thr Ala Ile Ala Leu Gly Gly Ala Asn Ile Leu
        770                 775                 780
```

-continued

Thr Lys Lys Gly Arg Gly Asp Ala Val Ala Leu Met Gly Gly Gly Ala
785                 790                 795                 800

Asn Val Leu Thr His Ile Gly Tyr Gly Ser Thr Thr Gly Val Met Leu
                805                 810                 815

Gly Gly Ala Asn Ile Leu Thr Lys Val Gly Asn Gly Asp Thr Thr Gly
            820                 825                 830

Ile Met Leu Gly Ile Gly Asn Val Leu Thr His Val Gly Asp Asp Gln
        835                 840                 845

Thr Leu Gly Val Met Gly Ala Ala Gly Asn Ile Phe Thr Lys Val Gly
850                 855                 860

Asp Gly Thr Ala Ile Ala Ala Met Ile Gly Ala Gly Asn Ile Phe Thr
865                 870                 875                 880

His Val Gly Lys Gly Asp Ala Trp Ala Leu Met Gly Gly Leu Gly Asn
                885                 890                 895

Ile Phe Thr Lys Val Gly Asp Gly Lys Ala Leu Ala Leu Met Ile Ala
            900                 905                 910

Ala Gly Asn Val Phe Thr His Val Gly Asn Gly Met Ser Val Ala Leu
        915                 920                 925

Met Leu Ala Lys Gly Asn Ile Ala Thr Lys Val Gly Asp Gly Thr Thr
930                 935                 940

Leu Ala Ala Met Ile Gly Glu Ala Asn Val Met Thr His Val Gly Asn
945                 950                 955                 960

Gly Ser Thr Phe Ala Ala Met Ile Gly Gln Gly Asn Ile Leu Thr Lys
                965                 970                 975

Ala Gly Asn Asp Leu Ala Leu Gly Leu Met Val Gly Glu Ala Asn Ile
            980                 985                 990

Tyr Ser His Val Gly Asp Gly Thr Ser Ile Gly Leu Leu Ala Gly Lys
        995                 1000                1005

Leu Asn Val Met Thr Lys Met Gly Asp Gly Thr Thr Leu Ala Ala
    1010                1015                1020

Met Phe Gly Glu Ala Asn Ile Met Thr His Tyr Gly Asp Gly Leu
    1025                1030                1035

Thr Gly Val Leu Ala Leu Gly Lys Ala Asn Ile Val Thr Lys Val
    1040                1045                1050

Gly Lys Gly Phe Met Gly Val Val Ala Ala Ala Glu Ala Asn Val
    1055                1060                1065

Val Thr His Met Gly Ala Ser Thr Thr Ala Ala Val Leu Leu Gly
    1070                1075                1080

Lys Gly Asn Ile Leu Thr Lys Glu Gly Ser Gly Thr Thr Val Gly
    1085                1090                1095

Leu Leu Ile Ser Asp Val Gly Asn Ile Met Thr His Ile Gly Asp
    1100                1105                1110

Gly Thr Thr Val Gly Phe Ala Lys Gly Lys Ala Asn Ile Ile Thr
    1115                1120                1125

Lys Val Gly Glu Gly Thr Gly Ile Asn Ala Val Trp Gly Glu Ala
    1130                1135                1140

Asn Ile Leu Thr His Val Gly Asn Gly Asp Arg Tyr Asn Phe Ala
    1145                1150                1155

Lys Gly Lys Ala Asn Ile Ile Thr Lys Val Gly Gly Met Arg Glu
    1160                1165                1170

Val Thr Val Val Gln Gly Asp Ala Asn Ile Ile Thr His Val Gly
    1175                1180                1185

Asn Gly Asp Asp Tyr Thr Gly Ala Trp Gly Lys Ala Asn Val Ile
    1190                1195                1200

```
Thr Lys Val Gly Asp Gly Asn Asn Val Leu Ala Lys Ala Asp
    1205            1210            1215

Ala Asn Ile Val Thr Gln Val Gly Asn Gly Asp Ser Phe Asn Ala
    1220            1225            1230

Leu Trp Ser Lys Gly Asn Ile Val Thr Lys Val Gly Asp Gly Met
    1235            1240            1245

Gln Val Thr Ala Ala Lys Gly Lys Ala Asn Ile Thr Thr Thr Val
    1250            1255            1260

Gly Asn Gly Leu Ser Val Thr Ala Thr His Gly Asp Leu Asn Val
    1265            1270            1275

Asn Thr Lys Val Gly Asp Gly Val Ser Val Asn Ala Val Trp Gly
    1280            1285            1290

Glu Tyr Asn Val Asn Thr Lys Val Gly Asn Gly Leu Asn Val Ala
    1295            1300            1305

Ile Met Lys Gly Lys Gly Asn Ala Asn Ile His Ile Gly Asp Gly
    1310            1315            1320

Leu Gly Ile Asn Ala Ser Tyr Ala Arg Asn Asn Val Ala Ile Lys
    1325            1330            1335

Val Gly Asn Gly Asp Phe Tyr Ser Leu Ser Ile Ala Glu Ser Asn
    1340            1345            1350

Thr Gln Ser Ser His Leu Ser Ser Leu Phe Glu Asn Ile Lys Gln
    1355            1360            1365

Thr Val Phe Asn Val Glu Gly Ser Gln Thr Ile Asn Tyr Leu Ile
    1370            1375            1380

Arg Gly Asp Glu Ala Asn Thr Ser Gly Val Asn Lys Gly Arg Gly
    1385            1390            1395

Ala Ile Asn Leu Thr Glu Val Ser Ala Ile Asp Gly Phe Gln Met
    1400            1405            1410

Asp Lys Ile Asp Glu Val Ser Ser Asp Leu Ala Asn Asn Leu Ser
    1415            1420            1425

Gly Ala Ile Thr Pro Val Glu Thr Pro Asp Ile Asn Val Ile Gln
    1430            1435            1440

Asn Asp Leu Gln Ile Gly Asp Asn Val Gly Ser Ala Gln Asp Gln
    1445            1450            1455

Ala Ser Pro His Ala Asp Ala Val Val Arg His Ala Lys Gln Asn
    1460            1465            1470

Lys Ala Ala Gln Asn Ala Leu Ser Asp Lys Glu Lys Ala Glu Ile
    1475            1480            1485

Asn His Gln Arg Leu Gln Gln Glu Lys Asp Lys Gln Leu Lys Thr
    1490            1495            1500

Ile Ser Lys Ser Gln Gly Gln Leu Glu Ser Thr Asn Gln Ala Ala
    1505            1510            1515

Leu Asn Thr Asn Gly Gln Val Gln Arg Asp Val Ile Ser Glu Glu
    1520            1525            1530

Ser Arg Gly Val Thr Glu Glu Leu Phe Ser Leu Thr Gln Gly Met
    1535            1540            1545

Gly Ala Leu Asn Asn Tyr Gly Asn Tyr Asp Gly Lys Ser Gly Asp
    1550            1555            1560

Glu Trp Arg Asn Arg Phe Ala Gly Gly Tyr Leu Asp Asn Ile Gln
    1565            1570            1575

Asn Lys Leu Asn Asp Ala Lys Leu Thr Ala Gln Lys Lys Leu Ala
    1580            1585            1590

Asp Ala Gln Gln His Phe Ile Asp Lys Arg Glu Thr Val Ile Thr
```

-continued

```
            1595                1600                1605

Ala Ile Lys Lys Ser Glu Val Gly Phe Thr Lys Ser Ala Glu Asn
    1610                1615                1620

Leu Asp Ser Ala Asp Asp Ile Val Asp Ala Glu Lys Lys Ala
    1625                1630                1635

Glu Gln Arg Lys Glu Glu Ala Leu Leu Gln Lys Gln Arg Ala Asp
    1640                1645                1650

Lys Ala Val Ser Asp Ala Asn Thr Ala Tyr Asp Lys Ala Lys Gln
    1655                1660                1665

Arg Gly Glu Ser Asp Ser Thr Ala Ala Glu Asn Lys Thr Ile Gln
    1670                1675                1680

Ala Gln Lys Asn Ala Lys Ser Val Lys Gln Ala Asp Asn Ala Lys
    1685                1690                1695

Pro Asp Arg Thr Gly Ala Ala Gly Ser Gly Leu Ser Gly Asn Ala
    1700                1705                1710

Tyr Ile Pro Ile Glu Val Glu Lys Ser Lys Ser His Ile Asp Pro
    1715                1720                1725

Ala Ser Lys Ala Glu Pro Asp Gly Trp Leu Ser Glu Asp Leu Ala
    1730                1735                1740

Leu Thr Ala Glu Asp Leu Ala Ala Leu Asn Asn Ala Gln Gln Ala
    1745                1750                1755

Val Asn Arg Leu Gln Leu Asn Lys Gly Met Arg Ser Glu Asn Thr
    1760                1765                1770

Gly Ala Ser Ile Met Ser Met Phe Thr Glu Thr Ser Ser Asp Gly
    1775                1780                1785

Ala Val Lys Ser Thr Leu Asn Lys Ser Arg Glu Leu Ile Arg Lys
    1790                1795                1800

Ala Pro Thr Ile Ser Gly Ile Asp Leu Gln Gly Leu Gly Gly Asn
    1805                1810                1815

Asn Pro Arg Ser His Ser Ser Val Leu Lys Lys Leu Glu Leu Ile
    1820                1825                1830

Leu Leu Lys Lys Asp Asn Lys Arg Phe Ile Asp Ser Thr Lys Arg
    1835                1840                1845

Arg Leu Gly Ser Ile Asn Thr Asp Leu Pro Ser Lys Ala Leu Val
    1850                1855                1860

Ala Val Arg Glu Ala Phe Asn Arg Thr Val Glu Gln Pro Asp Glu
    1865                1870                1875

Gln His Val Leu Gln Leu Glu Gln Thr Leu Ala His Trp Gln Gln
    1880                1885                1890

His Asp Pro Lys Glu Phe Thr Gln Arg Ser Lys Leu Val Lys Ser
    1895                1900                1905

Leu Arg Phe Glu Met Gly Glu Leu Val Ala His Ile Gln Ala Gln
    1910                1915                1920

Arg Ala Glu Ser Ala Gly Ile Leu Gly Ile Ala Val Ala Pro Glu
    1925                1930                1935

Gln Val Thr Gln Phe Gly Gln Val Ser Phe Asp Gly Ile Gly
    1940                1945                1950

Arg Val Val Gly Leu Lys Gly Asp Ile Ala Gln Ser Glu Ile Asn
    1955                1960                1965

Arg Leu Thr Asp Leu Gln Ile Lys Pro Leu Thr Gln Thr Asn Ser
    1970                1975                1980

Val Ala Glu Arg Glu Ala Pro Lys Thr Glu Asn Glu Ser Leu Ile
    1985                1990                1995
```

```
Val Phe Val Ser Arg Leu Gln Gln Glu Ala Ile Pro Glu Gly Lys
2000                2005                2010

Pro Leu Ile Glu Arg Ala Arg Lys Leu Trp Leu Thr Gly Gln Val
2015                2020                2025

Thr Asn Glu Lys Thr Lys Glu Leu Phe Lys Asp Ala Val Ala Gln
2030                2035                2040

Leu Gln Thr Tyr Pro Glu Leu His Thr Leu Ala Gln Gln Leu Leu
2045                2050                2055

Thr Asp Ala Asn Lys Glu Lys Ala Thr Gly Gln Tyr Ile Asp Asn
2060                2065                2070

Leu Phe Gly Arg His Phe Asp Ser Glu Leu Ala Tyr Glu Leu Val
2075                2080                2085

Lys Thr Ala Ser Pro Glu Ala Lys Asn Thr Ala Glu Arg Thr Gly
2090                2095                2100

Asn Phe Leu Val Glu Asp Phe Glu Arg Trp Ile Gly Asp Leu Tyr
2105                2110                2115

Pro Glu Gly Glu Lys Arg Asn Gly Ala Ile Asp Lys Lys Met Lys
2120                2125                2130

Ser Phe Ala Glu Ala Ile Asp Lys Asp Phe Arg Pro Trp Phe Ser
2135                2140                2145

Arg Val Pro Glu Val Thr Thr Phe Leu Asp Asp Pro Thr Phe Ala
2150                2155                2160

Asn Phe Lys Thr Met Met Thr Lys Val Asp Asp Gly Phe Ser Val
2165                2170                2175

Ile Lys Val Pro Phe Leu Ala Val Lys Met Ala Thr Thr Ser Gly
2180                2185                2190

Met Gly Met Asp Val Ala Asp Trp Lys Arg Lys Gly Asp Ser Phe
2195                2200                2205

Tyr Leu Asn Val Ile Thr Lys Ala Arg Ser Thr Ser Thr Glu Leu
2210                2215                2220

Thr Ala Gly Thr Asn Ala Glu Asp Val Lys Tyr Lys Val Lys Ile
2225                2230                2235

Thr Glu Lys Gln Thr Asn Asp Tyr Gly Thr Ala Leu Pro Tyr Gln
2240                2245                2250

Pro Ala Asn Asn Lys His Asp Asp Phe Leu Tyr Gly Arg Lys Val
2255                2260                2265

Ala Ala Gly Arg Ile Leu Thr Pro Gly Arg Glu Thr Ala Phe Glu
2270                2275                2280

Ser Asn Ala Leu Glu Arg Gly Gln Ser Val Val Thr Gly Ala Ser
2285                2290                2295

Gly Ser Thr Asn Ile Met Val His Leu Asn Asp Tyr Ile Ala Ser
2300                2305                2310

Lys Gln Pro Asp Phe Ser Thr Gly Gln Ser Tyr Leu Asn Thr Leu
2315                2320                2325

Ser Phe Leu Val Phe Asp Gly Gly His Ser Val Asn Glu Ser Leu
2330                2335                2340

Val Val Tyr Gln Ala Leu Gln Ala Thr Asp Glu Ile Lys Arg Lys
2345                2350                2355

Gln Ile Leu Asn Ser Tyr Thr Ala Asn Tyr Gln Asp Leu Ala Asp
2360                2365                2370

Ile Ala Gly Glu Ser Gly Lys Val Trp Val Asn Gln Ala Leu Asp
2375                2380                2385

Asn Ala Phe Lys Glu Thr Gln Glu Phe Tyr Gln Lys Tyr Ala Val
2390                2395                2400
```

-continued

```
Val Lys Pro Gln Ser Arg Pro Ala Val Glu Asp Leu Glu Gly Leu
    2405                2410                2415
Ser Gly Thr Asn Lys Gly Val Glu Pro Thr Ile Ile Gly Asp Ser
    2420                2425                2430
His Leu Lys Lys Pro Val Asp Gly Trp Gln Lys Val Asp Val Thr
    2435                2440                2445
Pro Gln Thr Asp Gly Arg Glu Thr Arg Phe Asp Gly Gln Ile Ile
    2450                2455                2460
Leu Gln Met Glu Asp Asp Pro Ile Ala Ala Arg Ala Ala Ala Asn
    2465                2470                2475
Leu Ala Gly Lys His Pro Asp Ser Ser Val Val Ile Gln Leu Asp
    2480                2485                2490
Ala Asn Gly Lys Tyr Arg Val Val Tyr Gly Asp Leu Ala Lys Leu
    2495                2500                2505
Ser Asn Lys Leu Arg Trp Gln Val Val Gly His Gly Arg Asp Thr
    2510                2515                2520
Ser Glu Gln Asn Asn Ile Arg Leu Ser Gly Tyr Ser Ala Asp Glu
    2525                2530                2535
Leu Ala Thr Lys Leu Lys Gln Phe Tyr Gln Ala Ala Lys Leu Gly
    2540                2545                2550
Lys Gln Ala Ile Ser Lys Pro Asp His Ile Ser Leu Val Gly Cys
    2555                2560                2565
Ser Leu Ile Ser Asp Asn Lys Arg Asp Gly Phe Ala Arg Arg Phe
    2570                2575                2580
Ile Thr Glu Leu Asp Lys Gln Gly Ile Arg Ser Asp Val Ser Ala
    2585                2590                2595
Arg Ser Ser Glu Val Ala Val Asp Ala Thr Gly Arg Lys Phe Thr
    2600                2605                2610
Arg Asp Glu Asn Asn Gln Trp Val Asn Asn Ser Pro Asp Asn Lys
    2615                2620                2625
Ile Val Leu Ser Leu Asn Ala Glu Asn Lys Leu Ile Thr His Thr
    2630                2635                2640
Glu Gln Val Arg Arg Gly Ile Ala Glu Ser Asp Ile Asp Phe Ala
    2645                2650                2655
Lys Val Gly Tyr Thr Gln Ala Asp Ser Val Thr Lys Gly Glu Ile
    2660                2665                2670
Ala Asp Asn Thr Glu Ile Phe Ile Lys Pro Gln Lys Arg Glu Lys
    2675                2680                2685
Val Asn Thr Ser Asp Asn Ser His Arg Gln Leu Ser Tyr Ser Gly
    2690                2695                2700
Asn Ile Gln Val Asp Val Gly Glu Gly Glu Phe Thr Ala Leu Asn
    2705                2710                2715
Trp Gly Thr Ser Asn Val Gly Ile Lys Val Gly Thr Gly Gly Phe
    2720                2725                2730
Lys Ser Leu Ala Phe Gly Asp Asn Asn Val Met Val His Ile Gly
    2735                2740                2745
His Gly Asp Ser Lys His Ser Val Asp Ile Gly Gly Tyr Gln Ala
    2750                2755                2760
Leu Glu Gly Ala Gln Met Phe Ile Gly Asn Arg Asn Val Ser Phe
    2765                2770                2775
Asn Gln Gly Arg Ser Asn Asp Leu Ile Val Met Met Asp Lys Ser
    2780                2785                2790
Ile Pro Thr Pro Pro Leu Val Asn Pro Phe Asp Asp Thr Ala Arg
```

-continued

```
            2795                2800                2805

Ile Ala Glu Val Leu Lys Gly Ile Ala Arg Ser Gly Glu Thr Gln
    2810                2815                2820

Asp Trp Leu Ala Ala Gln Asp Gln Gln Trp Thr Ile Ala Gly Ala
    2825                2830                2835

Arg Lys Phe Val Arg Asp Met Ser Gly Leu Asp Gln Thr Ser Ser
    2840                2845                2850

Val Asp Tyr Lys Thr Leu Leu Asp Leu Asp Ser Gln His Glu Arg
    2855                2860                2865

Ser Ser Arg Gly Leu Gln Asn Asp Ala Glu Ser Ala Leu Asn Lys
    2870                2875                2880

Lys Phe Asn Gln Trp Leu Gly Glu Asn Gly Asn Ser Ile Glu Met
    2885                2890                2895

Gly Lys Met Ser Arg Ala Asp Lys Phe Arg Gln Ala Asn Gln Lys
    2900                2905                2910

Leu Ala Phe Asn Phe Ala Val Gly Gly Arg Gly Ala Asp Ile Gln
    2915                2920                2925

Val Thr Thr Gly Asn Trp Asn Phe Thr Phe Gly Asp Asn Ile Gln
    2930                2935                2940

Ser Ile Leu Asp Thr Asn Leu Gly Ser Leu Phe Gly Leu Met Thr
    2945                2950                2955

Gln Gln Tyr Ser Ala Thr Gly Met Ala Lys Thr Thr Phe Thr Tyr
    2960                2965                2970

Thr Pro Gln Asp Leu Pro Arg Gln Leu Gln Asn Lys Leu Leu Gly
    2975                2980                2985

Arg Leu Ser Glu Val Gly Ala Asp Thr Thr Leu Ala Asp Ile Phe
    2990                2995                3000

Gly Val Asp Tyr Thr Ala Asp Gly Arg Ile Val Ser Arg Thr Gly
    3005                3010                3015

Lys Pro Val Asp Gly Glu Ala Met Leu Lys Glu Met Leu Glu Val
    3020                3025                3030

Ile Lys Glu Phe Ser Gly Asp Gln Leu Ala Ala Phe Thr Asn Pro
    3035                3040                3045

Gly Lys Leu Leu Asp Ser Leu Glu Ala Gly Ile Lys Ala Gly Glu
    3050                3055                3060

Asp Gly Val Arg Thr Phe Ala Glu Ser His Gly Leu Lys Glu Lys
    3065                3070                3075

Ala Pro Asp Lys Asn Gln Glu Gln Gly Ala Val Val Ser Thr Asn
    3080                3085                3090

Gly Asp Ser Ala Gln Ala Asn Asn Lys Ala Glu Arg Ala Phe Gly
    3095                3100                3105

Phe Asn Ser Leu Asn Leu Pro Asn Leu Phe Ala Thr Met Phe Ser
    3110                3115                3120

Lys Asp Lys Gln Ala Glu Met Gln Ser Leu Val Thr Asn Leu Lys
    3125                3130                3135

Glu Asn Leu Thr Ala Asp Leu Leu Asn Met Lys Gln Lys Thr Phe
    3140                3145                3150

Asp Phe Leu Arg Asn Ser Gly His Leu Gln Gly Asp Gly Asp Ile
    3155                3160                3165

Asn Val Ser Leu Gly Asn Tyr Asn Phe Asn Trp Gly Gly Asp Gly
    3170                3175                3180

Lys Asp Leu Gly Ala Tyr Leu Gly Asp Asn Asn Asn Phe Trp Gly
    3185                3190                3195
```

-continued

| | | | | | | | | | | | | | | |
|---|---|---|---|---|---|---|---|---|---|---|---|---|---|---|
| Gly | Arg | Gly | Asp | Val | Tyr | Tyr | Ser | Leu | Gly | Thr | Ser | Asn | Ile | |
| | 3200 | | | | 3205 | | | | 3210 | | | | | |
| Phe | Thr | Gly | Gly | Glu | Gly | Asn | Asp | Met | Gly | Val | Leu | Met | Gly | Arg |
| | 3215 | | | | 3220 | | | | 3225 | | | | | |
| Glu | Asn | Trp | Met | Phe | Gly | Asp | Gly | Asp | Thr | Ala | Val | Val | | |
| | 3230 | | | | 3235 | | | | 3240 | | | | | |
| Ala | Gly | Arg | Ile | Asn | His | Val | Phe | Met | Gly | Glu | Gly | Asn | Asp | Gln |
| | 3245 | | | | 3250 | | | | 3255 | | | | | |
| Thr | Phe | Val | Phe | Gly | Glu | Gly | Leu | Ile | Asp | Ala | Gly | Asn | Gly | |
| | 3260 | | | | 3265 | | | | 3270 | | | | | |
| Gln | Asp | Tyr | Val | Val | Thr | Ser | Gly | Asn | Tyr | Asn | Arg | Val | Asp | Thr |
| | 3275 | | | | 3280 | | | | 3285 | | | | | |
| Gly | Ala | Gly | Gln | Asp | Tyr | Ala | Val | Thr | Ile | Gly | Asn | Asn | Asn | Arg |
| | 3290 | | | | 3295 | | | | 3300 | | | | | |
| Val | Asp | Leu | Gly | Glu | Gly | Asp | Asp | Phe | Ala | Arg | Val | Phe | Gly | Asn |
| | 3305 | | | | 3310 | | | | 3315 | | | | | |
| Asp | Asn | Arg | Ile | Asp | Gly | Tyr | Ser | Gly | Asn | Asp | Thr | Ile | Lys | Leu |
| | 3320 | | | | 3325 | | | | 3330 | | | | | |
| Met | Gly | Tyr | His | Ala | Met | Ile | Asn | Gly | Gly | Glu | Gly | Asp | Asp | His |
| | 3335 | | | | 3340 | | | | 3345 | | | | | |
| Leu | Ile | Ala | Ala | Ala | Ile | Ser | Lys | Phe | Ser | Gln | Phe | Asn | Gly | Gly |
| | 3350 | | | | 3355 | | | | 3360 | | | | | |
| Asp | Gly | Gln | Asp | Leu | Leu | Val | Leu | Gly | Gly | Tyr | Gln | Asn | Ser | Phe |
| | 3365 | | | | 3370 | | | | 3375 | | | | | |
| Gln | Gly | Gly | Ala | Gly | Val | Asp | Ser | Phe | Val | Val | Ser | Ala | Glu | Val |
| | 3380 | | | | 3385 | | | | 3390 | | | | | |
| Ile | Asp | Asn | Arg | Val | Asn | Asp | Ile | Asn | Ala | Glu | Asp | Met | Ile | Leu |
| | 3395 | | | | 3400 | | | | 3405 | | | | | |
| Phe | Asn | Gly | Val | Asp | Trp | Lys | Asp | Leu | Trp | Phe | Gln | Arg | Ser | Gly |
| | 3410 | | | | 3415 | | | | 3420 | | | | | |
| Tyr | Asp | Leu | Val | Leu | Ser | Val | Asn | Arg | His | Thr | Gln | Asp | Asn | Thr |
| | 3425 | | | | 3430 | | | | 3435 | | | | | |
| Ala | Gln | Glu | Ile | Phe | Glu | Ser | Val | Gly | Ser | Val | Thr | Phe | Asn | Asp |
| | 3440 | | | | 3445 | | | | 3450 | | | | | |
| Tyr | Phe | Asn | Gly | His | Arg | Ala | Lys | Leu | Val | Thr | Gln | Met | Gly | Asp |
| | 3455 | | | | 3460 | | | | 3465 | | | | | |
| Lys | Asp | Lys | Ser | Gly | Glu | Tyr | Glu | Phe | Thr | Ala | Leu | Ser | Asp | Asn |
| | 3470 | | | | 3475 | | | | 3480 | | | | | |
| Ala | Val | Asp | Ser | Leu | Ile | Gln | Ala | Met | Ser | Ser | Phe | Ser | Pro | Thr |
| | 3485 | | | | 3490 | | | | 3495 | | | | | |
| Val | Gly | Asp | Asn | Gly | Phe | Ile | Glu | Ser | Leu | Gly | Ser | Lys | Ala | Arg |
| | 3500 | | | | 3505 | | | | 3510 | | | | | |
| Ala | Ala | Val | Ala | Thr | Ala | Trp | Ala | Asp | Val | Thr | Leu | Gly | Lys | Gly |
| | 3515 | | | | 3520 | | | | 3525 | | | | | |
| Lys | Phe | Ala | | | | | | | | | | | | |
| | 3530 | | | | | | | | | | | | | |

<210> SEQ ID NO 8
<211> LENGTH: 201
<212> TYPE: PRT
<213> ORGANISM: Xenorhabdus nematophila

<400> SEQUENCE: 8

| | | | | | | | | | | | | | | |
|---|---|---|---|---|---|---|---|---|---|---|---|---|---|---|
| Ser | Pro | Glu | Ser | His | Ile | Arg | Val | Asn | Asn | His | Asp | Val | Gly | Ser | Trp |
| 1 | | | | 5 | | | | | 10 | | | | | 15 | |

```
Glu Asn Ile Thr Val Lys Pro Gln Pro Glu Ser Gly Asp Ser Arg Phe
             20                  25                  30

Ser Gly Gln Ile Ile Gln Thr Glu Asn Asp Pro Val Ala Ala Lys
         35                  40                  45

Ala Ala Ala Asn Leu Ala Gly Lys His Pro Asp Ser Ser Val Ile Val
     50                  55                  60

Gln Leu Asp Ala Asn Gly Gln Tyr Arg Val Val Tyr Gly Asp Pro Ala
 65                  70                  75                  80

Asp Leu Ser Asn Lys Leu Gln Ser Gly Lys Leu Arg Trp Gln Ile Val
                 85                  90                  95

Gly His Gly Arg Glu Glu Ser Ala Gln Asn His Thr Arg Ile Ser Gly
            100                 105                 110

Tyr Ser Ala Asp Glu Leu Ala Leu Arg Leu Lys Gln Phe Ser Ile Asp
        115                 120                 125

Phe Lys Gln Ala Gly Lys Pro Asp His Ile Ser Leu Val Gly Cys Ser
    130                 135                 140

Leu Ile Ser Asp Asp Lys Arg Asn Gly Phe Ala Arg Arg Phe Ile Ser
145                 150                 155                 160

Ala Leu Asn Glu Gln Gly Val Arg Thr Thr Val Ser Ala Arg Ser Ser
                165                 170                 175

Glu Val Ala Val Asp Ser Ile Gly Arg Lys Tyr Thr Lys Asp Ala Gln
            180                 185                 190

Asp Gln Trp Val His Lys Leu Thr Asp
        195                 200

<210> SEQ ID NO 9
<211> LENGTH: 196
<212> TYPE: PRT
<213> ORGANISM: Xenorhabdus bovienii

<400> SEQUENCE: 9

Leu Pro Glu Gly Val Asp Arg Val Val Asn Asn Glu Asn Val Glu His
 1               5                  10                  15

Trp Glu Pro Ala Phe Val Lys Pro Gln Ala Glu Gly Gly Asp Ser Arg
             20                  25                  30

Phe Asn Ser Gln Val Ile Ile Gln Thr Glu Asn Asp Pro Val Ala Ala
         35                  40                  45

Lys Ala Ala Ala Arg Leu Ala Gly Lys His Pro Asp Ser Val Ile Val
     50                  55                  60

Gln Leu Asp Ala Asn Gly Arg Tyr Arg Val Val Tyr Gly Asp Pro Ala
 65                  70                  75                  80

Thr Leu Ser Gly Lys Leu Arg Trp Gln Ile Val Gly His Gly Arg Asp
                 85                  90                  95

Glu Ser Val Gln His His Thr Arg Met Ser Gly Tyr Ser Ala Asp Glu
            100                 105                 110

Leu Ala Leu Lys Leu Lys Gln Phe Arg Thr Asp Phe Lys Gln Ala Gly
        115                 120                 125

Ser Pro Asp His Ile Ser Leu Val Gly Cys Ser Leu Ile Ser Asp Asp
    130                 135                 140

Lys Arg Asp Gly Phe Ala Arg His Phe Ile Ser Glu Leu Asp Lys Gln
145                 150                 155                 160

Gly Ile Arg Thr Ile Val Ser Ala Arg Ser Ser Glu Val Ala Val Asp
                165                 170                 175

Ser Ile Gly Arg Lys Phe Thr Arg Asn Ala Glu Glu Gln Trp Val His
            180                 185                 190
```

Lys Leu Met Asp
        195

<210> SEQ ID NO 10
<211> LENGTH: 3103
<212> TYPE: PRT
<213> ORGANISM: Yersinia pseudotuberculosis

<400> SEQUENCE: 10

Met Pro Asn Gly Asn Glu Met Ala Gly Phe Tyr Ile Asn Lys Leu Ser
1               5                   10                  15

Leu Ser Gln Arg Leu Ser Ile Leu Ser Glu Thr Tyr Asp Arg Ile Asn
            20                  25                  30

Lys Asn Asn Lys Lys Glu Lys Phe Lys Tyr Ser Tyr Ala Asp Ile Glu
        35                  40                  45

Met Ile Lys Lys Arg Phe Ile Lys Tyr Ile Asp Ala Gln Leu Tyr Ser
    50                  55                  60

Leu Ile Arg Glu Gly Phe Ser Val Pro Thr Thr Leu Thr Gln Glu Glu
65                  70                  75                  80

Lys Ile Lys Ile Ala Asp Leu Ala Ile Asp Ala Ala Leu Tyr Asn Asp
                85                  90                  95

Tyr Gly Arg Phe Asn Glu Leu Ile Ile Tyr Ile Ser Ser Leu Gly Ile
            100                 105                 110

Ser Val Thr Pro Pro Leu Pro Gln Glu Glu Gly Gly Ser Arg Leu Tyr
        115                 120                 125

Ile Tyr Phe Ser Gly Asp Ile His Thr Tyr Met Asp Val Trp Arg Gly
    130                 135                 140

Asp Leu Leu Val Gly Ser Gly Thr Glu Leu Ser Asp Ile Gln Ser Ile
145                 150                 155                 160

Thr Gly Leu Arg Phe Met Ile Asp Met Ala Glu Ser Leu Lys Leu Asn
                165                 170                 175

Ile Ile Asn Pro Ser Asp Lys Ala Met Val Asp Leu Ile Asn His Leu
            180                 185                 190

Arg Tyr Lys Met Ile Ser Tyr Ala Ser Ser Phe Tyr Ala Thr Tyr Ser
        195                 200                 205

Ala Glu Arg Gly Gly Thr Val Tyr Leu Ser Ser Pro Gly Gly Leu Arg
    210                 215                 220

Ile Asn Asn Tyr Phe Trp Asn Ser Glu Leu Pro Val Leu Arg Ala Leu
225                 230                 235                 240

Gln Lys Gln Gly Leu Ile Gly Asp Ile Arg Ile Leu His Lys Pro Leu
                245                 250                 255

Glu Phe Tyr Lys Asp Thr Pro Leu Asp Glu Leu Gly Asp Leu Leu Thr
            260                 265                 270

Ala Lys Asp Leu Ser Met Thr Ala Glu Tyr Gln Phe Leu Pro Val Trp
        275                 280                 285

Leu Gln Glu Lys Leu Leu Val Ala Ile Tyr Gln Gln Trp Leu Asp Glu
    290                 295                 300

Glu Phe Gln Pro Ser Leu Phe Thr Val Arg Lys Glu Ile Ile Asn Thr
305                 310                 315                 320

Ile Asp Ile Asp Arg Asn Ala Pro Glu Val Glu Leu Leu Arg Tyr Phe
                325                 330                 335

Leu Ser Lys Ile His Glu Gln Leu Asp Glu Ile Thr Glu Tyr Lys Val
            340                 345                 350

Leu Ile Glu Ala Glu Arg Ile Asp Phe Ile Lys Lys Ile Ala Val
        355                 360                 365

```
Gly Ser Glu Ile Glu Ser Trp Leu Asp Asn Val Pro Ala Ile Asp Val
        370                 375                 380

Asn Glu Arg Lys Val Ile Leu Glu Asn Leu Leu Gln Lys Glu Ser Leu
385                 390                 395                 400

Leu Phe Ser Asn Val Arg Asp Ile Lys Lys Phe Pro Ile Pro Leu Asp
                405                 410                 415

Phe Asn Ser Asp Val Ile Asn Val Asn Thr Ser Lys Leu Lys Asn Thr
            420                 425                 430

Phe Ile Pro Phe Asn Leu Leu Arg Glu Lys Trp Asp Ile Ile Ile Ser
        435                 440                 445

Asp Arg Ser Leu Val Asp Gly Thr Leu Thr Ile His Phe Ser Ala Gly
    450                 455                 460

Arg Lys Ile Met Ile Lys Val Asp Ala Asn Arg Asn Gln Leu Lys Gln
465                 470                 475                 480

Met Ala Thr Leu Glu Arg Phe Leu Leu Ala Asn Phe Thr Pro Lys Asn
                485                 490                 495

Ala Pro Gln Asp Leu Gln Leu Ile Glu Asn Val Ile Met Ser Gly Asp
            500                 505                 510

Ala Val Leu Ala Glu Arg Lys Gly Asp Lys Gly Trp His Asn Asp Gln
        515                 520                 525

Gln Met Ile Glu Lys Val Lys Leu Ser Glu Phe Asp Tyr Phe Leu Lys
    530                 535                 540

Ser Asn Asp Leu Gly Ile Lys Ile Asn Asp Asn Gly Phe Val Leu Tyr
545                 550                 555                 560

Leu Ile Ser Asp Pro Glu Asp Ser Arg Asp Val Ile Ile Asn Pro Asn
                565                 570                 575

Asn Asp Tyr Asn Leu Lys Ser Ile Lys Asp Phe Ile Glu Asn Asn Tyr
            580                 585                 590

Leu Phe Phe Asp Asp Val Pro Glu Tyr Leu Ile Val Lys Lys Asn Ala
        595                 600                 605

Glu Asn Lys Glu Cys Ile Phe Ala His Asn Glu Arg Glu Thr Tyr Gln
    610                 615                 620

Val Ala Tyr Arg Asp Glu Gly Thr Trp Val Leu Leu Tyr Lys Lys Asp
625                 630                 635                 640

Leu Ser Asp Gln Ile Lys Ile Ile Asn Glu Ile Thr Thr Ser Val Asn
                645                 650                 655

Met Asn Asn Ala Glu Ser Arg Ser Val Ala Leu Ile Leu Cys Leu Leu
            660                 665                 670

Asn Lys His Val Arg Leu Val Ser Ile Leu Pro Asp Thr His Pro Lys
        675                 680                 685

Val Met Glu Asn Leu Leu Asp Ile Asp Ser Leu Leu Lys Asn Ser Lys
    690                 695                 700

His Pro Phe Ser His Pro His Tyr Asn Lys Ile Leu Asp Ser Leu Ser
705                 710                 715                 720

Asn Asp Ile Asn Asp Asn Val Asn Ser Leu Gln Glu Ile Lys Asp Phe
                725                 730                 735

Thr Arg Phe Phe Ser Tyr Asp Ile Lys Pro Gly Met Tyr Met Asn Thr
            740                 745                 750

Trp Asp Lys Ile Asp Lys Asn Val Val Leu Glu Tyr Ala Val Lys Gln
        755                 760                 765

Asn Asn Lys Asn Gln Tyr Pro Gln Phe Ile Val Leu Leu Gln Asp Asp
    770                 775                 780

Ser Leu Ser Lys Arg Val Gly Glu Val Leu Ser Ser Tyr His His Asp
785                 790                 795                 800
```

```
Lys Ser Val Val Leu Gln Phe Asp Ala Arg Ser Ser Glu Ala Arg Ile
                805                 810                 815

Ala Tyr Gly Val Pro Ser Asn Ile Ala Glu Met Gly Gly Phe Glu Leu
                820                 825                 830

Ser Phe Val Thr His Gly Ala Pro Asp Gly Leu Tyr Ser Phe Ser Ile
                835                 840                 845

Ala Asn Ile Ile Asp Ile Tyr Lys Leu Thr Thr Asn Ser Phe Ala Leu
                850                 855                 860

Pro Pro Pro Val Lys Ile Arg Leu Val Ile Cys Ser Ile Ala Asp Asn
865                 870                 875                 880

Gly Gln Gly Ala Gln Gly Phe Asn Gly Thr His Pro Ala Leu Gly Ile
                885                 890                 895

Val Asn Met Met His Gln Glu Gly Phe Asp Ile Pro Ile Leu Ala Tyr
                900                 905                 910

Thr Thr Lys Val Gly Val Ser Val Glu Tyr Pro Gly Glu Leu Val Val
                915                 920                 925

Phe Asn Ser Glu Asn Gln Gly Gly Val Leu Glu Asn Ile Asp Asp Tyr
                930                 935                 940

Gln Val Leu Tyr His Tyr Lys Asn Asn Ile Leu Leu Ile Asp Gly Ile
945                 950                 955                 960

Pro Ala Val Glu Leu Leu Leu Lys Asp Val Arg Asp Lys Ile Lys Ser
                965                 970                 975

Val Asp Gln Leu Ile Glu Ser Tyr Ser Gln Tyr Leu Val Pro Phe Phe
                980                 985                 990

Ser Asp Asn Asn Gly Val Ile Asp Arg Asn Leu Leu Glu Leu Thr Ile
                995                 1000                1005

Asn Asp Ser Asn Thr His Ser Lys Phe Glu Asn Phe Leu Asp Ile
        1010                1015                1020

Ile Arg Gln Arg Pro Glu Leu Arg Asn Ser Asp Asn Trp Gln Leu
        1025                1030                1035

Val Val Ala Asn Asn Ala Thr Gly Phe Leu Ile Thr Thr Leu Asp
        1040                1045                1050

Glu Pro Val Val Lys Tyr Pro Asp Ile Val Lys Val Asn Glu Trp
        1055                1060                1065

Asp Leu Pro Ala Ile Ala Asn Ile Asp Lys Thr Ala Thr Ala Ser
        1070                1075                1080

Gln Tyr Asp Met Gln Ile Val Phe Gln Cys Glu Asn Asn Pro Thr
        1085                1090                1095

Val Asn Arg Ala Ala Thr Arg Leu Ala Gly Lys His Ala Lys Asn
        1100                1105                1110

Ser Ile Ile Ile Gln Leu Asp Val Asp Asn Asn His Arg Ala Phe
        1115                1120                1125

Ile Ile Asp Asp Asn Ile His Ala Glu Trp Arg Glu Ile Ser His
        1130                1135                1140

Asn Glu Leu Val Thr Lys Leu Lys Ile Gln Pro Glu Asn Gly Lys
        1145                1150                1155

Ile Arg Trp Gln Val Val Gly His Gly Arg Ser Glu Gly Gly Asn
        1160                1165                1170

Asp Lys His Pro Thr Leu Ala Gly Gln Arg Pro Glu Gln Leu Thr
        1175                1180                1185

Ala Arg Leu Asn Gln Phe Ser Asp Tyr Leu Gln Thr Glu His Gln
        1190                1195                1200

Ile Asn Ile Ser Pro Gln Gln Val Ser Leu Val Gly Cys Ala Met
```

-continued

```
            1205                    1210                    1215
Ser Ser Ser Asp Arg Tyr Thr Ser Phe Ala His Lys Phe Met Ser
    1220                    1225                    1230
His Leu Asn Glu Asn Gly Ile Arg Thr Asn Val Ser Ala Ser Thr
    1235                    1240                    1245
Lys Ala Ile Glu Val Asp Pro Leu Gly His Lys His Asp Val Asp
    1250                    1255                    1260
Thr Pro Asp Ile Asp Ser Tyr Asn Asn Lys Tyr Leu Ser Ser Ile
    1265                    1270                    1275
Lys Gly Thr Glu Lys Leu Tyr Trp Asn Arg Trp Gly Glu Ile Thr
    1280                    1285                    1290
Thr Glu Arg Lys Lys Asp Ile Asn Gly Arg Leu Asn Asn Ile Asp
    1295                    1300                    1305
Ser Leu Leu Asp Asn Leu Ile Thr Arg Gln Leu Ser Val Asn Gln
    1310                    1315                    1320
Ile Asn Lys Lys Gln Gln Arg Lys Leu Ala Glu Ile Phe Pro Gln
    1325                    1330                    1335
Leu Thr Asp Lys Lys Leu Asn Lys Gly Glu Leu Leu Leu Thr Leu
    1340                    1345                    1350
His Asp Ser Trp Arg Met Gln Thr Leu Lys Tyr Asp Leu Leu Phe
    1355                    1360                    1365
Leu Gln Lys Ile Ser Asp Arg Pro Asp Phe Asp Thr Glu Leu Trp
    1370                    1375                    1380
Arg Val Thr Asp Arg Trp Arg Ile Thr Glu Thr Asp Gly Asn Thr
    1385                    1390                    1395
Leu Gln Asp Val Arg Ile Lys Ser Gly Ser Gln His Lys Thr Asp
    1400                    1405                    1410
Leu Ala Thr Tyr Pro His Ser Ile Thr Ser Asp Pro Asp Leu Lys
    1415                    1420                    1425
Thr Ser Asn Pro Lys Ala Arg Thr Ala Ile Phe Gly Arg Phe Gly
    1430                    1435                    1440
Tyr Gly Met Gln Gly Tyr Gly Phe Ile Ser Ala Leu Arg Leu Ser
    1445                    1450                    1455
Ala Asp Tyr Gln Arg Trp Met Ser Asn Gly Asp Leu Thr Glu Lys
    1460                    1465                    1470
Gln Glu Glu Glu Ile Gln Leu Gln Leu Ala Met Ala Trp Gly Gly
    1475                    1480                    1485
Ile Gly Ala Asn Leu Ala Thr Asp Gly Leu Gln Tyr Ala Phe Gly
    1490                    1495                    1500
Lys Trp Gly Ile Gly Tyr Leu Gln Lys Leu Val Ser Lys Gly Gly
    1505                    1510                    1515
Arg Leu Ser Pro Ala Leu Leu Ser Gln Leu Thr Leu Leu Lys Arg
    1520                    1525                    1530
Asn Pro Ala Leu Leu Leu Ala Pro Gly Phe Leu Lys Asp Leu Arg
    1535                    1540                    1545
Lys Leu Ala Leu Asn Gln Phe Ala His Gly Ala Ala Arg Phe Ser
    1550                    1555                    1560
Met Pro Leu Leu Ser Ala Leu Thr Ser Gly Ile Asp Ile Tyr Gln
    1565                    1570                    1575
Ala Tyr His Ala Phe Ser Gln Leu Ala Thr Glu Thr Asp Pro His
    1580                    1585                    1590
Val Arg Arg Asp Leu Ile Ala Ser Gly Val Phe Ser Thr Ile Asn
    1595                    1600                    1605
```

-continued

```
Ala Thr Ile Gly Leu Gly Val Ala Phe Ala Met Ala Met Gly Gly
1610                1615                1620

Thr Ala Ala Thr Ala Ala Gly Pro Ala Gly Ile Ala Leu Ala Phe
1625                1630                1635

Thr Met Ile Ile Val Gly Asp Ile Tyr Ser Ala Val Ser Gln Ile
1640                1645                1650

Glu Arg Ile Arg Asp Ile Val Pro Asp Met Thr Gly Ser Gln Arg
1655                1660                1665

Phe Glu Asn Gly Leu Arg Leu Phe Leu Lys Phe Gly Leu Thr Pro
1670                1675                1680

Gly Leu Asp Asn Gln Ile Arg Tyr Asn Gln Thr Met Glu Ser Val
1685                1690                1695

Tyr Gln Arg Gln Arg Asp Tyr Tyr Glu Ala Leu Leu Ala Ser Lys
1700                1705                1710

Gln Gly Val Asp Thr Leu Phe Tyr Ser Arg Gly Glu Ala Val Leu
1715                1720                1725

Lys Ala Ile Pro Phe Ile Lys Arg Asp Glu Arg Ser Gln Thr Glu
1730                1735                1740

Arg Asp Leu Glu Lys Ile Ser Ile Phe Ser Gly Asp Pro Phe Thr
1745                1750                1755

Asn Ala Lys Ile Tyr Thr Thr Tyr Ala Glu Met Gly Lys His Glu
1760                1765                1770

Tyr Tyr Glu Leu Asp Lys Ile Asn Asp Val Asp Tyr Val Ile
1775                1780                1785

Ala Asp Phe Phe Glu Asp Asn Arg Ser Val Val Lys Leu Gln
1790                1795                1800

Asn Lys Asn Leu His Gln Ala Phe Ser Glu Leu Asp Ile Asp Ser
1805                1810                1815

Thr Tyr Ser Pro Phe Ile Leu Ser Ala Asp Val Asp Arg Asn Gly
1820                1825                1830

Leu Asn Asp Phe Ile Val Ile Asn Glu Lys Tyr Asn Thr Thr Ile
1835                1840                1845

Ala Ser Arg Lys Asn Ser Val Gly Met Thr Val Ile Asp Asp Tyr
1850                1855                1860

Val Ser Arg Trp His Tyr Glu Leu Tyr Thr Trp Leu Ala Gln Pro
1865                1870                1875

Asp Gly Ser Tyr Leu Lys Ile Asp Thr Arg Leu Glu Trp Glu Lys
1880                1885                1890

Leu Phe His Ala Ile Glu Val Asp Lys Phe Asn Glu Val Val Phe
1895                1900                1905

Pro Val Leu Gly Asp Phe Asn Gly Asp Asn Val Phe Glu Leu Val
1910                1915                1920

Ile Phe His Asp Asp Lys Met Thr Thr Tyr His Tyr Asp Ser Leu
1925                1930                1935

Asp Phe Asn Gln Ser Gly Lys Asp Asn His Asn Val Ile Asn Ile
1940                1945                1950

Gly Asp Phe Ile Glu Pro Val Arg Leu Ala Phe Glu Gly Glu Lys
1955                1960                1965

Ser Lys Asn Tyr Pro Tyr Ser Leu Val Gly Asp Ile Asn Asn Asp
1970                1975                1980

Gly Phe Asp Asp Ile Leu Leu Leu Asn Lys Ser Gly Asp Met Leu
1985                1990                1995

His Leu Met Gly Asn Ser Ser Gly Val Phe Arg Gln His Lys Thr
2000                2005                2010
```

```
Lys Leu Ser Ser Glu Leu Thr Ser Leu Leu Ser Ser Ser Asn Leu
    2015                2020                2025

His Arg Ser Gln Leu Gln Leu Thr Asp Leu Asn Lys Asp Gly Gly
    2030                2035                2040

Leu Asp Leu Val Ile Ile Leu Asn Asp Gly Ile Tyr Tyr Gln Ala
    2045                2050                2055

Leu Gly Asp Lys Ile Asp Gly Glu Tyr His Phe Asp Thr Pro Ser
    2060                2065                2070

Met Val Asn Lys Ile Thr Ile Lys Thr Glu Gly Gly Asp Ser Val
    2075                2080                2085

Arg Tyr Gln Gln Asn Arg Leu Ser Gln Ile Asn Lys Asn Lys Ile
    2090                2095                2100

Ile Ala Ile Ser Pro Ser Asp Gln Gly Leu Asn Arg Leu Ile Ser
    2105                2110                2115

Leu Ser Asp Ser Gly Glu Leu Leu Ala His Pro Leu Arg Glu Ile
    2120                2125                2130

Lys Glu Asn Asp Val Ala Ala Leu Phe Asp Leu Gly Gly Gly Asp
    2135                2140                2145

Asp Val Ala Lys Gly Tyr His Lys Lys Lys Asn Ile Phe Thr Ile
    2150                2155                2160

Gly Ser Gly Phe Lys Gln Tyr Gln Gly Gly Glu Asn Ala Asp Thr
    2165                2170                2175

Phe Ile Leu Thr Ser Ala Ala Ala Ser Lys Ser His Ile Leu Ser
    2180                2185                2190

Gly Gly Glu Gly Asn Asp Thr Val Ala Leu Gly Glu Val Leu Gly
    2195                2200                2205

Asn Glu Ile Asp Ser Ile Ile Asp Ile Ser Lys Gly Tyr Tyr Ser
    2210                2215                2220

Gln Val Asn Gly Gly Val Glu Lys Gln Val Ala Leu Leu Tyr Asp
    2225                2230                2235

Phe Glu Asn Ile Leu Gly His Glu Asn Val Asn Asp Thr Ile Ile
    2240                2245                2250

Gly Asn Asp Val Asp Asn Tyr Leu Asn Gly Met Gly Gly Asp Asp
    2255                2260                2265

Lys Ile Trp Gly Asn Gly Gly Asn Asp Leu Leu Ala Leu Gln Ser
    2270                2275                2280

Gly Leu Ala Gln Gly Gly Thr Gly Leu Asp Ser Tyr His Ile Leu
    2285                2290                2295

Lys Ser Thr His Glu Lys Ser Leu Gln Ile Arg Ile Glu Glu Val
    2300                2305                2310

Ser Glu Asn Asn Asn Thr Asp Met Gln Ile Ser Asn Ile Phe Leu
    2315                2320                2325

Glu His Lys Leu Asn Gln Ile Lys Ser Ile Glu Leu Asp Asn Ile
    2330                2335                2340

Asp Val Leu Ile Asn Ile Asn Asn Asp Asn Gly Phe Met Thr Gln
    2345                2350                2355

Ile Arg Leu Val Gly Val Tyr Asn Ile Asn Asn Asn Gln Lys Gln
    2360                2365                2370

Gln Val Leu Asn Phe Thr Ile Gln Thr Val Asp Gly Phe Thr Met
    2375                2380                2385

Val Pro Leu Trp Pro Ser Tyr Leu Asn Glu Ile Thr Glu Phe Ser
    2390                2395                2400

Pro Asn Met Val Ala Tyr Tyr Ser Ser Leu Val Asp Arg Asn Tyr
```

-continued

```
        2405                2410                2415

Lys Glu Leu Val Gly Lys Gly Asp Pro Asp Ile Val Val Arg
    2420                2425                2430

Phe Ser Leu Asp Asn Gly Tyr Gln Gln Gln Val Thr His Leu
    2435                2440                2445

Gln Arg Val Glu Gly Glu Lys Asp Ile Val Leu Arg Gln Ala Ile
    2450                2455                2460

Leu Pro Asp Phe Ile Arg Leu Ser Pro Gln Glu His Ser Met Leu
    2465                2470                2475

Met Gly Phe Leu Pro Arg Tyr Glu Leu Leu Gly Asp Asn Lys Asp
    2480                2485                2490

Asn Leu Leu Gln Val Leu Ser Gly Glu Gly Leu Leu Glu Gly Arg
    2495                2500                2505

Gly Gly Gln Asp Thr Tyr Leu Ile Gln Glu Lys Glu Gly Ser Pro
    2510                2515                2520

Thr Asp Ile Ile Ile Asn Asn Phe Asp Asp Ser Leu Ala Ser Asp
    2525                2530                2535

Asn Leu Val Leu Ser Ser Trp Leu Leu Cys Asp Val Ile Val Glu
    2540                2545                2550

Arg Ser Asp Asp Asp Leu Leu Leu Arg Tyr Arg Asp Gln Pro Glu
    2555                2560                2565

Lys His Gln Ser Ile Arg Leu Val Asn Tyr Met Asn Asp Glu Arg
    2570                2575                2580

Tyr Arg His Leu Lys Ile Thr Asp Lys Ser Gly Gln Ser Gln Tyr
    2585                2590                2595

Arg Asp Pro Val Thr Gly Thr Phe Ile Asp Tyr Gln Ile Asn Leu
    2600                2605                2610

Asp Lys Asn Gly His Pro Phe Ile Ala Ala Gln Gln Ala Pro Val
    2615                2620                2625

Val Ser Ser Gly Asn Asp Glu Val Val Ile Asn Ser Ala Thr Phe
    2630                2635                2640

Leu Pro Gly Asn Tyr Ile Asp Thr Gly Asp Gly Asn Asp Ala Ile
    2645                2650                2655

Ile Tyr Ile Arg Gly His Glu Gly Thr Met Leu Lys Gly Gly Gly
    2660                2665                2670

Gly Asp Asp Thr Tyr Tyr Tyr Ser Ala Gly Ser Gly Ala Ile Asn
    2675                2680                2685

Ile Ala Asp Thr Ser Gly Leu Asp His Leu Tyr Leu Asp Lys His
    2690                2695                2700

Ile Leu Leu His Thr Leu Ser Ala Glu Arg Arg Glu Asn Asn Leu
    2705                2710                2715

Val Leu Asn Ile Ala Asp Asn Thr Ser Gly Arg Ile Ile Phe Val
    2720                2725                2730

Asp Trp Tyr Leu Ala Asp Glu Asn Lys Val Asp Phe Ile Trp Val
    2735                2740                2745

Glu Gly Ser Gln Ile Thr Phe Asp Glu Leu Phe Ser Leu Cys Pro
    2750                2755                2760

Tyr Ser Asp Glu Tyr Tyr Gln Leu Cys Gln Gln Leu Lys Ser Met
    2765                2770                2775

Gly Leu Ser Leu Thr Val Arg Gln Leu Ala Asp Leu Asp Ser Gln
    2780                2785                2790

Asp Gly Tyr Asn Thr Leu Asn Gln Leu Arg Thr Ile Lys Ala Trp
    2795                2800                2805
```

```
Ala Thr Lys Asn Pro Ile Tyr Asp Val Ala Asp Leu Asp Tyr Leu
    2810            2815                2820

Val Ala Met Ser Ser Ile Ala Trp Arg Gly Asn Ala Arg Asn Thr
    2825            2830                2835

Asp Pro Leu Pro Leu Ile Glu Gln Lys Ile Asp Ala Phe Phe Gln
    2840            2845                2850

Pro Leu Ile Ala Glu Arg Ile Ser Leu Thr Glu Glu His Val Thr
    2855            2860                2865

Trp Ile Gln Arg Glu Glu Phe Asp Thr Val Asp Ile Ala Lys Trp
    2870            2875                2880

Val Lys Asn Tyr His Leu Arg Ser Gln Asn Glu Ile Asn Tyr Leu
    2885            2890                2895

Leu Glu Gln Leu Gly Leu Leu Lys Glu Ser Pro Leu Ser Asp Lys
    2900            2905                2910

Ala Leu Asp Phe Thr Phe Lys Asn Arg Ile Asp Leu Ala Gln Ala
    2915            2920                2925

Asp Ile Glu Leu Cys Gln Gln Glu Cys Gly Ile Asn Arg Gln Ser
    2930            2935                2940

Leu Ile Asn Leu Ala Met Lys Tyr His Val Thr Gly Arg Gly His
    2945            2950                2955

Phe Glu Leu Leu Ile Ser Asn Ile Gln Val Leu Lys Glu Tyr Gly
    2960            2965                2970

Val Val Val Ser Glu Ser Glu Gln Pro Leu Val Leu Arg Lys Pro
    2975            2980                2985

Ile Asp Leu Arg Gln Tyr Phe Asn Gln Lys Asn Leu Thr Lys Asp
    2990            2995                3000

His Val Gly Arg Leu Ala Glu His Asp Met Ser Phe Asp Glu Leu
    3005            3010                3015

Thr Leu Leu Leu Asp Lys Asn Ile Pro Ile Glu Gln Ala Phe Thr
    3020            3025                3030

Gln Arg Leu Gln Thr Gln Leu Gly Pro Leu Lys Leu Phe Asn Asp
    3035            3040                3045

Glu Arg Val Leu Asn Gln Gly Asp Ile Phe Asp Gln Asp Ile Ser
    3050            3055                3060

Gln Leu Ala Glu Ala Met Gly Gly Leu Glu Ser Thr Glu Ser Tyr
    3065            3070                3075

Ser Leu Pro Leu Glu Arg Gln Thr Ala Met Ala Ile Thr Thr His
    3080            3085                3090

Gln Phe Val Ser Asp Ser Ile Ala Ala Tyr
    3095            3100

<210> SEQ ID NO 11
<211> LENGTH: 1449
<212> TYPE: PRT
<213> ORGANISM: Yersinia mollaretti

<400> SEQUENCE: 11

Met Gly Glu Thr Ile Asp Phe Ser Val Trp Glu Ser Pro Asp Gln Ala
1               5                   10                  15

Tyr Phe Thr Ser Leu Pro Asn Thr Pro Leu Glu Pro Glu Gly Thr His
            20                  25                  30

Tyr Glu Lys Thr Leu Ile Phe Gln Leu Gln Gly Asp Asp Thr Cys Phe
        35                  40                  45

Glu Ala Ser Arg Ala Leu Phe Asn Lys His Arg Tyr Thr Ser Glu Trp
    50                  55                  60
```

```
Leu Gln Leu Gly Asp Gly Lys Pro Ala Glu Val Phe Thr Trp Gly Glu
 65                  70                  75                  80

Thr Tyr Lys Lys Phe Val Tyr Thr Ser Pro Leu Lys Leu Asp Lys Glu
                 85                  90                  95

Gly Lys Ile Arg Ile Thr Leu Val Gly His Gly Glu Thr Glu Gly Asp
            100                 105                 110

Thr Thr Thr Phe Gly Gly Met Asn Ala Glu Thr Leu Lys Gly His Leu
        115                 120                 125

Ser Ser Leu Phe Ala Arg Leu Gly Ser Ser Val Leu Ile Lys Gly
    130                 135                 140

Ile Thr Leu Asn Leu Thr Gly Cys Ser Leu Leu Asn Pro Lys Gln Pro
145                 150                 155                 160

Leu Ala Asp Thr Leu Pro Gly Gln Leu Ala Ile Trp Leu Lys Gln Gln
                165                 170                 175

Ala Glu Ile Leu Gly Leu Asp Asp Ser Asn Trp Ser Val Asn Ala Arg
            180                 185                 190

Glu Asn Asp Leu Leu Val Leu Glu Asn Gly Lys Lys Glu Ile Arg Ile
        195                 200                 205

Asn Asp His Trp Ile Asn Lys Glu Val Ala Asp Ile His Gly Leu Val
210                 215                 220

Tyr Lys Thr Lys Leu Val Trp Asn Lys Glu Thr Gln Ser Leu Tyr Lys
225                 230                 235                 240

Leu Pro Leu Ser Ile Glu Glu Leu Gln Gln Val Thr Pro Tyr Ile Asp
                245                 250                 255

Asp Ala Ile Ala Thr His Asn Gln Leu Asp Ser Gln Ser Ala Thr Leu
            260                 265                 270

Leu Glu Glu Met His Arg Gln Val Ser Gln Arg Ile Ser Glu Leu Leu
        275                 280                 285

Leu Leu Asn Glu Lys His Glu Ser His Arg Asn Glu Ile Glu Gln Arg
290                 295                 300

Val Ser Glu Leu Leu Glu Leu Val Asn Leu Gly Asn Glu Trp Asn Asp
305                 310                 315                 320

Ala Ala Ser Gln Leu His Leu Asp Asn His Leu Asp Glu His Trp His
                325                 330                 335

Ala Thr Phe Thr Val Gln Ala Gly Glu Asn Gly Gly His Gln Val Ala
            340                 345                 350

Phe Val Asn Ser Leu Thr Asp Lys Ile Gln Tyr Ile Ser Thr Arg Glu
        355                 360                 365

Ser Ile Phe Ser Glu Phe Ser Gln Arg Tyr Glu Gln Leu Leu Gly His
370                 375                 380

Phe Ser Ser Gly Leu Met Leu Asp Lys Gln Ser Gly Lys Ile Ile Ala
385                 390                 395                 400

Lys Pro Asn Val Leu Glu Gly Glu Ala Ala His Thr Leu Asn Ala Ala
                405                 410                 415

Phe Met Leu Gln Thr Leu Met Asn Ile Asn Pro Ser Asn Gly Gly Ile
            420                 425                 430

Asn Ala Leu Ser Trp Pro Leu Gln Leu Gln Thr Tyr Thr Gln Leu Ala
        435                 440                 445

Gln Asn Thr Leu Gly Leu Val His Asp Val Ser Ala Val Ala Asn Leu
450                 455                 460

Val Lys Leu Ala Ser Ala Thr Glu Leu Lys Pro Leu Ser Ala Ala Thr
465                 470                 475                 480

Ser Leu Leu Gly Thr Val Ala Pro Gly Val Val Gly Leu Leu Leu Asp
                485                 490                 495
```

```
Ala Ala Asn Ile Leu Gly Met Ser Phe Gln Leu Ser Ala Ser Thr Asp
            500                 505                 510
Pro Val Glu Ile Asn Thr Thr Ile Ala Asn Leu Thr Leu Ser Ser Leu
            515                 520                 525
Met Val Gly Thr Asn Ile Ala Ala Leu Leu Thr Ser Leu Ser Ala Ala
            530                 535                 540
Ser Ala Ala Val Ser Gly Leu Leu Gly Met Val Ala Val Pro Leu Ala
545                 550                 555                 560
Gly Ile Ala Ala Gly Leu Pro Ala Leu Val Gly Asn Tyr Thr Thr Leu
            565                 570                 575
Ala Glu Gln Asn Lys Ser Ala Leu Thr Ala Phe Asp Ala Ile Gln Thr
            580                 585                 590
Ser Val Ser Gln Pro Asn Gln Leu Arg Lys Ile Ser Asp Ala Gly Gln
            595                 600                 605
Ser Pro Ile Val Trp Gly Leu Ala Met Gly Ala Val Val Asp Ser Ile
            610                 615                 620
Asn Phe Arg Asp Asn His Val His Phe Gly Ser Val Thr Ser Val Gly
625                 630                 635                 640
Ser Lys Gly Gly Ser Trp His Thr His Ser Gly His Trp Asp His Tyr
            645                 650                 655
Leu Ser Gly Pro Ser Ile Asp Tyr Gly Leu Lys Leu Asp Leu Tyr Leu
            660                 665                 670
Gly Leu Gly Leu Lys Glu His Thr Gln Glu Leu Asp Leu Thr Asp Ala
            675                 680                 685
Gln Ile Phe Leu Leu Pro Ala Ser Ala Gln Arg His Tyr Thr Phe Gly
            690                 695                 700
Tyr Asp Glu Ala Pro Gly Ile Arg Tyr Lys Asn Pro Ser Ala Leu Met
705                 710                 715                 720
Ala Leu Gly Gln Tyr Tyr Gly Ala Gln Phe Lys Trp Gly Phe Tyr Ala
            725                 730                 735
Leu Pro Thr Asp Trp Ala Ile Thr Arg Leu Thr Ala Glu Leu Phe Ser
            740                 745                 750
Thr Pro Ile Asn Val Gln Leu Asp Ser Arg Ala Arg Thr Leu Ile Val
            755                 760                 765
Pro Thr Leu Leu Asp Asp Thr Glu Arg Gly Lys Leu Phe Tyr Gln Leu
            770                 775                 780
Ile Gly Asn Gly Gly Glu Tyr Thr Leu Ile Met Pro Ser Lys Thr Val
785                 790                 795                 800
Ala Ile Thr Ile Thr Cys Ala Asp Ala Asp Lys Glu His Trp Ile Phe
            805                 810                 815
Asp Ile Glu Ala Leu Ile Lys Gln Ser Ser Val Val Asp Asn Lys Ile
            820                 825                 830
Val Leu Gly Ala Leu Leu Pro Glu Arg Ile Lys Ala Ile Thr Leu His
            835                 840                 845
Asn Asn Ile Leu Ser Val Gly Asp Gln Arg Ile Gln Phe Asn Gly Lys
850                 855                 860
Pro Pro Val His Leu Leu Leu Glu Ser Arg Leu Thr Leu Thr Gly Val
865                 870                 875                 880
Thr Lys Gln Asn Asn Ser Leu Pro Thr Leu Thr Leu Ala Leu Ser Val
            885                 890                 895
Gly Glu Gln Asn Ser Pro Pro Arg Pro Val Leu Met Phe Ser Asp Asp
            900                 905                 910
Thr Leu Leu Glu Gln Tyr Ala Ala Gln Ile Leu Gln Ala Val Arg Pro
```

-continued

```
               915                 920                 925
Leu Ala Ser Leu Val Ala Lys Ile Pro Phe Val Ala Gly Lys Ser Asn
        930                 935                 940
Gly Val Ile Asp Ile Ala Asn Asn Trp Leu Trp Leu Ala Gln Ser Gln
945                 950                 955                 960
Gly Gln Leu Leu Leu Cys Asp Gly Asn Arg Leu Ser Lys Ser Leu Phe
                965                 970                 975
Pro Lys Ser Ala Gln Val Leu Ile Gly Pro Asn Asp Lys Ile Met Ala
            980                 985                 990
Thr Gly Lys Met Gly Asp Leu Ser Phe Asn Ala Ile Leu Glu Gln Gln
            995                 1000                1005
Ser Gly Asn Ile Ala Val Ser Leu Ile Tyr Leu Glu Ile Val Ile
    1010                1015                1020
Ala Asp Ala Thr Ser Phe Ser Gln Ala Pro Phe Gln Glu Phe Ala
    1025                1030                1035
Asp His Ser Leu Gly Gly Val Ile Asp Ser Leu Leu Ala Arg Tyr
    1040                1045                1050
Pro Gly Ser Phe Ala Arg Glu Asn Leu Ser Phe Asn Pro Gln Gly
    1055                1060                1065
Val Trp Arg Phe Ala Ser Gln Gln Gly Glu Gly Phe Ser Phe Ala
    1070                1075                1080
Leu Ser Glu Arg Asp Leu Leu Ser Val Ser Asn Ala Asn Trp Ser
    1085                1090                1095
Asn Ser Gln Ala Glu Phe Ile Tyr Asn Asn Leu Tyr Ser Ser Thr
    1100                1105                1110
Thr Lys Thr Leu Glu Val Lys Ala Lys Ala Thr Thr Val Glu Leu
    1115                1120                1125
Asn Leu Ser Lys Gln Gln Leu Glu Leu Asn Trp Leu Asp Lys Asn
    1130                1135                1140
Thr Gln Ile Ile Ile Phe Tyr Gln Asp Asn Leu Ser Cys Ile Gly
    1145                1150                1155
Leu Ala Leu Asn Asp Ile Pro Val Ala Asn Leu Tyr Ile Ala Gly
    1160                1165                1170
Leu Ser Arg Lys Asn Arg Phe Thr Val Asn Ile Leu Asp His Thr
    1175                1180                1185
Gln Gln Ser Met Leu Leu Asn Ile Thr Asp Asn Asp Phe Val Met
    1190                1195                1200
Arg Ser Asn Leu Gly His Ser Ile Lys Val Ala Asn Ala Leu Asn
    1205                1210                1215
Met Glu Glu Ile Leu Phe Ser Phe Leu Asn Ser Gln Gln Met
    1220                1225                1230
Ser Phe Gln Lys Ile Lys Ala Asn Ile Leu Phe Ser Leu Asn Lys
    1235                1240                1245
Pro Ile Thr Gln Val Met Thr Tyr Phe Asn Leu Glu Ser Ile Pro
    1250                1255                1260
Asn Ala Glu Leu Ile Asp Gly Tyr Tyr His Phe Met Gly Lys Ser
    1265                1270                1275
Gly Leu Tyr Tyr Gln Ala Pro Met Asp Ile Ala Ala Ala Asn Lys
    1280                1285                1290
Ala Ala Asp Ile Ala Asp Ala Ala Asp Ile Thr His Ala Gln Ile
    1295                1300                1305
Gln Val Gln Gln Leu Ala Ser Ile Val Pro Phe Phe Asp Met
    1310                1315                1320
```

```
Glu  Pro  Glu  Pro  Thr  Leu  Ser  Asn  Gly  Arg  Ala  Phe  Thr  Val  Val
     1325                1330                    1335

Gly  Tyr  Lys  Gly  Pro  Gln  Ala  Tyr  Arg  Ile  Pro  Asn  Ile  Arg
     1340                1345                    1350

Ser  Ile  Ser  Ile  Leu  Leu  Gln  Ile  Ile  Gln  Gly  Gly  Thr  Ile  Phe
     1355                1360                    1365

Asn  Gly  Val  Lys  Phe  Gln  Asn  Ile  Asn  Leu  Asp  Thr  Phe  Phe  Pro
     1370                1375                    1380

Glu  Thr  Gly  Gln  Glu  Ala  Ile  Ile  Trp  Leu  Gln  Lys  Ile  Glu  Met
     1385                1390                    1395

Leu  Val  Thr  His  Ser  Gly  Gln  Asn  Gln  Phe  Ile  Gln  Arg  Leu  Met
     1400                1405                    1410

Phe  Gly  Ser  Gln  Pro  Asn  Thr  Ser  Ile  Glu  Ile  Asn  Ile  Arg  Asp
     1415                1420                    1425

Val  Lys  Lys  Phe  Ile  Asn  Asp  Tyr  Leu  Asn  Lys  Ala  Ile  Lys  Gln
     1430                1435                    1440

Gly  Gly  Trp  Val  Ser  Asn
     1445
```

<210> SEQ ID NO 12
<211> LENGTH: 2710
<212> TYPE: PRT
<213> ORGANISM: Clostridium difficile

<400> SEQUENCE: 12

```
Met  Ser  Leu  Ile  Ser  Lys  Glu  Glu  Leu  Ile  Lys  Leu  Ala  Tyr  Ser  Ile
1                     5                      10                      15

Arg  Pro  Arg  Glu  Asn  Glu  Tyr  Lys  Thr  Ile  Leu  Thr  Asn  Leu  Asp  Glu
                 20                      25                      30

Tyr  Asn  Lys  Leu  Thr  Thr  Asn  Asn  Asn  Glu  Asn  Lys  Tyr  Leu  Gln  Leu
             35                      40                      45

Lys  Lys  Leu  Asn  Glu  Ser  Ile  Asp  Val  Phe  Met  Asn  Lys  Tyr  Lys  Thr
50                   55                      60

Ser  Ser  Arg  Asn  Arg  Ala  Leu  Ser  Asn  Leu  Lys  Lys  Asp  Ile  Leu  Lys
65                   70                      75                      80

Glu  Val  Ile  Leu  Ile  Lys  Asn  Ser  Asn  Thr  Ser  Pro  Val  Glu  Lys  Asn
                 85                      90                      95

Leu  His  Phe  Val  Trp  Ile  Gly  Gly  Glu  Val  Ser  Asp  Ile  Ala  Leu  Glu
             100                     105                     110

Tyr  Ile  Lys  Gln  Trp  Ala  Asp  Ile  Asn  Ala  Glu  Tyr  Asn  Ile  Lys  Leu
         115                     120                     125

Trp  Tyr  Asp  Ser  Glu  Ala  Phe  Leu  Val  Asn  Thr  Leu  Lys  Lys  Ala  Ile
130                  135                     140

Val  Glu  Ser  Ser  Thr  Thr  Glu  Ala  Leu  Gln  Leu  Leu  Glu  Glu  Glu  Ile
145                  150                     155                     160

Gln  Asn  Pro  Gln  Phe  Asp  Asn  Met  Lys  Phe  Tyr  Lys  Lys  Arg  Met  Glu
                 165                     170                     175

Phe  Ile  Tyr  Asp  Arg  Gln  Lys  Arg  Phe  Ile  Asn  Tyr  Tyr  Lys  Ser  Gln
             180                     185                     190

Ile  Asn  Lys  Pro  Thr  Val  Pro  Thr  Ile  Asp  Asp  Ile  Ile  Lys  Ser  His
         195                     200                     205

Leu  Val  Ser  Glu  Tyr  Asn  Arg  Asp  Glu  Thr  Val  Leu  Glu  Ser  Tyr  Arg
     210                     215                     220

Thr  Asn  Ser  Leu  Arg  Lys  Ile  Asn  Ser  Asn  His  Gly  Ile  Asp  Ile  Arg
225                  230                     235                     240
```

-continued

```
Ala Asn Ser Leu Phe Thr Glu Gln Glu Leu Leu Asn Ile Tyr Ser Gln
            245                 250                 255

Glu Leu Leu Asn Arg Gly Asn Leu Ala Ala Ser Asp Ile Val Arg
        260                 265                 270

Leu Leu Ala Leu Lys Asn Phe Gly Gly Val Tyr Leu Asp Val Asp Met
        275                 280                 285

Leu Pro Gly Ile His Ser Asp Leu Phe Lys Thr Ile Ser Arg Pro Ser
        290                 295                 300

Ser Ile Gly Leu Asp Arg Trp Glu Met Ile Lys Leu Glu Ala Ile Met
305                 310                 315                 320

Lys Tyr Lys Lys Tyr Ile Asn Asn Tyr Thr Ser Glu Asn Phe Asp Lys
                325                 330                 335

Leu Asp Gln Gln Leu Lys Asp Asn Phe Lys Leu Ile Ile Glu Ser Lys
            340                 345                 350

Ser Glu Lys Ser Glu Ile Phe Ser Lys Leu Glu Asn Leu Asn Val Ser
        355                 360                 365

Asp Leu Glu Ile Lys Ile Ala Phe Ala Leu Gly Ser Val Ile Asn Gln
        370                 375                 380

Ala Leu Ile Ser Lys Gln Gly Ser Tyr Leu Thr Asn Leu Val Ile Glu
385                 390                 395                 400

Gln Val Lys Asn Arg Tyr Gln Phe Leu Asn Gln His Leu Asn Pro Ala
                405                 410                 415

Ile Glu Ser Asp Asn Asn Phe Thr Asp Thr Thr Lys Ile Phe His Asp
            420                 425                 430

Ser Leu Phe Asn Ser Ala Thr Ala Glu Asn Ser Met Phe Leu Thr Lys
        435                 440                 445

Ile Ala Pro Tyr Leu Gln Val Gly Phe Met Pro Glu Ala Arg Ser Thr
        450                 455                 460

Ile Ser Leu Ser Gly Pro Gly Ala Tyr Ala Ser Ala Tyr Tyr Asp Phe
465                 470                 475                 480

Ile Asn Leu Gln Glu Asn Thr Ile Glu Lys Thr Leu Lys Ala Ser Asp
                485                 490                 495

Leu Ile Glu Phe Lys Phe Pro Glu Asn Asn Leu Ser Gln Leu Thr Glu
            500                 505                 510

Gln Glu Ile Asn Ser Leu Trp Ser Phe Asp Gln Ala Ser Ala Lys Tyr
        515                 520                 525

Gln Phe Glu Lys Tyr Val Arg Asp Tyr Thr Gly Gly Ser Leu Ser Glu
        530                 535                 540

Asp Asn Gly Val Asp Phe Asn Lys Asn Thr Ala Leu Asp Lys Asn Tyr
545                 550                 555                 560

Leu Leu Asn Asn Lys Ile Pro Ser Asn Asn Val Glu Glu Ala Gly Ser
                565                 570                 575

Lys Asn Tyr Val His Tyr Ile Ile Gln Leu Gln Gly Asp Asp Ile Ser
            580                 585                 590

Tyr Glu Ala Thr Cys Asn Leu Phe Ser Lys Asn Pro Lys Asn Ser Ile
        595                 600                 605

Ile Ile Gln Arg Asn Met Asn Glu Ser Ala Lys Ser Tyr Phe Leu Ser
        610                 615                 620

Asp Asp Gly Glu Ser Ile Leu Glu Leu Asn Lys Tyr Arg Ile Pro Glu
625                 630                 635                 640

Arg Leu Lys Asn Lys Glu Lys Val Lys Val Thr Phe Ile Gly His Gly
                645                 650                 655

Lys Asp Glu Phe Asn Thr Ser Glu Phe Ala Arg Leu Ser Val Asp Ser
            660                 665                 670
```

```
Leu Ser Asn Glu Ile Ser Ser Phe Leu Asp Thr Ile Lys Leu Asp Ile
            675                 680                 685

Ser Pro Lys Asn Val Glu Val Asn Leu Leu Gly Cys Asn Met Phe Ser
        690                 695                 700

Tyr Asp Phe Asn Val Glu Thr Tyr Pro Gly Lys Leu Leu Leu Ser
705                 710                 715                 720

Ile Met Asp Lys Ile Thr Ser Thr Leu Pro Asp Val Asn Lys Asn Ser
                    725                 730                 735

Ile Thr Ile Gly Ala Asn Gln Tyr Glu Val Arg Ile Asn Ser Glu Gly
                740                 745                 750

Arg Lys Glu Leu Leu Ala His Ser Gly Lys Trp Ile Asn Lys Glu Glu
            755                 760                 765

Ala Ile Met Ser Asp Leu Ser Ser Lys Glu Tyr Ile Phe Phe Asp Ser
        770                 775                 780

Ile Asp Asn Lys Leu Lys Ala Lys Ser Lys Asn Ile Pro Gly Leu Ala
785                 790                 795                 800

Ser Ile Ser Glu Asp Ile Lys Thr Leu Leu Leu Asp Ala Ser Val Ser
                    805                 810                 815

Pro Asp Thr Lys Phe Ile Leu Asn Asn Leu Lys Leu Asn Ile Glu Ser
                820                 825                 830

Ser Ile Gly Asp Tyr Ile Tyr Tyr Glu Lys Leu Glu Pro Val Lys Asn
            835                 840                 845

Ile Ile His Asn Ser Ile Asp Asp Leu Ile Asp Glu Phe Asn Leu Leu
        850                 855                 860

Glu Asn Val Ser Asp Glu Leu Tyr Glu Leu Lys Lys Leu Asn Asn Leu
865                 870                 875                 880

Asp Glu Lys Tyr Leu Ile Ser Phe Glu Asp Ile Ser Lys Asn Asn Ser
                    885                 890                 895

Thr Tyr Ser Val Arg Phe Ile Asn Lys Ser Asn Gly Glu Ser Val Tyr
                900                 905                 910

Val Glu Thr Glu Lys Glu Ile Phe Ser Lys Tyr Ser Glu His Ile Thr
            915                 920                 925

Lys Glu Ile Ser Thr Ile Lys Asn Ser Ile Ile Thr Asp Val Asn Gly
        930                 935                 940

Asn Leu Leu Asp Asn Ile Gln Leu Asp His Thr Ser Gln Val Asn Thr
945                 950                 955                 960

Leu Asn Ala Ala Phe Phe Ile Gln Ser Leu Ile Asp Tyr Ser Ser Asn
                    965                 970                 975

Lys Asp Val Leu Asn Asp Leu Ser Thr Ser Val Lys Val Gln Leu Tyr
                980                 985                 990

Ala Gln Leu Phe Ser Thr Gly Leu Asn Thr Ile Tyr Asp Ser Ile Gln
            995                 1000                1005

Leu Val Asn Leu Ile Ser Asn Ala Val Asn Asp Thr Ile Asn Val
        1010                1015                1020

Leu Pro Thr Ile Thr Glu Gly Ile Pro Ile Val Ser Thr Ile Leu
        1025                1030                1035

Asp Gly Ile Asn Leu Gly Ala Ala Ile Lys Glu Leu Leu Asp Glu
        1040                1045                1050

His Asp Pro Leu Leu Lys Lys Glu Leu Glu Ala Lys Val Gly Val
        1055                1060                1065

Leu Ala Ile Asn Met Ser Leu Ser Ile Ala Ala Thr Val Ala Ser
        1070                1075                1080

Ile Val Gly Ile Gly Ala Glu Val Thr Ile Phe Leu Leu Pro Ile
```

```
              1085                1090                1095

Ala Gly Ile Ser Ala Gly Ile Pro Ser Leu Val Asn Asn Glu Leu
    1100                1105                1110

Ile Leu His Asp Lys Ala Thr Ser Val Val Asn Tyr Phe Asn His
    1115                1120                1125

Leu Ser Glu Ser Lys Lys Tyr Gly Pro Leu Lys Thr Glu Asp Asp
    1130                1135                1140

Lys Ile Leu Val Pro Ile Asp Asp Leu Val Ile Ser Glu Ile Asp
    1145                1150                1155

Phe Asn Asn Asn Ser Ile Lys Leu Gly Thr Cys Asn Ile Leu Ala
    1160                1165                1170

Met Glu Gly Gly Ser Gly His Thr Val Thr Gly Asn Ile Asp His
    1175                1180                1185

Phe Phe Ser Ser Pro Ser Ile Ser Ser His Ile Pro Ser Leu Ser
    1190                1195                1200

Ile Tyr Ser Ala Ile Gly Ile Glu Thr Glu Asn Leu Asp Phe Ser
    1205                1210                1215

Lys Lys Ile Met Met Leu Pro Asn Ala Pro Ser Arg Val Phe Trp
    1220                1225                1230

Trp Glu Thr Gly Ala Val Pro Gly Leu Arg Ser Leu Glu Asn Asp
    1235                1240                1245

Gly Thr Arg Leu Leu Asp Ser Ile Arg Asp Leu Tyr Pro Gly Lys
    1250                1255                1260

Phe Tyr Trp Arg Phe Tyr Ala Phe Phe Asp Tyr Ala Ile Thr Thr
    1265                1270                1275

Leu Lys Pro Val Tyr Glu Asp Thr Asn Ile Lys Ile Lys Leu Asp
    1280                1285                1290

Lys Asp Thr Arg Asn Phe Ile Met Pro Thr Ile Thr Thr Asn Glu
    1295                1300                1305

Ile Arg Asn Lys Leu Ser Tyr Ser Phe Asp Gly Ala Gly Gly Thr
    1310                1315                1320

Tyr Ser Leu Leu Leu Ser Ser Tyr Pro Ile Ser Thr Asn Ile Asn
    1325                1330                1335

Leu Ser Lys Asp Asp Leu Trp Ile Phe Asn Ile Asp Asn Glu Val
    1340                1345                1350

Arg Glu Ile Ser Ile Glu Asn Gly Thr Ile Lys Lys Gly Lys Leu
    1355                1360                1365

Ile Lys Asp Val Leu Ser Lys Ile Asp Ile Asn Lys Asn Lys Leu
    1370                1375                1380

Ile Ile Gly Asn Gln Thr Ile Asp Phe Ser Gly Asp Ile Asp Asn
    1385                1390                1395

Lys Asp Arg Tyr Ile Phe Leu Thr Cys Glu Leu Asp Asp Lys Ile
    1400                1405                1410

Ser Leu Ile Ile Glu Ile Asn Leu Val Ala Lys Ser Tyr Ser Leu
    1415                1420                1425

Leu Leu Ser Gly Asp Lys Asn Tyr Leu Ile Ser Asn Leu Ser Asn
    1430                1435                1440

Thr Ile Glu Lys Ile Asn Thr Leu Gly Leu Asp Ser Lys Asn Ile
    1445                1450                1455

Ala Tyr Asn Tyr Thr Asp Glu Ser Asn Asn Lys Tyr Phe Gly Ala
    1460                1465                1470

Ile Ser Lys Thr Ser Gln Lys Ser Ile Ile His Tyr Lys Lys Asp
    1475                1480                1485
```

-continued

| | | | | | | | | | | |
|---|---|---|---|---|---|---|---|---|---|---|
| Ser | Lys | Asn | Ile | Leu | Glu | Phe | Tyr | Asn | Asp | Ser | Thr | Leu | Glu | Phe |
| 1490 | | | | | 1495 | | | | | 1500 | | | | |

Ser Lys Asn Ile Leu Glu Phe Tyr Asn Asp Ser Thr Leu Glu Phe
1490                1495                1500

Asn Ser Lys Asp Phe Ile Ala Glu Asp Ile Asn Val Phe Met Lys
1505                1510                1515

Asp Asp Ile Asn Thr Ile Thr Gly Lys Tyr Tyr Val Asp Asn Asn
1520                1525                1530

Thr Asp Lys Ser Ile Asp Phe Ser Ile Ser Leu Val Ser Lys Asn
1535                1540                1545

Gln Val Lys Val Asn Gly Leu Tyr Leu Asn Glu Ser Val Tyr Ser
1550                1555                1560

Ser Tyr Leu Asp Phe Val Lys Asn Ser Asp Gly His His Asn Thr
1565                1570                1575

Ser Asn Phe Met Asn Leu Phe Leu Asp Asn Ile Ser Phe Trp Lys
1580                1585                1590

Leu Phe Gly Phe Glu Asn Ile Asn Phe Val Ile Asp Lys Tyr Phe
1595                1600                1605

Thr Leu Val Gly Lys Thr Asn Leu Gly Tyr Val Glu Phe Ile Cys
1610                1615                1620

Asp Asn Asn Lys Asn Ile Asp Ile Tyr Phe Gly Glu Trp Lys Thr
1625                1630                1635

Ser Ser Ser Lys Ser Thr Ile Phe Ser Gly Asn Gly Arg Asn Val
1640                1645                1650

Val Val Glu Pro Ile Tyr Asn Pro Asp Thr Gly Glu Asp Ile Ser
1655                1660                1665

Thr Ser Leu Asp Phe Ser Tyr Glu Pro Leu Tyr Gly Ile Asp Arg
1670                1675                1680

Tyr Ile Asn Lys Val Leu Ile Ala Pro Asp Leu Tyr Thr Ser Leu
1685                1690                1695

Ile Asn Ile Asn Thr Asn Tyr Tyr Ser Asn Glu Tyr Tyr Pro Glu
1700                1705                1710

Ile Ile Val Leu Asn Pro Asn Thr Phe His Lys Lys Val Asn Ile
1715                1720                1725

Asn Leu Asp Ser Ser Ser Phe Glu Tyr Lys Trp Ser Thr Glu Gly
1730                1735                1740

Ser Asp Phe Ile Leu Val Arg Tyr Leu Glu Glu Ser Asn Lys Lys
1745                1750                1755

Ile Leu Gln Lys Ile Arg Ile Lys Gly Ile Leu Ser Asn Thr Gln
1760                1765                1770

Ser Phe Asn Lys Met Ser Ile Asp Phe Lys Asp Ile Lys Lys Leu
1775                1780                1785

Ser Leu Gly Tyr Ile Met Ser Asn Phe Lys Ser Phe Asn Ser Glu
1790                1795                1800

Asn Glu Leu Asp Arg Asp His Leu Gly Phe Lys Ile Ile Asp Asn
1805                1810                1815

Lys Thr Tyr Tyr Tyr Asp Glu Asp Ser Lys Leu Val Lys Gly Leu
1820                1825                1830

Ile Asn Ile Asn Asn Ser Leu Phe Tyr Phe Asp Pro Ile Glu Phe
1835                1840                1845

Asn Leu Val Thr Gly Trp Gln Thr Ile Asn Gly Lys Lys Tyr Tyr
1850                1855                1860

Phe Asp Ile Asn Thr Gly Ala Ala Leu Thr Ser Tyr Lys Ile Ile
1865                1870                1875

Asn Gly Lys His Phe Tyr Phe Asn Asn Asp Gly Val Met Gln Leu
1880                1885                1890

```
Gly Val Phe Lys Gly Pro Asp Gly Phe Glu Tyr Phe Ala Pro Ala
    1895                1900                1905

Asn Thr Gln Asn Asn Asn Ile Glu Gly Gln Ala Ile Val Tyr Gln
    1910                1915                1920

Ser Lys Phe Leu Thr Leu Asn Gly Lys Lys Tyr Tyr Phe Asp Asn
    1925                1930                1935

Asn Ser Lys Ala Val Thr Gly Trp Arg Ile Ile Asn Asn Glu Lys
    1940                1945                1950

Tyr Tyr Phe Asn Pro Asn Asn Ala Ile Ala Ala Val Gly Leu Gln
    1955                1960                1965

Val Ile Asp Asn Asn Lys Tyr Tyr Phe Asn Pro Asp Thr Ala Ile
    1970                1975                1980

Ile Ser Lys Gly Trp Gln Thr Val Asn Gly Ser Arg Tyr Tyr Phe
    1985                1990                1995

Asp Thr Asp Thr Ala Ile Ala Phe Asn Gly Tyr Lys Thr Ile Asp
    2000                2005                2010

Gly Lys His Phe Tyr Phe Asp Ser Asp Cys Val Val Lys Ile Gly
    2015                2020                2025

Val Phe Ser Thr Ser Asn Gly Phe Glu Tyr Phe Ala Pro Ala Asn
    2030                2035                2040

Thr Tyr Asn Asn Asn Ile Glu Gly Gln Ala Ile Val Tyr Gln Ser
    2045                2050                2055

Lys Phe Leu Thr Leu Asn Gly Lys Lys Tyr Tyr Phe Asp Asn Asn
    2060                2065                2070

Ser Lys Ala Val Thr Gly Trp Gln Thr Ile Asp Ser Lys Lys Tyr
    2075                2080                2085

Tyr Phe Asn Thr Asn Thr Ala Glu Ala Ala Thr Gly Trp Gln Thr
    2090                2095                2100

Ile Asp Gly Lys Lys Tyr Tyr Phe Asn Thr Asn Thr Ala Glu Ala
    2105                2110                2115

Ala Thr Gly Trp Gln Thr Ile Asp Gly Lys Lys Tyr Tyr Phe Asn
    2120                2125                2130

Thr Asn Thr Ala Ile Ala Ser Thr Gly Tyr Thr Ile Ile Asn Gly
    2135                2140                2145

Lys His Phe Tyr Phe Asn Thr Asp Gly Ile Met Gln Ile Gly Val
    2150                2155                2160

Phe Lys Gly Pro Asn Gly Phe Glu Tyr Phe Ala Pro Ala Asn Thr
    2165                2170                2175

Asp Ala Asn Asn Ile Glu Gly Gln Ala Ile Leu Tyr Gln Asn Glu
    2180                2185                2190

Phe Leu Thr Leu Asn Gly Lys Lys Tyr Tyr Phe Gly Ser Asp Ser
    2195                2200                2205

Lys Ala Val Thr Gly Trp Arg Ile Ile Asn Asn Lys Lys Tyr Tyr
    2210                2215                2220

Phe Asn Pro Asn Asn Ala Ile Ala Ala Ile His Leu Cys Thr Ile
    2225                2230                2235

Asn Asn Asp Lys Tyr Tyr Phe Ser Tyr Asp Gly Ile Leu Gln Asn
    2240                2245                2250

Gly Tyr Ile Thr Ile Glu Arg Asn Asn Phe Tyr Phe Asp Ala Asn
    2255                2260                2265

Asn Glu Ser Lys Met Val Thr Gly Val Phe Lys Gly Pro Asn Gly
    2270                2275                2280

Phe Glu Tyr Phe Ala Pro Ala Asn Thr His Asn Asn Asn Ile Glu
```

```
                2285                2290                2295

Gly Gln Ala Ile Val Tyr Gln Asn Lys Phe Leu Thr Leu Asn Gly
    2300                2305                2310

Lys Lys Tyr Tyr Phe Asp Asn Asp Ser Lys Ala Val Thr Gly Trp
    2315                2320                2325

Gln Thr Ile Asp Gly Lys Lys Tyr Tyr Phe Asn Leu Asn Thr Ala
    2330                2335                2340

Glu Ala Ala Thr Gly Trp Gln Thr Ile Asp Gly Lys Lys Tyr Tyr
    2345                2350                2355

Phe Asn Leu Asn Thr Ala Glu Ala Ala Thr Gly Trp Gln Thr Ile
    2360                2365                2370

Asp Gly Lys Lys Tyr Tyr Phe Asn Thr Asn Thr Phe Ile Ala Ser
    2375                2380                2385

Thr Gly Tyr Thr Ser Ile Asn Gly Lys His Phe Tyr Phe Asn Thr
    2390                2395                2400

Asp Gly Ile Met Gln Ile Gly Val Phe Lys Gly Pro Asn Gly Phe
    2405                2410                2415

Glu Tyr Phe Ala Pro Ala Asn Thr Asp Ala Asn Asn Ile Glu Gly
    2420                2425                2430

Gln Ala Ile Leu Tyr Gln Asn Lys Phe Leu Thr Leu Asn Gly Lys
    2435                2440                2445

Lys Tyr Tyr Phe Gly Ser Asp Ser Lys Ala Val Thr Gly Leu Arg
    2450                2455                2460

Thr Ile Asp Gly Lys Lys Tyr Tyr Phe Asn Thr Asn Thr Ala Val
    2465                2470                2475

Ala Val Thr Gly Trp Gln Thr Ile Asn Gly Lys Lys Tyr Tyr Phe
    2480                2485                2490

Asn Thr Asn Thr Ser Ile Ala Ser Thr Gly Tyr Thr Ile Ile Ser
    2495                2500                2505

Gly Lys His Phe Tyr Phe Asn Thr Asp Gly Ile Met Gln Ile Gly
    2510                2515                2520

Val Phe Lys Gly Pro Asp Gly Phe Glu Tyr Phe Ala Pro Ala Asn
    2525                2530                2535

Thr Asp Ala Asn Asn Ile Glu Gly Gln Ala Ile Arg Tyr Gln Asn
    2540                2545                2550

Arg Phe Leu Tyr Leu His Asp Asn Ile Tyr Tyr Phe Gly Asn Asn
    2555                2560                2565

Ser Lys Ala Ala Thr Gly Trp Val Thr Ile Asp Gly Asn Arg Tyr
    2570                2575                2580

Tyr Phe Glu Pro Asn Thr Ala Met Gly Ala Asn Gly Tyr Lys Thr
    2585                2590                2595

Ile Asp Asn Lys Asn Phe Tyr Phe Arg Asn Gly Leu Pro Gln Ile
    2600                2605                2610

Gly Val Phe Lys Gly Ser Asn Gly Phe Glu Tyr Phe Ala Pro Ala
    2615                2620                2625

Asn Thr Asp Ala Asn Asn Ile Glu Gly Gln Ala Ile Arg Tyr Gln
    2630                2635                2640

Asn Arg Phe Leu His Leu Leu Gly Lys Ile Tyr Tyr Phe Gly Asn
    2645                2650                2655

Asn Ser Lys Ala Val Thr Gly Trp Gln Thr Ile Asn Gly Lys Val
    2660                2665                2670

Tyr Tyr Phe Met Pro Asp Thr Ala Met Ala Ala Ala Gly Gly Leu
    2675                2680                2685
```

-continued

Phe Glu Ile Asp Gly Val Ile Tyr Phe Phe Gly Val Asp Gly Val
         2690              2695              2700

Lys Ala Pro Gly Ile Tyr Gly
    2705             2710

<210> SEQ ID NO 13
<211> LENGTH: 2367
<212> TYPE: PRT
<213> ORGANISM: Clostridium difficile

<400> SEQUENCE: 13

Met Ser Leu Val Asn Arg Lys Gln Leu Glu Lys Met Ala Asn Val Arg
1               5                   10                  15

Phe Arg Val Gln Glu Asp Glu Tyr Val Ala Ile Leu Asp Ala Leu Glu
            20                  25                  30

Glu Tyr His Asn Met Ser Glu Asn Thr Val Val Glu Lys Tyr Leu Lys
        35                  40                  45

Leu Lys Asp Ile Asn Ser Leu Thr Asp Thr Tyr Ile Asp Thr Tyr Lys
    50                  55                  60

Lys Ser Gly Arg Asn Lys Ala Leu Lys Lys Phe Lys Glu Tyr Leu Val
65                  70                  75                  80

Ile Glu Ile Leu Glu Leu Lys Asn Ser Asn Leu Thr Pro Val Glu Lys
                85                  90                  95

Asn Leu His Phe Ile Trp Ile Gly Gly Gln Ile Asn Asp Thr Ala Ile
            100                 105                 110

Asn Tyr Ile Asn Gln Trp Lys Asp Val Asn Ser Asp Tyr Asn Val Asn
        115                 120                 125

Val Phe Tyr Asp Ser Asn Ala Phe Leu Ile Asn Thr Leu Lys Lys Thr
    130                 135                 140

Ile Ile Glu Ser Ala Ser Asn Asp Thr Leu Glu Ser Phe Arg Glu Asn
145                 150                 155                 160

Leu Asn Asp Pro Glu Phe Asn His Thr Ala Phe Phe Arg Lys Arg Met
                165                 170                 175

Gln Ile Ile Tyr Asp Lys Gln Gln Asn Phe Ile Asn Tyr Tyr Lys Ala
            180                 185                 190

Gln Lys Glu Glu Asn Pro Asp Leu Ile Ile Asp Asp Ile Val Lys Thr
        195                 200                 205

Tyr Leu Ser Asn Glu Tyr Ser Lys Asp Ile Asp Glu Leu Asn Ala Tyr
    210                 215                 220

Ile Glu Glu Ser Leu Asn Lys Val Thr Glu Asn Ser Gly Asn Asp Val
225                 230                 235                 240

Arg Asn Phe Glu Glu Phe Lys Thr Gly Glu Val Phe Asn Leu Tyr Glu
                245                 250                 255

Gln Glu Ser Val Glu Arg Trp Asn Leu Ala Gly Ala Ser Asp Ile Leu
            260                 265                 270

Arg Val Ala Ile Leu Lys Asn Ile Gly Gly Val Tyr Leu Asp Val Asp
        275                 280                 285

Met Leu Pro Gly Ile His Pro Asp Leu Phe Lys Asp Ile Asn Lys Pro
    290                 295                 300

Asp Ser Val Lys Thr Ala Val Asp Trp Glu Glu Met Gln Leu Glu Ala
305                 310                 315                 320

Ile Met Lys His Lys Glu Tyr Ile Pro Glu Tyr Thr Ser Lys His Phe
                325                 330                 335

Asp Thr Leu Asp Glu Glu Val Gln Ser Ser Phe Glu Ser Val Leu Ala
            340                 345                 350

-continued

```
Ser Lys Ser Asp Lys Ser Glu Ile Phe Leu Pro Leu Gly Asp Ile Glu
        355                 360                 365
Val Ser Pro Leu Glu Val Lys Ile Ala Phe Ala Lys Gly Ser Ile Ile
        370                 375                 380
Asn Gln Ala Leu Ile Ser Ala Lys Asp Ser Tyr Cys Ser Asp Leu Leu
385                 390                 395                 400
Ile Lys Gln Ile Gln Asn Arg Tyr Lys Ile Leu Asn Asp Thr Leu Gly
                405                 410                 415
Pro Ile Ile Ser Gln Gly Asn Asp Phe Asn Thr Thr Met Asn Asn Phe
                420                 425                 430
Gly Glu Ser Leu Gly Ala Ile Ala Asn Glu Asn Ile Ser Phe Ile
                435                 440                 445
Ala Lys Ile Gly Ser Tyr Leu Arg Val Gly Phe Tyr Pro Glu Ala Asn
        450                 455                 460
Thr Thr Ile Thr Leu Ser Gly Pro Thr Ile Tyr Ala Gly Ala Tyr Lys
465                 470                 475                 480
Asp Leu Leu Thr Phe Lys Glu Met Ser Ile Asp Thr Ser Ile Leu Ser
                485                 490                 495
Ser Glu Leu Arg Asn Phe Glu Phe Pro Lys Val Asn Ile Ser Gln Ala
                500                 505                 510
Thr Glu Gln Glu Lys Asn Ser Leu Trp Gln Phe Asn Glu Glu Arg Ala
        515                 520                 525
Lys Ile Gln Phe Glu Glu Tyr Lys Lys Asn Tyr Phe Glu Gly Ala Leu
        530                 535                 540
Gly Glu Asp Asp Asn Leu Asp Phe Ser Gln Asn Thr Val Thr Asp Lys
545                 550                 555                 560
Glu Tyr Leu Leu Glu Lys Ile Ser Ser Thr Lys Ser Ser Glu Gly
                565                 570                 575
Gly Tyr Val His Tyr Ile Val Gln Leu Gln Gly Asp Lys Ile Ser Tyr
                580                 585                 590
Glu Ala Ala Cys Asn Leu Phe Ala Lys Asn Pro Tyr Asp Ser Ile Leu
        595                 600                 605
Phe Gln Arg Asn Ile Glu Asp Ser Glu Val Ala Tyr Tyr Tyr Asn Pro
        610                 615                 620
Thr Asp Ser Glu Ile Gln Glu Ile Asp Lys Tyr Arg Ile Pro Asp Arg
625                 630                 635                 640
Ile Ser Asp Arg Pro Lys Ile Lys Leu Thr Phe Ile Gly His Gly Lys
                645                 650                 655
Ala Glu Phe Asn Thr Asp Ile Phe Ala Gly Leu Asp Val Asp Ser Leu
                660                 665                 670
Ser Ser Glu Ile Glu Thr Ala Ile Gly Leu Ala Lys Glu Asp Ile Ser
        675                 680                 685
Pro Lys Ser Ile Glu Ile Asn Leu Leu Gly Cys Asn Met Phe Ser Tyr
        690                 695                 700
Ser Val Asn Val Glu Glu Thr Tyr Pro Gly Lys Leu Leu Leu Arg Val
705                 710                 715                 720
Lys Asp Lys Val Ser Glu Leu Met Pro Ser Met Ser Gln Asp Ser Ile
                725                 730                 735
Ile Val Ser Ala Asn Gln Tyr Glu Val Arg Ile Asn Ser Glu Gly Arg
                740                 745                 750
Arg Glu Leu Leu Asp His Ser Gly Glu Trp Ile Asn Lys Glu Glu Ser
        755                 760                 765
Ile Ile Lys Asp Ile Ser Ser Lys Glu Tyr Ile Ser Phe Asn Pro Lys
        770                 775                 780
```

```
Glu Asn Lys Ile Ile Val Lys Ser Lys Asn Leu Pro Glu Leu Ser Thr
785                 790                 795                 800

Leu Leu Gln Glu Ile Arg Asn Asn Ser Asn Ser Ser Asp Ile Glu Leu
                805                 810                 815

Glu Glu Lys Val Met Leu Ala Glu Cys Glu Ile Asn Val Ile Ser Asn
        820                 825                 830

Ile Glu Thr Gln Val Val Glu Glu Arg Ile Glu Glu Ala Lys Ser Leu
            835                 840                 845

Thr Ser Asp Ser Ile Asn Tyr Ile Lys Asn Glu Phe Lys Leu Ile Glu
        850                 855                 860

Ser Ile Ser Glu Ala Leu Cys Asp Leu Lys Gln Gln Asn Glu Leu Glu
865                 870                 875                 880

Asp Ser His Phe Ile Ser Phe Glu Asp Ile Ser Glu Thr Asp Glu Gly
                885                 890                 895

Phe Ser Ile Arg Phe Ile Asn Lys Glu Thr Gly Glu Ser Ile Phe Val
            900                 905                 910

Glu Thr Glu Lys Thr Ile Phe Ser Glu Tyr Ala Asn His Ile Thr Glu
        915                 920                 925

Glu Ile Ser Lys Ile Lys Gly Thr Ile Phe Asp Thr Val Asn Gly Lys
    930                 935                 940

Leu Val Lys Lys Val Asn Leu Asp Thr Thr His Glu Val Asn Thr Leu
945                 950                 955                 960

Asn Ala Ala Phe Phe Ile Gln Ser Leu Ile Glu Tyr Asn Ser Ser Lys
                965                 970                 975

Glu Ser Leu Ser Asn Leu Ser Val Ala Met Lys Val Gln Val Tyr Ala
            980                 985                 990

Gln Leu Phe Ser Thr Gly Leu Asn Thr Ile Thr Asp Ala Ala Lys Val
        995                 1000                1005

Val Glu Leu Val Ser Thr Ala Leu Asp Glu Thr Ile Asp Leu Leu
    1010                1015                1020

Pro Thr Leu Ser Glu Gly Leu Pro Ile Ile Ala Thr Ile Ile Asp
    1025                1030                1035

Gly Val Ser Leu Gly Ala Ala Ile Lys Glu Leu Ser Glu Thr Ser
    1040                1045                1050

Asp Pro Leu Leu Arg Gln Glu Ile Glu Ala Lys Ile Gly Ile Met
    1055                1060                1065

Ala Val Asn Leu Thr Thr Ala Thr Thr Ala Ile Ile Thr Ser Ser
    1070                1075                1080

Leu Gly Ile Ala Ser Gly Phe Ser Ile Leu Leu Val Pro Leu Ala
    1085                1090                1095

Gly Ile Ser Ala Gly Ile Pro Ser Leu Val Asn Asn Glu Leu Val
    1100                1105                1110

Leu Arg Asp Lys Ala Thr Lys Val Val Asp Tyr Phe Lys His Val
    1115                1120                1125

Ser Leu Val Glu Thr Glu Gly Val Phe Thr Leu Leu Asp Asp Lys
    1130                1135                1140

Val Met Met Gln Gln Asp Asp Leu Val Ile Ser Glu Ile Asp Phe
    1145                1150                1155

Asn Asn Asn Ser Ile Val Leu Gly Lys Cys Glu Ile Trp Arg Met
    1160                1165                1170

Glu Gly Gly Ser Gly His Thr Val Thr Asp Asp Ile Asp His Phe
    1175                1180                1185

Phe Ser Ala Pro Ser Ile Thr Tyr Arg Glu Pro His Leu Ser Ile
```

```
                 1190                1195                1200

Tyr Asp Val Leu Glu Val Gln Lys Glu Leu Asp Leu Ser Lys
1205                1210                1215

Asp Leu Met Val Leu Pro Asn Ala Pro Asn Arg Val Phe Ala Trp
1220                1225                1230

Glu Thr Gly Trp Thr Pro Gly Leu Arg Ser Leu Glu Asn Asp Gly
1235                1240                1245

Thr Lys Leu Leu Asp Arg Ile Arg Asp Asn Tyr Glu Gly Glu Phe
1250                1255                1260

Tyr Trp Arg Tyr Phe Ala Phe Ile Ala Asp Ala Leu Ile Thr Thr
1265                1270                1275

Leu Lys Pro Arg Tyr Glu Asp Thr Asn Ile Arg Ile Asn Leu Asp
1280                1285                1290

Ser Asn Thr Arg Ser Phe Ile Val Pro Ile Ile Thr Thr Glu Tyr
1295                1300                1305

Ile Arg Glu Lys Leu Ser Tyr Ser Phe Tyr Gly Ser Gly Gly Thr
1310                1315                1320

Tyr Ala Leu Pro Leu Ser Gln Tyr Asn Met Gly Ile Asn Ile Glu
1325                1330                1335

Leu Ser Glu Ser Asp Val Trp Ile Ile Asp Val Asp Asn Val Val
1340                1345                1350

Arg Asp Val Thr Ile Glu Ser Asp Lys Ile Lys Lys Gly Asp Leu
1355                1360                1365

Ile Glu Gly Ile Leu Ser Thr Leu Ser Ile Glu Glu Asn Lys Ile
1370                1375                1380

Ile Leu Asn Ser His Glu Ile Asn Phe Ser Gly Glu Val Asn Gly
1385                1390                1395

Ser Asn Gly Phe Val Ser Leu Thr Phe Ser Ile Leu Glu Gly Ile
1400                1405                1410

Asn Ala Ile Ile Glu Val Asp Leu Leu Ser Lys Ser Tyr Lys Leu
1415                1420                1425

Leu Ile Ser Gly Glu Leu Lys Ile Leu Met Leu Asn Ser Asn His
1430                1435                1440

Ile Gln Gln Lys Ile Asp Tyr Ile Gly Phe Asn Ser Glu Leu Gln
1445                1450                1455

Lys Asn Ile Pro Tyr Ser Phe Val Asp Ser Glu Gly Lys Glu Asn
1460                1465                1470

Gly Phe Ile Asn Gly Ser Thr Lys Glu Gly Leu Phe Val Ser Glu
1475                1480                1485

Leu Pro Asp Val Val Leu Ile Ser Lys Val Tyr Met Asp Asp Ser
1490                1495                1500

Lys Pro Ser Phe Gly Tyr Tyr Ser Asn Asn Leu Lys Asp Val Lys
1505                1510                1515

Val Ile Thr Lys Asp Asn Val Asn Ile Leu Thr Gly Tyr Tyr Leu
1520                1525                1530

Lys Asp Asp Ile Lys Ile Ser Leu Ser Leu Thr Leu Gln Asp Glu
1535                1540                1545

Lys Thr Ile Lys Leu Asn Ser Val His Leu Asp Glu Ser Gly Val
1550                1555                1560

Ala Glu Ile Leu Lys Phe Met Asn Arg Lys Gly Ser Thr Asn Thr
1565                1570                1575

Ser Asp Ser Leu Met Ser Phe Leu Glu Ser Met Asn Ile Lys Ser
1580                1585                1590
```

```
Ile Phe Val Asn Phe Leu Gln Ser Asn Ile Lys Phe Ile Leu Asp
1595                1600                1605

Ala Asn Phe Ile Ile Ser Gly Thr Thr Ser Ile Gly Gln Phe Glu
1610                1615                1620

Phe Ile Cys Asp Glu Asn Asn Asn Ile Gln Pro Tyr Phe Ile Lys
1625                1630                1635

Phe Asn Thr Leu Glu Thr Asn Tyr Thr Leu Tyr Val Gly Asn Arg
1640                1645                1650

Gln Asn Met Ile Val Glu Pro Asn Tyr Asp Leu Asp Asp Ser Gly
1655                1660                1665

Asp Ile Ser Ser Thr Val Ile Asn Phe Ser Gln Lys Tyr Leu Tyr
1670                1675                1680

Gly Ile Asp Ser Cys Val Asn Lys Val Val Ile Ser Pro Asn Ile
1685                1690                1695

Tyr Thr Asp Glu Ile Asn Ile Thr Pro Val Tyr Glu Thr Asn Asn
1700                1705                1710

Thr Tyr Pro Glu Val Ile Val Leu Asp Ala Asn Tyr Ile Asn Glu
1715                1720                1725

Lys Ile Asn Val Asn Ile Asn Asp Leu Ser Ile Arg Tyr Val Trp
1730                1735                1740

Ser Asn Asp Gly Asn Asp Phe Ile Leu Met Ser Thr Ser Glu Glu
1745                1750                1755

Asn Lys Val Ser Gln Val Lys Ile Arg Phe Val Asn Val Phe Lys
1760                1765                1770

Asp Lys Thr Leu Ala Asn Lys Leu Ser Phe Asn Phe Ser Asp Lys
1775                1780                1785

Gln Asp Val Pro Val Ser Glu Ile Ile Leu Ser Phe Thr Pro Ser
1790                1795                1800

Tyr Tyr Glu Asp Gly Leu Ile Gly Tyr Asp Leu Gly Leu Val Ser
1805                1810                1815

Leu Tyr Asn Glu Lys Phe Tyr Ile Asn Asn Phe Gly Met Met Val
1820                1825                1830

Ser Gly Leu Ile Tyr Ile Asn Asp Ser Leu Tyr Tyr Phe Lys Pro
1835                1840                1845

Pro Val Asn Asn Leu Ile Thr Gly Phe Val Thr Val Gly Asp Asp
1850                1855                1860

Lys Tyr Tyr Phe Asn Pro Ile Asn Gly Gly Ala Ala Ser Ile Gly
1865                1870                1875

Glu Thr Ile Ile Asp Asp Lys Asn Tyr Tyr Phe Asn Gln Ser Gly
1880                1885                1890

Val Leu Gln Thr Gly Val Phe Ser Thr Glu Asp Gly Phe Lys Tyr
1895                1900                1905

Phe Ala Pro Ala Asn Thr Leu Asp Glu Asn Leu Glu Gly Glu Ala
1910                1915                1920

Ile Asp Phe Thr Gly Lys Leu Ile Ile Asp Glu Asn Ile Tyr Tyr
1925                1930                1935

Phe Glu Asp Asn Tyr Arg Gly Ala Val Glu Trp Lys Glu Leu Asp
1940                1945                1950

Gly Glu Met His Tyr Phe Ser Pro Glu Thr Gly Lys Ala Phe Lys
1955                1960                1965

Gly Leu Asn Gln Ile Gly Asp Asp Lys Tyr Tyr Phe Asn Ser Asp
1970                1975                1980

Gly Val Met Gln Lys Gly Phe Val Ser Ile Asn Asp Asn Lys His
1985                1990                1995
```

```
Tyr Phe Asp Asp Ser Gly Val Met Lys Val Gly Tyr Thr Glu Ile
    2000                2005                2010

Asp Gly Lys His Phe Tyr Phe Ala Glu Asn Gly Glu Met Gln Ile
    2015                2020                2025

Gly Val Phe Asn Thr Glu Asp Gly Phe Lys Tyr Phe Ala His His
    2030                2035                2040

Asn Glu Asp Leu Gly Asn Glu Gly Glu Glu Ile Ser Tyr Ser
    2045                2050                2055

Gly Ile Leu Asn Phe Asn Asn Lys Ile Tyr Tyr Phe Asp Asp Ser
    2060                2065                2070

Phe Thr Ala Val Val Gly Trp Lys Asp Leu Glu Asp Gly Ser Lys
    2075                2080                2085

Tyr Tyr Phe Asp Glu Asp Thr Ala Glu Ala Tyr Ile Gly Leu Ser
    2090                2095                2100

Leu Ile Asn Asp Gly Gln Tyr Tyr Phe Asn Asp Asp Gly Ile Met
    2105                2110                2115

Gln Val Gly Phe Val Thr Ile Asn Asp Lys Val Phe Tyr Phe Ser
    2120                2125                2130

Asp Ser Gly Ile Ile Glu Ser Gly Val Gln Asn Ile Asp Asp Asn
    2135                2140                2145

Tyr Phe Tyr Ile Asp Asp Asn Gly Ile Val Gln Ile Gly Val Phe
    2150                2155                2160

Asp Thr Ser Asp Gly Tyr Lys Tyr Phe Ala Pro Ala Asn Thr Val
    2165                2170                2175

Asn Asp Asn Ile Tyr Gly Gln Ala Val Glu Tyr Ser Gly Leu Val
    2180                2185                2190

Arg Val Gly Glu Asp Val Tyr Tyr Phe Gly Glu Thr Tyr Thr Ile
    2195                2200                2205

Glu Thr Gly Trp Ile Tyr Asp Met Glu Asn Glu Ser Asp Lys Tyr
    2210                2215                2220

Tyr Phe Val Pro Glu Thr Lys Lys Ala Cys Lys Gly Ile Asn Leu
    2225                2230                2235

Ile Asp Asp Ile Lys Tyr Tyr Phe Asp Glu Lys Gly Ile Met Arg
    2240                2245                2250

Thr Gly Leu Ile Ser Phe Glu Asn Asn Asn Tyr Tyr Phe Asn Glu
    2255                2260                2265

Asn Gly Glu Ile Gln Phe Gly Tyr Ile Asn Ile Glu Asp Lys Met
    2270                2275                2280

Phe Tyr Phe Gly Glu Asp Gly Val Met Gln Ile Gly Val Phe Asn
    2285                2290                2295

Thr Pro Asp Gly Phe Lys Tyr Phe Ala His Gln Asn Thr Leu Asp
    2300                2305                2310

Glu Asn Phe Glu Gly Glu Ser Ile Asn Tyr Thr Gly Trp Leu Gly
    2315                2320                2325

Leu Asp Glu Lys Arg Tyr Tyr Phe Thr Asp Glu Tyr Ile Ala Ala
    2330                2335                2340

Thr Gly Ser Val Ile Ile Asp Gly Glu Glu Tyr Tyr Phe Asp Pro
    2345                2350                2355

Asp Thr Ala Gln Leu Val Ile Ser Glu
    2360                2365

<210> SEQ ID NO 14
<211> LENGTH: 2178
<212> TYPE: PRT
```

<213> ORGANISM: Clostridium noveyi

<400> SEQUENCE: 14

```
Met Leu Ile Thr Arg Glu Gln Leu Met Lys Ile Ala Ser Ile Pro Leu
1               5                   10                  15

Lys Arg Lys Glu Pro Glu Tyr Asn Leu Ile Leu Asp Ala Leu Glu Asn
            20                  25                  30

Phe Asn Arg Asp Ile Glu Gly Thr Ser Val Lys Glu Ile Tyr Ser Lys
        35                  40                  45

Leu Ser Lys Leu Asn Glu Leu Val Asp Asn Tyr Gln Thr Lys Tyr Pro
    50                  55                  60

Ser Ser Gly Arg Asn Leu Ala Leu Glu Asn Phe Arg Asp Ser Leu Tyr
65                  70                  75                  80

Ser Glu Leu Arg Glu Leu Ile Lys Asn Ser Arg Thr Ser Thr Ile Ala
                85                  90                  95

Ser Lys Asn Leu Ser Phe Ile Trp Ile Gly Pro Ile Ser Asp Gln
            100                 105                 110

Ser Leu Glu Tyr Tyr Asn Met Trp Lys Met Phe Asn Lys Asp Tyr Asn
        115                 120                 125

Ile Arg Leu Phe Tyr Asp Lys Asn Ser Leu Leu Val Asn Thr Leu Lys
    130                 135                 140

Thr Ala Ile Ile Gln Glu Ser Ser Lys Val Ile Ile Glu Gln Asn Gln
145                 150                 155                 160

Ser Asn Ile Leu Asp Gly Thr Tyr Gly His Asn Lys Phe Tyr Ser Asp
                165                 170                 175

Arg Met Lys Leu Ile Tyr Arg Tyr Lys Arg Glu Leu Lys Met Leu Tyr
            180                 185                 190

Glu Asn Met Lys Gln Asn Asn Ser Val Asp Asp Ile Ile Ile Asn Phe
        195                 200                 205

Leu Ser Asn Tyr Phe Lys Tyr Asp Ile Gly Lys Leu Asn Asn Gln Lys
    210                 215                 220

Glu Asn Asn Asn Lys Met Ile Ala Ile Gly Ala Thr Asp Ile Asn
225                 230                 235                 240

Thr Glu Asn Ile Leu Thr Asn Lys Leu Lys Ser Tyr Tyr Tyr Gln Glu
                245                 250                 255

Leu Ile Gln Thr Asn Asn Leu Ala Ala Ala Ser Asp Ile Leu Arg Ile
            260                 265                 270

Ala Ile Leu Lys Lys Tyr Gly Gly Val Tyr Cys Asp Leu Asp Phe Leu
        275                 280                 285

Pro Gly Val Asn Leu Ser Leu Phe Asn Asp Ile Ser Lys Pro Asn Gly
    290                 295                 300

Met Asp Ser Asn Tyr Trp Glu Ala Ala Ile Phe Glu Ala Ile Ala Asn
305                 310                 315                 320

Glu Lys Lys Leu Met Asn Asn Tyr Pro Tyr Lys Tyr Met Glu Gln Val
                325                 330                 335

Pro Ser Glu Ile Lys Glu Arg Ile Leu Ser Phe Val Arg Asn His Asp
            340                 345                 350

Ile Asn Asp Leu Ile Leu Pro Leu Gly Asp Ile Lys Ile Ser Gln Leu
        355                 360                 365

Glu Ile Leu Leu Ser Arg Leu Lys Ala Ala Thr Gly Lys Lys Thr Phe
    370                 375                 380

Ser Asn Ala Phe Ile Ile Ser Asn Asn Asp Ser Leu Thr Leu Asn Asn
385                 390                 395                 400

Leu Ile Ser Gln Leu Glu Asn Arg Tyr Glu Ile Leu Asn Ser Ile Ile
```

```
                    405                 410                 415
Gln Glu Lys Phe Lys Ile Cys Glu Thr Tyr Asp Ser Tyr Ile Asn Ser
                420                 425                 430

Val Ser Glu Leu Val Leu Glu Thr Thr Pro Lys Asn Leu Ser Met Asp
            435                 440                 445

Gly Ser Ser Phe Tyr Gln Gln Ile Ile Gly Tyr Leu Ser Ser Gly Phe
        450                 455                 460

Lys Pro Glu Val Asn Ser Thr Val Phe Ser Gly Pro Asn Ile Tyr
465                 470                 475                 480

Ser Ser Ala Thr Cys Asp Thr Tyr His Phe Ile Lys Asn Thr Phe Asp
                485                 490                 495

Met Leu Ser Ser Gln Asn Gln Glu Ile Phe Glu Ala Ser Asn Asn Leu
            500                 505                 510

Tyr Phe Ser Lys Thr His Asp Glu Phe Lys Ser Ser Trp Leu Leu Arg
        515                 520                 525

Ser Asn Ile Ala Glu Lys Glu Phe Gln Lys Leu Ile Lys Thr Tyr Ile
    530                 535                 540

Gly Arg Thr Leu Asn Tyr Glu Asp Gly Leu Asn Phe Asn Lys Trp Lys
545                 550                 555                 560

Arg Val Thr Thr Ser Glu Leu Leu Lys Val Ile Glu Glu Val Asn Ser
                565                 570                 575

Thr Lys Ile Tyr Glu Asn Tyr Asp Leu Asn Met Ile Leu Gln Ile Gln
            580                 585                 590

Gly Asp Asp Ile Ser Tyr Glu Ser Ala Val Asn Val Phe Gly Lys Asn
        595                 600                 605

Pro Asn Lys Ser Ile Leu Ile Gln Gly Val Asp Phe Ala Asn Val
    610                 615                 620

Phe Tyr Phe Glu Asn Gly Ile Val Gln Ser Asp Ile Asn Asn Ile
625                 630                 635                 640

Leu Ser Arg Phe Asn Asp Ile Lys Lys Ile Lys Leu Thr Leu Ile Gly
                645                 650                 655

His Gly Glu Asn Val Phe Asn Pro Lys Leu Phe Gly Gly Lys Thr Val
            660                 665                 670

Asn Asp Leu Tyr Thr Asn Ile Ile Lys Pro Lys Leu Gln His Leu Leu
        675                 680                 685

Glu Arg Glu Gly Val Ile Leu Lys Asn Lys Tyr Leu Lys Ile Asn Ile
    690                 695                 700

Leu Gly Cys Tyr Met Phe Thr Pro Lys Val Asp Ile Asn Ser Thr Phe
705                 710                 715                 720

Val Gly Lys Leu Phe Asn Lys Ile Ser Arg Asp Leu Gln Pro Lys Gly
                725                 730                 735

Phe Ser Lys Asn Gln Leu Glu Ile Ser Ala Asn Lys Tyr Ala Ile Arg
            740                 745                 750

Ile Asn Arg Glu Gly Lys Arg Glu Val Leu Asp Tyr Phe Gly Lys Trp
        755                 760                 765

Val Ser Asn Thr Asp Leu Ile Ala Glu Gln Ile Ser Asn Lys Tyr Val
    770                 775                 780

Val Tyr Trp Asn Glu Val Glu Asn Thr Leu Ser Ala Arg Val Glu Gln
785                 790                 795                 800

Leu Asn Lys Val Ala Glu Phe Ala Lys Asp Ile Asn Ser Ile Ile Gln
                805                 810                 815

Thr Thr Asn Asn Gln Glu Leu Lys Gln Ser Leu Val Asn Thr Tyr Ala
            820                 825                 830
```

-continued

```
Asp Leu Ile Thr Thr Leu Tyr Ser Glu Leu Leu Lys Glu Asp Ile Pro
        835                 840                 845

Phe Glu Leu Asp Asn Ile Gln Ile Lys Glu Arg Ile Ile Leu Asn Glu
    850                 855                 860

Ile Ser Arg Leu His Asp Phe Ser Asn Ile Ile Leu Asp Phe Tyr Gln
865                 870                 875                 880

Lys Asn Asn Ile Ser Asn Asn Met Ile Ile Leu Phe Asp Ser Ile Ile
            885                 890                 895

Lys Glu Lys Asp Tyr Tyr Asn Val Lys Leu Ala Asn Lys Ile Thr Gly
                900                 905                 910

Glu Thr Ser Val Ile Lys Thr Tyr Ser Asp Ser Leu Trp Asn Phe Thr
        915                 920                 925

Asn Lys Tyr Lys Lys Ile Val Asp Asp Ile Lys Gly Ile Ile Val Lys
    930                 935                 940

Asp Ile Asn Gly Glu Phe Ile Lys Lys Ala Asp Phe Glu Ile Glu Gln
945                 950                 955                 960

Asn Pro Ser Leu Leu Asn Ser Ala Met Leu Met Gln Leu Leu Ile Asp
            965                 970                 975

Tyr Lys Pro Tyr Thr Glu Ile Leu Thr Asn Met Asn Thr Ser Leu Lys
                980                 985                 990

Val Gln Ala Tyr Ala Gln Ile Phe  Gln Leu Ser Ile Gly  Ala Ile Gln
        995                1000                1005

Glu Ala  Thr Glu Ile Val Thr  Ile Ile Ser Asp Ala  Leu Asn Ala
    1010                1015                1020

Asn Phe  Asn Ile Leu Ser Lys  Leu Lys Val Gly Ser  Ser Val Ala
    1025                1030                1035

Ser Val  Ile Ile Asp Gly Ile  Asn Leu Ile Ala Ala  Leu Thr Glu
    1040                1045                1050

Leu Lys  Asn Val Lys Thr Asn  Phe Glu Arg Lys Leu  Ile Glu Ala
    1055                1060                1065

Lys Val  Gly Met Tyr Ser Ile  Gly Phe Ile Leu Glu  Ser Ser Ser
    1070                1075                1080

Leu Ile  Ser Gly Leu Leu Gly  Ala Thr Ala Val Ser  Glu Ile Leu
    1085                1090                1095

Gly Val  Ile Ser Val Pro Ala  Gly Ile Leu Val  Gly Leu Pro
    1100                1105                1110

Ser Leu  Val Asn Asn Ile Leu  Val Leu Gly Glu Lys  Tyr Asn Gln
    1115                1120                1125

Ile Leu  Asp Tyr Phe Ser Lys  Phe Tyr Pro Ile Val  Gly Lys Asn
    1130                1135                1140

Pro Phe  Ser Ile Gln Asp Asn  Ile Ile Ile Pro Tyr  Asp Asp Ile
    1145                1150                1155

Ala Ile  Thr Glu Leu Asn Phe  Lys Tyr Asn Lys Phe  Lys Tyr Gly
    1160                1165                1170

Tyr Ala  Lys Ile Ser Gly Leu  Lys Val Gly Leu Val  Thr His Ile
    1175                1180                1185

Gly Glu  Asn Ile Asp His Tyr  Phe Ser Ala Pro Ser  Leu Asp His
    1190                1195                1200

Tyr Ile  Glu Leu Ser Ile Tyr  Pro Ala Leu Lys Leu  Asn Asp Thr
    1205                1210                1215

Asn Leu  Pro Lys Gly Asn Val  Val Leu Leu Pro Ser  Gly Leu Asn
    1220                1225                1230

Lys Val  Tyr Lys Pro Glu Ile  Ser Ala Ile Ala Gly  Ala Asn Ser
    1235                1240                1245
```

-continued

```
Gln Glu Gly Asn Gly Val Glu Val Leu Asn Leu Ile Arg Asn Tyr
    1250                1255                1260
Tyr Val Asp Ser Asn Gly Asn Thr Lys Phe Pro Trp Lys Tyr Glu
1265                1270                1275
Ala Pro Phe Glu Tyr Ser Phe Ser Tyr Met Arg Val Glu Tyr Phe
1280                1285                1290
Asp Thr Lys Val Asn Val Ile Leu Asp Asn Glu Asn Lys Thr Leu
1295                1300                1305
Ile Ile Pro Val Leu Thr Ile Asp Glu Met Arg Asn Lys Ile Ser
1310                1315                1320
Tyr Glu Ile Leu Gly Asp Gly Gly Gln Tyr Asn Val Ile Leu Pro
1325                1330                1335
Val Asn Gln Thr Asn Ile Asn Ile Val Ser Asn Lys Asn Asp Ile
1340                1345                1350
Trp Asn Phe Asp Val Ser Tyr Ile Val Lys Glu Ser Lys Ile Glu
1355                1360                1365
Asp Asn Lys Phe Val Leu Asp Gly Phe Ile Asn Asn Ile Phe Ser
1370                1375                1380
Thr Leu Lys Val Ser Asn Asp Gly Phe Lys Ile Gly Lys Gln Phe
1385                1390                1395
Ile Ser Ile Lys Asn Thr Pro Arg Ala Ile Asn Leu Ser Phe Lys
1400                1405                1410
Ile Asn Asn Asn Ile Val Ile Val Ser Ile Tyr Leu Asn His Glu
1415                1420                1425
Lys Ser Asn Ser Ile Thr Ile Ile Ser Ser Asp Leu Asn Asp Ile
1430                1435                1440
Lys Asn Asn Phe Asp Asn Leu Leu Asp Asn Ile Asn Tyr Ile Gly
1445                1450                1455
Leu Gly Ser Ile Ser Asp Asn Thr Ile Asn Cys Ile Val Arg Asn
1460                1465                1470
Asp Glu Val Tyr Met Glu Gly Lys Ile Phe Leu Asn Glu Lys Lys
1475                1480                1485
Leu Val Phe Ile Gln Asn Glu Leu Glu Leu His Leu Tyr Asp Ser
1490                1495                1500
Val Asn Lys Asp Ser Gln Tyr Leu Ile Asn Asn Pro Ile Asn Asn
1505                1510                1515
Val Val Lys Tyr Lys Asp Gly Tyr Ile Val Glu Gly Thr Phe Leu
1520                1525                1530
Ile Asn Ser Thr Glu Asn Lys Tyr Ser Leu Tyr Ile Glu Asn Asn
1535                1540                1545
Lys Ile Met Leu Lys Gly Leu Tyr Leu Glu Ser Ser Val Phe Lys
1550                1555                1560
Thr Ile Gln Asp Lys Ile Tyr Ser Lys Glu Lys Val Asn Asp Tyr
1565                1570                1575
Ile Leu Ser Leu Ile Lys Lys Phe Phe Thr Val Asn Ile Gln Leu
1580                1585                1590
Cys Pro Phe Met Ile Val Ser Gly Val Asp Glu Asn Asn Arg Tyr
1595                1600                1605
Leu Glu Tyr Met Leu Ser Thr Asn Asn Lys Trp Ile Ile Asn Gly
1610                1615                1620
Gly Tyr Trp Glu Asn Asp Phe Asn Asn Tyr Lys Ile Val Asp Phe
1625                1630                1635
Glu Lys Cys Asn Val Ile Val Ser Gly Ser Asn Lys Leu Asn Ser
```

-continued

```
            1640                1645                1650

Glu Gly Asp Leu Ala Asp Thr Ile Asp Val Leu Asp Lys Asp Leu
    1655                1660                1665

Glu Asn Leu Tyr Ile Asp Ser Val Ile Ile Pro Lys Val Tyr
    1670                1675                1680

Thr Lys Lys Ile Ile Ile His Pro Ile Pro Asn Asn Pro Gln Ile
    1685                1690                1695

Asn Ile Ile Asn Thr Gln Ser Ile His Asp Lys Cys His Leu Ile
    1700                1705                1710

Ile Asp Ser Val Leu Thr Asn Asn Tyr His Trp Glu Ser Asp Gly
    1715                1720                1725

Asp Asp Leu Ile Ile Thr Asn Gly Leu Asp Ile Asn Ile Arg Ile
    1730                1735                1740

Leu Gln Gly Leu Ser Phe Gly Phe Lys Tyr Lys Asn Ile Tyr Leu
    1745                1750                1755

Lys Phe Ser Asn Tyr Asp Glu Leu Ser Leu Asn Asp Phe Leu Leu
    1760                1765                1770

Gln Asn Tyr Asn Val Lys Gly Leu Tyr Tyr Ile Asn Gly Glu Leu
    1775                1780                1785

His Tyr Lys Asn Ile Pro Gly Asp Thr Phe Glu Tyr Gly Trp Ile
    1790                1795                1800

Asn Ile Asp Ser Arg Trp Tyr Phe Phe Asp Ser Ile Asn Leu Ile
    1805                1810                1815

Ala Lys Lys Gly Tyr Gln Glu Ile Glu Gly Glu Arg Tyr Tyr Phe
    1820                1825                1830

Asn Pro Asn Thr Gly Val Gln Glu Ser Gly Val Phe Leu Thr Pro
    1835                1840                1845

Asn Gly Leu Glu Tyr Phe Thr Asn Lys His Ala Ser Ser Lys Arg
    1850                1855                1860

Trp Gly Arg Ala Ile Asn Tyr Thr Gly Trp Leu Thr Leu Asp Gly
    1865                1870                1875

Asn Lys Tyr Tyr Phe Gln Ser Asn Ser Lys Ala Val Thr Gly Leu
    1880                1885                1890

Gln Lys Ile Ser Asp Lys Tyr Tyr Phe Asn Asp Asn Gly Gln
    1895                1900                1905

Met Gln Ile Lys Trp Gln Ile Ile Asn Asn Asn Lys Tyr Tyr Phe
    1910                1915                1920

Asp Gly Asn Thr Gly Glu Ala Ile Ile Gly Trp Phe Asn Asn Asn
    1925                1930                1935

Lys Glu Arg Tyr Tyr Phe Asp Ser Glu Gly Arg Leu Leu Thr Gly
    1940                1945                1950

Tyr Gln Val Ile Gly Asp Lys Ser Tyr Tyr Phe Ser Asp Asn Ile
    1955                1960                1965

Asn Gly Asn Trp Glu Glu Gly Ser Gly Val Leu Lys Ser Gly Ile
    1970                1975                1980

Phe Lys Thr Pro Ser Gly Phe Lys Leu Phe Ser Glu Gly Asp
    1985                1990                1995

Lys Ser Ala Ile Asn Tyr Lys Gly Trp Leu Asp Leu Asn Gly Asn
    2000                2005                2010

Lys Tyr Tyr Phe Asn Ser Asp Ser Ile Ala Val Thr Gly Ser Tyr
    2015                2020                2025

Asn Ile Lys Gly Ile Gln Tyr Tyr Phe Asn Pro Lys Thr Ala Val
    2030                2035                2040
```

-continued

```
Leu Thr Asn Gly Trp Tyr Thr Leu Asp Asn Asn Tyr Tyr Val
    2045                2050                2055

Ser Asn Gly His Asn Val Leu Gly Tyr Gln Asp Ile Asp Gly Lys
    2060                2065                2070

Gly Tyr Tyr Phe Asp Pro Ser Thr Gly Ile Gln Lys Ala Gly Val
    2075                2080                2085

Phe Pro Thr Pro Asn Gly Leu Arg Tyr Phe Thr Met Lys Pro Ile
    2090                2095                2100

Asp Gly Gln Arg Trp Gly Gln Cys Ile Asp Tyr Thr Gly Trp Leu
    2105                2110                2115

His Leu Asn Gly Asn Lys Tyr Tyr Phe Gly Tyr Tyr Asn Ser Ala
    2120                2125                2130

Val Thr Gly Trp Arg Val Leu Gly Gly Lys Arg Tyr Phe Phe Asn
    2135                2140                2145

Ile Lys Thr Gly Ala Ala Thr Thr Gly Leu Leu Thr Leu Ser Gly
    2150                2155                2160

Lys Arg Tyr Tyr Phe Asn Glu Lys Gly Glu Gln Leu Thr Leu Val
    2165                2170                2175
```

```
<210> SEQ ID NO 15
<211> LENGTH: 2364
<212> TYPE: PRT
<213> ORGANISM: Clostridium sordellii

<400> SEQUENCE: 15

Met Asn Leu Val Asn Lys Ala Gln Leu Gln Lys Met Val Tyr Val Lys
1               5                   10                  15

Phe Arg Ile Gln Glu Asp Glu Tyr Val Ala Ile Leu Asn Ala Leu Glu
                20                  25                  30

Glu Tyr His Asn Met Ser Glu Ser Val Val Glu Lys Tyr Leu Lys
            35                  40                  45

Leu Lys Asp Ile Asn Asn Leu Thr Asp Asn Tyr Leu Asn Thr Tyr Lys
    50                  55                  60

Lys Ser Gly Arg Asn Lys Ala Leu Lys Lys Phe Lys Glu Tyr Leu Thr
65                  70                  75                  80

Met Glu Val Leu Glu Leu Lys Asn Asn Ser Leu Thr Pro Val Glu Lys
                85                  90                  95

Asn Leu His Phe Ile Trp Ile Gly Gly Gln Ile Asn Asp Thr Ala Ile
            100                 105                 110

Asn Tyr Ile Asn Gln Trp Lys Asp Val Asn Ser Asp Tyr Thr Val Lys
        115                 120                 125

Val Phe Tyr Asp Ser Asn Ala Phe Leu Ile Asn Thr Leu Lys Lys Thr
    130                 135                 140

Ile Val Glu Ser Ala Thr Asn Asn Thr Leu Glu Ser Phe Arg Glu Asn
145                 150                 155                 160

Leu Asn Asp Pro Glu Phe Asp Tyr Asn Lys Phe Tyr Arg Lys Arg Met
                165                 170                 175

Glu Ile Ile Tyr Asp Lys Gln Lys His Phe Ile Asp Tyr Tyr Lys Ser
            180                 185                 190

Gln Ile Glu Glu Asn Pro Glu Phe Ile Ile Asp Asn Ile Ile Lys Thr
        195                 200                 205

Tyr Leu Ser Asn Glu Tyr Ser Lys Asp Leu Glu Ala Leu Asn Lys Tyr
    210                 215                 220

Ile Glu Glu Ser Leu Asn Lys Ile Thr Ala Asn Asn Gly Asn Asp Ile
225                 230                 235                 240
```

```
Arg Asn Leu Glu Lys Phe Ala Asp Glu Asp Leu Val Arg Leu Tyr Asn
            245                 250                 255

Gln Glu Leu Val Glu Arg Trp Asn Leu Ala Ala Ala Ser Asp Ile Leu
        260                 265                 270

Arg Ile Ser Met Leu Lys Glu Asp Gly Gly Val Tyr Leu Asp Val Asp
    275                 280                 285

Ile Leu Pro Gly Ile Gln Pro Asp Leu Phe Lys Ser Ile Asn Lys Pro
290                 295                 300

Asp Ser Ile Thr Asn Thr Ser Trp Glu Met Ile Lys Leu Glu Ala Ile
305                 310                 315                 320

Met Lys Tyr Lys Glu Tyr Ile Pro Gly Tyr Thr Ser Lys Asn Phe Asp
                325                 330                 335

Met Leu Asp Glu Glu Val Gln Arg Ser Phe Glu Ser Ala Leu Ser Ser
            340                 345                 350

Lys Ser Asp Lys Ser Glu Ile Phe Leu Pro Leu Asp Asp Ile Lys Val
        355                 360                 365

Ser Pro Leu Glu Val Lys Ile Ala Phe Ala Asn Asn Ser Val Ile Asn
    370                 375                 380

Gln Ala Leu Ile Ser Leu Lys Asp Ser Tyr Cys Ser Asp Leu Val Ile
385                 390                 395                 400

Asn Gln Ile Lys Asn Arg Tyr Lys Ile Leu Asn Asp Asn Leu Asn Pro
                405                 410                 415

Ser Ile Asn Glu Gly Thr Asp Phe Asn Thr Thr Met Lys Ile Phe Ser
            420                 425                 430

Asp Lys Leu Ala Ser Ile Ser Asn Glu Asp Asn Met Met Phe Met Ile
        435                 440                 445

Lys Ile Thr Asn Tyr Leu Lys Val Gly Phe Ala Pro Asp Val Arg Ser
    450                 455                 460

Thr Ile Asn Leu Ser Gly Pro Gly Val Tyr Thr Gly Ala Tyr Gln Asp
465                 470                 475                 480

Leu Leu Met Phe Lys Asp Asn Ser Thr Asn Ile His Leu Leu Glu Pro
                485                 490                 495

Glu Leu Arg Asn Phe Glu Phe Pro Lys Thr Lys Ile Ser Gln Leu Thr
            500                 505                 510

Glu Gln Glu Ile Thr Ser Leu Trp Ser Phe Asn Gln Ala Arg Ala Lys
        515                 520                 525

Ser Gln Phe Glu Glu Tyr Lys Lys Gly Tyr Phe Glu Gly Ala Leu Gly
    530                 535                 540

Glu Asp Asp Asn Leu Asp Phe Ala Gln Asn Thr Val Leu Asp Lys Asp
545                 550                 555                 560

Tyr Val Ser Lys Lys Ile Leu Ser Ser Met Lys Thr Arg Asn Lys Glu
                565                 570                 575

Tyr Ile His Tyr Ile Val Gln Leu Gln Gly Asp Lys Ile Ser Tyr Glu
            580                 585                 590

Ala Ser Cys Asn Leu Phe Ser Lys Asp Pro Tyr Ser Ser Ile Leu Tyr
        595                 600                 605

Gln Lys Asn Ile Glu Gly Ser Glu Thr Ala Tyr Tyr Tyr Val Ala
    610                 615                 620

Asp Ala Glu Ile Lys Glu Ile Asp Lys Tyr Arg Ile Pro Tyr Gln Ile
625                 630                 635                 640

Ser Asn Lys Arg Asn Ile Lys Leu Thr Phe Ile Gly His Gly Lys Ser
                645                 650                 655

Glu Phe Asn Thr Asp Thr Phe Ala Asn Leu Asp Val Asp Ser Leu Ser
            660                 665                 670
```

```
Ser Glu Ile Glu Thr Ile Leu Asn Leu Ala Lys Ala Asp Ile Ser Pro
            675                 680                 685

Lys Tyr Ile Glu Ile Asn Leu Leu Gly Cys Asn Met Phe Ser Tyr Ser
    690                 695                 700

Ile Ser Ala Glu Glu Thr Tyr Pro Gly Lys Leu Leu Lys Ile Lys
705                 710                 715                 720

Asp Arg Val Ser Glu Leu Met Pro Ser Ile Ser Gln Asp Ser Ile Thr
                725                 730                 735

Val Ser Ala Asn Gln Tyr Glu Val Arg Ile Asn Glu Glu Gly Lys Arg
            740                 745                 750

Glu Ile Leu Asp His Ser Gly Lys Trp Ile Asn Lys Glu Glu Ser Ile
        755                 760                 765

Ile Lys Asp Ile Ser Ser Lys Glu Tyr Ile Ser Phe Asn Pro Lys Glu
    770                 775                 780

Asn Lys Ile Ile Val Lys Ser Lys Tyr Leu His Glu Leu Ser Thr Leu
785                 790                 795                 800

Leu Gln Glu Ile Arg Asn Asn Ala Asn Ser Ser Asp Ile Asp Leu Glu
                805                 810                 815

Lys Lys Val Met Leu Thr Glu Cys Glu Ile Asn Val Ala Ser Asn Ile
            820                 825                 830

Asp Arg Gln Ile Val Glu Gly Arg Ile Glu Glu Ala Lys Asn Leu Thr
        835                 840                 845

Ser Asp Ser Ile Asn Tyr Ile Lys Asn Glu Phe Lys Leu Ile Glu Ser
    850                 855                 860

Ile Ser Asp Ser Leu Tyr Asp Leu Lys His Gln Asn Gly Leu Asp Asp
865                 870                 875                 880

Ser His Phe Ile Ser Phe Glu Asp Ile Ser Lys Thr Glu Asn Gly Phe
                885                 890                 895

Arg Ile Arg Phe Ile Asn Lys Glu Thr Gly Asn Ser Ile Phe Ile Glu
            900                 905                 910

Thr Glu Lys Glu Ile Phe Ser Glu Tyr Ala Thr His Ile Ser Lys Glu
        915                 920                 925

Ile Ser Asn Ile Lys Asp Thr Ile Phe Asp Asn Val Asn Gly Lys Leu
    930                 935                 940

Val Lys Lys Val Asn Leu Asp Ala Ala His Glu Val Asn Thr Leu Asn
945                 950                 955                 960

Ser Ala Phe Phe Ile Gln Ser Leu Ile Glu Tyr Asn Thr Thr Lys Glu
                965                 970                 975

Ser Leu Ser Asn Leu Ser Val Ala Met Lys Val Gln Val Tyr Ala Gln
            980                 985                 990

Leu Phe Ser Thr Gly Leu Asn Thr Ile Thr Asp Ala Ser Lys Val Val
        995                 1000                1005

Glu Leu Val Ser Thr Ala Leu Asp Glu Thr Ile Asp Leu Leu Pro
    1010                1015                1020

Thr Leu Ser Glu Gly Leu Pro Ile Ile Ala Thr Ile Ile Asp Gly
    1025                1030                1035

Val Ser Leu Gly Ala Ala Ile Lys Glu Leu Ser Glu Thr Asn Asp
    1040                1045                1050

Pro Leu Leu Arg Gln Glu Ile Glu Ala Lys Ile Gly Ile Met Ala
    1055                1060                1065

Val Asn Leu Thr Ala Ala Ser Thr Ala Ile Val Thr Ser Ala Leu
    1070                1075                1080

Gly Ile Ala Ser Gly Phe Ser Ile Leu Leu Val Pro Leu Ala Gly
```

```
                    1085              1090              1095
Ile Ser Ala Gly Ile Pro Ser Leu Val Asn Asn Glu Leu Ile Leu
    1100              1105              1110
Gln Asp Lys Ala Thr Lys Val Ile Asp Tyr Phe Lys His Ile Ser
    1115              1120              1125
Leu Ala Glu Thr Glu Gly Ala Phe Thr Leu Leu Asp Asp Lys Ile
    1130              1135              1140
Ile Met Pro Gln Asp Asp Leu Val Leu Ser Glu Ile Asp Phe Asn
    1145              1150              1155
Asn Asn Ser Ile Thr Leu Gly Lys Cys Glu Ile Trp Arg Ala Glu
    1160              1165              1170
Gly Gly Ser Gly His Thr Leu Thr Asp Asp Ile Asp His Phe Phe
    1175              1180              1185
Ser Ser Pro Ser Ile Thr Tyr Arg Lys Pro Trp Leu Ser Ile Tyr
    1190              1195              1200
Asp Val Leu Asn Ile Lys Lys Glu Lys Ile Asp Phe Ser Lys Asp
    1205              1210              1215
Leu Met Val Leu Pro Asn Ala Pro Asn Arg Val Phe Gly Tyr Glu
    1220              1225              1230
Met Gly Trp Thr Pro Gly Phe Arg Ser Leu Asp Asn Asp Gly Thr
    1235              1240              1245
Lys Leu Leu Asp Arg Ile Arg Asp His Tyr Glu Gly Gln Phe Tyr
    1250              1255              1260
Trp Arg Tyr Phe Ala Phe Ile Ala Asp Ala Leu Ile Thr Lys Leu
    1265              1270              1275
Lys Pro Arg Tyr Glu Asp Thr Asn Val Arg Ile Asn Leu Asp Gly
    1280              1285              1290
Asn Thr Arg Ser Phe Ile Val Pro Val Ile Thr Thr Glu Gln Ile
    1295              1300              1305
Arg Lys Asn Leu Ser Tyr Ser Phe Tyr Gly Ser Gly Gly Ser Tyr
    1310              1315              1320
Ser Leu Ser Leu Ser Pro Tyr Asn Met Asn Ile Asp Leu Asn Leu
    1325              1330              1335
Val Glu Asn Asp Thr Trp Val Ile Asp Val Asp Asn Val Val Lys
    1340              1345              1350
Asn Ile Thr Ile Glu Ser Asp Glu Ile Gln Lys Gly Glu Leu Ile
    1355              1360              1365
Glu Asn Ile Leu Ser Lys Leu Asn Ile Glu Asp Asn Lys Ile Ile
    1370              1375              1380
Leu Asn Asn His Thr Ile Asn Phe Tyr Gly Asp Ile Asn Glu Ser
    1385              1390              1395
Asn Arg Phe Ile Ser Leu Thr Phe Ser Ile Leu Glu Asp Ile Asn
    1400              1405              1410
Ile Ile Ile Glu Ile Asp Leu Val Ser Lys Ser Tyr Lys Ile Leu
    1415              1420              1425
Leu Ser Gly Asn Cys Met Lys Leu Ile Glu Asn Ser Ser Asp Ile
    1430              1435              1440
Gln Gln Lys Ile Asp His Ile Gly Phe Asn Gly Glu His Gln Lys
    1445              1450              1455
Tyr Ile Pro Tyr Ser Tyr Ile Asp Asn Glu Thr Lys Tyr Asn Gly
    1460              1465              1470
Phe Ile Asp Tyr Ser Lys Lys Glu Gly Leu Phe Thr Ala Glu Phe
    1475              1480              1485
```

-continued

| | | | | | | | | | | |
|---|---|---|---|---|---|---|---|---|---|---|
| Ser | Asn | Glu | Ser | Ile | Ile | Arg | Asn | Ile | Tyr | Met | Pro | Asp | Ser | Asn |
| | 1490 | | | | 1495 | | | | 1500 | |

Ser Asn Glu Ser Ile Ile Arg Asn Ile Tyr Met Pro Asp Ser Asn
    1490                1495                1500

Asn Leu Phe Ile Tyr Ser Ser Lys Asp Leu Lys Asp Ile Arg Ile
    1505                1510                1515

Ile Asn Lys Gly Asp Val Lys Leu Leu Ile Gly Asn Tyr Phe Lys
    1520                1525                1530

Asp Asp Met Lys Val Ser Leu Ser Phe Thr Ile Glu Asp Thr Asn
    1535                1540                1545

Thr Ile Lys Leu Asn Gly Val Tyr Leu Asp Glu Asn Gly Val Ala
    1550                1555                1560

Gln Ile Leu Lys Phe Met Asn Asn Ala Lys Ser Ala Leu Asn Thr
    1565                1570                1575

Ser Asn Ser Leu Met Asn Phe Leu Glu Ser Ile Asn Ile Lys Asn
    1580                1585                1590

Ile Phe Tyr Asn Asn Leu Asp Pro Asn Ile Glu Phe Ile Leu Asp
    1595                1600                1605

Thr Asn Phe Ile Ile Ser Gly Ser Asn Ser Ile Gly Gln Phe Glu
    1610                1615                1620

Leu Ile Cys Asp Lys Asp Lys Asn Ile Gln Pro Tyr Phe Ile Asn
    1625                1630                1635

Phe Lys Ile Lys Glu Thr Ser Tyr Thr Leu Tyr Val Gly Asn Arg
    1640                1645                1650

Gln Asn Leu Ile Val Glu Pro Ser Tyr His Leu Asp Asp Ser Gly
    1655                1660                1665

Asn Ile Ser Ser Thr Val Ile Asn Phe Ser Gln Lys Tyr Leu Tyr
    1670                1675                1680

Gly Ile Asp Arg Tyr Val Asn Lys Val Ile Ile Ala Pro Asn Leu
    1685                1690                1695

Tyr Thr Asp Glu Ile Asn Ile Thr Pro Val Tyr Lys Pro Asn Tyr
    1700                1705                1710

Ile Cys Pro Glu Val Ile Ile Leu Asp Ala Asn Tyr Ile Asn Glu
    1715                1720                1725

Lys Ile Asn Val Asn Ile Asn Asp Leu Ser Ile Arg Tyr Val Trp
    1730                1735                1740

Asp Asn Asp Gly Ser Asp Leu Ile Leu Ile Ala Asn Ser Glu Glu
    1745                1750                1755

Asp Asn Gln Pro Gln Val Lys Ile Arg Phe Val Asn Val Phe Lys
    1760                1765                1770

Ser Asp Thr Ala Ala Asp Lys Leu Ser Phe Asn Phe Ser Asp Lys
    1775                1780                1785

Gln Asp Val Ser Val Ser Lys Ile Ile Ser Thr Phe Ser Leu Ala
    1790                1795                1800

Ala Tyr Ser Asp Gly Phe Phe Asp Tyr Glu Phe Gly Leu Val Ser
    1805                1810                1815

Leu Asp Asn Asp Tyr Phe Tyr Ile Asn Ser Phe Gly Asn Met Val
    1820                1825                1830

Ser Gly Leu Ile Tyr Ile Asn Asp Ser Leu Tyr Tyr Phe Lys Pro
    1835                1840                1845

Pro Lys Asn Asn Leu Ile Thr Gly Phe Thr Thr Ile Asp Gly Asn
    1850                1855                1860

Lys Tyr Tyr Phe Asp Pro Thr Lys Ser Gly Ala Ala Ser Ile Gly
    1865                1870                1875

Glu Ile Thr Ile Asp Gly Lys Asp Tyr Tyr Phe Asn Lys Gln Gly
    1880                1885                1890

-continued

```
Ile Leu Gln Val Gly Val Ile Asn Thr Ser Asp Gly Leu Lys Tyr
    1895                1900                1905

Phe Ala Pro Ala Gly Thr Leu Asp Glu Asn Leu Glu Gly Glu Ser
    1910                1915                1920

Val Asn Phe Ile Gly Lys Leu Asn Ile Asp Gly Lys Ile Tyr Tyr
    1925                1930                1935

Phe Glu Asp Asn Tyr Arg Ala Ala Val Glu Trp Lys Leu Leu Asp
    1940                1945                1950

Asp Glu Thr Tyr Tyr Phe Asn Pro Lys Thr Gly Glu Ala Leu Lys
    1955                1960                1965

Gly Leu His Gln Ile Gly Asp Asn Lys Tyr Tyr Phe Asp Asp Asn
    1970                1975                1980

Gly Ile Met Gln Thr Gly Phe Ile Thr Ile Asn Asp Lys Val Phe
    1985                1990                1995

Tyr Phe Asn Asn Asp Gly Val Met Gln Val Gly Tyr Ile Glu Val
    2000                2005                2010

Asn Gly Lys Tyr Phe Tyr Phe Gly Lys Asn Gly Glu Arg Gln Leu
    2015                2020                2025

Gly Val Phe Asn Thr Pro Asp Gly Phe Lys Phe Phe Gly Pro Lys
    2030                2035                2040

Asp Asp Asp Leu Gly Thr Glu Glu Gly Glu Leu Thr Leu Tyr Asn
    2045                2050                2055

Gly Ile Leu Asn Phe Asn Gly Lys Ile Tyr Phe Phe Asp Ile Ser
    2060                2065                2070

Asn Thr Ala Val Val Gly Trp Gly Thr Leu Asp Asp Gly Ser Thr
    2075                2080                2085

Tyr Tyr Phe Asp Asp Asn Arg Ala Glu Ala Cys Ile Gly Leu Thr
    2090                2095                2100

Val Ile Asn Asp Cys Lys Tyr Tyr Phe Asp Asp Asn Gly Ile Arg
    2105                2110                2115

Gln Leu Gly Phe Ile Thr Ile Asn Asp Asn Ile Phe Tyr Phe Ser
    2120                2125                2130

Glu Ser Gly Lys Ile Glu Leu Gly Tyr Gln Asn Ile Asn Gly Asn
    2135                2140                2145

Tyr Phe Tyr Ile Asp Glu Ser Gly Leu Val Leu Ile Gly Val Phe
    2150                2155                2160

Asp Thr Pro Asp Gly Tyr Lys Tyr Phe Ala Pro Leu Asn Thr Val
    2165                2170                2175

Asn Asp Asn Ile Tyr Gly Gln Ala Val Lys Tyr Ser Gly Leu Val
    2180                2185                2190

Arg Val Asn Glu Asp Val Tyr Tyr Phe Gly Glu Thr Tyr Lys Ile
    2195                2200                2205

Glu Thr Gly Trp Ile Glu Asn Glu Thr Asp Lys Tyr Tyr Phe Asp
    2210                2215                2220

Pro Glu Thr Lys Lys Ala Tyr Lys Gly Ile Asn Val Val Asp Asp
    2225                2230                2235

Ile Lys Tyr Tyr Phe Asp Glu Asn Gly Ile Met Arg Thr Gly Leu
    2240                2245                2250

Ile Ser Phe Glu Asn Asn Asn Tyr Tyr Phe Asn Glu Asp Gly Lys
    2255                2260                2265

Met Gln Phe Gly Tyr Leu Asn Ile Lys Asp Lys Met Phe Tyr Phe
    2270                2275                2280

Gly Lys Asp Gly Lys Met Gln Ile Gly Val Phe Asn Thr Pro Asp
```

-continued

```
                    2285                2290                2295

Gly Phe Lys Tyr Phe Ala His Gln Asn Thr Leu Asp Glu Asn Phe
2300                2305                2310

Glu Gly Glu Ser Ile Asn Tyr Thr Gly Trp Leu Asp Leu Asp Gly
    2315                2320                2325

Lys Arg Tyr Tyr Phe Thr Asp Glu Tyr Ile Ala Ala Thr Gly Ser
    2330                2335                2340

Leu Thr Ile Asp Gly Tyr Asn Tyr Tyr Phe Asp Pro Asp Thr Ala
    2345                2350                2355

Glu Leu Val Val Ser Glu
    2360

<210> SEQ ID NO 16
<211> LENGTH: 4196
<212> TYPE: PRT
<213> ORGANISM: Bordetella pertussis

<400> SEQUENCE: 16

Met Asn Lys His Cys Phe Lys Leu Val His Ser Pro Ala Leu Gly Met
1               5                   10                  15

Leu Val Pro Val His Glu His Arg Thr Gly Arg Pro Leu Arg Gly Ala
            20                  25                  30

Arg Arg Ala Met Ala Val Thr Leu Ala Val Leu Ala Pro Ala Gly Ala
        35                  40                  45

Ala Ala Ala Gly Gly Ile Ala Pro Gln Gly Ala Thr Gln Val Ala Pro
    50                  55                  60

Ala Arg Asn Gly Val Pro Val Ile Gln Ile Ala Ala Pro Asp Ala Thr
65                  70                  75                  80

Gly Ile Ser His Asn Arg Tyr Thr Glu Phe Asn Val Arg Gln Pro Gly
                85                  90                  95

Val Val Leu Asn Asn Ser Thr Ala Glu Gly Val Ser Ala Leu Ala Gly
            100                 105                 110

Arg Ile Ser Gly Asn Pro Gly Leu Arg Gly Pro Ala Arg Ala Ile Leu
        115                 120                 125

Asn Glu Val Thr Gly Val Ser Pro Thr Thr Leu Glu Gly Ala Leu Glu
    130                 135                 140

Val Phe Gly Pro Ala Ala Asp Val Leu Val Ala Asn Pro Asn Gly Leu
145                 150                 155                 160

Thr Ala Asn Gly Leu Ser Thr Ile Asn Ile Arg Gly Leu Thr Leu Ser
                165                 170                 175

Thr Gly Arg Pro Gly Ala Gly Gly Val Leu Asp Val Ala Arg Gly Arg
            180                 185                 190

Leu Glu Ile Gly Pro His Gly Val Asn Thr Ala Gly Leu Ser Tyr Phe
        195                 200                 205

Asp Leu Val Ala Arg Thr Val Ala Leu His Gly Pro Val Gly Ala Gly
    210                 215                 220

Asp Gly Gln Pro Pro Ala Asp Ile Asn Val Ala Gly Ala Asn Arg
225                 230                 235                 240

Tyr Asp Tyr Gly Arg Arg Thr Arg Leu Gln Pro Thr Gly Arg Pro Ala
                245                 250                 255

Ala Ala Pro Asp Ala Ser Ala Gly His Ala Ile Asp Gly Ser Ala Ala
            260                 265                 270

Gly Ala Met Tyr Gly Arg His Ile Thr Leu Val Ser Ser Asp Ala Gly
        275                 280                 285

Leu Gly Ala Arg His Arg Gly Leu Val Ser Ala Ala Gly His Ile Ala
```

```
              290                 295                 300
Ile Asp Ala Ala Gly Gly Val Ser Val Gln Ala Leu Ala Ala His Ala
305                 310                 315                 320

Ala Ser Asp Gly Thr Ala Gly Ser Ala Thr Ile Arg Ala Gly Gly Asp
                325                 330                 335

Ala Leu Ile Gly Ser Val Ile Ala Phe Gly Gly Asp Ile Glu Val Arg
                340                 345                 350

Ala Ala Ala Gly Arg Ile Ala Thr His Gly Ala Leu Asn Ala Pro Arg
                355                 360                 365

Gly Arg Val Arg Leu Gln Ala Gly Asp Ala Leu Ala Val His Gly Pro
370                 375                 380

Val Gln Ala Ala Arg Val Ala Leu Ala Thr Arg Gly Asp Ala Ser Ile
385                 390                 395                 400

Ala Ala Asp Leu His Ala Thr Arg Asp Gly Val Ser Leu Ala Ala Arg
                405                 410                 415

Asn Ala Thr Leu Ala His Ala Arg Val Ile Ala Thr Pro Pro Ala Ala
                420                 425                 430

Gln Ala Arg Pro Ser Thr Pro Ala Ile Asp Ile Ala Leu Ser Gly Thr
                435                 440                 445

Leu Thr Leu Arg Gly Thr Leu His Asp Ala Asp Gly Asp Gly Arg Arg
450                 455                 460

Ile Glu Gly Thr Ser Val Ala Leu Ala Asn Gly Met Pro Val Ile Val
465                 470                 475                 480

Asp Thr Arg Gln Pro Gln Arg Ala Val Pro Asn Ala Leu Leu Ala Ser
                485                 490                 495

Asp Ala Gly Leu Tyr Ala Ala Ser Gln Pro Ile Ser Ile Arg Ala Ala
                500                 505                 510

Gly Leu Arg Asn Glu Gly Gly Ala Ile Asp Ser Thr Gly Thr Gly Gln
                515                 520                 525

Gly His Ile Gly Leu Arg Ile Gly Gly Pro Ala Val Asn Leu Gly Tyr
                530                 535                 540

Ile Ala Thr His Gly Thr Leu Glu Ala Thr Val Asp Gly Thr Leu Glu
545                 550                 555                 560

Asn Arg Met Leu Leu Ser Ala Ala Ala Leu Arg Val Ala Thr His Asp
                565                 570                 575

Leu Ser Asn His Ala Ala Met Thr Ala Ser Gly Pro Asp Thr Gly Thr
                580                 585                 590

Pro Ala Leu Asp Leu Ser Val Gln His Arg Val Glu Asn Ala Gly Ser
                595                 600                 605

Leu Leu Ala Ala Arg Gly Ala Leu Arg Leu Gly Gly Ala Glu Leu
610                 615                 620

Ser Ile Val Asn Gln Pro Ala Gly Phe Met Leu Ala His Gly Gln Asp
625                 630                 635                 640

Ile Ala Ala Ala Arg Leu Ala Asn Ala Gly Thr Leu Ser Ser Thr Ala
                645                 650                 655

Ala Gly Thr Leu Thr Leu Ala Gly Asp Leu Glu Asn Ser Gly Val Leu
                660                 665                 670

Gln Ser Ala His Ala Leu Arg Val Gln Ala Arg Ile Ala Ser Arg
                675                 680                 685

Gly Arg Leu Ala Thr Ala Thr Asp Gly Ala Gly Leu Thr Leu Ala Ala
                690                 695                 700

Asp Glu Asn Leu Thr Leu Ala Gly Arg Thr Ser Ser Ala Gly Ala Leu
705                 710                 715                 720
```

```
Leu Ala Arg Ala Gly Ala Ala Leu Val Asn Glu Gly Ile Val Thr Ala
                725                 730                 735

Arg Gln Asp Leu Ser Trp Arg Ala Arg Asp Ile Val Asn Ala Ala
            740                 745                 750

Gly Asn Val Val Ala Arg Ser Val Asp Met Arg Ala Gly Gln Gly Phe
            755                 760                 765

Asp His Arg Gly Ala Ile Gly Ser Val Thr Asp Leu Val Leu Lys Ala
            770                 775                 780

Ala Arg Ile Asp Ser Ala Gly Val Leu Arg Ala Asn Gln Asp Ile Asp
785                 790                 795                 800

Met His Ala Asp Ala Met Arg Leu Lys Ala Gly Ala Arg Thr Leu
                805                 810                 815

Ala Gly Arg Asp Leu Ala Leu Ala Ala Asp Gln Leu Glu Gln Ser Gly
            820                 825                 830

Met Ala Gln Ala Gly Arg Thr Leu Thr Ala Thr Ala Gly Ala Leu Glu
                835                 840                 845

Asn Asp Gly Leu Leu Asp Ala Ala Asp Ala Lys Leu Arg Thr Thr Arg
            850                 855                 860

Ala Phe Val Asn Arg Gly Gln Ile Gln Ala Asp Met Leu Gln Ala Gln
865                 870                 875                 880

Gly Pro Gln Ile Arg Asn Ala Gly Val Leu Arg Thr Gly Ala Leu Leu
            885                 890                 895

Ala Leu Gln Ala Ala Gly Arg Leu Glu Asn Thr Gly Gly Met Ala Ala
            900                 905                 910

Ser Gly Ser Leu Ser Ile Ala Ala Ala Gly Pro Phe Ala Asn Ser Gly
            915                 920                 925

Thr Met Gly Ala Asn Gly Asp Ala Ser Phe Ala Leu Ser Ser Phe Ala
            930                 935                 940

Asn Thr Gly Ser Ile Ser Val Gly Gly Asp Leu Ala Leu Arg Leu Pro
945                 950                 955                 960

Asp Val Glu Leu Thr Leu Asp Ala Asp His Arg Leu Pro Val Ser Gln
                965                 970                 975

Gly Thr Thr Leu Leu Gln Val Ala Ser Leu Asp Asn Arg Ala Arg Ser
            980                 985                 990

Glu Thr Pro Gly Arg Leu Ser Val Gln Ala Arg Gly Ala Ile Arg Asn
            995                 1000                1005

Gln Asp Thr Leu Ala Ala Gly Gln Gly Leu Trp Leu Glu Ser Ala
        1010                1015                1020

Ala Asn Asp Ile Glu Asn Gly Ala Gly Ala Leu Leu Trp Ser Gly
        1025                1030                1035

Ala Asp Leu Arg Leu Arg Gly Thr Arg Ile Ile Asn Arg Glu Ala
        1040                1045                1050

Ala Ile Ile Glu Ser Ala Ala Gly Met Val Leu Asp Ala Arg Ala
        1055                1060                1065

Glu Ile Asp Asn Gly Leu Gly Ile Ile Arg Ala Gly Gly Asp Leu
        1070                1075                1080

Trp Ala Asp Ala Pro Leu Leu Arg Asn Ser Gly Arg Leu Gly Gly
        1085                1090                1095

Arg Ile Val Pro Ala Gly Asp Ala Ala Ile Gly Gly Gly Thr Tyr
        1100                1105                1110

Asp His Tyr His Ser Ala Ala Val Val Trp His Glu Leu Phe Thr
        1115                1120                1125

Ala Gly Ala Ala Gly Ile Arg Val Pro Arg Tyr Asp Gly Lys Asp
        1130                1135                1140
```

-continued

```
Val Arg Val Ala Gln Ser Val Gln Ala Gly Gly Asn Leu His
    1145                1150                1155

Leu Asn Gln Gly Glu Gln Lys Gly Arg Gln Ala Arg Val Ser Asn
    1160                1165                1170

Gln Gly Arg Ile Glu Ala Ala Gly Met Ala Leu Val Asp Gly Asn
    1175                1180                1185

Val Asp Asn Ala Ser Leu His Leu Ser Leu Ser Val Asp Glu Tyr
    1190                1195                1200

Leu Arg Arg Pro Leu Ala Ala Pro Ile Val Leu Arg Ala Thr Asp
    1205                1210                1215

Ser Arg Ala Gln His Val Ile Pro Ala Phe Trp Lys Phe His Thr
    1220                1225                1230

Leu Tyr Glu Phe Leu Asp Phe Leu Leu Ser Asn Asn Glu Pro Arg
    1235                1240                1245

Tyr Ile Trp Gly Tyr Tyr Arg Thr Trp Pro Glu Trp Ala Phe Gln
    1250                1255                1260

Thr Leu Arg Asn Leu Asp Leu Gly Tyr Ala Gly Ala Pro Asp Pro
    1265                1270                1275

Thr Ala Pro Pro Val Pro Arg Pro Pro Val Leu Asp Pro Gln Ala
    1280                1285                1290

Lys Ala Ser Thr Thr Pro Ala Ala Gln Ala Leu Val Ala Gln Tyr
    1295                1300                1305

His Lys Asp Leu Ala Glu Tyr Ala Thr Ala Leu Glu Ala Ala Gln
    1310                1315                1320

Arg Ala Glu Ala Ile Arg Thr Ala Arg Gln Arg Val Asp Gly Ala
    1325                1330                1335

Leu Arg Ala Arg Tyr Gly Glu Lys Leu Ala Gln Leu Lys Thr Arg
    1340                1345                1350

Thr Pro Glu Val Asp Ala Ala Val Ala Ala Leu Ala Gln Thr Ile
    1355                1360                1365

Phe Asp Ala Arg Ala Lys Pro Ala Ala Glu Val Glu Lys Leu Ile
    1370                1375                1380

Ala Ala Ala Leu Cys Ser Pro Arg Ala Gln Ala Cys Ala Ala Gly
    1385                1390                1395

Thr Ala Arg Ile Ala Gln Leu Leu Asp Gln Ala Ser Leu Pro Pro
    1400                1405                1410

Arg Arg Pro Ala Val Ala Leu Phe Ala Gln Ala Met Ala Ala Val
    1415                1420                1425

Leu Gly Pro Asp Trp His Gly Pro Val Gly His Ala Thr Leu Met
    1430                1435                1440

Ala Arg Tyr Ala Asp Phe Lys Arg Arg Val Ala Thr Gln Gly Arg
    1445                1450                1455

Ala Ala Gly Gly Glu Leu Ala Phe Tyr Pro Ala Gln Gln Thr Val
    1460                1465                1470

Leu Ala Gly Gly Ala Gly Leu Val Leu Ser Gly Gly Arg Val Thr
    1475                1480                1485

Asn Gly Glu Asn Val Ala Gly Leu Leu Ala Arg Asn Met Thr Val
    1490                1495                1500

His Ile Gly Glu Gln Arg Ile Glu Thr Pro Arg Gly Ser Ile Asp
    1505                1510                1515

Ala Ile Arg His Pro Asp Ala Gly Pro Ala Val Thr Val Lys Asp
    1520                1525                1530

Ser Ile His Ala Leu Leu Glu Asn Arg Arg Leu Phe Ala Arg Thr
```

-continued

```
           1535                1540                1545

Ala Pro Ala Arg Ala Ala Ala Gly Pro Gly Gly Pro Asp Val Pro
    1550                1555                1560

Ala Thr Pro Pro Gly Leu Pro Gln Pro Leu Tyr Glu Thr Arg Leu
    1565                1570                1575

Ser Tyr Leu Asp Gln Ser His Tyr Tyr Gly Ser Gln Tyr Phe Phe
    1580                1585                1590

Asp Leu Ile Arg Tyr Arg Pro Asp Arg Pro Leu Arg Thr Ile Gly
    1595                1600                1605

Asp Asn Tyr Phe Glu Thr Arg Leu Ile Arg Glu Gln Ile Ala Arg
    1610                1615                1620

Ala Met Gly Gly His Glu Tyr Arg Asn Ala Val Arg Gly Leu Ala
    1625                1630                1635

Leu Val Gln Ser Leu Met Asp Ala Ala Pro Leu Ala Ala Ala Glu
    1640                1645                1650

Leu Gly Leu Arg Val Gly Gln Ala Pro Thr Ala Glu Gln Leu Ala
    1655                1660                1665

Arg Ala Thr Arg Asp Phe Val Trp Tyr Val Arg Glu Thr Val Asp
    1670                1675                1680

Gly Gln Glu Val Leu Val Pro Arg Val Tyr Leu Thr Arg Ala Thr
    1685                1690                1695

Arg Thr Ala Ala Ser Ala Thr Arg Glu Ala Gly Gly Ala Leu Met
    1700                1705                1710

Ala Ser Ala Gly Thr Val Leu Ala Asp Thr Gly Gly Ala Ala Ile
    1715                1720                1725

Glu Ser Gly Asn Ala Ala Phe Leu Gly Lys Asp Val Ile Leu Asp
    1730                1735                1740

Ala Ala Gly Gly Ala Val Arg Leu Ile Asn Asp Lys Gly Ile Ala
    1745                1750                1755

Gly Gly Ala Arg Ala Leu Gly Thr Leu Ala Ile Arg Gly Gly Asp
    1760                1765                1770

Ile Ala Ile Gln Gly Gly Leu Leu Asp Ala Ala Gln Ala Tyr Leu
    1775                1780                1785

Thr Gly Glu Arg Val Ser Leu Ala Ala Ser Ala Arg Tyr Asp Ala
    1790                1795                1800

His Gly Arg Leu Val Ser Arg His Asp Ala Arg Leu Asn Gly Arg
    1805                1810                1815

Ala Asp Ala Ala Gly Leu Leu Tyr Ile Ala Ala Lys Arg Leu Asp
    1820                1825                1830

Ser Ala Gly Ala Thr Leu Ser Gly Asp His Val Arg Leu Glu Ala
    1835                1840                1845

Asp Lys Val Arg Leu Gly Gly Leu Tyr Asp Val Asp Ser Ser Tyr
    1850                1855                1860

Ser Gln Thr Ser Arg Tyr Gly Leu Gly Lys Ala Trp Trp Leu Leu
    1865                1870                1875

Ser Ser Gln Thr Glu Thr Ala Thr Ala Ser His Ala Arg Phe Gln
    1880                1885                1890

Gly Thr Thr Leu Glu Gly Ala Ile Leu Ser Gly Arg Ala Thr Asp
    1895                1900                1905

Met Asp Ile Glu Gly Ser Ser Ala Arg Phe Gln Gln Thr Asp Leu
    1910                1915                1920

Gln Val Ala His Asp Phe Lys Ala Arg Ala Ala Ala Asp Tyr Ala
    1925                1930                1935
```

-continued

```
Tyr Ala Glu Arg Ala Lys Arg Val Asp Gln Leu Phe Leu Arg Leu
    1940                1945                1950

Ser Ala Gly Ala Gly Gly Tyr Glu Ala Gly Ile Asp Leu Ser Ala
    1955                1960                1965

Gln Gly Gly Leu Gln Ala His Ala Gly Arg Gly Gln Thr Ala Gly
    1970                1975                1980

Ala His Ala Ser Ala Gly Phe Glu Ser Thr Arg Glu Tyr Glu Arg
    1985                1990                1995

Ser Arg Met Thr His Tyr Arg Asn Ala Asp Leu Asn Phe Gly Ala
    2000                2005                2010

Gly Leu Leu Ala Val Gly Asn Thr Ala Asp Leu Gly Gly Ala Asp
    2015                2020                2025

Ile Asn Arg Asp Arg Tyr Gly Gln Gly Ala Ser Thr Ala Ser Asp
    2030                2035                2040

Ala Ile Pro Gly Asp Leu Leu Arg Ile Arg Ala Ala Arg Val Ala
    2045                2050                2055

Ala Thr Lys Tyr Leu Asp Val Thr Asp Ser Leu Thr Ala Ser Ser
    2060                2065                2070

Tyr Leu Arg Ala Ser Ile Asp Gly Ala Leu Thr Ser Ser Val Ala
    2075                2080                2085

Thr Ala Ala Thr Arg Leu Gly Asp Thr Leu Ala Glu Ala Arg Gln
    2090                2095                2100

Glu Asn Ser Gln Val His Ala Gly Gln Met Ala Leu Gln Met Ala
    2105                2110                2115

Gly Glu Ala Thr Gln Leu Ala Thr Thr Asp Thr Ala Ala Leu Ser
    2120                2125                2130

Ile Ser Ala Thr Phe Ala Ala Gly Tyr Ala Asp Ser His Arg Asn
    2135                2140                2145

Thr Gln Thr Glu Asn Thr Asn Tyr Phe Gly Gly Asn Leu Asp Ile
    2150                2155                2160

Arg Ala Thr Glu Gln Asp Ile Asp Leu Ala Gly Thr Lys Phe Ser
    2165                2170                2175

Gly Ala Asp Trp Leu Ala Leu Ser Ala Arg Arg Asp Ile Asn Val
    2180                2185                2190

Arg Ala Ala Ala Ser Arg Tyr Gln Glu Ser Gly Glu Gln His Asp
    2195                2200                2205

Leu Gln Leu His Gln Thr Ile Asn Ala Gly Ala Asn Ala Met Gln
    2210                2215                2220

Ala Ala Ala Gly Val Gly Val Thr Ala Gly Leu Ser Gly Ser His
    2225                2230                2235

Met Val Arg His Gly Ala Gly Gln Thr Tyr Glu Gly Ser Ala Leu
    2240                2245                2250

Arg Ala Thr Gln Leu His Leu Gln Ala Arg Asp Leu Asn Leu Asp
    2255                2260                2265

Ala Ser Met Ala Gln Ala Thr Arg Met Asp Leu His Val Ala Arg
    2270                2275                2280

Asp Leu Asn Ala Ile Ser Arg Gln Asp Glu Gln Arg Phe Ala Gln
    2285                2290                2295

Thr Gly Gly Asn Trp Glu Val Ser Leu Gly Ala Ala Ile Gln Asn
    2300                2305                2310

Arg Thr Leu Val Ala Pro Val Gly Thr Ile Gly Ala Gly Val Arg
    2315                2320                2325

His Glu His Asp Tyr Gln Ala Leu Thr Gln Asn Gly Gln Ala Gly
    2330                2335                2340
```

-continued

```
Leu Leu Ala Ser Gln Gly Leu Arg Ala Thr Val Gly Arg Asp Ala
    2345            2350                2355

Arg Leu Arg Gly Ala Ile Ile Ala Asp Ala Ser Asn Gln Gly Gly
    2360            2365                2370

Met Asp Ile Ala Gly Arg Ile His Ala Glu Ala Leu His Asp Tyr
    2375            2380                2385

Arg Asp Lys Asp Gly Phe Glu Thr Gly Ala Ser Val Gly Ile Ser
    2390            2395                2400

Ser Thr Thr Leu Asn Pro Thr Leu Ser Leu Thr Leu Gly Arg Pro
    2405            2410                2415

Ala Val Glu Gln Tyr Arg Ala Val Arg Gln Ala Thr Ile Ala Met
    2420            2425                2430

Gly Ala Ala Pro Gly Ala Pro Arg Tyr Thr Ala Arg Gly Gly Val
    2435            2440                2445

Ser Gly Arg Leu Asn Thr Asp Ser Gly Gln Ala Val Val Val Gln
    2450            2455                2460

Arg Ala Glu Arg Trp Ala Ser Ala Arg Thr Glu Phe Ser Phe Asp
    2465            2470                2475

Gln Pro Ser Arg Arg Asp Lys Ala Asp Ser Gly Ser Pro Gly Ala
    2480            2485                2490

Arg Pro Ala His Pro Gly Ala Ala Lys Ala Pro Ala Leu Pro Leu
    2495            2500                2505

Ala Arg Pro Leu Thr Ser Val Leu Ala Gly Pro Ser Ser Thr Ser
    2510            2515                2520

Pro Thr Ala Asn Pro Ala Ala Pro Gly Ile Ala Ala Gln Pro
    2525            2530                2535

Ala Pro Ala Ser Pro Gly Arg Asp Ala Pro Lys Pro Asp Pro Tyr
    2540            2545                2550

Ala Asn Arg Val Ile Val Gln Leu Ala Gln Asp Val Ala Thr
    2555            2560                2565

Gln Ala Ala Gln Ala Leu Phe His Lys His Ala Glu Gln Ser Asp
    2570            2575                2580

Trp Tyr Arg Gln Ala Asp Asp Gly Ser Leu His Pro Val His Pro
    2585            2590                2595

Leu Arg Ala Ala Ala Ala Gly Pro Thr Lys Ile Gln Leu Val Gly
    2600            2605                2610

His Gly Ser Ala Asp Arg Gln Ala Leu Ser Gly His Asp Gly His
    2615            2620                2625

Ala Val Ala Gly Ile Val Gln Gln Leu Arg Glu Arg Leu Pro Pro
    2630            2635                2640

Ala Ala Ala Leu Ala Lys Val Ala Leu Val Gly Cys Asp Thr Asp
    2645            2650                2655

Cys Ala Ser Gly Ala Ser Leu Arg Gly Asp Val Ala Gln Arg Leu
    2660            2665                2670

Ala Ala Asp Gly Ala Gln Pro Ala Pro Ala Val Ser Gly Tyr Ile
    2675            2680                2685

Gly Arg Leu Glu Val Asp Ala Ala Gly Arg Lys His Ala Val Ala
    2690            2695                2700

Gln Gly Gly Leu Gly Asp Val Asp Pro Glu Ala Arg Ala Gln Gly
    2705            2710                2715

Thr Gln Pro Val Pro Arg Val Phe Ser His Gly Pro Val Asn Ile
    2720            2725                2730

Ala Gln Ser Gly Gln Ala Arg Gln Leu Val Ile Asp Gly His Gly
```

```
                  2735                2740                2745
Ser Trp Val Arg Pro Asp Arg Ala Val Ala Pro Ser Tyr Ser Gly
    2750                2755                2760

Thr Val Arg Leu Pro Ala Gly Thr Arg Met His Phe Tyr Ser Asp
    2765                2770                2775

Asp Gly Gln Met Val Ser Ala Ile Pro Leu Arg Asn Ile Pro Asp
    2780                2785                2790

Asn Pro Glu Arg Ala Trp Arg Ala Gln Pro Phe Ser Glu Arg Ile
    2795                2800                2805

Ser Ser Glu Arg Ile Arg Arg Val Ala Asn Ala Ala Lys Val Pro
    2810                2815                2820

Phe Asp Val Ala Arg Gln Gly Phe Glu Thr Ser Thr Gln Val Arg
    2825                2830                2835

Glu Ile Ala Ala Pro Gly Thr Ala Val Lys Asn Tyr Leu Leu Thr
    2840                2845                2850

Pro Ile Asp Pro Gln Arg Asp Ala Ala Leu Ala Phe His Gln Ser
    2855                2860                2865

Arg Ser Gln Ala Asp Val Asp Leu Ala Ser Ala Ala Pro Gly Lys
    2870                2875                2880

Gly Ala Leu Leu Ser Asp Leu Leu Leu Ala Val Ala Ala Ser Gly
    2885                2890                2895

His Ser Tyr Pro Leu Ile His Tyr Thr Cys Cys Arg Gly Glu Phe
    2900                2905                2910

Gln Arg Pro Gly Ser Asp Thr Pro Ser Pro Gln Leu Pro Pro His
    2915                2920                2925

Glu Leu Leu Ile Arg Ser Trp Leu Ala Ser Ser Ala Pro Val His
    2930                2935                2940

Ala Leu Pro Leu Pro Pro Ser Ser Arg Gly Thr Leu Pro Gly Ala
    2945                2950                2955

Asp Pro Tyr Ala Leu Arg Ser Ile Val Gln Leu Gly Thr Asp Ala
    2960                2965                2970

Ala Thr Ala Arg Ala Ala Ala Leu His Gly Lys His Pro Ala
    2975                2980                2985

Asn Ser Asn Trp Tyr Leu Gln Thr Arg Asp Gly Leu Glu Pro
    2990                2995                3000

Val Arg Gln Ala Ala Gly Pro Ala Ala Gly Pro His Lys Val Gln
    3005                3010                3015

Phe Val Gly His Gly Asp Val Tyr His Gly Val Pro Leu Leu Gly
    3020                3025                3030

Gly Asn Ala Ala Ala Thr Leu Ala Asp Leu Leu Asn Gln Val Glu
    3035                3040                3045

Gln His Ser Pro Ala Gly Ala Arg Leu Asp Lys Ile Ala Leu Val
    3050                3055                3060

Gly Cys Asp Thr Asp Cys Thr Gly Arg Pro Ser Leu Arg Glu Pro
    3065                3070                3075

Phe Arg Gln Ser Leu Ala Ala Arg Pro Asp Ala Pro Ala Leu Thr
    3080                3085                3090

Val Thr Gly Tyr Ile Gly Arg Ile Asp Val Asp Ser Ala Gly Arg
    3095                3100                3105

Lys Arg Arg Val Ala Thr Gly Gly Leu Gly Asp Arg Pro Pro Ala
    3110                3115                3120

Asp Glu Pro Ala Ser Pro Arg Pro Pro Ala Gln Pro Ala Ala Pro
    3125                3130                3135
```

```
Gly Pro Gly Ala Ala Thr Pro Ser Ser Ala Pro Ser Ala Pro Val
    3140                3145                3150

Ala Ala Arg Leu Phe Thr His Gly Pro Ile Thr Leu Ser Gln Ser
    3155                3160                3165

Glu Asn Ala Arg Gln Leu Leu Ile Gln Gly His Ser Gly Trp Thr
    3170                3175                3180

Arg Pro Pro Ala Gly Thr Ser Gly Ala Gly Glu Ile Pro Ala Gly
    3185                3190                3195

Trp Leu Arg Leu Pro Ser Gly Thr Arg Met His Phe Tyr Ser Val
    3200                3205                3210

Asp Asn Gln Gln Thr Ser Gly Val Pro Val Gln Ala Ile Pro Arg
    3215                3220                3225

Asn Pro Glu Leu Ala Trp Leu Gly Arg Pro Phe Val Arg Glu Phe
    3230                3235                3240

Pro Ala Ser Val Ile Arg Gln Phe Ala His Ala Arg Gln Ala Pro
    3245                3250                3255

Phe Asp Val Ala Arg Ala Ala Leu Val Glu Ser Thr Arg Val Gln
    3260                3265                3270

Glu Val Ala Ala Ala Gly Ala Leu Val Lys Asn Tyr Arg Leu Ala
    3275                3280                3285

Pro Ala Ile Asp Pro Leu Val Thr Gly Val Glu Gln Phe His Ala
    3290                3295                3300

Gln Arg Arg Gln Gly Asp Val Asp Met Ala Val Ala Arg Glu Arg
    3305                3310                3315

Ala Ser Leu Ser Asp Val Leu Ala Ala Val Glu Ala Ser Gly His
    3320                3325                3330

His Tyr Pro Leu Leu His Phe Thr Cys Cys Arg Gly Glu Thr Thr
    3335                3340                3345

Pro Pro Gly Ala Pro Pro Asp Ala Val Ala Pro Leu Ala Pro
    3350                3355                3360

Val Ser Ala Arg Tyr Leu Gln Gln Trp Arg Glu Arg Ser Gly Val
    3365                3370                3375

Ala Gln Pro Arg Pro Pro Thr Pro Leu Gly Ala Glu Pro Pro Val
    3380                3385                3390

His Gly Pro Asp Arg Tyr Gly His Arg Thr Ile Val Gln Leu Gly
    3395                3400                3405

Ser Asp Ala Leu Thr Glu Thr Ala Ala Arg Arg Leu Phe Arg Lys
    3410                3415                3420

His Ala Gly Asn Ala Ser Trp Tyr Ser Gln Asp Ala Ser Gly Gln
    3425                3430                3435

Leu Thr Gln Val Arg Ala Pro Ala Ala Pro Ala Thr Gly Pro Gln
    3440                3445                3450

Lys Ile Gln Phe Val Gly His Gly Ser Ile Leu Glu Gly Met Pro
    3455                3460                3465

Leu Leu Gly Gly Asn Asn Ala Ala Gln Leu Ala Arg Met Leu Pro
    3470                3475                3480

Ala Ile Arg Gln Gly Leu Pro Ala Thr Ala Arg Val Glu Lys Ile
    3485                3490                3495

Thr Leu Val Gly Cys Asn Thr Gly Cys Ala Ser Arg Ala Ser Leu
    3500                3505                3510

Arg Asn Leu Leu Asn His Tyr Leu Ile Thr Thr Ala Gly Leu Ser
    3515                3520                3525

Ala Glu Val Lys Gly Tyr Ala Gly Arg Val Asp Val Asp Ala Ala
    3530                3535                3540
```

```
Gly His Lys Gln Ile Val Glu  Gln Gly Gly Leu Gly  Asn Thr Pro
    3545             3550                3555

Pro Pro Glu Ala Ala Pro Ala  Pro Arg Val Phe Arg  His Gly Asn
    3560             3565                3570

Val Thr Leu Ser Gln Ser Gly  Glu Ala Arg Gln Leu  Thr Ile Val
    3575             3580                3585

Gly His Gly Phe Trp Pro Arg  Pro Gly Pro Ala Asp  Gln Pro Asp
    3590             3595                3600

Gly Ala Ser Pro Pro Gly Trp  Val Arg Leu Pro Ala  Asn Thr Ser
    3605             3610                3615

Met Tyr Phe Tyr Ser Arg Glu  Asn Gln Leu Val Gly  Gly Leu Pro
    3620             3625                3630

Ser Gln Ala Ala Leu Arg Ala  Pro Met Leu Ala Ala  Gln Gly Gln
    3635             3640                3645

Gly Ala Ala Glu Leu Phe Ser  Arg Ala Val Ile Arg  Gly Phe Ala
    3650             3655                3660

His Arg His Gln Leu Pro Phe  Asp Val Ala Arg His  Thr Leu Val
    3665             3670                3675

Gly Ala Thr Arg Pro Gln Asp  Ile Gly Glu Pro Gly  Ala Leu Ile
    3680             3685                3690

Lys Asp Tyr Val Val Ser Pro  Ala Pro Glu Thr Gly  Leu Gly Ala
    3695             3700                3705

Ile Glu Asp Phe His Ala Ala  Arg Gln Gln Pro Asp  Met Asp Leu
    3710             3715                3720

Ala Gln Ala Ala Pro Gly Ser  Glu Ile Arg Leu Ser  Glu Ile Leu
    3725             3730                3735

Gln Ala Val Ala Gln Ser Gly  Val Arg Tyr Asp Leu  Ile His Tyr
    3740             3745                3750

Ala Cys Cys Arg Ala Glu Ile  Pro Ala Thr Asp Thr  Pro Thr Gln
    3755             3760                3765

Gln Val Ala Thr Pro Val Pro  Ala Pro Asp Lys Leu  Val Ile Gln
    3770             3775                3780

Gln Trp His Ser Gly Ala Gly  Ala Ala Arg Pro Pro  Ser Pro Gln
    3785             3790                3795

Ala Gln Ala Gln Ala Pro Tyr  Gly Pro Asp Arg Tyr  Ala His Arg
    3800             3805                3810

Val Ile Val Gln Leu Gly Ser  Asp Thr Val Thr Glu  Ser Ala Ala
    3815             3820                3825

Arg Arg Leu Phe Arg Lys His  Ala Ala Thr Ser Leu  Trp Tyr Gly
    3830             3835                3840

Gln Thr Leu Glu Gly Thr Leu  Met Leu Lys Gln Gly  Gly Asp Thr
    3845             3850                3855

Pro Ala Ala Gly Pro Leu Lys  Ile Gln Phe Val Gly  His Gly Gly
    3860             3865                3870

Pro Arg Tyr Ser Met Pro Leu  Leu Gly Gly Asn Thr  Pro Ala Glu
    3875             3880                3885

Leu Ala Gln Met Ala Ser Thr  Ile Gln His Ala Gly  Pro Pro Ser
    3890             3895                3900

Gln Leu Glu Lys Val Thr Leu  Val Gly Cys Gln Thr  Asp Cys Val
    3905             3910                3915

Ala Arg Pro Ser Leu Arg Lys  Leu Phe Ser Thr Ala  Leu Ala Thr
    3920             3925                3930

Glu His Gly Leu Thr Pro Ala  Val Thr Gly Tyr Ala  Gly Arg Val
```

```
                    3935                3940                3945

Asp Val  Asp Ala Ala Gly Arg  Lys Arg Ile Val Glu  Gln Gly Gly
    3950                3955                3960

Leu Asn  Glu Pro Arg Ala Gln  Ala Gly Ala Ser Thr  Ala Ala Pro
    3965                3970                3975

Asn Arg  Ile Val Gln Ser Val  Ala His Gly Val Ala  Leu Ser Gln
    3980                3985                3990

Ser Gly  Gln Ala Arg Gln Leu  Val Val Leu Ala His  Gly Gly Trp
    3995                4000                4005

Lys Asp  Lys Thr Thr Ser Arg  Tyr Leu Arg Arg Val  Arg Gly Asp
    4010                4015                4020

Gly Tyr  Thr Glu Leu Pro Ala  Asn Thr Arg Ile Asp  Tyr Tyr Thr
    4025                4030                4035

Glu Asp  Gly Ile Pro Thr Lys  Gly Phe Ala Val Tyr  Gln Glu Val
    4040                4045                4050

Thr Ala  Arg Ala Asn Asp Thr  Tyr Thr Gly Leu Gln  Pro Thr Leu
    4055                4060                4065

Ala Ile  Ser Pro Ala Asp Leu  Glu Ala Leu Ala Arg  Met His Asn
    4070                4075                4080

Thr Ser  Pro Gln Ala Leu Thr  Asp Ala Met Leu Ala  Ser Ala Val
    4085                4090                4095

Gly Arg  Arg Glu Ser Ile Ile  Gly Ala Ala Thr Met  Lys Asp Tyr
    4100                4105                4110

Ala Leu  Tyr Tyr His Glu Gln  Phe Ala Leu Asn Phe  Leu Arg Arg
    4115                4120                4125

His Asn  Ala Asp Gly Ser Ser  Ala Asp Val Asp Leu  Ala Ile Ile
    4130                4135                4140

Thr Glu  Pro Thr His Lys Arg  His Leu Ser Asp Val  Leu Lys Ala
    4145                4150                4155

Ala Gly  Glu Ser Gly Ala His  Tyr Asp Val Val His  Phe Gly Ala
    4160                4165                4170

Cys Arg  Val Gly Arg Cys Arg  Asn Ala Ala Ala Glu  Met Gly Ala
    4175                4180                4185

Ser Ala  Thr Ser Arg Leu Pro  Pro
    4190                4195

<210> SEQ ID NO 17
<211> LENGTH: 211
<212> TYPE: PRT
<213> ORGANISM: Vibrio cholerae

<400> SEQUENCE: 17

Ala Leu Ala Asp Gly Lys Ile Leu His Asn Gln Asn Val Asn Ser Trp
1               5                   10                  15

Gly Pro Ile Thr Val Thr Pro Thr Thr Asp Gly Gly Glu Thr Arg Phe
            20                  25                  30

Asp Gly Gln Ile Ile Val Gln Met Glu Asn Asp Pro Val Val Ala Lys
        35                  40                  45

Ala Ala Ala Asn Leu Ala Gly Lys His Ala Glu Ser Ser Val Val Val
    50                  55                  60

Gln Leu Asp Ser Asp Gly Asn Tyr Arg Val Val Tyr Gly Asp Pro Ser
65                  70                  75                  80

Lys Leu Asp Gly Lys Leu Arg Trp Gln Leu Val Gly His Gly Arg Asp
                85                  90                  95

His Ser Glu Thr Asn Asn Thr Arg Leu Ser Gly Tyr Ser Ala Asp Glu
```

```
                    100                 105                 110
Leu Ala Val Lys Leu Ala Lys Phe Gln Gln Ser Phe Asn Gln Ala Glu
            115                 120                 125

Asn Ile Asn Asn Lys Pro Asp His Ile Ser Ile Val Gly Cys Ser Leu
        130                 135                 140

Val Ser Asp Asp Lys Gln Lys Gly Phe Gly His Gln Phe Ile Asn Ala
145                 150                 155                 160

Met Asp Ala Asn Gly Leu Arg Val Asp Val Ser Val Arg Ser Ser Glu
                165                 170                 175

Leu Ala Val Asp Glu Ala Gly Arg Lys His Thr Lys Asp Ala Asn Gly
            180                 185                 190

Asp Trp Val Gln Lys Ala Glu Asn Asn Lys Val Ser Leu Ser Trp Asp
        195                 200                 205

Ala Gln Gly
    210

<210> SEQ ID NO 18
<211> LENGTH: 5
<212> TYPE: PRT
<213> ORGANISM: Artificial
<220> FEATURE:
<223> OTHER INFORMATION: Peptide linker utilized for fusing first
      polypeptide and second polypeptide in fusion protein

<400> SEQUENCE: 18

Gly Gly Gly Gly Ser
1               5
```